United States Patent
Brown et al.

(10) Patent No.: US 7,250,442 B2
(45) Date of Patent: Jul. 31, 2007

(54) DIHYDROINDOL-2-ONE DERIVATIVES AS STEROID HORMONE NUCLEAR RECEPTOR MODULATORS

(75) Inventors: Matthew Lee Brown, San Francisco, CA (US); Timothy Alan Grese, Indianapolis, IN (US); Prabhakar Kondaji Jadhav, Zionsville, IN (US); David Andrew Neel, Zionsville, IN (US); Mitchell Irvin Steinberg, South Bend, IN (US); Peter Ambrose Lander, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 317 days.

(21) Appl. No.: 10/506,175

(22) PCT Filed: Mar. 11, 2003

(86) PCT No.: PCT/US03/06152

§ 371 (c)(1),
(2), (4) Date: Aug. 31, 2004

(87) PCT Pub. No.: WO03/078394

PCT Pub. Date: Sep. 25, 2003

(65) Prior Publication Data

US 2005/0054712 A1 Mar. 10, 2005

(51) Int. Cl.
*C61K 31/405* (2006.01)
*C61K 31/40* (2006.01)
*C07D 209/04* (2006.01)
*C07D 209/36* (2006.01)
*C07D 209/34* (2006.01)

(52) U.S. Cl. .................. 514/415; 514/418; 548/469; 548/484; 548/486; 548/487

(58) Field of Classification Search ............ 514/415, 514/418; 548/469, 484, 486, 487
See application file for complete search history.

(56) References Cited

U.S. PATENT DOCUMENTS

| 3,558,653 A | 1/1971 | Coyne et al. |
| 3,705,869 A * | 12/1972 | Benedetto et al. .......... 524/104 |
| 4,016,173 A | 4/1977 | Darmory et al. |
| 4,053,483 A | 10/1977 | Pujol et al. |
| 4,904,575 A | 2/1990 | Ono et al. |
| 5,696,130 A | 12/1997 | Jones et al. |
| 5,914,431 A | 6/1999 | Fennhoff |
| 5,994,544 A | 11/1999 | Jones et al. |
| 6,008,210 A | 12/1999 | Weber |
| 6,017,924 A | 1/2000 | Edwards et al. |
| 6,093,708 A | 7/2000 | Weber |
| 6,121,450 A | 9/2000 | Jones et al. |
| 6,147,066 A | 11/2000 | Petit et al. |
| 6,166,013 A | 12/2000 | Coghlan et al. |
| 6,329,416 B1 | 12/2001 | Grubb et al. |

FOREIGN PATENT DOCUMENTS

| GB | 1 420 310 | 1/1976 |
| SU | 757 530 | 8/1980 |
| SU | 755782 | 8/1980 |
| WO | WO 96/19458 | 6/1996 |
| WO | WO 00/06137 | 2/2000 |
| WO | WO 01/19770 | 3/2001 |
| WO | WO 01/52847 | 7/2001 |

OTHER PUBLICATIONS

Petynin et al., Zhurnal Obshchei Khimii (1957), 27, 731-4.*
Klumpp et al., J. Org. Chem., 1998, 63, 4481-4484.*
Neel et al., Bio. & Med. Chem. Lett., 15, 2005, 2553-2557.*
Neel, et al., Bioorganic & Medicinal Chemistry Letters, vol. 15, 2005, pp. 2553-2557.*
Witkop, Bernhard, "Two-fold Wagner-Meerwein Rearrangements," Journal of the American Chemical Society, vol. 73, pp. 5664-5669; XP002244339 (1951).
Klumpp, D, et al., "Preparation of 3,3-Diaryloxindoles by Superacid-induced condensation of Isatins and aromatics with a Combinatorial Approach," Journal of Organic Chemistry, vol. 63, pp. 4481-4484; XP002244340 (1998).
Petyunin, P, et al., "N-Alkyl derivatives of 3,3-diaryloxindoles," Zhurnal Obshchei Khim, vol. 27, pp. 1554-1557; XP009012299 (1957).

* cited by examiner

*Primary Examiner*—Joseph K. McKane
*Assistant Examiner*—Susannah Chung
(74) *Attorney, Agent, or Firm*—Alexander Wilson

(57) ABSTRACT

The present invention relates to methods of treating pathological disorders susceptible to steroid hormone nuclear receptor modulation, particularly congestive heart failure, comprising administering to a patient in need thereof an effective amount of a compound of the formula: I or a pharmaceutically acceptable salt thereof. In addition, the present invention provides novel pharmaceutical compounds of Formula I, including the pharmaceutically acceptable salts thereof, as well as pharmaceutical compositions which comprise as an active ingredient a compound of Formula I

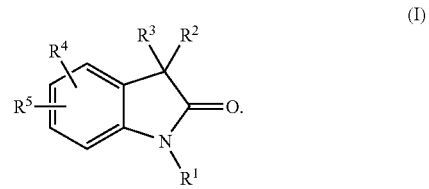

9 Claims, No Drawings

DIHYDROINDOL-2-ONE DERIVATIVES AS STEROID HORMONE NUCLEAR RECEPTOR MODULATORS

BACKGROUND OF THE INVENTION

Nuclear hormone receptors are an evolutionarily conserved class of intracellular receptor proteins which have been termed "ligand dependent transcription factors". Evans et al., SCIENCE, 240: 889 (1988). The nuclear hormone receptor gene superfamily encodes structurally-related receptor proteins for glucocorticoids (e.g. cortisol, corticosterone, cortisone), androgens, mineralocorticoids (e.g. aldosterone), progestins, estrogen, and thyroid hormone. Also included within this superfamily of nuclear receptors are receptor proteins for vitamin D, retinoic acid, 9-cis retinoic acid, as well as those receptors for which no cognate ligands have been identified ("orphan receptors") Ribeiro et al., Annual Rev. Med., 46:443-453 (1995). Steroid hormone receptors represent a subset of the nuclear hormone receptor superfamily. So named according to the cognate ligand which complexes with the receptor in its native state, the steroid hormone nuclear receptors include the glucocorticoid receptor (GR), the androgen receptor (AR), the mineralocorticoid receptor (MR), the estrogen receptor (ER), and the progesterone receptor (PR). Tenbaum et al., Int. J. Biochem. Cell. Bio., 29(12):1325-1341(1997).

In contrast to membrane bound receptors, nuclear hormone receptors encounter their respective ligands following entry of the ligand into the cell. Once ligand binding occurs, the ligand-receptor complex modulates transcription of target genes within the cell nucleus. For example, most ligand-free nuclear receptors are bound in a complex with heat shock proteins (hsps) in the cytoplasm. Following entry of circulating hormone into the cell, hormone binding elicits a conformational change in the receptor, dissociating the receptor from the hsp. The ligand bound receptors form hetero-dimers that translocate to the nucleus where they bind to particular hormone response elements (HREs) in the promoter regions of target genes.

The HRE-receptor complex then, in turn, regulates transcription of proximally-located genes. (see Ribeiro et al., supra.). On the other hand, thyroid hormone receptors (TRs) and other non-steroid receptors such as vitamin D receptor (VDR) and retinoic acid receptors (RAR) are bound to their respective HRE in the absence of hsps and/or cognate ligand. Hormones released from the circulation enter the cell, binding in the nucleus to these receptors which, in turn, hetero-dimerize to other nuclear receptors such as 9-cis retinoic acid (RXR). As with the steroid hormone nuclear receptors, following ligand binding, the ligand-bound receptor complex again regulates transcription of neighboring genes.

Mineralocorticoids and glucocorticoids exert profound influences on a multitude of physiological functions by virtue of their diverse roles in growth, development, and maintenance of homeostasis. The actions are mediated by the MR and GR which share approximately 94% homology in their respective DNA binding regions, and approximately 57% homology in their respective ligand-binding domains. Kino et al., J. of Endocrinology, 169, 437-445 (2001). In visceral tissues, such as the kidney and the gut, MR regulates sodium retention, potassium excretion, and water balance in response to aldosterone. In addition, MR expression in the brain appears to play a role in the control of neuronal excitability, in the negative feedback regulation of the hypothalamo-pituitary-adrenal axis, and in the cognitive aspects of behavioral performance. Castren et al., J. of Neuroendocrinology, 3, 461-466 (1993). GR, which is ubiquitously expressed in almost all tissues and organ systems, and the presence of glucocorticoids, appears crucial for the integrity of central nervous system function and the maintenance of cardiovascular, metabolic, and immune homeostasis. Kino et al., J. of Endocrinology, 169,437-445 (2001).

Elevations in aldosterone levels, or excess stimulation of mineralocorticoid receptors, are linked to several pathological disorders or pathologic disease states including, Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels. Hadley, M. E., ENDOCRINOLOGY, $2^{nd}$ Ed., pp. 366-381, (1988); and Brilla et al., Journal of Molecular and Cellular Cardiology, 25 (5), pp. 563-575 (1993). Additionally, elevated aldosterone levels have been increasingly implicated with congestive heart failure (CHF). In CHF, the failing heart triggers hormonal mechanisms in other organs in response to the attending reductions in blood flow and blood pressure seen with CHF. In particular, the kidney activates the renin-angiotensin-aldosterone system (RAAS) causing an increase in aldosterone production by the adrenals which, in turn, promotes water and sodium retention, potassium loss, and further edema. Although historically it was believed that aldosterone participated in the etiology of CHF only as a result of its salt retaining effects, several recent studies have implicated elevated aldosterone levels with events in extra-adrenal tissues and organs, such as myocardial and vascular fibrosis, direct vascular damage, and baroreceptor dysfunction. Pitt et al., New Eng. J. Med., 341:709-717 (1999). These findings are particularly significant since angiotensin converting enzyme (ACE) inhibitors, which were once thought to completely abolish aldosterone production, are now believed to only transiently suppress aldosterone production which has been shown to occur in extra-adrenal tissues including the heart and vasculature. Weber, New Eng. J. Med., 341:753-755 (1999); Fardella and Miller, Annu. Rev. Nutr., 16:443-470 (1996).

The involvement of aldosterone acting via MR in CHF was confirmed in the recently completed RALES (Randomized Aldactone Evaluation Study) study. Pitt et al., New Eng. J. Med., 341:709-717 (1999). The RALES study demonstrated that the use of Aldactone™ (spironolactone), a well-known competitive MR antagonist, in combination with standard CHF therapy, reduced cardiac related mortality by 30% and frequency of hospitalization by 35% in patients suffering from advanced CHF. However, spironolactone therapy has also been implicated with attending side effects such as gastric bleeding, diarrhea, azotemia, hyperchloremic metabolic acidosis an type-4 renal tubule acidosis, nausea, gynecomastia, erectile dysfunction, hyperkalemia, and irregular menses. Thus, the mineralocorticoid receptor represents a viable target for CHF therapy either alone or in combination with conventional CHF therapies such as vasodilators (ACE inhibitors), inotropics (digoxin), diuretics, or beta blockers. Molecules, and preferably non-steroidals, which bind to the mineralocorticoid receptor and modulate receptor activity without the attending side effects of current therapies would be particularly desirable.

Glucocorticoids (e.g. cortisol, corticosterone, and cortisone), and the glucocorticoid receptor, have also been implicated in the etiology of a variety of pathological disorders or pathologic disease states. For example, cortisol hyposecretion is implicated in the pathogenesis of Addison's Disease and may result in muscle weakness, increased melanin pigmentation of the skin, weight loss, hypotension, and hypoglycemia. On the other hand, excessive or prolonged secretion of glucocorticoids has been correlated to Cushing's Syndrome and may also result in obesity, hypertension, glucose intolerance, hyperglycemia, diabetes mellitus, osteoporosis, polyuria, and polydipsia. Hadley, M. E., ENDOCRINOLOGY, $2_{nd}$ Ed., pp. 366-381, (1988). Further, Coghlan et al., U.S. Pat. No. 6,166,013, issued Dec. 26, 2000, discloses that GR selective agents could modulate GR activity and, thus, be useful in the treatment of inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome. Coghlan et al. also discloses that GR modulators are especially useful in disease states involving systemic inflammation such as inflammatory bowel disease, systemic lupus erythematosus, polyartitis nodosa, Wegener's granulomatosis, giant cell arthritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis; and that GR modulating compounds have been used as immunostimulants, repressors, and as wound healing and tissue repair agents.

In addition, Coghlan et al. discloses that GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, and cutaneous T-cell lymphoma.

Thus, it is clear that a ligand which has affinity for steroid hormone nuclear receptors, and particularly for MR and/or GR, could be used to modulate (i.e. antagonize, agonize, partially antagonize, partially agonize) receptor activity and therby influence a multitude of physiological functions related to alterations in steroid hormone levels and/or steroid hormone receptor activity. In this regard, such ligands could be useful to treat a wide range of pathological disorders susceptible to steroid hormone nuclear receptor modulation.

Several art references disclose oxindole derivative molecules useful as, inter alia, photographic coupling agents, intermediates in polyimide synthesis, and chemical catalysts. Further, oxindole-derivative compounds have also been disclosed as having pharmcologic utility as, inter alia, anti-inflammatory agents, laxative agents, and analgesic agents. Surprisingly, however, and in accordance with the present invention, applicants have discovered a series of oxindole-derivative compounds with affinity for steroid hormone nuclear receptors, and particularly MR and GR. Such compounds could modulate receptor activity and, thus, have utility in treating pathological disorders related to alterations in steroid hormone level and/or to alterations in steroid hormone nuclear receptor activity. As a further embodiment, the present invention also provides a novel series of novel non-steroidal oxindole-derivative compounds that exhibit steroid hormone nuclear receptor affinity and modulating activity. Such methods and compounds could address a long felt and continuing need for safe and effective pharmaceutical interventions without the attending side effects of steroidal-type agents. The treatment of steroid hormone related pathological disorders is hereby furthered.

The following references describe examples of the state of the art as it relates to the present invention.

U.S. Pat. No. 4,904,575 and Japanese Patent No. JP01105248 disclose indolinone compounds as photographic coupling agents.

Russian Patent No. SU757530 discloses 3,3-diaryl-2-indolinone-1-acetic acid derivatives as anti-inflammatory agents.

Russian Patent No. SU75782 discloses 3,3-di-para-tolyl-5-bromo-1-aminomethyl-2-indolinone derivatives as anti-inflammatory agents.

U.S. Pat. No. 3,705,869 and U.S. Pat. No. 4,016,173 disclose the synthesis of oxindole diamines useful for preparing polimide polymers.

U.S. Pat. No. 4,053,483 discloses 3,3-bis-4-hydroxyphenyl-2-indolinone compounds as laxative agents.

U.S. Pat. No. 3,558,653 discloses 1-aminoalkyl-3,3-diphenyl-indolinones compounds as anti-inflammatory agents.

U.S. Pat. No. 5,914,431 discloses cocatalysts for the synthesis of bisphenols.

U.S. Pat. No. 6,329,416 discloses combination treatment regimes using 3,3 substitutted indoline derivative PR antagonists.

Published International PCT Application WO 96/19458 and U.S. Pat. Nos. 5,696,130; 5,994,544; 6,017,924, and 6,121,450 disclose quinoline derivative analogs as steroid hormone receptor modulators.

Published International PCT Application WO 00/06137 and U.S. Pat. No. 6,166,013 disclose triphenylmethane compounds as glucocorticoid receptor modulators.

U.S. Pat. No. 6,147,066 discloses anti-mineralocorticoid receptor compounds for use in treating drug withdrawal syndrome.

U.S. Pat. Nos. 6,008,210 and 6,093,708 disclose spirolactone compounds, such as spironolactone and epoxymexrenone, with affinity for the mineralocorticoid receptor for use in the treatment of myocardial fibrosis.

SUMMARY OF THE INVENTION

The present invention is directed to the discovery that oxindole-derivative compounds of the present invention, as defined below, are modulators of steroid hormone nuclear receptors. Accordingly, the present invention provides a method of treating a pathological disorder susceptible to steroid hormone nuclear receptor modulation comprising administering to a patient in need thereof an effective amount of a compound of the formula:

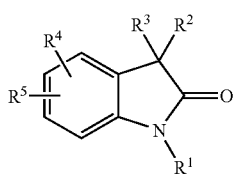

Formula I wherein

R¹ represents $(C_1-C_6)$alkyl, halo$(C_1-C_6)$alkyl, $(C_3-C_7)$cycloalkyl, $(C_3-C_7)$cycloalkoxy, $(C_1-C_4)$alkyl-$(C_3-C_7)$cycloalkyl, $(C_1-C_4)$alkyl-$(C_1-C_6)$alkoxy, $(C_1-C_4)$alkyl-$(C_3-C_7)$cycloalkoxy, $(C_1-C_4)$alkyl-substituted$(C_3-C_7)$cycloalkyl, $(C_2-C_6)$alkenyl, $(C_2-C_6)$alkynyl, aryl, substituted aryl, $(C_1-C_4)$alkyl-aryl, $(C_1-C_4)$alky-substituted aryl, heterocycle, substituted heterocycle, $(C_1-C_4)$alkyl-heterocycle, $(C_1-C_4)$alkyl-substituted heterocycle, $CH_2CN$ or $CH_2COR^7$;

R² represents $(C_1-C_6)$alkyl, halo$(C_1-C_6)$alkyl, hydroxy$(C_1-C_6)$alkyl, $(C_3-C_7)$cycloalkyl, $(C_1-C_6)$alkyl-$(C_3-C_7)$cycloalkyl, $(C_1-C_6)$alkyl-$(C_1-C_6)$alkoxy, $(C_2-C_6)$alkenyl, or a group of the formula:

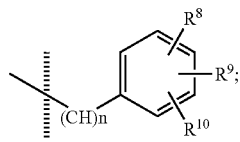

wherein n is 0, 1, or 2;

R³ represents a group of the formula:

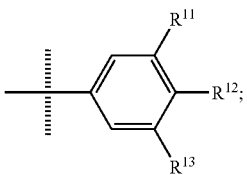

R⁴ and R⁵ each independently represent hydrogen, halo, hydroxy, $(C_1-C_4)$alkyl, $(C_1-C_4)$alkoxy, $(C_3-C_5)$cyclkoalkyl, $CF_3$, $OCF_3$, $CHF_2$, $OCHF_2$, $CF_2CF_3$, cyano, nitro, amino, $NH—(C_1-C_6)$alkylamine, or $N,N—(C_1-C_6)$dialkylamine;

R⁷ represents $(C_1-C_6)$alkyl, $(C_3-C_7)$cycloalkyl, $NH(C_3-C_7)$cycloalkyl, $(C_1-C_4)$alkoxy, aryl, heterocycle, or an aryl or heterocycle optionally substituted with 1-2 substituents independently selected from the group consisting of:
  $(C_1-C_4)$alkyl, $(C_3-C_7)$cycloalkyl, halo, hydroxy, $(C_1-C_4)$alkoxy, $CF_3$, $OCF_3$, $CHF_2$, $OCHF_2$, $CF_2CF_3$, cyano, nitro, amino, $NH—(C_1-C_6)$alkylamine,and $N,N—(C_1-C_6)$dialkylamine;

R⁸ through R¹⁰ each independently represent hydrogen, hydroxyl, $(C_1-C_4)$alkyl, $(C_1-C_4)$alkoxy, halo, nitro, amino, $NH(C_1-C_6)$alkylamine, $N,N—(C_1-C_4)$dialkylamine, or $NHR^{14}$; or R⁸ and R⁹, or R⁹ and R¹⁰, together with the carbon atoms to which each are attached, form a benzofused heterocyclic ring;

R¹¹ and R¹³ each independently represent hydrogen, hydroxyl, $(C_1-C_4)$alkyl, $(C_1-C_4)$alkoxy, halo, nitro, amino, $NH(C_1-C_6)$alkylamine, $N,N—(C_1-C_4)$dialkylamine;

R¹² represents hydrogen, hydroxyl, $(C_1-C_4)$alkyl, halo, nitro, amino, $NH(C_1-C_6)$alkylamine, $N,N—(C_1-C_4)$dialkylamine; and R¹⁴ represents acyl or $(C_1-C_4)$alkylsulfonyl; or a pharmaceutically acceptable salt thereof.

Examples of such pathological disorders include Conn's Syndrome, secondary hyperaldosteronism, increased sodium retention and edema, increased magnesium and potassium excretion (diuresis), increased water retention, hypertension, Bartter's Syndrome, disorders associated with excess catecholamine levels, diastolic and systolic congestive heart failure, myocardial infarction, isolated systolic and combined systolic/diastolic hypertension, peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, glucose intolerance, hyperglycemia, diabetes mellitus, osteoporosis, polyuria, and polydipsia, leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, chronic primary adrenal insufficiency, secondary adrenal insufficiency, cerebral edema, thrombocytopenia, and Little's syndrome, inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, and cutaneous T-cell lymphoma, and disorders associated with impaired cognitive function.

As a particular aspect, the present invention provides a method of treating a pathological disorder susceptible to mineralocorticoid or glucocorticoid receptor modulation comprising administering to a patient in need thereof an effective amount of a compound of Formula I, as described more fully herein and above. As a more particular aspect, the present invention provides a method of treating a pathological disorder susceptible to mineralocorticoid or glucocorticoid receptor antagonism comprising administering to a patient in need thereof an effective amount of a compound of Formula I, as described herein and above.

Certain of the oxindole-derivative compounds corresponding to Formula I are believed to be novel and, thus, to constitute another embodiment of the present invention. As such, the present invention also provides a novel compound of Formula I:

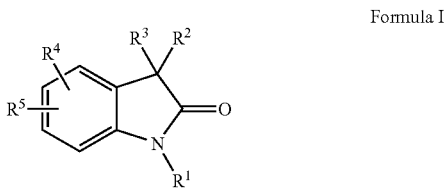

Formula I wherein

R¹ represents halo($C_1$-$C_6$)alkyl, ($C_3$-$C_7$)cycloalkyl, ($C_3$-$C_7$)cycloalkoxy, ($C_1$-$C_4$)alkyl-($C_3$-$C_7$)cycloalkyl, ($C_1$-$C_4$)alkyl-($C_1$-$C_6$)alkoxy, ($C_1$-$C_4$)alkyl-($C_3$-$C_7$)cycloalkoxy, ($C_1$-$C_4$)alkyl-substituted($C_3$-$C_7$)cyclkoalkyl, ($C_2$-$C_6$)alkenyl, ($C_2$-$C_6$)alkynyl, aryl, substituted aryl, ($C_1$-$C_4$)alkyl-aryl, ($C_1$-$C_4$)alky-substituted aryl, heterocycle, substituted heterocycle, ($C_1$-$C_4$)alkyl-heterocycle, ($C_1$-$C_4$)alkyl-substituted heterocycle, $CH_2CN$ or $CH_2COR^7$, with the proviso that R¹ is other than phenyl or benzyl;

R² represents ($C_1$-$C_6$)alkyl, halo($C_1$-$C_6$)alkyl, hydroxy ($C_1$-$C_6$)alkyl, ($C_3$-$C_7$)cycloalkyl, ($C_1$-$C_6$)alkyl-($C_3$-$C_7$)cycloalkyl, ($C_1$-$C_6$)alkyl-($C_1$-$C_6$)alkoxy, ($C_2$-$C_6$)alkenyl, or a group of the formula:

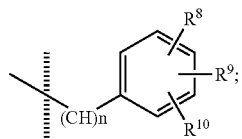

wherein n is 0, 1, or 2;

R³ represents a group of the formula:

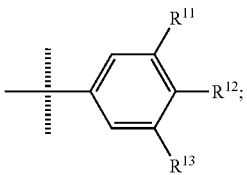

R⁴ and R⁵ each independently represent hydrogen, halo, hydroxy, ($C_1$-$C_4$)alkyl, ($C_1$-$C_4$)alkoxy, ($C_3$-$C_5$)cyclkoalkyl, $CF_3$, $OCF_3$, $CHF_2$, $OCHF_2$, $CF_2CF_3$, cyano, nitro, amino, NH—($C_1$-$C_6$)alkylamine, or N,N—($C_1$-$C_6$)dialkylamine;

R⁷ represents ($C_1$-$C_6$)alkyl, ($C_3$-$C_7$)cycloalkyl, NH($C_3$-$C_7$)cycloalkyl, ($C_1$-$C_4$)alkoxy, aryl, heterocycle, or an aryl or heterocycle optionally substituted with 1-2 substituents independently selected from the group consisting of:

($C_1$-$C_4$)alkyl, ($C_3$-$C_7$)cycloalkyl, halo, hydroxy, ($C_1$-$C_4$) alkoxy, $CF_3$, $OCF_3$, $CHF_2$, $OCHF_2$, $CF_2CF_3$, cyano, nitro, amino, NH—($C_1$-$C_6$)alkylamine, and N,N—($C_1$-$C_6$)dialkylamine;

R⁸ through R¹⁰ each independently represent hydrogen, hydroxyl, ($C_1$-$C_4$)alkyl, ($C_1$-$C_4$)alkoxy, halo, nitro, amino, NH($C_1$-$C_6$)alkylamine, N,N—($C_1$-$C_4$)dialkylamine, or $NHR_{14}$; or R⁸ and R⁹, or R⁹ and R¹⁰, together with the carbon atoms to which each are attached, form a benzofused heterocyclic ring;

R¹¹ and R¹³ each independently represent hydrogen, hydroxyl, ($C_1$-$C_4$)alkyl, ($C_1$-$C_4$)alkoxy, halo, nitro, amino, NH($C_1$-$C_6$)alkylamine, N,N—($C_1$-$C_4$)dialkylamine, with the proviso that where R¹² is hydrogen, hydroxy, ($C_1$-$C_4$) alkyl, halo, amino, NH($C_1$-$C_6$)alkylamine, or N,N—($C_1$-$C_4$) dialkylamine, then at least one of R¹¹ and R¹³ is other than hydrogen;

R¹² represents hydrogen, hydroxyl, ($C_1$-$C_4$)alkyl, halo, nitro, amino, NH($C_1$-$C_6$)alkylamine, N,N—($C_1$-$C_4$)dialkylamine; and R¹⁴ represents acyl or ($C_1$-$C_4$)alkylsulfonyl, or a pharmaceutically acceptable salt thereof.

In another embodiment, the present invention provides a method of treating a pathological disorder susceptible to steroid hormone nuclear receptor modulation comprising administering to a patient in need thereof an effective amount of a novel compound of Formula I, or a pharmaceutically acceptable salt thereof, as described more fully herein and above. Examples of such pathological disorders include Conn's Syndrome, secondary hyperaldosteronism, increased sodium retention and edema, increased magnesium and potassium excretion (diuresis), increased water retention, hypertension, Bartter's Syndrome, disorders associated with excess catecholamine levels, diastolic and systolic congestive heart failure, myocardial infarction, isolated systolic and combined systolic/diastolic hypertension, peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, glucose intolerance, hyperglycemia, diabetes mellitus, osteoporosis, polyuria, and polydipsia, leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, chronic primary adrenal insufficiency, secondary adrenal insufficiency, cerebral edema, thrombocytopenia, and Little's syndrome, inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, and cutaneous T-cell lymphoma, and disorders associated with impaired cognitive function.

As a particular aspect, the present invention provides a method of treating a pathological disorder susceptible to mineralocorticoid or glucocorticoid receptor modulation comprising administering to a patient in need thereof an effective amount of a novel compound of Formula I, as described herein and above. More particularly, the present invention provides a method of treating a pathological disorder susceptible to mineralocorticoid or glucocorticoid receptor antagonism comprising administering to a patient in need thereof an effective amount of a novel compound of Formula I, as described herein and above. As an even more particular aspect, the present invention provides a method of treating systolic and/or diastaolic congestive heart failure comprising administering to a patient in need thereof an effective amount of a novel compound of Formula I, as described herein and above.

In addition, the present invention also provides a method of modulating a steroid hormone nuclear receptor comprising administering to a patient in need thereof an effective amount of a compound of Formula I, or a pharmaceutically acceptable salt thereof. More particularly, the present invention provides a method of modulating MR or GR comprising administering to a patient in need thereof an effective amount of a compound of Formula I, or a pharmaceutically acceptable salt thereof, as described herein and above. As an even more particular aspect, the present invention provides a method of modulating MR or GR comprising administering to a patient in need thereof an effective amount of a novel compound of Formula I, as described herein and above. More particular still, the present invention provides a method of antagonizing MR or GR comprising administering to a patient in need thereof an effective amount of a compound of Formula I, or a novel compound of Formula I, all as described herein and above.

In addition, the present invention provides pharmaceutical compositions of compounds of Formula I, including any pharmaceutically acceptable salts and hydrates thereof, comprising a compound of Formula I in combination with a pharmaceutically acceptable carrier, diluent or excipient. More particularly, the present invention provides pharmaceutical compositions comprising a novel compound of Formula I in combination with a pharmaceutically acceptable carrier, diluent or excipient. This invention also encompasses novel intermediates, and processes for the synthesis of the compounds of Formula I.

The present invention also provides the use of a compound of Formula I, or a pharmaceutically acceptable salt thereof, for the manufacture of a medicament for treating a pathological disorder susceptible to steroid hormone nuclear receptor modulation. More particularly, the present invention provides the use of a novel compound of Formula I, or a pharmaceutically acceptable salt thereof, for the manufacture of a medicament for treating a pathological disorder susceptible to steroid hormone nuclear receptor modulation. As an even more particular aspect, the present invention provides the use of a novel compound of Formula I for the manufacture of a medicament for treating congestive heart failure.

DETAILED DESCRIPTION OF THE INVENTION

The present invention provides compounds with affinity for steroid hormone nuclear receptors, particularly MR and/or GR, which could be used to modulate (i.e. antagonize, agonize, partially antagonize, partially agonize) receptor activity and therby influence physiological functions related to steroid hormone levels and/or steroid hormone receptor activity. In this regard, such ligands are believed to be useful in treating or preventing a multitude of pathological disorders susceptible to steroid hormone nuclear receptor modulation. Thus, methods for the treatment or prevention of pathological disorders susceptible to steroid hormone nuclear receptor modulation constitute an important embodiment of the present invention. As a particular aspect, the present invention provides compounds useful as minerlaocorticoid or glucorcorticoid receptor modulators. As a more particular aspect, the present invention provides compounds useful as minerlaocorticoid or glucocorticoid receptor antagonists. In addition, certain of the compounds of Formula I are believed to be novel and, thus, to constitute yet another important embodiment of the present invention.

As will be understood by the skilled artisan, some of the compounds useful for the methods of the present invention may be available for prodrug formulation. As used herein, the term "prodrug" refers to a compound of Formula I which has been structurally modified such that in vivo the prodrug is converted, for example, by hydrolytic, oxidative, reductive, or enzymatic cleavage, into the parent molecule ("drug") as given by Formula I. Such prodrugs may be, for example, metabolically labile ester derivatives of the parent compound where said parent molecule bears a carboxylic acid group. Conventional procedures for the selection and preparation of suitable prodrugs are well known to one of ordinary skill in the art.

It is also understood that many of the steroid hormone nuclear receptor modulators of the present invention may exist as pharmaceutically acceptable salts and, as such, pharmaceutically acceptable salts are therefore included within the scope of the present invention. The term "pharmaceutically acceptable salt" as used herein, refers to salts of the compounds of Formula I, which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. It is further understood by the skilled reader that salt forms of pharmaceutical compounds are commonly used because they are often more readily crystallized, or more readily purified, than are the free bases. In all cases, the use of the pharmaceutical compounds of the present invention as salts is contemplated in the description herein. Hence, it is understood that where compounds of Formula I are capable of forming salts, the pharmaceutically acceptable salts are encompassed in the names provided herein.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napththalene-2-sulfonate, mandelate and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. All such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As used herein the term "Pg" refers to a suitable oxygen or nitrogen protecting group. Suitable oxygen or nitrogen protecting groups, as used herein, refers to those groups intended to protect or block the oxygen or nitrogen group against undesirable reactions during synthetic procedures. Whether the term "Pg", as used herein, represents an oxygen protecting group or a nitrogen protecting group will be readily apparent to the ordinarily skilled artisan. The suitability of the oxygen or nitrogen protecting group used will depend upon the conditions that will be employed in subsequent reaction steps wherein protection is required, and is well within the knowledge of one of ordinary skill in the art.

Commonly used nitrogen protecting groups are disclosed in Greene, "Protective Groups In Organic Synthesis," (John Wiley & Sons, New York (1981)). Suitable nitrogen protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl,.alpha.,.alpha.-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Commonly used oxygen protecting groups are also disclosed in Greene (supra). Suitable oxygen protecting groups comprise alkyl groups such as methyl, ethyl, and the like; silyl groups such as t-butyldimethylsilyl, t-butyldiphenylsilyl, triisopropylsilyl, and the like, with t-butyldimethylsilyl being preferred. Other commonly used oxygen protecting groups include benzyl, 4-nitrophenyl methyl, benzoyl, and the like.

As used herein the term "$(C_1-C_4)$alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "$(C_1-C_4)$alkyl" is included within the definition of "$(C_1-C_6)$alkyl".

As used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. It is understood that the terms "$(C_1-C_4)$alkyl" and "$(C_1-C_6)$alkyl" are included within the definition of "$(C_1-C_{10})$alkyl".

As used herein, the terms "Me", "Et", "Pr", "iPr", "Bu" and "t-Bu" refer to methyl, ethyl, propyl, isopropyl, butyl and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methoxy, ethoxy, n-propoxy, isopropoxy, n-butoxy, and the like. As used herein the term "$(C_1-C_6)$alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like. It is understood that the term "$(C_1-C_4)$alkoxy" is included within the definition of "$(C_1-C_6)$alkoxy".

As used herein, the term "hydroxy$(C_1-C_4)$alkyl" refers to a straight or branched, monovalent, saturated aliphatic chain of 1 to 4 carbon atoms bearing a hydroxyl group attached to one of the carbon atoms. As used herein, the term "hydroxy "($C_1$-$C_6$)alkyl" refers to a straight or branched, monovalent, saturated aliphatic chain of 1 to 6 carbon atoms bearing a hydroxyl group attached to one of the carbon atoms. It is understood that the term "hydroxy($C_1$-$C_4$)alkyl" is included within the definition of "hydroxy($C_1$-$C_6$)alkyl".

As used herein, the term "($C_1$-$C_6$)alkyl-($C_1$-$C_6$)alkoxy" refers to a straight or branched, monovalent, saturated aliphatic chain of 1 to 6 carbon atoms which has a ($C_1$-$C_6$) alkoxy group attached to the aliphatic chain. The term "($C_1$-$C_6$)alkoxymethylene" refers to a methylene group bearing a ($C_1$-$C_6$)alkoxy group. "($C_1$-$C_6$)alkoxy($C_1$-$C_6$) alkoxy-methylene refers to a methylene group bearing a ($C_1$-$C_6$)alkoxy group which, in turn, bears an additional ($C_1$-$C_6$)alkoxy group attached to the aliphatic chain.

As used herein, the terms "halo", "halide" or "hal" of "Hal" refer to a chlorine, bromine, iodine or fluorine atom, unless otherwise specified herein.

As used herein, the term "halo($C_1$-$C_4$)alkyl" refers to a straight or branched, monovalent, saturated aliphatic chain of 1 to 4 carbon atoms bearing one or more halo groups attached to one or more of the carbon atoms. As used herein, the term "halo($C_1$-$C_6$)alkyl" refers to a straight or branched, monovalent, saturated aliphatic chain of 1 to 6 carbon atoms bearing one or more halo groups attached to one or more of the carbon atoms. It is understood that the term "halo($C_1$-$C_4$)alkyl" is included within the definition of "hydroxy($C_1$-$C_6$)alkyl".

As used herein the term "($C_2$-$C_6$)alkenyl" refers to a straight or branched, monovalent, unsaturated aliphatic chain having from two to six carbon atoms and having a double bond. Typical ($C_2$-$C_6$)alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein the term "($C_2$-$C_6$)alkynyl" refers to a straight or branched, monovalent, unsaturated aliphatic chain having from two to six carbon atoms and having a triple bond.

As used herein, the term "acyl" refers to a hydrogen or a ($C_1$-$C_6$)alkyl group attached to a carbonyl group. Typical acyl groups include formyl, acetyl, propionyl, butyryl, valeryl, and caproyl.

As used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like. The term "substituted aryl" refers to an aryl group optionally substituted with one to three moieties, preferably one or two, chosen from the group consisting of acyl, halogen, hydroxy, cyano, nitro, amino, ($C_1$-$C_6$)alkyl, ($C_1$-$C_4$)alkylsulfonyl, halo($C_1$-$C_6$)alkyl, ($C_1$-$C_6$)alkoxy, ($C_1$-$C_6$)alkylthio, ($C_3$-$C_7$)cycloalkyl, ($C_1$-$C_4$)alkyl-($C_3$-$C_7$) cycloalkyl, aryl, ($C_1$-$C_4$)alkyl-aryl, heterocycle, ($C_1$-$C_4$) alkyl-heterocycle, ($C_1$-$C_4$)alkoxy-heterocycle, ($C_1$-$C_6$) alkoxycarbonyl, N,N($C_1$-$C_6$)dialkylamine, NH($C_1$-$C_6$) alkylamine, NHSO$_2$($C_1$-$C_4$)alkyl, ($C_1$-$C_4$)alkyl-N,N—($C_1$-$C_6$)dialkylamine, ($C_1$-$C_4$)alkoxy-N,N—($C_1$-$C_6$) dialkylamine difluoromethyl, difluoromethoxy, trifluoromethyl, trifluoromethoxy, $CF_2CF_3$, benzoyl, phenoxy, or an aryl or heterocycle group further substituted with one to two moieties selected from the group consisting of:
($C_1$-$C_4$)alkyl,
($C_3$-$C_7$)cycloalkyl,
halo,
hydroxy,
($C_1$-$C_4$)alkoxy,
$CF_3$,
$OCF_3$,
$CHF_2$,
$OCHF_2$,
$CF_2CF_3$,
cyano,
nitro,
amino,
NH($C_1$-$C_4$)alkylamine, and
N,N—($C_1$-$C_4$)dialkylamine;

As used herein, the term "($C_1$-$C_6$)alkyl-aryl" refers to a straight or branched, monovalent, saturated aliphatic chain of 1 to 6 carbon atoms which has an aryl group attached to the aliphatic chain. "($C_1$-$C_4$)alkyl-aryl" refers to a straight or branched, monovalent, saturated aliphatic chain of 1 to 4 carbon atoms which has an aryl group attached to the aliphatic chain. It is understood that the term "($C_1$-$C_4$)alkyl-aryl" is included within the definition of "($C_1$-$C_6$)alkyl-aryl. Examples of "($C_1$-$C_6$)alkyl-aryl" include the following:

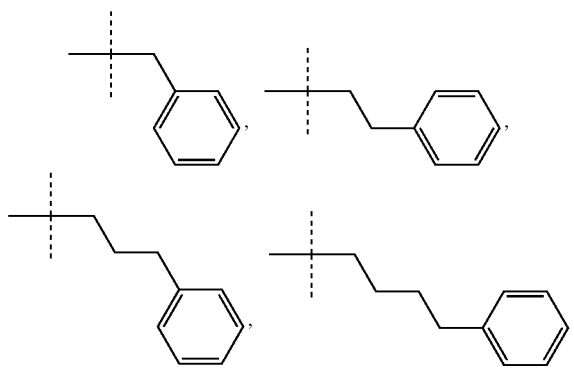

and the like.

As used herein, the term "($C_1$-$C_4$)alkyl-substituted aryl" refers to a straight or branched, monovalent, saturated aliphatic chain of 1 to 4 carbon atoms which has an optionally substituted aryl group attached to the aliphatic chain. Examples of "($C_1$-$C_4$)alkyl-substituted aryl" include methylbenzyl, phenylbenzyl, nitrobenzyl, methoxybenzyl, chlorobenzyl, bromobenzyl, dimethlybenzyl, aminobenzyl, dichlorobenzyl, and the like.

As used herein, the term "aryl($C_1$-$C_6$)alkoxy" refers to an oxygen atom bearing a straight or branched, monovalent, saturated aliphatic chain of 1 to 6 carbon atoms wherein said aliphatic chain, in turn, bears an aryl group.

As used herein the term "($C_3$-$C_{10}$)cycloalkyl" refers to a saturated hydrocarbon ring structure composed of one or more fused or unfused rings containing from three to ten carbon atoms. Typical ($C_3$-$C_{10}$)cycloalkyl groups include cyclopropyl, cyclobutyl, cyclopentyl, cyclohexyl, cycloheptyl, cyclooctyl, adamantanyl, and the like. "($C_3$-$C_7$)cycloalkyl" refers to a saturated hydrocarbon ring structure composed of one or more fused or unfused rings containing from three to seven carbon atoms. It is understood that the definition of "($C_3$-$C_7$)cycloalkyl" is included within the definition of "($C_3$-$C_{10}$)cycloalkyl". The term "substituted ($C_3$-$C_7$)cycloalkyl" refers to a "($C_3$-$C_7$)cycloalkyl group optionally substituted with one or two moieties chosen from the group consisting of halogen, hydroxy, cyano, nitro, amino, ($C_1$-$C_6$)alkyl, ($C_1$-$C_6$)alkoxy, ($C_1$-$C_4$)alkyl-($C_3$-$C_{10}$) cycloalkyl, ($C_1$-$C_4$)alkyl-aryl, ($C_1$-$C_6$)alkoxycarbonyl, N,N ($C_1$-$C_6$)dialkylamine, NH($C_1$-$C_6$)alkylamine, ($C_1$-$C_4$)alkyl- N,N—$C_1$-$C_6$dialkylamine, difluoromethyl, difluoromethoxy, trifluoromethyl, and trifluoromethoxy.

As used herein, the term "($C_1$-$C_4$)alkyl-($C_3$-$C_7$)cycloalkyl" refers to a straight or branched, monovalent, saturated aliphatic chain of 1 to 4 carbon atoms which has a ($C_3$-$C_7$)cycloalkyl attached to the aliphatic chain. Included within the term "($C_1$-$C_4$)alkyl-($C_3$-$C_7$)cycloalkyl" are the following:

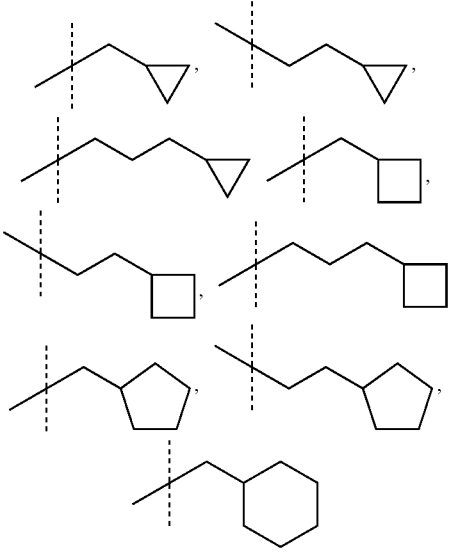

and the like. As used herein, the term "($C_1$-$C_4$)alkyl-substituted ($C_3$-$C_7$)cycloalkyl" refers to a straight or branched, monovalent, saturated aliphatic chain of 1 to 4 carbon atoms bearing an optionally substituted ($C_3$-$C_7$)cycloalkyl group attached to the aliphatic chain.

As used herein the term "($C_3$-$C_7$)cycloalkoxy" refers to an oxygen atom bearing a saturated hydrocarbon ring structure composed of one or more fused or unfused rings containing from three to seven carbon atoms.

As used herein, the term "($C_1$-$C_6$)alkoxycarbonyl" refers to a carbonyl group having a ($C_1$-$C_6$)alkyl group attached to the carbonyl carbon through an oxygen atom. Examples of this group include t-butoxycarbonyl, methoxycarbonyl, ethoxycarbonyl and the like. It is understood that the term "($C_1$-$C_4$)alkoxycarbonyl" is included within the definition of "($C_1$-$C_6$)alkoxycarbonyl".

As used herein the term "heterocycle" refers to a saturated or unsaturated, five- or six-membered ring, which contains one to four heteroatoms selected from the group consisting of oxygen, sulfur, and nitrogen. It is understood that the remaining atoms are carbon and that the heterocycle may be attached at any point which provides for a stable structure. Examples of heterocycle groups include thiophenyl, furyl, tetrahydrofuryl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl, and the like. As used herein, the term "benzofused heterocyclic ring" refers to a saturated or unsaturated, five- or six-membered ring, which contains one to four heteroatoms selected from the group consisting of oxygen, sulfur, and nitrogen, and which is fused to a phenyl group. Representative "benzofused heterocyclic rings" include benzoxazole, benzimidazole, benzofuran, benzothiophene, benzothiazole, azaindole, and indole.

The term "substituted heterocycle" represents a heterocycle group optionally substituted with one or two moieties chosen from the group consisting of acyl, halogen, hydroxy, cyano, nitro, amino, ($C_1$-$C_6$)alkyl, ($C_1$-$C_4$)alkylsulfonyl, halo($C_1$-$C_6$)alkyl, ($C_1$-$C_6$)alkoxy, ($C_1$-$C_6$)alkylthio, ($C_3$-$C_7$) cycloalkyl, ($C_1$-$C_4$)alkyl-($C_3$-$C_7$)cycloalkyl, aryl, ($C_1$-$C_4$) alkyl-aryl, heterocycle, ($C_1$-$C_4$)alkyl-heterocycle, ($C_1$-$C_4$) alkoxy-heterocycle, ($C_1$-$C_6$)alkoxycarbonyl, N,N($C_1$-$C_6$) dialkylamine, NH($C_1$-$C_6$)alkylamine, NHSO$_2$($C_1$-$C_4$)alkyl, ($C_1$-$C_4$)alkyl-N,N—$C_1$-$C_6$dialkylamine, ($C_1$-$C_4$)alkoxy-N, N—$C_1$-$C_6$dialkylamine, difluoromethyl, difluoromethoxy, trifluoromethyl, trifluoromethoxy, $CF_2CF_3$, or an aryl or heterocycle group further substituted with one to two moieties selected from the group consisting of:

($C_1$-$C_4$)alkyl,
($C_3$-$C_7$)cycloalkyl,
halo,
hydroxy,
($C_1$-$C_4$)alkoxy,
$CF_3$,
$OCF_3$,
$CHF_2$,
$OCHF_2$,
$CF_2CF_3$,
cyano,
nitro,
amino,
NH($C_1$-$C_4$)alkylamine, and
N,N—($C_1$-$C_4$)dialkylamine;

Examples of substituted heterocycle include methylisoxazole, nitrofuryl, (trifluoromethylphenyl)thiazolyl, cyclobutyloxadiazolyl, (methoxyphenyl)oxadiazolyl, dimethylisoxazolyl, and the like.

As used herein, the term "($C_1$-$C_4$)alkyl-heterocycle" refers to a straight or branched, monovalent, saturated aliphatic chain of 1 to 4 carbon atoms which has a heterocycle group attached to the aliphatic chain. Examples of "($C_1$-$C_4$)alkyl-heterocycle" include:

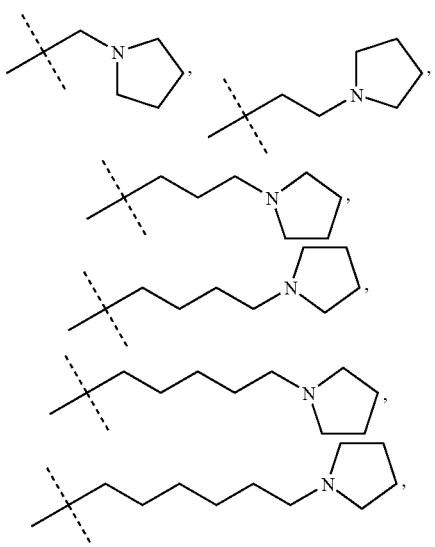

-continued

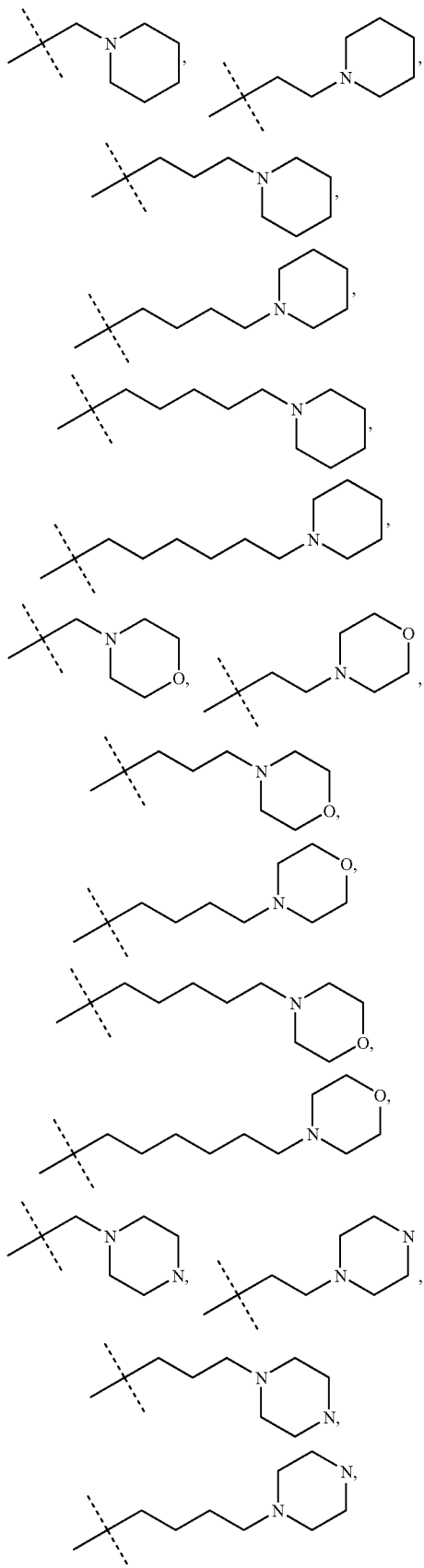

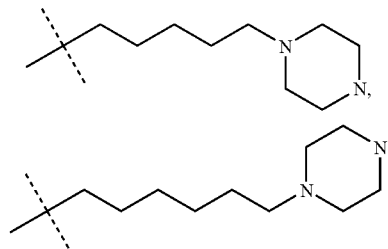

and the like.

The term "$(C_1-C_4)$alkyl-substituted heterocycle" refers to a straight or branched, monovalent, saturated aliphatic chain of 1 to 4 carbon atoms bearing an optionally substituted heterocycle group attached to the aliphatic chain.

As used herein, the term "$(C_1-C_4)$alkoxy-heterocycle" refers to an oxygen atom bearing a straight or branched, monovalent, saturated aliphatic chain of 1 to 4 carbon atoms which has a heterocycle group attached to the aliphatic chain. Examples of "$(C_1-C_4)$alkoxy-heterocycle" include:

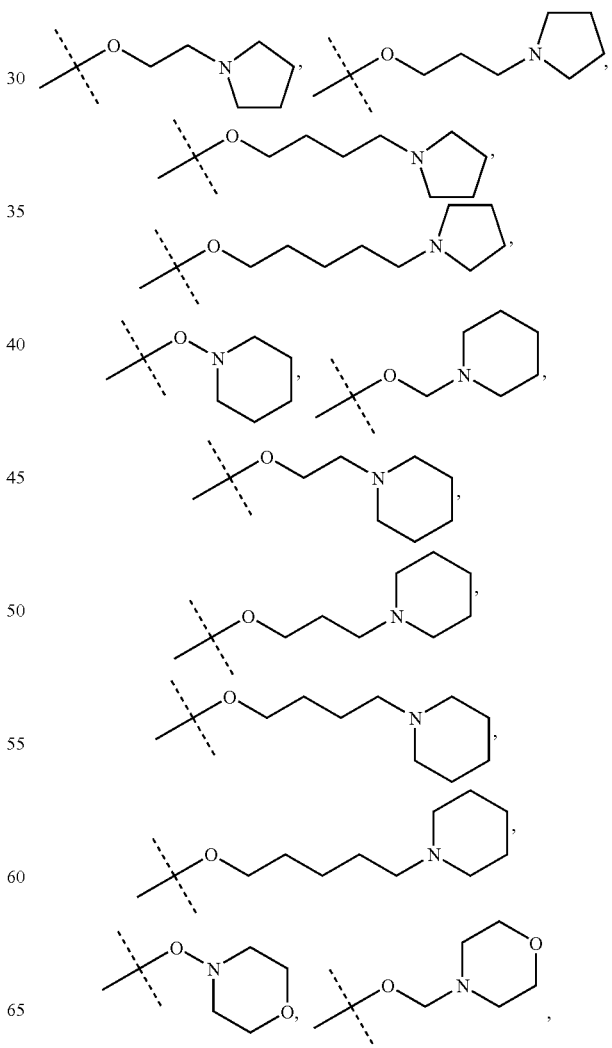

-continued

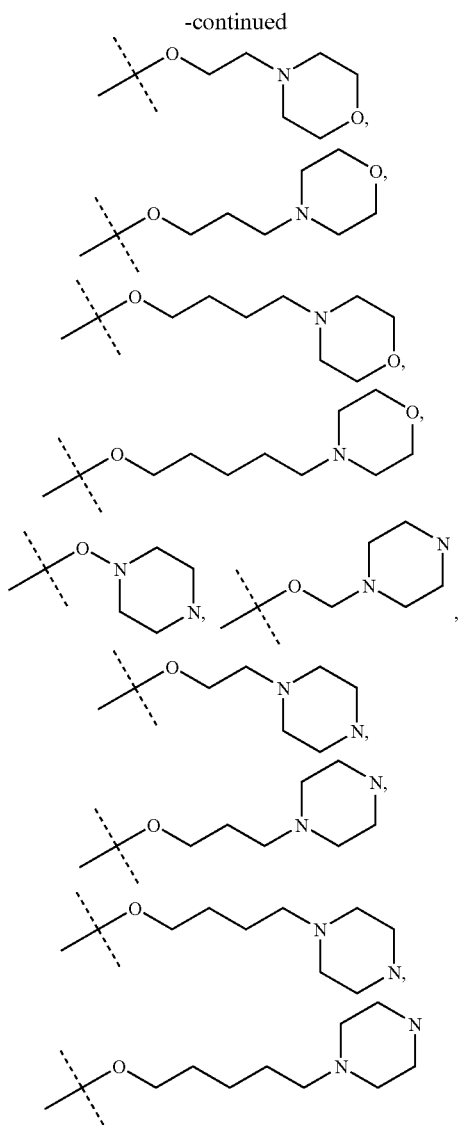

and the like.

As used herein the term "NH(C$_3$-C$_7$)cycloalkyl" refers to an amino group substituted with a saturated hydrocarbon ring structure composed of one or more fused or unfused rings containing from three to seven carbon atoms.

As used herein the term "N,N—(C$_1$-C$_6$)dialkylamine" refers to a nitrogen atom substituted with two straight or branched, monovalent, saturated aliphatic chains of 1 to 6 carbon atoms. Included within the term "N,N—(C$_1$-C$_6$) dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like. "NH—(C$_1$-C$_6$)alkylamine" refers to a nitrogen atom substituted with a straight or branched, monovalent, saturated aliphatic chains of 1 to 6 carbon atoms.

As used herein the term "(C$_1$-C$_6$)alkyl-N,N—C$_1$-C$_6$dialkylamine" refers to straight or branched, monovalent, saturated aliphatic chain of 1 to 6 carbon atoms which has an N,N—(C$_1$-C$_6$)dialkylamine attached to the aliphatic chain. Included within the term "(C$_1$-C$_6$)alkyl-N,N—(C$_1$-C$_6$)dialkylamine" are the following:

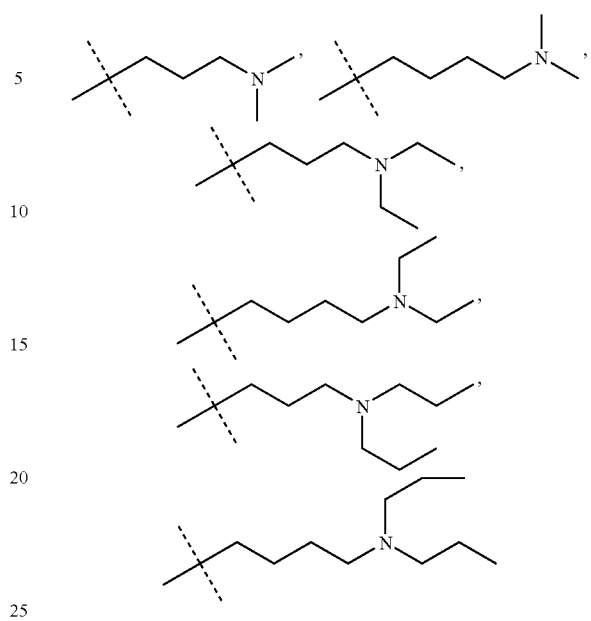

and the like.

As used herein the term "(C$_1$-C$_6$)alkoxy-N,N—(C$_1$-C$_6$) dialkylamine" refers to an oxygen atom bearing a straight or branched, monovalent, saturated aliphatic chain of 1 to 6 carbon atoms which has an N,N—C$_1$-C$_6$ dialkylamine attached to the aliphatic chain. Included within the term "C$_1$-C$_6$ alkoxy-N,N—(C$_1$-C$_6$)dialkylamine" are the following:

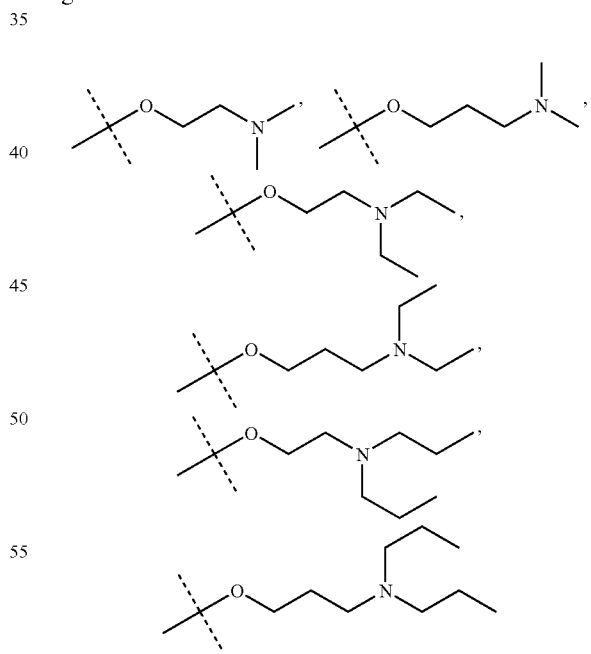

and the like.

The designation "⎯■" refers to a bond that protrudes forward out of the plane of the page.

The designation "⋯⋯" refers to a bond that protrudes backward out of the plane of the page.

As used herein, the term "steroid hormone nuclear receptor modulator" refers to those nuclear hormone receptor ligands which bind to any one of GR, MR, AR, ER, or PR, of the larger class of nuclear hormone receptors, and either agonize, antagonize, partially agonize, or partially antagonize the receptor's activity.

As used herein the term "mineralocorticoid receptor" or "MR" refers to the mineralocorticoid receptor subtype, of the larger class of nuclear hormone receptors, which binds the mineralocorticoid hormone aldosterone, as its cognate ligand. The term "mineralocorticoid receptor modulator" or "mineralocorticoid modulator" or "MR modulator" as used herein, refers to those nuclear hormone receptor ligands which bind to the mineralocorticoid receptor subtype and modulate (i.e. agonize, antagonize, partially agonize, or partially antagonize) the receptor activity activity. As a particular embodiment, the present invention provides antagonists of MR activity As used herein the term "glucocorticoid receptor" or "GR" refers to the gluoocorticoid receptor subtype, of the larger class of nuclear hormone receptors, which binds the glucocorticoid hormones cortisol, corticosterone, or cortisone as its cognate ligand. The term "glucocorticoid receptor modulator" or "glucocorticoid modulator" or "GR modulator", as used herein, refers to those nuclear hormone receptor ligands which bind to the gluoocorticoid receptor subtype and modulate (i.e. agonize, antagonize, partially agonize, or partially antagonize) the receptor activity.

As used herein, the term "disorder susceptible to steroid hormone nuclear receptor modulation" refers to any pathological disorder, of any origin, known or believed to be responsive to administration of a modulator (i.e. agonist, antagonist, partial agonist, or partial antagonist) of a steroid hormone nuclear receptor. Such pathological disorders include Conn's Syndrome, secondary hyperaldosteronism, increased sodium retention and edema, increased magnesium and potassium excretion (diuresis), increased water retention, hypertension, Bartter's Syndrome, disorders associated with excess catecholamine levels, diastolic and systolic congestive heart failure, myocardial infarction, isolated systolic and combined systolic/diastolic hypertension, peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, glucose intolerance, hyperglycemia, diabetes mellitus, osteoporosis, polyuria, and polydipsia, leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, chronic primary adrenal insufficiency, secondary adrenal insufficiency, cerebral edema, thrombocytopenia, and Little's syndrome, inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, and cutaneous T-cell lymphoma, and disorders associated with impaired cognitive function.

As used herein the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is charachterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As appreciated by one of skill in the art, pathological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of pathological disorders contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human. As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as a mineralocorticoid receptor modulator. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the steroid hormone nuclear receptor modulator is administered as a combination of compounds, one of the compounds may be administered by one route, such as oral, and the other may be administered by the transdermal, percutaneous, pulmonary, intravenous, intramuscular, intranasal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmceutical compositions and, therefore, pharmaceutical compositions incorporating compounds of Formula I, and more particularly the novel compounds of Formula I, are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, including the pharmaceutically acceptable salts and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

The following discussion provides typical procedures for preparing pharmaceutical compositions incorporating the compounds of the present invention. However, the following is in no way intended to limit the scope of the pharmaceutical compositons provided by the present invention.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It is understood by one of ordinary skill in the art that the procedures as described above can also be readily applied to a method of treating pathological disorders susceptible to steroid hormone nuclear receptor modulation, and particularly congestive heart failure.

Particular Aspects of the Methods and Uses of the Invention

The following list sets out several groupings of particular substituents and particular variables for compounds of Formula I. It will be understood that certain methods and uses as described herein, employing compounds of Formula I having such particular substituents or variables, represent particular aspects of the methods and uses of the present invention. It will be further understood that each of these groupings of particular substituents and particular variables may be combined with other provided groupings, to create still additional particular aspects of the methods and uses of the present invention.

Thus, a particular aspect of the methods and uses of the present invention is one wherein the compound to be administered is a compound of Formula I, wherein:

a) $R^1$ represents $(C_1-C_6)$alkyl, $(C_3-C_7)$cycloalkyl, $(C_3-C_7)$cycloalkoxy, $(C_1-C_6)$alkyl-$(C_3-C_7)$cycloalkyl, $(C_1-C_6)$alkyl-$(C_1-C_6)$alkoxy, $(C_2-C_6)$alkenyl, aryl, substituted aryl, $(C_1-C_4)$alkyl-aryl, $(C_1-C_4)$alky-substituted aryl, heterocycle, substituted heterocycle, $(C_1-C_4)$alkyl-heterocycle, $(C_1-C_4)$alkyl-substituted heterocycle, or $CH_2COR^7$;

b) $R^1$ represents $(C_1-C_6)$alkyl, substituted aryl, $(C_1-C_4)$alky-substituted aryl, heterocycle, substituted heterocycle, $(C_1-C_4)$alkyl-heterocycle, or $(C_1-C_4)$alkyl-substituted heterocycle;

c) $R^1$ represents substituted aryl, $(C_1-C_4)$alky-substituted aryl, heterocycle, substituted heterocycle, $(C_1-C_4)$alkyl-heterocycle, or $(C_1-C_4)$alkyl-substituted heterocycle;

d) $R^1$ represents substituted aryl, $(C_1-C_4)$alky-substituted aryl, substituted heterocycle, or $(C_1-C_4)$alkyl-substituted heterocycle;

e) $R^1$ represents $(C_1-C_6)$alkyl;

f) $R^1$ represents methyl, ethyl, propyl, or isopropyl;

g) $R^1$ represents $(C_1-C_4)$alkyl-aryl;

h) $R^1$ represents $(C_1-C_4)$alkyl-aryl wherein aryl is phenyl or naphthyl;

i) $R^1$ represents $(C_1-C_4)$alkyl-aryl wherein $(C_1-C_4)$alkyl is methyl or ethyl;

j) $R^1$ represents benzyl, naphthalen-2-ylmethyl, or naphthalene-1-ylmethyl;

k) $R^1$ represents $(C_1-C_4)$alkyl-substituted aryl;

l) $R^1$ represents $(C_1-C_4)$alkyl-substituted aryl wherein said aryl moiety is substituted one to three times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethyl, difluoromethoxy, trifluoromethyl, trifluoromethoxy, and benzoyl;

m) $R_1$ represents $(C_1-C_4)$alkyl-substituted aryl wherein said aryl moiety is substituted one to two times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethyl, difluoromethoxy, trifluoromethyl, trifluoromethoxy, and benzoyl;

n) $R^1$ represents $(C_1-C_4)$alkyl-substituted aryl wherein said aryl moiety is substituted one to two times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethoxy, trifluoromethyl, trifluoromethoxy, and benzoyl o) $R^1$ represents $(C_1-C_4)$alkyl-substituted aryl wherein said aryl moiety is phenyl;

p) $R^1$ represents $(C_1-C_4)$alkyl-substituted aryl wherein said aryl moiety is phenyl and said phenyl is substituted one to two times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethyl, difluoromethoxy, trifluoromethyl, trifluoromethoxy, and benzoyl;

q) $R^1$ represents substituted benzyl;

r) $R^1$ represents substituted benzyl wherein the phenyl moiety is substituted one to two times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethyl, difluoromethoxy, trifluoromethyl, trifluoromethoxy, and benzoyl;

s) $R^1$ represents benzyl wherein the phenyl moiety is substituted one to two times with a halo group;

t) $R^1$ represents benzyl wherein the phenyl moiety is substituted one to two times with a hydroxy group;

u) $R^1$ represents benzyl wherein the phenyl moiety is substituted one to two times with a cyano, nitro, or amino group;

v) $R^1$ represents benzyl wherein the phenyl moiety is substituted one to two times with a $(C_1-C_6)$alkyl group;

w) $R^1$ represents benzyl wherein the phenyl moiety is substituted one to two times with a $(C_1-C_4)$alkylsulfonyl group;

x) $R^1$ represents benzyl wherein the phenyl moiety is substituted one to two times with a $(C_1-C_6)$alkoxy group;

y) $R^1$ represents benzyl wherein the phenyl moiety is substituted with a phenyl group;

z) $R^1$ represents benzyl wherein the phenyl moiety is substituted with a heterocycle group, aa) $R^1$ represents benzyl wherein the phenyl moiety is substituted with an $(C_1-C_6)$alkoxycarbonyl group, bb) $R^1$ represents benzyl wherein the phenyl moiety is substituted one to two times with a difluoromethyl, difluoromethoxy, trifluoromethyl, or trifluoromethoxy group;

cc) $R^1$ represents 4-methoxy-benzyl, 3-methoxy benzyl, 4-Hydroxy-benzyl, 4-fluoro-benzyl, 2-Fluoro-benzyl, 4-Bromo-benzyl, 2,6-difluoro-benzyl, 2-Bromo-benzyl, 3-Bromo-benzyl, 2,4-Difluoro-benzyl, 2,3-Difluoro-benzyl, 2,6-difluoro-benzyl, 2-Chloro-benzyl, 3-Chloro-benzyl, 3,4-Dichloro-benzyl, 2,6-dichloro-benzyl, 2-Chloro-6-fluoro-benzyl, 4-Bromo-2-fluoro-benzyl, 4-Chloro-2-fluoro-benzyl, 2-methyl-benzyl, 2,6-Dimethyl-benzyl, 2-cyano-benzyl, 4-methoxycarbonyl benzyl, 3-methoxycarbonyl benzyl, 4-methanesulfonyl-benzyl, 4-tert-butyl benzyl, 2-Difluoromethoxy-benzyl, 2-trifluoromethyl-benzyl, 3-trifluoromethoxy-benzyl, 3-trifluoromethyl-benzyl, 4-trifluoromethyl-benzyl, 4-trifluoromethoxy-benzyl, 2,4-Bis-trifluoromethyl-benzyl, 3,5-Bis-trifluoromethyl-benzyl, 2-Fluoro-3-methyl-benzyl, 2-Fluoro-5-trifluoromethyl-benzyl, 4-nitro-benzyl, 2-nitro-benzyl, 3-nitro-benzyl, 2-Amino-benzyl, 3-Aminobenzyl, 4-Amino-benzyl, 4-Benzoyl-benzyl, 4-Benzyloxy-benzyl, 1-Biphenyl-2-ylmethyl, or 4-[1,2,3]thiadiazol-4-yl-benzyl;

dd) $R^1$ represents $(C_1-C_6)$alkyl-$(C_3-C_7)$cycloalkyl;

ee) $R^1$ represents $(C_1-C_6)$alkyl-$(C_3-C_7)$cycloalkyl wherein $(C_1-C_6)$alkyl is methyl or ethyl;

ff) $R^1$ represents cyclohexylmethyl, 2-cyclohexylethyl, or cyclopropylmethyl;

gg) $R^1$ represents $(C_1-C_4)$alkyl-heterocycle;

hh) $R^1$ represents $(C_1-C_4)$alkyl-heterocycle wherein said $(C_1-C_4)$alkyl moiety is methyl or ethyl;

ii) $R^1$ represents $(C_1-C_4)$alkyl-heterocycle wherein said heterocycle moiety is pyridinyl, pyrimidinyl, furanyl, quinolinyl, isoxazolyl, thiazolyl, or oxadiazolyl;

jj) $R^1$ represents $(C_1-C_4)$alkyl-heterocycle wherein said heterocycle moiety is pyridinyl, pyrimidinyl, furanyl, quinolinyl, isoxazolyl, thiazolyl, or oxadiazolyl and said $(C_1-C_4)$alkyl moiety is methyl or ethyl;

kk) $R^1$ represents $((C_1-C_4)$alkyl-heterocycle wherein said heterocycle moiety is pyridinyl or quinolinyl and said $(C_1-C_4)$alkyl moiety is methyl or ethyl;

ll) $R^1$ represents quinolin-2-ylmethyl, pyridin-2-ylmethyl, pyridin-3-ylmethyl, pyridin-4-ylmethyl, or 2-pyridin-2-ylethyl;

mm) $R^1$ represents $(C_1-C_4)$alkyl-substituted heterocycle;

nn) $R^1$ represents $(C_1-C_4)$alkyl-substituted heterocycle wherein said $(C_1-C_4)$alkyl moiety is methyl or ethyl;

oo) $R^1$ represents $(C_1-C_4)$alkyl-substituted heterocycle wherein said heterocycle moiety is substituted one to two times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$alkyl-heterocycle, $(C_1-C_6)$alkoxycarbonyl, N,N$(C_1-C_6)$dialkylamine, NH$(C_1-C_6)$alkylamine, NHSO$_2(C_1-C_4)$alkyl, $(C_1-C_4)$alkyl-N,N—$C_1$-$C_6$dialkylamine, $(C_1-C_4)$alkoxy-N,N—$C_1$-$C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, N,N$(C_1-C_6)$dialkylamine, or NH$(C_1-C_6)$alkylamine;

pp) $R^1$ represents $(C_1-C_4)$alkyl-substituted heterocycle wherein said heterocycle moiety is substituted one to two times independently with a substituent selected from the group consisting of acyl, nitro, $(C_1-C_6)$alkyl, $(C_1-C_6)$alkoxy, $(C_3-C_7)$cycloalkyl, phenyl, heterocycle, and aryl further substituted one to two times independently with $(C_1-C_6)$alkoxy, $(C_1-C_6)$alkoxycarbonyl, or trifluoromethyl;

qq) $R^1$ represents $(C_1-C_4)$alkyl-substituted heterocycle wherein said heterocycle moiety is pyridinyl, pyrimidinyl, furanyl, quinolinyl, isoxazolyl, thiazolyl, or oxadiazolyl;

rr) $R^1$ represents $(C_1-C_4)$alkyl-substituted heterocycle wherein said heterocycle moiety is furanyl, isoxazolyl, thiazolyl, or oxadiazolyl;

ss) $R^1$ represents $(C_1-C_4)$alkyl-substituted heterocycle wherein said $(C_1-C_4)$alkyl moiety is methyl or ethyl; said heterocycle moiety is furanyl, isoxazolyl, thiazolyl, or oxadiazolyl; and said heterocycle moiety is substituted one to two times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$alkyl-heterocycle, $(C_1-C_6)$alkoxycarbonyl, N,N$(C_1-C_6)$dialkylamine, NH$(C_1-C_6)$alkylamine, NHSO$_2(C_1-C_4)$alkyl, $(C_1-C_4)$alkyl-N,N—$C_1$-$C_6$dialkylamine, $(C_1-C_4)$alkoxy-N,N—$C_1$-$C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, N,N$(C_1-C_6)$dialkylamine, or NH$(C_1-C_6)$alkylamine;

tt) $R^1$ represents 5-Furan-2-yl-[1,2,4]oxadiazol-3-ylmethyl, 2-methoxycarbonyl-furan-5-ylmethyl, 5-nitro-furan-2-ylmethyl, 5-(2-methoxy-phenyl)-[1,2,4]oxadiazol-3-ylmethyl, 5-(4-methoxy-phenyl)-[1,2,4]oxadiazol-3-ylmethyl, 3,5-Dimethyl-isoxazol-4-ylmethyl, 2-methyl-thiazol-4-ylmethyl, 2-Ethyl-thiazol-4-ylmethyl, 2-phenyl-thiazol-4-ylmethyl, 2-(4-methoxy-phenyl)-thiazol-4-ylmethyl, 2-(4trifluoromethyl-phenyl)-thiazol-4-ylmethyl, 2-(4-methyl-thiazol-5-yl)-ethyl, 5-Cyclobutyl-[1,2,4]oxadiazol-3-ylmethyl, 3-(3-methoxycarbonyl-phenyl)-[1,2,4]oxadiazol-5-ylmethyl, or 3-(4-methoxy-phenyl)-[1,2,4]oxadiazol-5-ylmethyl;

uu) $R^1$ represents $(C_1-C_6)$alkyl-$(C_1-C_6)$alkoxy;

vv) $R^1$ represents $(C_1-C_6)$alkyl-$(C_1-C_6)$alkoxy wherein said alkoxy moiety is methoxy or ethoxy;

ww) $R^1$ represents $(C_1-C_6)$alkyl-$(C_1-C_6)$alkoxy wherein said alkyl moiety is methyl or ethyl;

xx) $R^1$ represents $(C_2-C_6)$alkenyl;

yy) $R^1$ represents allyl, 2-methylallyl, or 3-methyl-but-2-enyl;

zz) $R^1$ represents $(C_2-C_6)$alkynyl;

aaa) $R^1$ represents prop-2-ynyl bbb) $R^1$ represents $CH_2COR^7$ wherein $R^7$ is selected from the group consisting of aryl, $(C_1-C_6)$alkoxy, NH—$(C_3-C_7)$cycloalkyl, and aryl optionally substituted with one to two substituents independently selected from the group consisting of $(C_1-C_6)$alkyl, $(C_1-C_6)$alkoxy, and halo;

ccc) $R^1$ represents $CH_2COR^7$ wherein $R^7$ is 2-methoxyphenyl, 3-methoxy-phenyl, 4-methoxy-phenyl, naphthalene-2-yl, 4-bromophenyl, 2,5-dimethoxy-phenyl, NH-cyclohexyl, ethoxy;

ddd) $R^1$ represents acetic acid ethyl ester, 2-(2-methoxyphenyl)-2-oxo-ethyl, 2-(3-methoxy-phenyl)-2-oxo-ethyl, 2-(4-methoxy-phenyl)-2-oxo-ethyl, 2-naphthalen-2-yl-2-oxo-ethyl, 2-(4-Bromo-phenyl)-2-oxo-ethyl, 2-(2,5-Dimethoxy-phenyl)-2-oxo-ethyl, or N-cyclohexyl-acetamidyl eee) $R^1$ represents $(C_3-C_7)$cycloalkyl;

fff) $R^1$ represents cyclopropyl, cyclopentyl, or cyclohexyl;

ggg) $R^1$ represents $(C_3-C_7)$cycloalkoxy;

hhh) $R^1$ represents aryl;

iii) $R^1$ represents phenyl or naphthyl;

jjj) $R^1$ represents substituted aryl;

kkk) $R^1$ represents substituted aryl wherein said aryl moiety is phenyl or naphthyl;

lll) $R^1$ represents substituted aryl wherein said aryl moiety is phenyl or naphthyl substituted one to three times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$alkyl-heterocycle, $(C_1-C_6)$alkoxycarbonyl, N,N$(C_1-C_6)$dialkylamine, NH$(C_1-C_6)$alkylamine, NHSO$_2(C_1-C_4)$ alkyl, $(C_1-C_4)$alkyl-N,N—$C_1-C_6$dialkylamine, $(C_1-C_4)$ alkoxy-N,N—$C_1-C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$ alkoxy, difluoromethyl, difluoromethoxy, trifluoromethyl, trifluoromethoxy, $CF_2CF_3$, nitro, amino, N,N$(C_1-C_6)$dialkylamine, or NH$(C_1-C_6)$alkylamine;

mmm) $R^1$ represents substituted aryl wherein said aryl moiety is phenyl or naphthyl substituted one to two times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$ alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$ alkyl-heterocycle, $(C_1-C_6)$alkoxycarbonyl, N,N$(C_1-C_6)$ dialkylamine, NH$(C_1-C_6)$alkylamine, NHSO$_2$$(C_1-C_4)$ alkyl, $(C_1-C_4)$alkyl-N,N—$C_1-C_6$dialkylamine, $(C_1-C_4)$ alkoxy-N,N—$C_1-C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$ alkoxy, difluoromethyl, difluoromethoxy, trifluoromethyl, trifluoromethoxy, $CF_2CF_3$, nitro, amino, N,N$(C_1-C_6)$dialkylamine, or NH$(C_1-C_6)$alkylamine;

mmm) $R^1$ represents substituted aryl wherein said aryl moiety is phenyl substituted one to two times independently with a substituent selected from the group consisting of $(C_1-C_6)$alkyl, $(C_1-C_6)$alkoxy, halo, heterocycle, N,N$(C_1-C_6)$dialkylamine, NH$(C_1-C_6)$alkylamine, trifluoromethyl, trifluoromethoxy, difluoromethyl, difluoromethoxy or a heterocycle further substituted with one to two moieties selected from the group consisting of $(C_1-C_6)$alkyl, $(C_3-C_7)$cycloalkyl, halogen, hydroxy, $(C_1-C_6)$ alkoxy, difluoromethyl, difluoromethoxy, trifluoromethyl, trifluoromethoxy, $CF_2CF_3$, nitro, amino, N,N$(C_1-C_6)$dialkylamine, or NH$(C_1-C_6)$alkylamine;

ooo) $R^1$ represents substituted aryl wherein said aryl moiety is phenyl substituted one to two times independently with a substituent selected from the group consisting of $(C_1-C_6)$alkyl, $(C_1-C_6)$alkoxy, halo, heterocycle, N,N$(C_1-C_6)$ dialkylamine, NH$(C_1-C_6)$alkylamine, trifluoromethyl, trifluoromethoxy, difluoromethyl, difluoromethoxy or a heterocycle further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, N,N$(C_1-C_6)$ dialkylamine, or NH$(C_1-C_6)$alkylamine, further provided that at least one of the substitutions occurs at the meta position of said phenyl moiety;

ppp) $R^1$ represents substituted aryl wherein said aryl moiety is phenyl substituted one to two times independently with a substituent selected from the group consisting of $(C_1-C_6)$alkyl, $(C_1-C_6)$alkoxy, halo, heterocycle, N,N$(C_1-C_6)$ dialkylamine, NH$(C_1-C_6)$alkylamine, trifluoromethyl, trifluoromethoxy, difluoromethyl, or difluoromethoxy, further provided that at least one of the substitutions occurs at the meta position of said phenyl moiety;

qqq) $R^1$ represents substituted aryl wherein said aryl moiety is phenyl substituted one to two times independently with a substituent selected from the group consisting of $(C_1-C_6)$alkyl, $(C_1-C_6)$alkoxy, halo, heterocycle, trifluoromethyl, trifluoromethoxy, difluoromethoxy, or difluoromethyl, further provided that at least one of the substitutions occurs at the meta position of said phenyl moiety;

rrr) $R^1$ represents 4-methyl phenyl, 2-methyl phenyl, 3-methyl phenyl, 3-trifluoromethyl-phenyl, 3-isopropyl-phenyl, 4-methoxy-phenyl, 3-methoxy-phenyl, 3,4-Dimethoxy-phenyl, 3-Ethoxy-phenyl, 2-Chloro-phenyl, 3-Fluoro-phenyl, 3-Bromo-phenyl, 3-trifluoromethoxy phenyl, or 4-trifluoromethyl-phenyl sss) $R^1$ represents heterocycle;

ttt) $R^1$ represents pyridinyl, pyrimidinyl, furanyl, quinolinyl, isoxazolyl, thiazolyl, or oxadiazolyl;

uuu) $R^1$ represents pyridinyl, pyrimidinyl, furanyl, thiazolyl, oxadiazolyl;

vvv) $R^1$ represents pyridin-3-yl or pyridin-4-yl;

www) $R^1$ represents substituted heterocycle;

xxx) $R^1$ represents substituted heterocycle wherein said heterocycle moiety is pyridinyl, pyrimidinyl, furanyl, thiazolyl, or oxadiazolyl substituted one to two times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$ alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$ alkyl-heterocycle, $(C_1-C_6)$alkoxycarbonyl, N,N$(C_1-C_6)$ dialkylamine, NH$(C_1-C_6)$alkylamine, NHSO$_2$$(C_1-C_4)$ alkyl, $(C_1-C_4)$alkyl-N,N—$C_1-C_6$dialkylamine, $(C_1-C_4)$ alkoxy-N,N—$C_1-C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$ alkoxy, difluoromethyl, difluoromethoxy, trifluoromethyl, trifluoromethoxy, $CF_2CF_3$, nitro, amino, N,N$(C_1-C_6)$dialkylamine, or NH$(C_1-C_6)$alkylamine;

yyy) $R^1$ represents substituted heterocycle wherein said heterocycle moiety is pyridinyl, pyrimidinyl, furanyl, thiazolyl, or oxadiazolyl substituted one to two times independently with a substituent selected from the group consisting of acyl, nitro, $(C_1-C_6)$alkyl, $(C_1-C_6)$alkoxy, $(C_3-C_7)$cycloalkyl, phenyl, heterocycle, and aryl further substituted one to two times independently with $(C_1-C_6)$ alkoxy, $(C_1-C_6)$alkoxycarbonyl, or trifluoromethyl;

zzz) $R^1$ represents 2-methoxy-pyrimidin-4-yl;

aaaa) $R^2$ represents hydroxy, $(C_1-C_6)$alkyl, hydroxy$(C_1-C_6)$ alkyl or a group of the formula

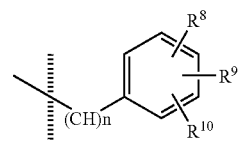

wherein n is 0 or 1;

bbbb) $R^2$ represents hydroxy, $(C_1-C_6)$alkyl, hydroxy$(C_1-C_6)$ alkyl or a group of the formula

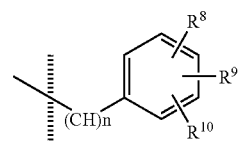

wherein n is 0 or 1 and $R^8$ through $R^{10}$ each independently represent hydrogen, hydroxy, $(C_1-C_4)$alkyl, halo, nitro, amino, $(C_1-C_4)$alkoxy, or $NHR^{14}$;

cccc) $R^2$ represents a group of the formula

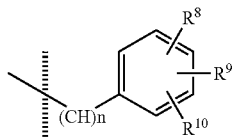

wherein n is 0 or 1 and $R^8$ through $R^{10}$ each independently represent hydrogen, hydroxy, $(C_1-C_4)$alkyl, halo, nitro, amino, $(C_1-C_4)$alkoxy, or $NHR^{14}$ and $R^{14}$ represents $CO(CH_3)$ or $SO_2(CH_3)$;

dddd) $R^2$ represents 4-hydroxy-3,5-dimethyl phenyl, 4-hydroxy-3-ethyl phenyl, 2-hydroxy-5-ethyl phenyl, 4-hydroxy-3-methyl phenyl, 4-hydroxy phenyl, 4-hydroxy-3,5-dichloro phenyl, 5-fluoro-2-hydroxy-3-methoxy phenyl, 5-fluoro-2-hydroxy-3-methyl phenyl, 5-fluoro-2-hydroxy-4-methyl phenyl, 4-amino-3,5-dimethyl phenyl, 4-amino phenyl, 4-nitro phenyl, 2-hydroxy-3,4-dimethyl phenyl, 2-hydroxy-3,5-dimethyl phenyl, 2-hydroxy-4-methyl phenyl, 2-hydroxy-5-methyl phenyl, 3,4-dihydroxy-5-methyl phenyl, 4-hydroxy-3-methyl-5-propyl phenyl, 3,4-dimethyl phenyl, 3,4,5-trimethyl phenyl, 4-amino-3-chloro-5-methyl phenyl, 4-amino-3-methyl phenyl, 2,4-dihydroxy phenyl, 2,4-dihydroxy-3-methyl phenyl, 2-hydroxy-3-ethyl phenyl, 2-hydroxy phenyl, 3-hydroxy benzyl, 3-methoxy benzyl, 4-hydroxy benzyl, or 4-methoxy benzyl;

eeee) $R^2$ represents 4-hydroxy-3,5-dimethyl phenyl, 4-hydroxy-3-ethyl phenyl, 4-hydroxy-3-methyl phenyl, 4-hydroxy phenyl, 4-hydroxy-3,5-dichloro phenyl, 4-amino-3,5-dimethyl phenyl, 4-amino phenyl, 4-nitro phenyl, 2-hydroxy-3,4-dimethyl phenyl, 2-hydroxy-3,5-dimethyl phenyl, 2-hydroxy-4,5-dimethyl phenyl 2-hydroxy-5-methyl phenyl, 3,4-dihydroxy-5-methyl phenyl, 4-hydroxy-3-methyl-5-propyl phenyl, 3,4-dimethyl phenyl, 3,4,5-trimethyl phenyl, 4-amino-3-chloro-5-methyl phenyl, 4-amino-3-methyl phenyl, 2,4-dihydroxy phenyl, 2,4-dihydroxy-3-methyl phenyl, 2-hydroxy-3-ethyl phenyl, or 2-hydroxy phenyl;

ffff) $R^2$ represents 4-hydroxy-3,5-dimethyl phenyl;

gggg) $R^2$ represents hydroxy, $(C_1-C_6)$alkyl, or hydroxy$(C_1-C_6)$alkyl;

hhhh) $R^2$ represents methyl, ethyl, propyl, or 3-hydroxypropyl;

iiii) $R^3$ represents a group of the formula:

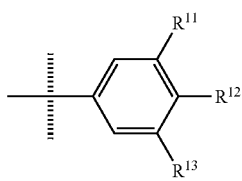

wherein $R^{11}$ and $R^{13}$ each independently represent hydrogen, $(C_1-C_4)$alkyl, or halo; and $R^{12}$ represents hydrogen, halo, $(C_1-C_4)$alkyl, hydroxy, or amino;

jjjj) $R^3$ represents 4-hydroxy-3,5-dimethyl phenyl, 4-hydroxy-3-ethyl phenyl, 4-hydroxy-3-methyl phenyl, 4-hydroxy phenyl, 4-hydroxy-3,5-dichloro phenyl, 3,5-dimethyl phenyl, or 3,4,5-trimethyl phenyl;

kkkk) $R^3$ represents 4-hydroxy-3,5-dimethyl-phenyl;

llll) $R^4$ and $R^5$ each independently represent hydrogen, halo, hydroxy, $(C_1-C_4)$alkyl, $(C_1-C_4)$alkoxy, $CF_3$, $OCF_3$, $CHF_2$, $OCEF_2$, $CF_2CF_3$, cyano, nitro, or amino;

mmmm) $R^4$ and $R^5$ each independently represent hydrogen, halo, $(C_1-C_4)$alkyl, or $(C_1-C_4)$alkoxy; or nnnn) $R^4$ and $R^5$ each independently represent hydrogen, bromo, chloro, methyl, ethyl, or methoxy.

Particular Aspects of the Novel Compounds of the Invention

As discussed previously, certain compounds of Formula I are believed to be novel and, thus, to represent another embodiment of the present invention. The following list sets out several groupings of particular substituents and particular variables of the novel compounds of Formula I. It will be understood that novel compounds of Formula I having such particular substituents and variables represent particular aspects of the present invention. It will be further understood that each of these groupings may be combined with other provided groupings, to create still additional particular aspects of the present invention.

Thus, a particular aspect of the novel compounds of Formula I is one wherein:

a) $R^1$ represents $(C_3-C_7)$cycloalkyl, $(C_3-C_7)$cycloalkoxy, $(C_1-C_6)$alkyl-$(C_3-C_7)$cycloalkyl, $(C_1-C_6)$alkyl-$(C_1-C_6)$alkoxy, $(C_2-C_6)$alkenyl, aryl, substituted aryl, $(C_1-C_4)$alkyl-aryl, $(C_1-C_4)$alky-substituted aryl, heterocycle, substituted heterocycle, $(C_1-C_4)$alkyl-heterocycle, $(C_1-C_4)$alkyl-substituted heterocycle, or $CH_2COR^7$, with the proviso that $R^1$ is other than phenyl or benzyl;

b) $R^1$ represents substituted aryl, $(C_1-C_4)$alky-substituted aryl, heterocycle, substituted heterocycle, $(C_1-C_4)$alkyl-heterocycle, or $(C_1-C_4)$alkyl-substituted heterocycle;

c) $R^1$ represents substituted aryl, $(C_1-C_4)$alky-substituted aryl, substituted heterocycle, or $(C_1-C_4)$alkyl-substituted heterocycle;

d) $R^1$ represents $(C_1-C_4)$alkyl-aryl, with the proviso that $R^1$ is other than benzyl;

e) $R^1$ represents $(C_1-C_4)$alkyl-aryl wherein aryl is phenyl or naphthyl, with the proviso that $R^1$ is other than benzyl;

f) $R^1$ represents $(C_1-C_4)$alkyl-aryl wherein $(C_1-C_4)$alkyl is methyl or ethyl, with the proviso that $R^1$ is other than benzyl;

g) $R^1$ represents naphthalen-2-ylmethyl, or naphthalene-1-ylmethyl;

h) $R^1$ represents $(C_1-C_4)$alkyl-substituted aryl;

i) $R^1$ represents $(C_1-C_4)$alkyl-substituted aryl wherein said aryl moiety is substituted one to three times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethyl, difluoromethoxy, trifluoromethyl, trifluoromethoxy, and benzoyl;

j) $R^1$ represents $(C_1-C_4)$alkyl-substituted aryl wherein said aryl moiety is substituted one to two times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethyl, difluoromethoxy, trifluoromethyl, trifluoromethoxy, and benzoyl;

k) $R^1$ represents $(C_1-C_4)$alkyl-substituted aryl wherein said aryl moiety is substituted one to two times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethoxy, trifluoromethyl, trifluoromethoxy, and benzoyl l) $R^1$ represents $(C_1-C_4)$alkyl-substituted aryl wherein said aryl moiety is phenyl;

m) $R^1$ represents $(C_1-C_4)$alkyl-substituted aryl wherein said aryl moiety is phenyl and said phenyl is substituted one to two times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethyl, difluoromethoxy, trifluoromethyl, trifluoromethoxy, and benzoyl;

n) $R^1$ represents substituted benzyl;

o) $R^1$ represents substituted benzyl wherein the phenyl moiety is substituted one to two times independently with a substituent selected from the group consisting of halogen, hydroxy, cyano, nitro, amino, $(C_1-C_6)$alkyl, $(C_1-C_4)$alkylsulfonyl, $(C_1-C_6)$alkoxy, aryl, heterocycle, $(C_1-C_6)$alkoxycarbonyl, difluoromethyl, difluoromethoxy, trifluoromethyl, trifluoromethoxy, and benzoyl;

p) $R^1$ represents substituted benzyl wherein the phenyl moiety is substituted one to two times with a halo group;

q) $R^1$ represents substituted benzyl wherein the phenyl moiety is substituted one to two times with a hydroxy group;

r) $R^1$ represents substituted benzyl wherein the phenyl moiety is substituted one to two times with a cyano, nitro, or amino group;

s) $R^1$ represents substituted benzyl wherein the phenyl moiety is substituted one to two times with a $(C_1-C_6)$alkyl group;

t) $R^1$ represents substituted benzyl wherein the phenyl moiety is substituted one to two times with a $(C_1-C_4)$alkylsulfonyl group;

u) $R^1$ represents substituted benzyl wherein the phenyl moiety is substituted one to two times with a $(C_1-C_6)$alkoxy group;

v) $R^1$ represents substituted benzyl wherein the phenyl moiety is substituted with a phenyl group;

w) $R^1$ represents substituted benzyl wherein the phenyl moiety is substituted with a heterocycle group, x) $R^1$ represents substituted benzyl wherein the phenyl moiety is substituted with an $(C_1-C_6)$alkoxycarbonyl group, y) $R^1$ represents substituted benzyl wherein the phenyl moiety is substituted one to two times with a difluoromethyl, difluoromethoxy, trifluoromethyl, or trifluoromethoxy group;

z) $R^1$ represents 4-methoxy-benzyl, 3-methoxy benzyl, 4-Hydroxy-benzyl, 4-fluoro-benzyl, 2-Fluoro-benzyl, 4Bromo-benzyl, 2,6-difluoro-benzyl, 2-Bromo-benzyl, 3-Bromo-benzyl, 2,4-Difluoro-benzyl, 2,3-Difluoro-benzyl, 2,6-difluoro-benzyl, 2-Chloro-benzyl, 3-Chloro-benzyl, 3,4-Dichloro-benzyl, 2,6-dichloro-benzyl, 2-Chloro-6-fluoro-benzyl, 4-Bromo-2-fluoro-benzyl, 4-Chloro-2-fluoro-benzyl, 2-methyl-benzyl, 2,6-Dimethyl-benzyl, 2-cyano-benzyl, 4-methoxycarbonyl benzyl, 3-methoxycarbonyl benzyl, 4methanesulfonyl-benzyl, 4-tert-butyl benzyl, 2-Difluoromethoxy-benzyl, 2-trifluoromethyl-benzyl, 3-trifluoromethoxy-benzyl, 3-trifluoromethyl-benzyl, 4-trifluoromethyl-benzyl, 4-trifluoromethoxy-benzyl, 2,4-Bis-trifluoromethyl-benzyl, 3,5-Bis-trifluoromethyl-benzyl, 2-Fluoro-3-methyl-benzyl, 2-Fluoro-5-trifluoromethyl-benzyl, 4-nitro-benzyl, 2-nitro-benzyl, 3-nitro-benzyl, 2-Amino-benzyl, 3-Amino-benzyl, 4-Amino-benzyl, 4-Benzoyl-benzyl, 4-Benzyloxy-benzyl, 1-Biphenyl-2-ylmethyl, or 4-[1,2,3]thiadiazol-4-yl-benzyl;

aa) $R^1$ represents $(C_1-C_6)$alkyl-$(C_3-C_7)$cycloalkyl;

bb) $R^1$ represents $(C_1-C_6)$alkyl-$(C_3-C_7)$cycloalkyl wherein $(C_1-C_6)$alkyl is methyl or ethyl;

cc) $R^1$ represents cyclohexylmethyl, 2-cyclohexylethyl, or cyclopropylmethyl;

dd) $R^1$ represents $(C_1-C_4)$alkyl-heterocycle;

ee) $R^1$ represents $(C_1-C_4)$alkyl-heterocycle wherein said $(C_1-C_4)$alkyl moiety is methyl or ethyl;

ff) $R^1$ represents $(C_1-C_4)$alkyl-heterocycle wherein said heterocycle moiety is pyridinyl, pyrimidinyl, furanyl, quinolinyl, isoxazolyl, thiazolyl, or oxadiazolyl;

gg) $R^1$ represents $(C_1-C_4)$alkyl-heterocycle wherein said heterocycle moiety is pyridinyl, pyrimidinyl, furanyl, quinolinyl, isoxazolyl, thiazolyl, or oxadiazolyl and said $(C_1-C_4)$alkyl moiety is methyl or ethyl;

hh) $R^1$ represents $((C_1-C_4)$alkyl-heterocycle wherein said heterocycle moiety is pyridinyl or quinolinyl and said $(C_1-C_4)$alkyl moiety is methyl or ethyl;

ii) $R^1$ represents quinolin-2-ylmethyl, pyridin-2-ylmethyl, pyridin-3-ylmethyl, pyridin-4-ylmethyl, or 2-pyridin-2-ylethyl;

jj) $R^1$ represents $(C_1-C_4)$alkyl-substituted heterocycle;

kk) $R^1$ represents $(C_1-C_4)$alkyl-substituted heterocycle wherein said $(C_1-C_4)$alkyl moiety is methyl or ethyl;

ll) $R^1$ represents $(C_1-C_4)$alkyl-substituted heterocycle wherein said heterocycle moiety is substituted one to two times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$alkyl-heterocycle, $(C_1-C_6)$alkoxycarbonyl, N,N($C_1-C_6$)dialkylamine, NH$(C_1-C_6)$alkylamine, NHSO$_2(C_1-C_4)$alkyl, $(C_1-C_4)$alkyl-N,N—$C_1$-$C_6$dialkylamine, $(C_1-C_4)$alkoxy-N,N—$C_1$-$C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, N,N($C_1-C_6$)dialkylamine, or NH$(C_1-C_6)$alkylamine;

mm) $R^1$ represents $(C_1-C_4)$alkyl-substituted heterocycle wherein said heterocycle moiety is substituted one to two times independently with a substituent selected from the group consisting of acyl, nitro, $(C_1-C_6)$alkyl, $(C_1-C_6)$alkoxy, $(C_3-C_7)$cycloalkyl, phenyl, heterocycle, and aryl further substituted one to two times independently with $(C_1-C_6)$alkoxy, $(C_1-C_6)$alkoxycarbonyl, or trifluoromethyl;

nn) $R^1$ represents $(C_1-C_4)$alkyl-substituted heterocycle wherein said heterocycle moiety is pyridinyl, pyrimidinyl, furanyl, quinolinyl, isoxazolyl, thiazolyl, or oxadiazolyl;

oo) $R^1$ represents $(C_1-C_4)$alkyl-substituted heterocycle wherein said heterocycle moiety is furanyl, isoxazolyl, thiazolyl, or oxadiazolyl;

pp) $R^1$ represents $(C_1-C_4)$alkyl-substituted heterocycle wherein said $(C_1-C_4)$alkyl moiety is methyl or ethyl; said heterocycle moiety is furanyl, isoxazolyl, thiazolyl, or oxadiazolyl; and said heterocycle moiety is substituted one to two times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$alkyl-heterocycle, $(C_1-C_6)$alkoxycarbonyl, $N,N(C_1-C_6)$dialkylamine, $NH(C_1-C_6)$alkylamine, $NHSO_2(C_1-C_4)$alkyl, $(C_1-C_4)$alkyl-N,N—$C_1-C_6$dialkylamine, $(C_1-C_4)$alkoxy-N,N—$C_1-C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, $N,N(C_1-C_6)$dialkylamine, or $NH(C_1-C_6)$alkylamine;

qq) $R^1$ represents 5-Furan-2-yl-[1,2,4]oxadiazol-3-ylmethyl, 2-methoxycarbonyl-furan-5-ylmethyl, 5-nitro-furan-2-ylmethyl, 5-(2-methoxy-phenyl)-[1,2,4]oxadiazol-3-ylmethyl, 5-(4-methoxy-phenyl)-[1,2,4]oxadiazol-3-ylmethyl, 3,5-Dimethyl-isoxazol-4-ylmethyl, 2-methyl-thiazol-4-ylmethyl, 2-Ethyl-thiazol-4-ylmethyl, 2-phenyl-thiazol-4-ylmethyl, 2-(4-methoxy-phenyl)-thiazol-4-ylmethyl, 2-(4-trifluoromethyl-phenyl)-thiazol-4-ylmethyl, 2-(4-methyl-thiazol-5-yl)-ethyl, 5-Cyclobutyl-[1,2,4]oxadiazol-3-ylmethyl, 3-(3-methoxycarbonyl-phenyl)-[1,2,4]oxadiazol-5-ylmethyl, or 3-(4-methoxy-phenyl)-[1,2,4]oxadiazol-5-ylmethyl;

rr) $R^1$ represents $(C_1-C_6)$alkyl-$(C_1-C_6)$alkoxy;

ss) $R^1$ represents $(C_1-C_6)$alkyl-$(C_1-C_6)$alkoxy wherein said alkoxy moiety is methoxy or ethoxy;

tt) $R^1$ represents $(C_1-C_6)$alkyl-$(C_1-C_6)$alkoxy wherein said alkyl moiety is methyl or ethyl;

uu) $R^1$ represents $(C_2-C_6)$alkenyl;

vv) $R^1$ represents allyl, 2-methylallyl, or 3-methyl-but-2-enyl;

ww) $R^1$ represents $(C_2-C_6)$alkynyl;

xx) $R^1$ represents prop-2-ynyl yy) $R^1$ represents $CH_2COR^7$ wherein $R^7$ is selected from the group consisting of aryl, $(C_1-C_6)$alkoxy, NH—$(C_3-C_7)$cycloalkyl, and aryl optionally substituted with one to two substituents independently selected from the group consisting of $(C_1-C_6)$alkyl, $(C_1-C_6)$alkoxy, and halo;

zz) $R^1$ represents $CH_2COR^7$ wherein $R^7$ is 2-methoxy-phenyl, 3-methoxy-phenyl, 4-methoxy-phenyl, naphthalene-2-yl, 4-bromophenyl, 2,5-dimethoxy-phenyl, NH—cyclohexyl, ethoxy;

aaa) $R^1$ represents acetic acid ethyl ester, 2-(2-methoxy-phenyl)-2-oxo-ethyl, 2-(3-methoxy-phenyl)-2-oxo-ethyl, 2-(4-methoxy-phenyl)-2-oxo-ethyl, 2-naphthalen-2-yl-2-oxo-ethyl, 2-(4-Bromo-phenyl)-2-oxo-ethyl, 2-(2,5-Dimethoxy-phenyl)-2-oxo-ethyl, or N-cyclohexyl-acetamidyl bbb) $R^1$ represents $(C_3-C_7)$cycloalkyl;

ccc) $R^1$ represents cyclopropyl, cyclopentyl, or cyclohexyl;

ddd) $R^1$ represents $(C_3-C_7)$cycloalkoxy;

eee) $R^1$ represents aryl, with the proviso that $R^1$ is other than phenyl;

fff) $R^1$ represents naphthalen-1-yl or naphthalen-2-yl;

ggg) $R^1$ represents substituted aryl;

hhh) $R^1$ represents substituted aryl wherein said aryl moiety is phenyl or naphthyl;

iii) $R^1$ represents substituted aryl wherein said aryl moiety is phenyl or naphthyl substituted one to three times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$alkyl-heterocycle, $(C_1-C_6)$alkoxycarbonyl, $N,N(C_1-C_6)$dialkylamine, $NH(C_1-C_6)$alkylamine, $NHSO_2(C_1-C_4)$alkyl, $(C_1-C_4)$alkyl-N,N—$C_1-C_6$dialkylamine, $(C_1-C_4)$alkoxy-N,N—$C_1-C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, $N,N(C_1-C_6)$dialkylamine, or $NH(C_1-C_6)$alkylamine;

jjj) $R^1$ represents substituted aryl wherein said aryl moiety is phenyl or naphthyl substituted one to two times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$alkyl-heterocycle, $(C_1-C_6)$alkoxycarbonyl, $N,N(C_1-C_6)$dialkylamine, $NH(C_1-C_6)$alkylamine, $NHSO_2(C_1-C_4)$alkyl, $(C_1-C_4)$alkyl-N,N—$C_1-C_6$dialkylamine, $(C_1-C_4)$alkoxy-N,N—$C_1-C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, $N,N(C_1-C_6)$dialkylamine, or $NH(C_1-C_6)$alkylamine;

kkk) $R^1$ represents substituted aryl wherein said aryl moiety is phenyl substituted one to two times independently with a substituent selected from the group consisting of $(C_1-C_6)$alkyl, $(C_1-C_6)$alkoxy, halo, heterocycle, $N,N(C_1-C_6)$dialkylamine, $NH(C_1-C_6)$alkylamine, trifluoromethyl, trifluoromethoxy, difluoromethyl, difluoromethoxy or a heterocycle further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, $N,N(C_1-C_6)$dialkylamine, or $NH(C_1-C_6)$alkylamine;

lll) $R^1$ represents substituted aryl wherein said aryl moiety is phenyl substituted one to two times independently with a substituent selected from the group consisting of $(C_1-C_6)$alkyl, $(C_1-C_6)$alkoxy, halo, heterocycle, $N,N(C_1-C_6)$dialkylamine, $NH(C_1-C_6)$alkylamine, trifluoromethyl, trifluoromethoxy, difluoromethyl, difluoromethoxy or a heterocycle further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, $N,N(C_1-C_6)$dialkylamine, or $NH(C_1-C_6)$alkylamine, further provided that at least one of the substitutions occurs at the meta position of said phenyl moiety;

mmm) $R^1$ represents substituted aryl wherein said aryl moiety is phenyl substituted one to two times independently with a substituent selected from the group consisting of $(C_1-C_6)$alkyl, $(C_1-C_6)$alkoxy, halo, heterocycle, $N,N(C_1-C_6)$dialkylamine, $NH(C_1-C_6)$alkylamine, trifluoromethyl, trifluoromethoxy, difluoromethoxy, or difluoromethyl, further provided that at least one of the substitutions occurs at the meta position of said phenyl moiety;

nnn) $R^1$ represents substituted aryl wherein said aryl moiety is phenyl substituted one to two times independently with a substituent selected from the group consisting of $(C_1-C_6)$alkyl, $(C_1-C_6)$alkoxy, halo, heterocycle, trifluoromethyl, trifluoromethoxy, difluoromethoxy, or difluoromethyl, further provided that at least one of the substitutions occurs at the meta position of said phenyl moiety;

ooo) R¹ represents 4-methyl phenyl, 2-methyl phenyl, 3-methyl phenyl, 3-trifluoromethyl-phenyl, 3-isopropyl-phenyl, 4-methoxy-phenyl, 3-methoxy-phenyl, 3,4-Dimethoxy-phenyl, 3-Ethoxy-phenyl, 2-Chloro-phenyl, 3-Fluoro-phenyl, 3-Bromo-phenyl, 3-trifluoromethoxy phenyl, or 4-trifluoromethyl-phenyl ppp) R¹ represents heterocycle;

qqq) R¹ represents pyridinyl, pyrimidinyl, furanyl, quinolinyl, isoxazolyl, thiazolyl, or oxadiazolyl;

rrr) R¹ represents pyridinyl, pyrimidinyl, furanyl, thiazolyl, oxadiazolyl;

sss) R¹ represents pyridin-3-yl or pyridin-4-yl;

ttt) R¹ represents substituted heterocycle;

uuu) R¹ represents substituted heterocycle wherein said heterocycle moiety is pyridinyl, pyrimidinyl, furanyl, thiazolyl, or oxadiazolyl substituted one to two times independently with a substituent selected from the group consisting of acyl, halogen, hydroxy, cyano, nitro, amino, $(C_1-C_6)$alkyl, halo$(C_1-C_6)$alkyl, $(C_1-C_6)$alkoxy, $(C_1-C_6)$alkylthio, $(C_3-C_7)$cycloalkyl, $(C_1-C_4)$alkyl-$(C_3-C_7)$cycloalkyl, aryl, $(C_1-C_4)$alkyl-aryl, heterocycle, $(C_1-C_4)$alkyl-heterocycle, $(C_1-C_6)$alkoxycarbonyl, N,N$(C_1-C_6)$dialkylamine, NH$(C_1-C_6)$alkylamine, NHSO₂$(C_1-C_4)$alkyl, $(C_1-C_4)$alkyl-N,N—$C_1-C_6$dialkylamine, $(C_1-C_4)$alkoxy-N,N—$C_1-C_6$dialkylamine, difluoromethyl, difluoromethoxy, trifluoromethyl, trifluoromethoxy, or an aryl or heterocycle group further substituted with one to two moieties selected from the group consisting of $(C_1-C_6)$alkyl, $(C_3-C_7)$cycloalkyl, halogen, hydroxy, $(C_1-C_6)$alkoxy, difluoromethyl, difluoromethoxy, trifluoromethyl, trifluoromethoxy, $CF_2CF_3$, nitro, amino, N,N$(C_1-C_6)$dialkylamine, or NH$(C_1-C_6)$alkylamine;

vvv) R¹ represents substituted heterocycle wherein said heterocycle moiety is pyridinyl, pyrimidinyl, furanyl, thiazolyl, or oxadiazolyl substituted one to two times independently with a substituent selected from the group consisting of acyl, nitro, $(C_1-C_6)$alkyl, $(C_1-C_6)$alkoxy, $(C_3-C_7)$cycloalkyl, phenyl, heterocycle, and aryl further substituted one to two times independently with $(C_1-C_6)$alkoxy, $(C_1-C_6)$alkoxycarbonyl, or trifluoromethyl;

www) R¹ represents 2-methoxy-pyrimidin-4-yl;

xxx) R² represents hydroxy, $(C_1-C_6)$alkyl, hydroxy$(C_1-C_6)$alkyl or a group of the formula

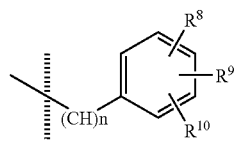

wherein n is 0 or 1;

yyy) R² represents hydroxy, $(C_1-C_6)$alkyl, hydroxy$(C_1-C_6)$alkyl or a group of the formula

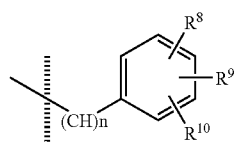

wherein n is 0 or 1 and R⁸ through R¹⁰ each independently represent hydrogen, hydroxy, $(C_1-C_4)$alkyl, halo, nitro, amino, $(C_1-C_4)$alkoxy, or NHR¹⁴;

zzz) R² represents a group of the formula

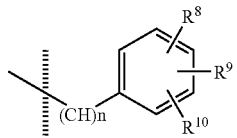

wherein n is 0 and R⁸ through R¹⁰ each independently represent hydrogen, hydroxy, $(C_1-C_4)$alkyl, halo, nitro, amino, $(C_1-C_4)$alkoxy, or NHR¹⁴ and R¹⁴ represents CO(CH₃) or SO₂(CH₃);

dddd) R² represents 4-hydroxy-3,5-dimethyl phenyl, 4-hydroxy-3-ethyl phenyl, 2-hydroxy-5-ethyl phenyl, 4-hydroxy-3-methyl phenyl, 4-hydroxy phenyl, 4-hydroxy-3,5-dichloro phenyl, 5-fluoro-2-hydroxy-3-methoxy phenyl, 5-fluoro-2-hydroxy-3-methyl phenyl, 5-fluoro-2-hydroxy-4-methyl phenyl, 4-amino-3,5-dimethyl phenyl, 4-amino phenyl, 4-nitro phenyl, 2-hydroxy-3,4-dimethyl phenyl, 2-hydroxy-3,5-dimethyl phenyl, 2-hydroxy-5-methyl phenyl, 2-hydroxy-4-methyl phenyl, 3,4-dihydroxy-5-methyl phenyl, 4-hydroxy-3-methyl-5-propyl phenyl, 3,4-dimethyl phenyl, 3,4,5-trimethyl phenyl, 4-amino-3-chloro-5-methyl phenyl, 4-amino-3-methyl phenyl, 2,4-dihydroxy phenyl, 2,4-dihydroxy-3-methyl phenyl, 2-hydroxy-3-ethyl phenyl, 2-hydroxy phenyl, 3-hydroxy benzyl, 3-methoxy benzyl, 4-hydroxy benzyl, or 4-methoxy benzyl;

eeee) R² represents 4-hydroxy-3,5-dimethyl phenyl, 4-hydroxy-3-ethyl phenyl, 4-hydroxy-3-methyl phenyl, 4-hydroxy phenyl, 4-hydroxy-3,5-dichloro phenyl, 4-amino-3,5-dimethyl phenyl, 4-amino phenyl, 4-nitro phenyl, 2-hydroxy-3,4-dimethyl phenyl, 2-hydroxy-3,5-dimethyl phenyl, 2-hydroxy-4,5-dimethyl phenyl 2-hydroxy-5-methyl phenyl, 3,4-dihydroxy-5-methyl phenyl, 4-hydroxy-3-methyl-5-propyl phenyl, 3,4-dimethyl phenyl, 3,4,5-trimethyl phenyl, 4-amino-3-chloro-5-methyl phenyl, 4-amino-3-methyl phenyl, 2,4-dihydroxy phenyl, 2,4-dihydroxy-3-methyl phenyl, 2-hydroxy-3-ethyl phenyl, or 2-hydroxy phenyl;

ffff) R² represents 4-hydroxy-3,5-dimethyl phenyl;

gggg) R² represents hydroxy, $(C_1-C_6)$alkyl, or hydroxy$(C_1-C_6)$alkyl;

hhhh) R² represents methyl, ethyl, propyl, or 3-hydroxypropyl;

iiii) R³ represents a group of the formula:

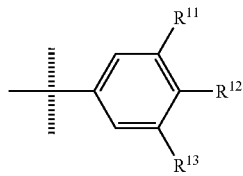

wherein R¹¹ and R¹³ each independently represent hydrogen, $(C_1-C_4)$alkyl, or halo; and R¹² represents hydrogen, halo, $(C_1-C_4)$alkyl, hydroxy, or amino, with the proviso that at least one of R¹¹ and R¹³ is other than hydrogen;

jjjj) R³ represents 4-hydroxy-3,5-dimethyl phenyl, 4-hydroxy-3-ethyl phenyl, 4-hydroxy-3-methyl phenyl, 4-hydroxy-3,5-dichloro phenyl, 3,5-dimethyl phenyl, or 3,4,5-trimethyl phenyl;

kkkk) R³ represents 4-hydroxy-3,5-dimethyl-phenyl;

llll) $R^4$ and $R^5$ each independently represent hydrogen, halo, hydroxy, $(C_1-C_4)$alkyl, $(C_1-C_4)$alkoxy, $CF_3$, $OCF_3$, $CHF_2$, $OCHF_2$, $CF_2CF_3$, cyano, nitro, or amino;

mmmm) $R^4$ and $R^5$ each independently represent hydrogen, halo, $(C_1-C_4)$alkyl, or $(C_1-C_4)$alkoxy; or nnnn) $R^4$ and $R^5$ each independently represent hydrogen, bromo, chloro, methyl, ethyl, or methoxy.

Compounds of Formula I, including the novel compounds of Formula I, can be chemically prepared, for example, by following the synthetic routes set forth in the Schemes below. However, the following discussion is not intended to be limiting to the scope of the present invention in any way. For example, the specific synthetic steps for the routes described herein may be combined in different ways, or with steps from different schemes, to prepare other compounds of Formula I. All substituents, unless otherwise indicated, are as previously defined. The reagents and starting materials are readily available to one of ordinary skill in the art. For example, certain reagents or starting materials can be prepared by one of ordinary skill in the art following procedures disclosed in Song, H. N., et. al.; *Syn. Comm.* (1999), 29, 3303-3311; Olah, G. A., et. al.; *J. Org. Chem.* (1998), 63, 4481-4484; and Hewawasam, P. and Erway, M; *Tetrahedron Lett.* (1998), 39, 3981-3984. Other necessary reagents and starting material maybe made by procedures which are selected from standard techniques of organic and heterocyclic chemistry, techniques which are analogous to the syntheses of known structurally similar compounds, and the procedures described in the Examples, including any novel procedures.

Scheme I provides procedures for the synthesis of compounds of Formula I wherein, for example, R2 and R3 are substituted phenyl groups, R9 and R12 are hydroxy, and R8 and R10, and R11 and R13 are each independently $(C_1-C_6)$ alkyl or hydrogen.

In Scheme I, step A, the compound of structure (1) is treated in a Friedel-Crafts reaction with phenols by methods known in the art (Song, H. N., et. al.; *Syn. Comm.* (1999), 29, 3303-3311). For example, isatin (1), or substituted isatin, is treated with a phenol or substituted phenol of structure (2) (wherein R and R" are each independently $C_1-C_6$ alkyl or hydrogen) in acetic acid with a Lewis acid such as aluminum chloride, ferric chloride, zinc chloride, or the like at about 50-120° C. for about 1 to 24 h. The product can then be isolated by standard methods such as filtration and washing with water.

In Scheme I, step B, the hydroxyl moieties of compound (3) are protected with a silyl protecting group such as tert-butyldimethylsilyl, tert-butyldiphenylsilyl, or triisopropylsilyl under conditions commonly used in the art. For example, compound (2) is treated with imidazole and a compound of formula Pg-Hal (wherein Pg is tert-butyldimethylsilyl and Hal is chloro atom), in dichloromethane or other halogenated solvent at ambient temperature to the reflux temperature of the solvent for a period of 1-24 h. The product (compound (4)) can be isolated by aqueous workup followed by chromatographic techniques well known in the art.

In Scheme 1, step C, the compound of structure (4) is treated with an appropriate base and a compound of formula R1-Hal, wherein R1 represents an alkylating agent and Hal represents a chloro, bromo or iodo atom. For example, compound (4) is dissolved in a suitable organic solvent, such as tetrahydrofuran, dioxane, or dimethylformamide and treated with about 1 to 2 equivalents of a compound of formula R1-Hal and an excess of a suitable organic base, such as sodium hydride, potassium t-butoxide, potassium, sodium or lithium bis(trimethylsilyl)amide or 2-tert-butyl-imino-2-diethylamino-1,3-dimethyl-perhydro-1,3,2-diazaphosphorine (BEMP). The reaction can be performed at 0°

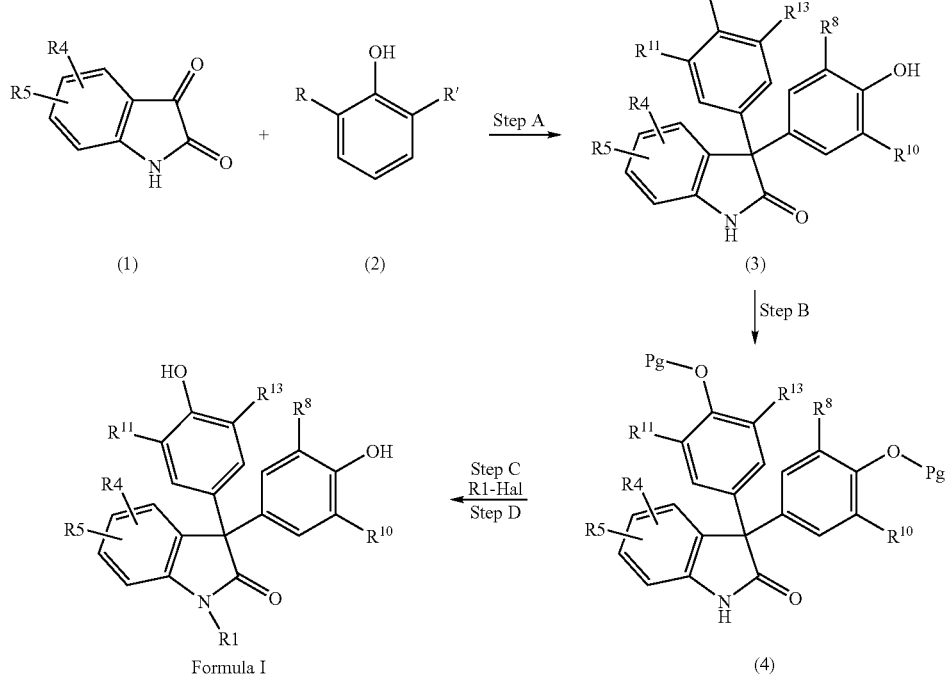

Scheme I

C. to the refluxing temperature of the solvent for about 3-24 h to give the desired intermediate. The product can be isolated by standard aqueous workup procedures or treated in situ (step D) with a silyl deprotecting reagent commonly used in the art such as cesium fluoride or tetrabutylammonium fluoride (TBAF) and the product of Formula I isolated by aqueous workup and recrystallization techniques well known in the art.

Schemes I(a) through I(g) below provide a variety of procedures for synthesizing additional compounds of Formula I wherein, for example, R2 and R3 are substituted phenyl groups, R9 and R12 are hydroxy, and R8, R10, R11 and R13 are each independently $(C_1-C_6)$alkyl or hydrogen.

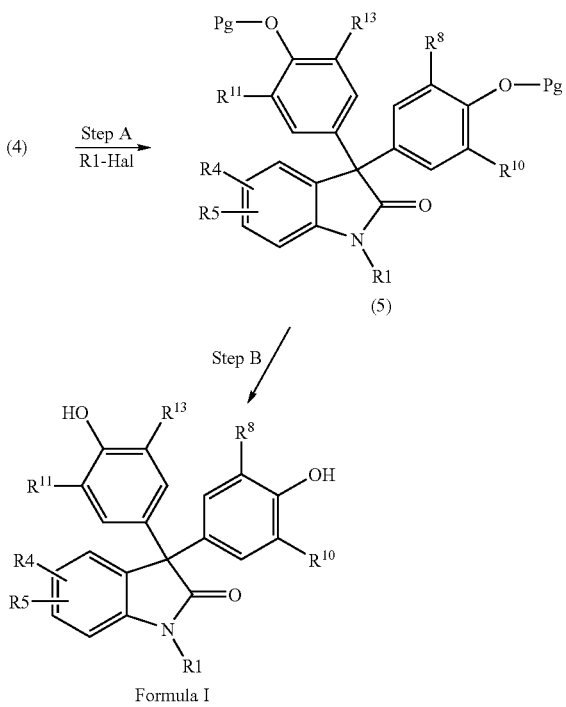

Scheme I(a)

In Scheme I(a), step A, the compound of structure (4), wherein Pg is a suitable silyl protecting group, is treated under standard conditions with a compound of formula R1-Hal wherein R1 is a suitable leaving group and Hal represents a chloro, bromo or iodo atom to provide a compound of structure (5). For example, compound (4) is dissolved in a suitable organic solvent, such as anhydrous tetrahydrofuran and treated with about 3 equivalents of a suitable organic base, such as lithium bis(trimethylsilyl)amide, followed by a solution of a catalytic amount of sodium iodide (when Hal is chloro or bromo atom) and about 3 equivalents of R1-Hal in anhydrous tetrahydrofuran. Examples of other suitable organic solvents include 1,4-dioxane, diethyl ether, glymes, dimethylformamide, and the like. Examples of R1-Hal suitable for the methods of the present scheme include 2,3-difluorobenzyl bromide, 4-nitrobenzyl bromide, 3-methoxybenzyl bromide, 2-methoxyphenacyl bromide, 4-difluoromethoxybenzyl bromide, 2-chloromethylquinoline hydrochloride, allyl bromide, 1-iodopentane, iodoacetonitrile, and the like. The reaction is stirred at about 50-60° C. for about 12-24 hours. The compound (5) is then isolated using standard procedures known in the art, such as column chromatography. The crude material can then be purified by standard methods such as chromatography on silica gel with a suitable eluent, such as ethyl acetate/hexanes, to provide purified compound (5).

In Scheme I(a), step B, the silyl protecting groups are removed from compound (5) to provide the compound of Formula I under conditions well known in the art. For example, compound (5) is dissolved in a suitable solvent such as methanol or tetrahydrofuran and then treated with about 2-10 equivalents of cesium fluoride or tetrabutyl ammonium fluoride at about 0-60° C. for about 1-24 h. The compound of Formula I is then isolated and can be purified by standard techniques known well in the art. For example, the crude compound of Formula I is dissolved in water and then extracted with a suitable solvent such as ethyl acetate. The organic extracts are dried over anhydrous sodium sulfate, filtered, and then concentrated. The residue can then be triturated with, for example, diethyl ether to provide the purified compound of Formula I.

Where R1 is, for example, a nitro or amino substituted benzyl, compounds of Formula I may be synthesized according to the procedures provided in Scheme I(b).

Scheme I(b)

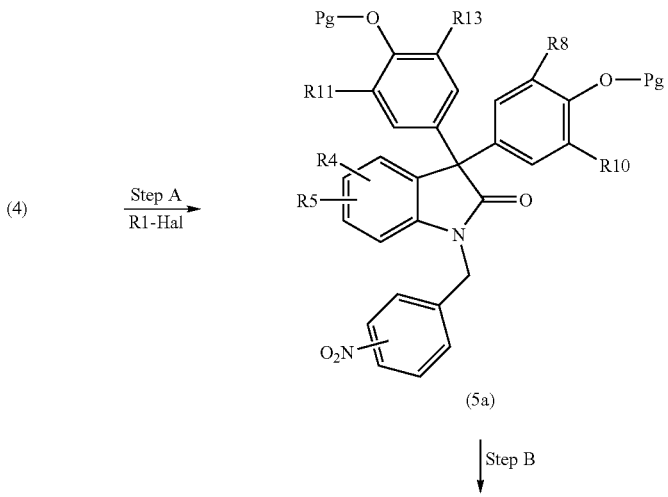

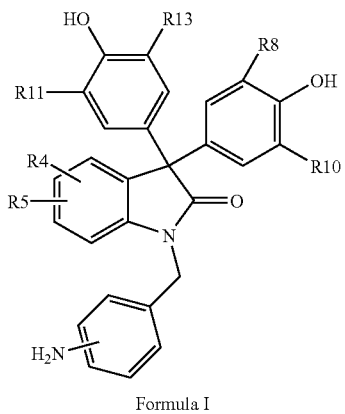

Formula I

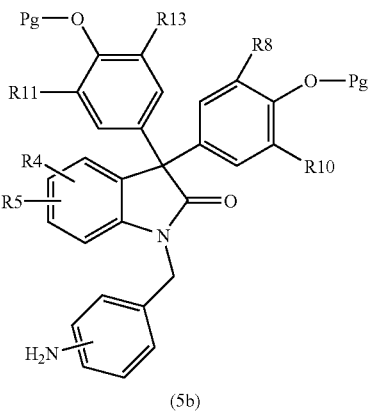

(5b)

In Scheme I(b), step A, the compound of structure (4), wherein Pg is a suitable silyl protecting group, is treated under standard conditions with a compound of the formula R1-Hal, wherein R1 is a nitrobenzyl group and hal represents a chloro, bromo or iodo atom, to provide a compound of structure (5a) (wherein R1 is a nitro substituted benzyl). For example, compound (4) is dissolved in a suitable organic solvent, such as anhydrous tetrahydrofuran and treated with about 3 equivalents of a suitable organic base, such as lithium bis(trimethylsilyl)amide, followed by a solution of a catalytic amount of sodium iodide (when halide is chloro or bromo atom) and about 3 equivalents of nitrobenzyl halide in anhydrous tetrahydrofuran. Examples of other suitable organic solvents include 1,4-dioxane, diethyl ether, glymes, and the like. The reaction is stirred at about 0-60° C. for about 12-24 hours. The compound (5a) is then isolated using standard procedures known in the art, such as column chromatography. The crude material can then be purified by methods well known in the art such as chromatography on silica gel with a suitable eluent, such as ethyl acetate/hexanes, to provide purified compound (5a).

In Scheme I(b), step B, the nitroaryl substituents are converted to anilines using conditions well known in the art. For example a mixture of compound (5), wherein R1 is nitro substituted benzyl, and about 2-4 equivalents of tin(II) chloride dihydrate is dissolved in an acceptable solvent or solvent mixture such as 1:1 methanol:tetrahydrofuran and allowed to stir for about 2-24 hours. The reaction mixture is then concentrated under reduced pressure and the crude product (5b), wherein R1 is amino-substituted benzyl, is then purified using techniques well known in the art. For example, the residue is dissolved in ethyl acetate and washed with 1N aqueous sodium hydroxide. The organic solution is then dried over anhydrous sodium sulfate, filtered, and then concentrated under vacuum to provide crude compound (5b). This crude material can then be purified by standard methods known in the art, such as flash chromatography on silica gel with a suitable eluent such as ethyl acetate/hexanes, to provide purified compound (5b) wherein R1 is amino-substituted benzyl.

In Scheme I(b), step C, the silyl protecting groups are removed from compound (5) to provide the compound of Formula I under conditions well known in the art. For example, compound (5b) is dissolved in a suitable solvent such as methanol or tetrahydrofuran and then treated with about 2-10 equivalents of cesium fluoride or tetrabutylammonium fluoride (TBAF) at about 0-60° C. for about 1-24 h. The compound of Formula I is then isolated and can be purified by standard techniques known well in the art. For example, the crude compound of Formula I is dissolved in water and then extracted with a suitable solvent such as ethyl acetate. The organic extracts are dried over anhydrous sodium sulfate, filtered, and then concentrated. The residue can then be triturated with diethyl ether to provide the purified compound of Formula I.

Scheme I(c) provides procedures for synthesizing compounds of Formula I wherein R1 represents, for example, a benzenesulfonyl group.

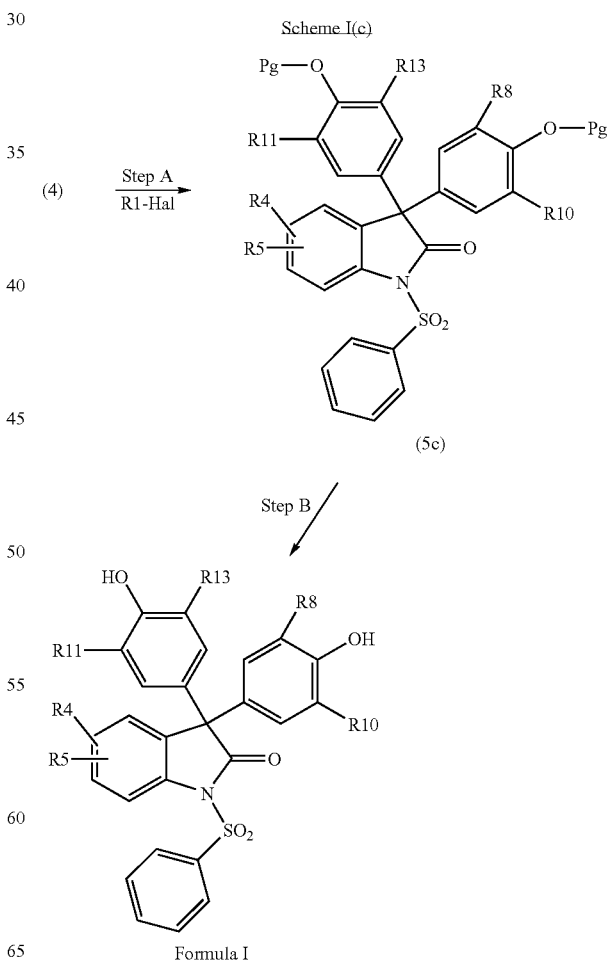

Scheme I(c)

In Scheme I(c), step A, the compound of structure (4), wherein Pg is a suitable silyl protecting group, is treated under standard conditions with a compound of formula R1-Hal where R1 is a suitable leaving group and Hal represents a chloro or fluoro atom to provide a compound of structure (5c). For example, compound (1) is dissolved in a suitable organic solvent, such as anhydrous tetrahydrofuran and treated with about 1 equivalent of a suitable organic base, such as sodium hydride, followed by the addition of about 2 equivalents of R1-Hal. Examples of compounds of the formula R1-Hal, suitable for the methods of the present scheme, include m-nitrobenzenesulfonyl chloride, p-nitrobenzenesulfonyl chloride, p-bromobenzenesulfonyl chloride, p-toluenesulfonyl chloride, benzenesulfonyl chloride, methanesulfonyl chloride, trifluoromethanesulfonyl chloride, and the like. The reaction is stirred at room temperature for about 1-4 hours. The compound (5c), wherein R1 is, for example, a benzenesulfonyl or substituted-benzenesulfonyl group, is then isolated using standard procedures, such as column chromatography. The crude material can then be purified by chromatography on silica gel with a suitable eluent, such as ethyl acetate/hexanes, to provide purified compound (5c).

In Scheme I(c), step B, the silyl protecting groups are removed from compound (5c) to provide the compound of Formula I under conditions well known in the art, and as previously discussed herein.

Scheme I(d) provides yet additional procedures for synthesizing compounds of Formula I wherein for example R2 and R3 are substituted phenyl groups, R9 and R12 are hydroxy, and R8, R10, R11 and R13 are each independently $(C_1-C_6)$alkyl or hydrogen.

In Scheme I(d), step A, the compound of structure (4) wherein Pg is a silyl protecting group, is treated under standard conditions with a compound of formula R1-OH, wherein R1-OH is a primary or secondary alcohol, to provide compounds of structure (5) and (5d). For example, compound (4), 4-8 equivalents of (4-diphenylphosphanyl-phenyl)-dimethyl-amine or triphenylphosphine, and about 4 equivalents of R1-OH are dissolved in a suitable organic solvent, such as anhydrous tetrahydrofuran, and treated with about 4-8 equivalents of diethyl azodicarboxylate or diisopropyl azodicarboxylate. Examples of compounds of the general formula R1-OH, suitable for the present synthesis, include butanol, diethylene glycol monomethylether, cyclopentanol, 2-(4-methyl-thiazol-5-yl)-ethanol, 2-(2-hydroxy-ethylethanol, and the like. The reaction mixture is then allowed to stir for about 3-24 hours. Compounds (5) and (5d) are isolated and can be purified by standard techniques well known in the art. For example the reaction mixture is diluted with ethyl acetate and then washed with 3:1 water:brine. The organic layer is then dried over anhydrous magnesium sulfate, filtered, and then the volatiles are removed under reduced pressure. The compounds (5) and (5d) can then be purified by chromatography on silica gel with a suitable eluent, such as ethyl acetate/hexanes, to provide purified compounds (5) and (5d).

In Scheme I(d), step B, the silyl protecting groups are removed from compound (5) or (5d) to provide the compound of Formula I under conditions well known in the art. For example, compound (5) is dissolved in a suitable solvent such as tetrahydrofuran and then treated with about 2-2.5 equivalents of tetrabutylammonium fluoride. The compound of Formula I is then isolated and can be purified by standard

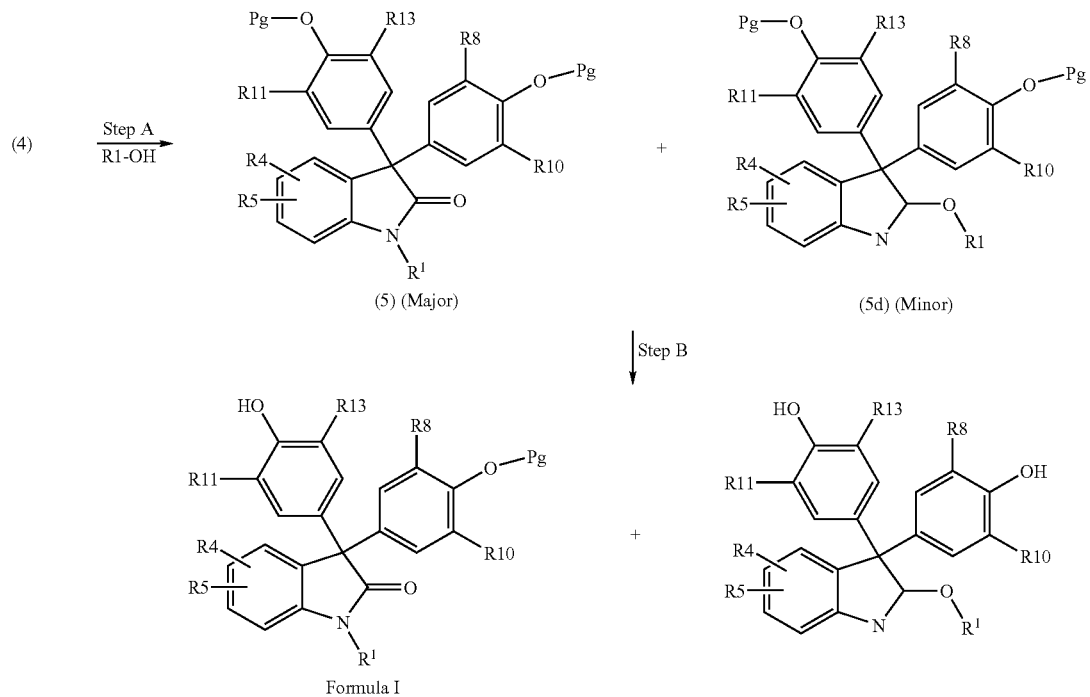

techniques known well in the art. For example the reaction mixture is diluted with ethyl acetate and then washed with 3:1 water:brine. The organic layer is then dried over anhydrous magnesium sulfate, filtered, and then the volatiles are removed under reduced pressure. The crude compound of Formula I can then be purified by chromatography on silica gel with a suitable eluent, such as ethyl acetate/hexanes, to provide the purified compound of Formula I.

Scheme I(e) provides further procedures for synthesizing compounds of Formula I. The methods of Scheme I(e) are particularly useful where it is desired that R1 be, for example, an aryl, substituted aryl, heterocycle, or substituted heterocycle group.

using standard procedures, such as chromatography techniques. For example, the reaction mixture is filtered through Celite. The filtrate can then be purified by chromatography on silica gel with a suitable eluent, such as dichloromethane/hexanes, to provide purified compound (5e).

In Scheme I(e), step B, compound (5e) is deprotected under standard conditions well known in the art to provide the compound of Formula I. For example, compound (5e) is dissolved in an organic solvent, such as tetrahydrofuran, under an atmosphere of nitrogen, and about 2.5 equivalents of a tetrabutylammonium fluoride in tetrahydrofuran is

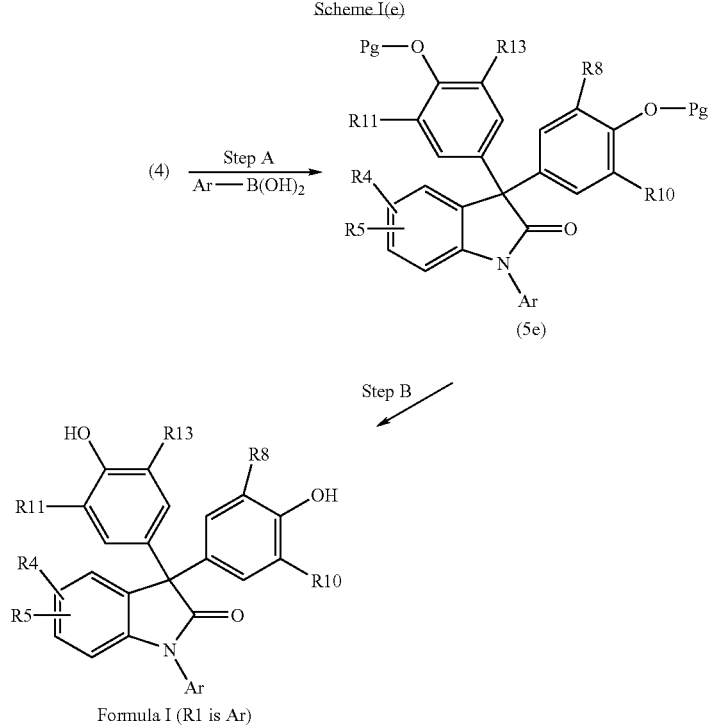

In Scheme I(e), step A, the compound of structure (4), wherein Pg is a silyl protecting group, is treated under standard conditions with a compound of formula Ar—B(OH)$_2$, wherein Ar represents an appropriately substituted or unsubstituted aryl or heterocyclic ring, to provide the compound of structure (5e). For example, compound (4) is dissolved in a suitable organic solvent, such as methylene chloride and treated with about 2 equivalents of a compound of formula Ar—B(OH)$_2$, 2 equivalents of a suitable organic base, such as triethylamine, 1 equivalent of a suitable Cu (II) source, such as copper (II) acetate, and a drying agent, such as molecular sieves. Examples of compounds of the general formula Ar—B(OH)$_2$, suitable for the present synthesis methods, include phenylboronic acid, 4-methoxyphenylboronic acid, 2-chlorophenylboronic acid, 3-fluorophenylboronic acid, pyridine-3-boronic acid, and the like. The reaction mixture is stirred for about 16 to 200 hours at a temperature of about 25° C. under ambient atmosphere. The compound (5e) wherein R1 is, for example, aryl, substituted aryl, heterocycle, or substituted heterocycle, is then isolated added. The reaction mixture is stirred at room temperature for about 1 to 2 hours. The reaction is quenched and the compound of Formula (I) is isolated. The crude product can then be purified by standard techniques well known in the art. For example, the reaction is quenched with saturated aqueous ammonium chloride. Water is added and the quenched reaction is extracted with a suitable organic solvent, such as ethyl acetate. The organic extract is dried over anhydrous sodium sulfate, filtered, and concentrated to provide crude compound of Formula (I). This crude material can then be purified by chromatography on silica gel with a suitable eluent, such as ethyl acetate/hexanes, to provide purified compound of Formula I (wherein R1 is aryl, substituted aryl, heterocycle, or substituted heterocycle).

Scheme I(f) provides yet further procedures for synthesizing compounds of Formula I. In particular, Scheme I(f) provides compounds of Formula I wherein R1 is, for example, an alkyl-heterocycle or alkyl-(substituted)heterocycle group.

Scheme I(f)

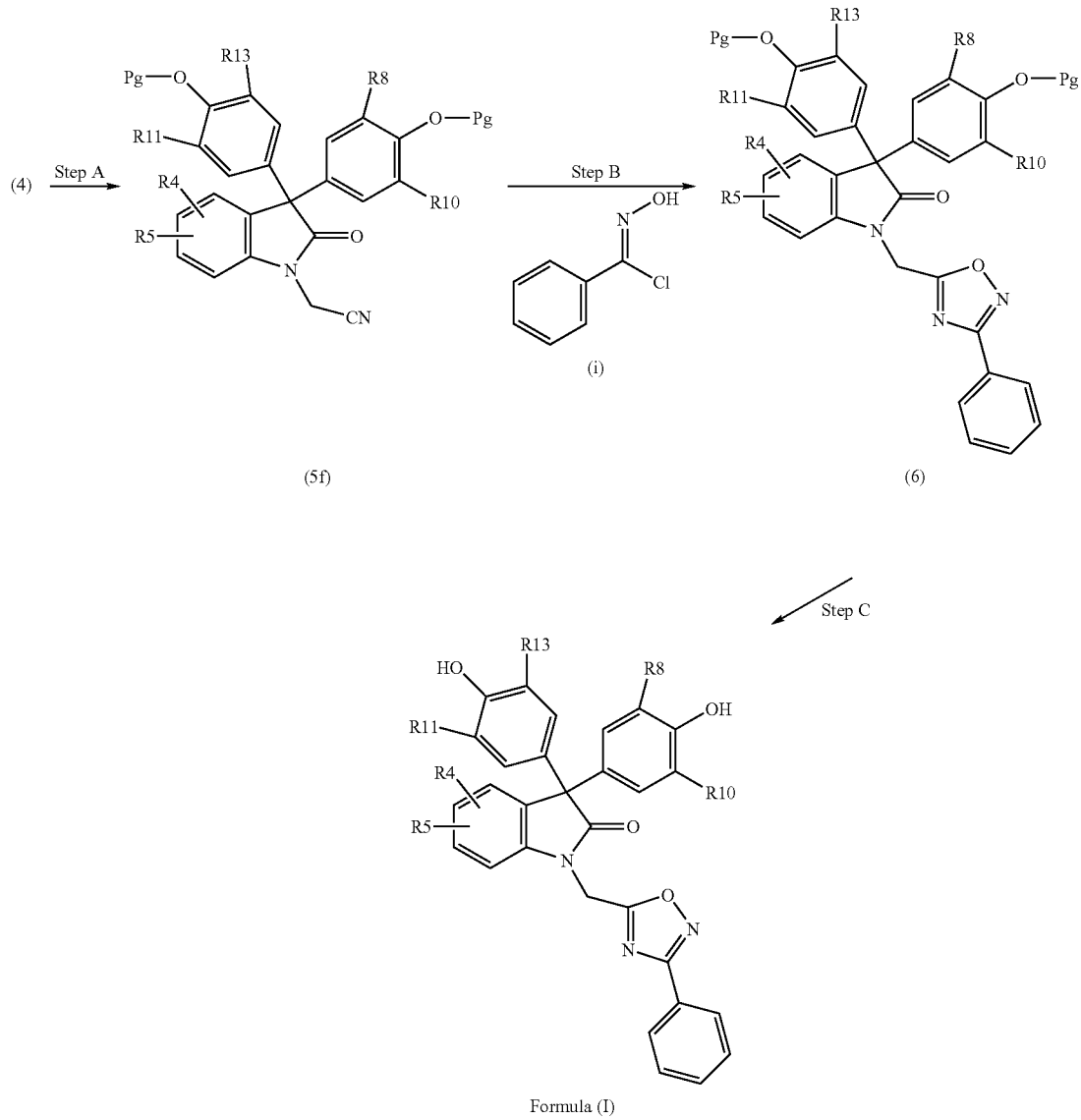

Formula (I)

In Scheme I(f), step A, compound (4), wherein Pg is a silyl protecting group, is alkylated with, for example, bromoacetonitrile to provide the compound of structure (5f) wherein R1 is —CH2—CN. For example, compound (4) is dissolved in a suitable organic solvent, such as N,N-dimethylformamide, under an atmosphere of nitrogen. The reaction is cooled to a temperature of 0° C., and about 1.1 equivalents of a suitable base, such as potassium t-butoxide in tetrahydrofuran, is added. The reaction mixture is then treated with about 1.1 equivalents of bromoacetonitrile. Upon completion of the addition, the reaction is allowed to warm to room temperature, and the reaction is stirred at room temperature for about 18 hours. The compound (5), wherein R1 is —CH$_2$CN, is then isolated and can be purified by standard techniques well known in the art. For example, the reaction is diluted with water and extracted with diethyl ether. The organic extracts are combined, washed with brine, dried over sodium sulfate, filtered, and concentrated to provide crude compound (5f). The crude product can then be purified by methods well known in the art such as chromatography on silica gel with a suitable eluent, such as ethyl acetate/hexanes, to provide purified compound (5f) wherein R1 is —CH$_2$CN.

In Scheme I(f), step B, compound (5f) is combined with, for example, a compound of structure (i), prepared by one of ordinary skill following procedures known in he art, to provide the compound of structure (6) wherein R1 is an alkyl-heterocycle or alkyl-(substituted) heterocycle. For example, compound (5f), wherein R1 is —CH$_2$CN, is dissolved in an organic solvent, such as diethyl ether, and about 7 equivalents of a compound of structure (i) is added. The reaction mixture is then treated with base, such as triethylamine, in diethyl ether, and the reaction is stirred at room temperature for about 16 to 18 hours. The compound (6) is then isolated and can be purified using standard techniques. For example, the reaction is diluted with an organic solvent suitable for extraction, such as ethyl acetate, then washed with water. The organic extract is dried over sodium sulfate, filtered, and concentrated to provide crude compound (6). The crude material can then be purified by chromatography on silica gel with a suitable eluent such as ethyl acetate/hexanes, to provide purified compound (6) wherein R1 is alkyl-heterocycle or alkyl-substituted heterocycle.

In Scheme I(f), step C, compound (6) is deprotected under standard conditions well known in the art to provide the compound of Formula I, wherein R1 is alkyl-heterocycle or alkyl-substituted heterocycle. For example, compound (6) is dissolved in an organic solvent, such as tetrahydrofuran, under an atmosphere of nitrogen, and about 2.5 equivalents of tetrabutylammonium fluoride in tetrahydrofuran is added. The reaction mixture is stirred at room temperature for about 1 to 2 hours. The reaction is then quenched and compound of Formula I is isolated and can be purified by standard techniques well known in the art. For example, the reaction is quenched with saturated aqueous ammonium chloride. Water is added and the quenched reaction is extracted with a suitable organic solvent, such as ethyl acetate. The organic extract is dried over anhydrous sodium sulfate, filtered, and concentrated to provide crude compound of Formula I. The crude material can then be purified by chromatography on silica gel with a suitable eluent, such as ethyl acetate/hexanes, to provide purified compound of Formula I, wherein R1 is an alkyl-heterocycle or an alkyl-substituted heterocycle.

Scheme I(g) provides still additional procedures for synthesizing compounds of Formula I wherein, for example, R1 is a heterocycle or substituted heterocycle.

In Scheme I(g), step A, compound (4), wherein Pg is a suitable silyl protecting group, is alkylated with, for example, a substituted or unsubstituted heterocycle to provide the compound of structure (5g) wherein R1 is, for example, heterocycle or substituted heterocycle. For example, compound (4) is dissolved in an organic solvent, such as tetrahydrofuran, under an atmosphere of nitrogen. The reaction is cooled to 0° C., and about 1.1 equivalents of a suitable base, such as potassium t-butoxide in tetrahydrofuran, is added. The reaction mixture is then treated with about 1.1 equivalents of a heterocycle such as 2,4-dichloropyrimidine. Upon completion of the addition, the reaction is heated to about 55° C., and the reaction is stirred at this temperature for about 18 hours. The compound (5g), wherein R1 is, for example, a substituted or unsubstituted heterocycle, is then isolated and can be purified by standard techniques well known in the art. For example, the reaction is diluted with water and extracted with diethyl ether. The organic extracts are combined, dried over sodium sulfate, filtered, and concentrated to provide crude compound (5g). The crude product can then be purified by chromatography on silica gel with a suitable eluent, such as ethyl acetate/hexanes, to provide purified compound (5g), wherein R1 is a substituted or unsubstituted heterocycle such as 2-chloropyrimidine.

In scheme I(g), step B, the compound of structure (5g), wherein R1 is a halo substituted heterocycle can be converted to a compound wherein R1 is an alkoxy substituted heterocycle. For example compound (5g), wherein R1 is

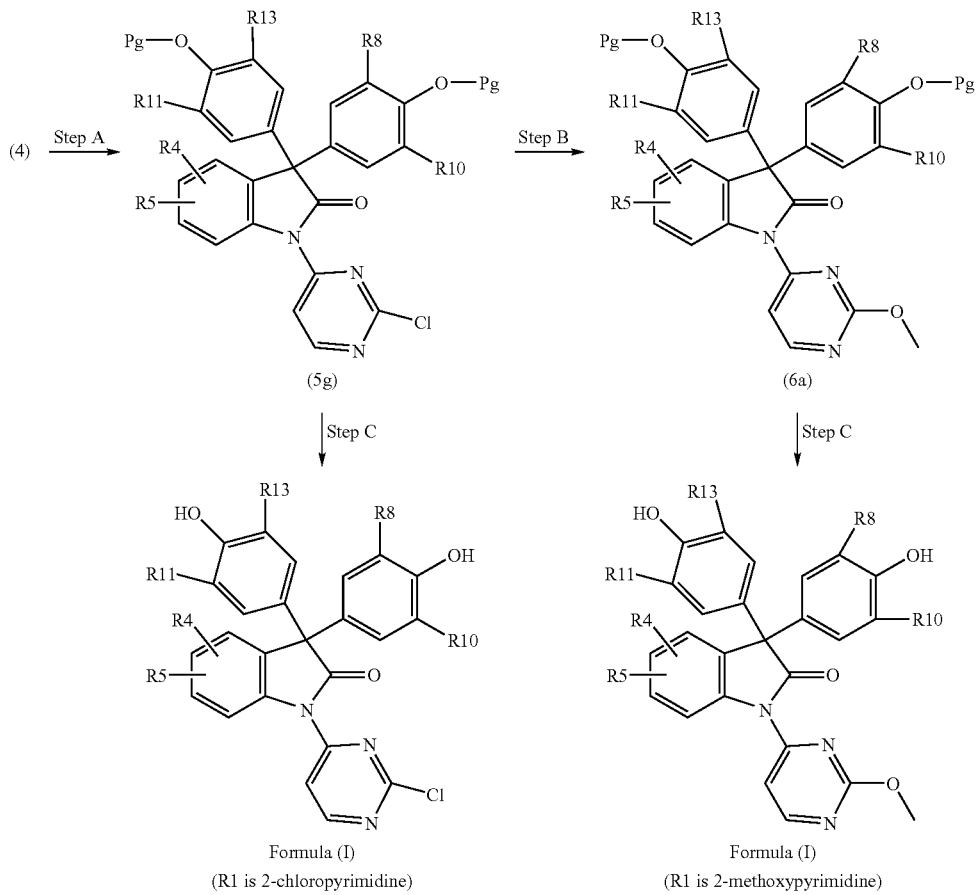

2-chloropyrimidine can be treated with sodium methoxide in methanol under an atmosphere of nitrogen. Tetrahydrofuran is added, and the reaction is stirred at room temperature for about 3 hours. The crude material is isolated by standard techniques well known to one of ordinary skill. For example, the reaction is diluted with diethyl ether and water. The organic extracts are combined, dried over anhydrous sodium sulfate, filtered, and concentrated under vacuum to provide crude compound of structure (6a) wherein R1 is, for example, 2-methoxypyrimidine.

In Scheme I(g), step C, compound (5g) or (6a) is deprotected under standard conditions well known in the art to provide the compound of Formula I wherein R1 is substituted or unsubstituted heterocycle. For example, compound (5g) or (6a) is dissolved in an organic solvent, such as tetrahydrofuran, under an atmosphere of nitrogen, and about 2.5 equivalents of tetrabutylammonium fluoride in tetrahydrofuran is added. The reaction mixture is stirred at room temperature for about 1 to 2 hours. The reaction is then quenched and compound of Formula I is isolated and purified by standard techniques. For example, the reaction is quenched with saturated aqueous ammonium chloride. Water is added and the quenched reaction is extracted with a suitable organic solvent, such as ethyl acetate. The organic extract is dried over anhydrous sodium sulfate, filtered, and concentrated to provide crude compound of Formula I wherein R1 is an unsubstituted or substituted heterocycle (for example, 2-chloro- or 2-methoxypyrimimidine). The crude material can then be purified by chromatography on silica gel with a suitable eluent, such as ethyl acetate/hexanes, to provide purified compound of Formula I.

Scheme II provides procedures for the synthesis of compounds of Formula I wherein, for example, R2 and R3 are substituted phenyl groups; R9 and R12 are hydroxy; R8 and R11 are both hydrogen, (C$_1$-C$_4$)alkyl, or halo; and R10 and R13 are both hydrogen, (C$_1$-C$_4$)alkyl, or halo.

compound of formula R1-Hal, wherein R1 represents an alkylating agent and Hal represents a chloro, bromo or iodo atom, to provide the compound of structure (7). For example, compound (1) is dissolved in a suitable organic solvent, such as acetone, 2-butanone, tetrahydrofuran, dioxane, dimethylformamide, or the like and treated with about 1 to 2 equivalents of a compound of formula R1-Hal and an excess of a suitable organic base, such as cesium carbonate, sodium hydride, potassium t-butoxide, potassium, sodium or lithium bis(trimethylsilyl)amide or 2-tert-butylimino-2-diethylamino-1,3-dimethyl-perhydro-1,3,2-diazaphosphorine (BEMP). The reaction can be performed at 0° C. to the refluxing temperature of the solvent for about 3-24 h to give the compound of structure (7). The product can be isolated by standard aqueous workup procedures and crystallization techniques well known in the art.

In Scheme II, step B, the compound of structure (7) is treated with a phenol or a substituted phenol in a solvent such as trifluoromethanesulfonic acid using methods known in the art (Olah, G. A., et. al.; *J. Org. Chem.* (1998), 63, 4481-4484) at about 0-50° C. for about 1-2 h. The compound of Formula I can be isolated by standard procedures such as quenching with ice, extracting with ethyl acetate followed by washing with aqueous sodium bicarbonate. The product can then be purified by chromatographic or crystallization techniques well known in the art.

Scheme III provides procedures for the synthesis of compounds of Formula I wherein, for example, R2 and R3 are substituted phenyl groups; R9 is hydroxy and R12 is hydrogen; R8 and R10 are (C$_1$-C$_6$)alkyl; and R11 and R13 are each independently hydrogen or (C$_1$-C$_6$)alkyl.

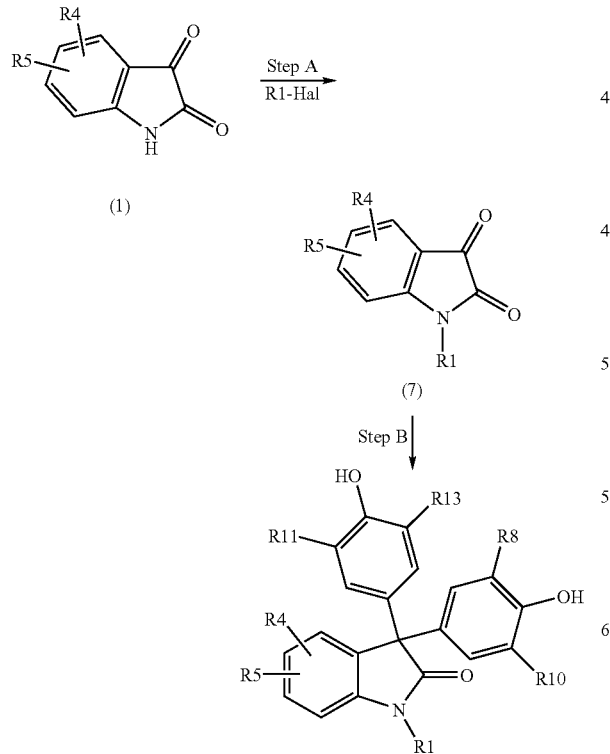

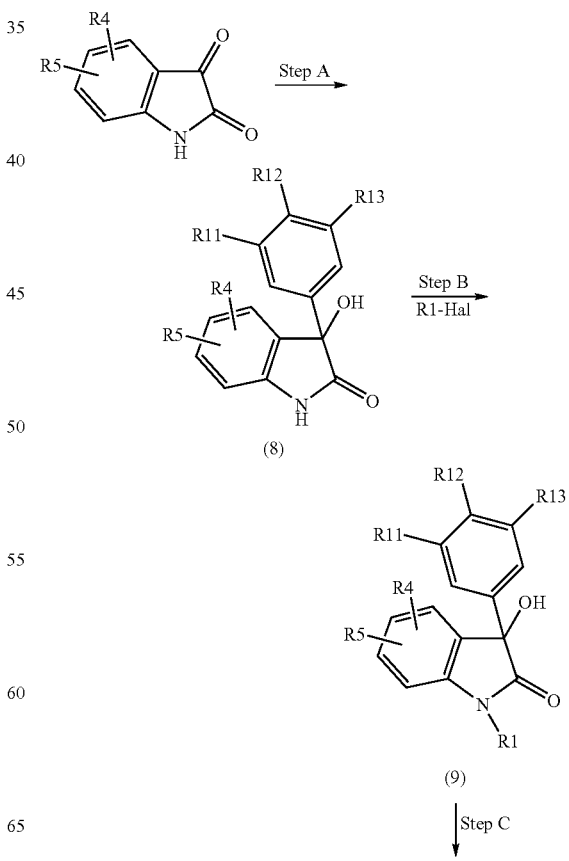

In Scheme II, step A, isatin or a substituted isatin of structure (1) is treated with an appropriate base and with a

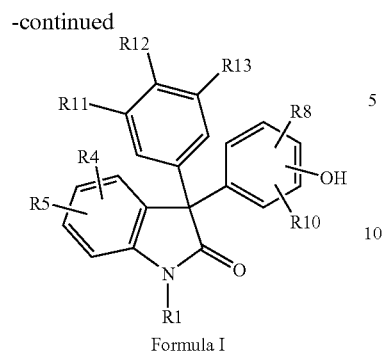

Formula I

In Scheme III, step A, isatin or a substituted isatin of structure (1) is treated with a Grignard reagent to obtain a tertiary alcohol of structure (8). For example, compound (1) in a solvent such as tetrahydrofuran, diethyl ether, or the like is treated with 2 equivalents of an aryl magnesium bromide, aryl magnesium chloride, or an aryl lithium at a temperature of about 0-50° C. for about 4-24 h. The product can be isolated by common aqueous workup procedures followed by recrystallization techniques well known in the art.

In Scheme III, step B, compound (8) is treated with an appropriate base and with a compound of formula R1-Hal, wherein R1 is an alkylating agent and Hal represents a chloro, bromo or iodo atom, to provide the compound of structure (9). For example, compound (1) is dissolved in a suitable organic solvent, such as acetone, 2-butanone, tetrahydrofuran, dioxane, acetonitrile, dimethylformamide, or the like and treated with about 1 to 2 equivalents of a compound of formula R1-Hal and an excess of a suitable organic base, such as cesium carbonate or 2-tert-butylimino-2-diethylamino-1,3-dimethyl-perhydro-1,3,2-diazaphosphorine (BEMP). The reaction can be performed at 0° C. to the refluxing temperature of the solvent for about 3-24 h to give compounds of structure (9). The product can be isolated by standard aqueous workup procedures and crystallization techniques well known in the art.

In Scheme III, step C, the compound of structure (9) is treated with a phenol or a substituted phenol in a solvent such as trifluoroacetic acid at about 0-50° C. for about 1-2 h. The compound of Formula I can then be isolated by quenching with ice, extractimg with ethyl acetate, followed by washing with aqueous sodium bicarbonate. The product can then be purified by chromatographic or crystallization techniques well known in the art.

Scheme IV provides procedures for the synthesis of compounds of Formula I wherein, for example, R2 and R3 are substituted phenyl groups; R9 and R12 are hydroxy; R8 and R10 are hydrogen; and R11 and R13 are $(C_1\text{-}C_6)$alkyl.

Scheme IV

In Scheme IV, step A, the compound of structure (10) is treated with a compound of the formula Pg-Hal (wherein Pg is a sutiable oxygen protecting group, such as benzyl, and Hal represents a chloro, bromo, or iodo atom), in the presence of an appropriate base, to give the protected phenol compound of structure (11). For example, using methods known in the art, compound (10) is treated with an appropriate base such as cesium carbonate or potassium carbonate in a solvent such as acetone, 2-butanone, dimethylformamide, or the like at about 20-100° C. for about 1-24 h to provide compound (11). Compound (11) can be isolated by common aqueous extraction procedures and purified by chromatography techniques well known in the art.

In Scheme IV, step B, compound (11) is treated with an alkyl lithium to make an aryl lithium reagent and reacted with an N-alkylated isatin such as N-benzylisatin to give the compound of structure (12). For example, the aryl lithium is generated using alkyl lithium reagents common in the art, such as n-butyl lithium or t-butyl lithium, in a solvent such as tetrahydrofuran, dioxane, ethylene glycol, dimethyl ether, or the like at about −70° C. for about 15-30 min. The N-benzylisatin is added and the temperature allowed to warm to ambient temperature for about 4-24 h. The reaction is quenched with ammonium chloride solution and compound (12) can then be isolated by common extraction methods. The product can then be purified by chromatographic techniques well known in the art.

In Scheme IV, step C, the compound of structure (12) is treated with phenol in a solvent such as trifluoroacetic acid at about 0-50° C. for about 1-2 h. The compound of Formula I can then be isolated by quenching with ice and extracting with ethyl acetate, followed by washing with aqueous sodium bicarbonate. The product can then be purified by chromatographic or crystallization techniques well known in the art.

Scheme V provides procedures for the synthesis of intermediates which, in turn, may be employed in procedures of subsequent Schemes to synthesize yet additional compounds of Formula I.

temperature of about −50 to 0° C. for about 4-24 h. The product can be isolated by common aqueous workup techniques followed by recrystallization techniques well known in the art.

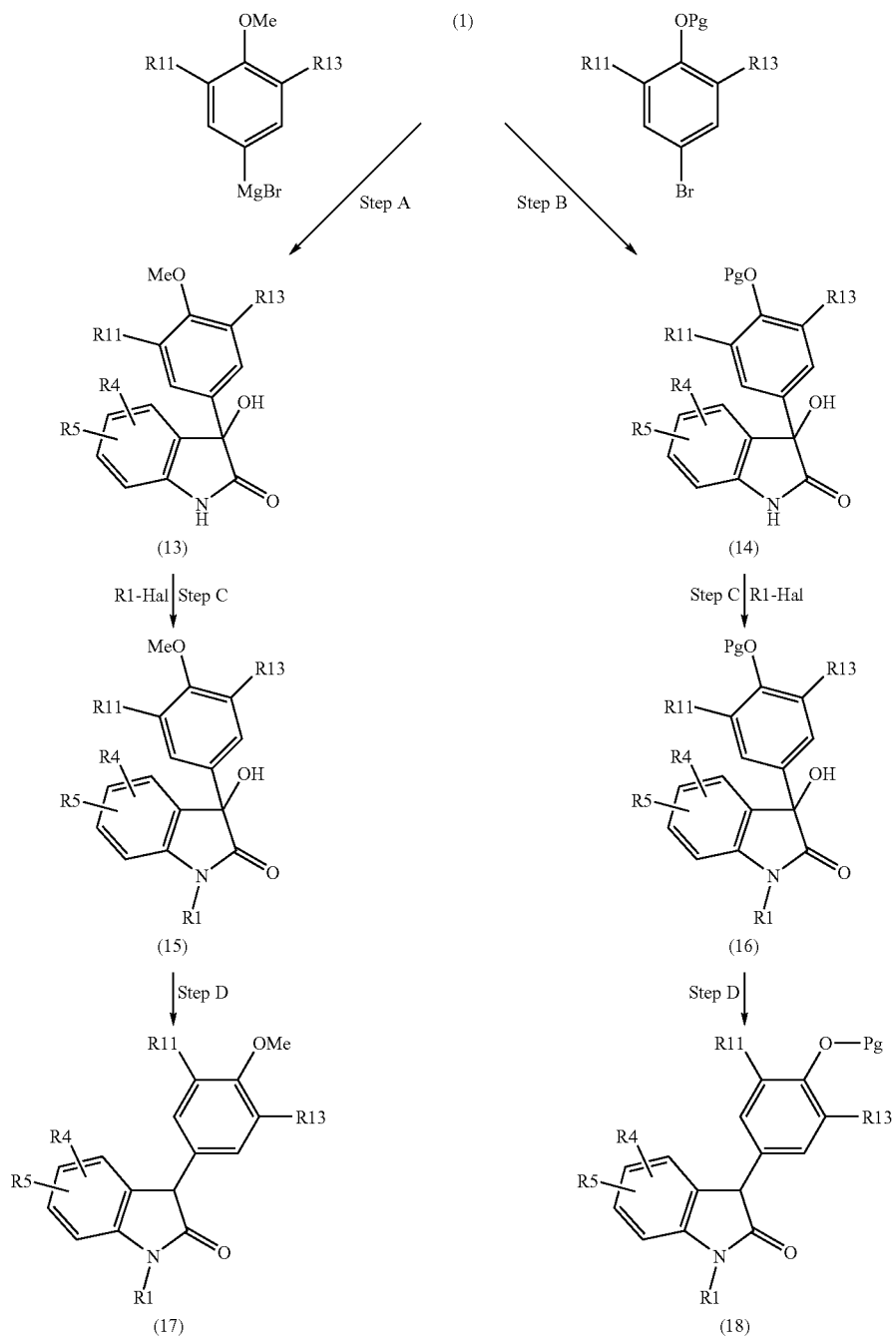

In Scheme V, step A, isatin or a substituted isatin of structure (1) is treated with a Grignard reagent to obtain a tertiary alcohol of structure (13). For example, compound (1), in a solvent such as tetrahydrofuran or diethyl ether, or the like, is treated with 2 equivalents of an aryl magnesium bromide, aryl magnesium chloride, or aryl lithium at a Alternatively, in Scheme V, step B, compound (1) can be treated with an aryl lithium reagent to yield compound (14), wherein the aryl is a protected 3,5-dimethylphenol, synthesized by methods well known in th art. (suitable protecting groups include silyl groups such as t-butyldimethyl silyl, t-butyldiphenyl silyl, triisopropyl silyl, and the like). For example, the aryl lithium is generated using alkyl lithium reagents common in the art such as n-butyl lithium or t-butyl lithium in a solvent such as tetrahydrofuran, dioxane or ethylene glycol dimethyl ether at −75 to −70° C. for about 15-30 min. The isatin is added and the temperature allowed to warm to about −30 to −40° C. for about 2-3 h and then up to 15° C. over another 1-2 h. The reaction is quenched with ammonium chloride solution and compound (14) isolated by common extraction methods. The product can be purified by chromatographic or recrystallization techniques well known in the art.

In Scheme V, step C, compound (13) or (14) is treated with an appropriate base and a compound of formula R1-Hal, wherein R1 represents an alkylating agent and Hal represents a chloro, bromo or iodo atom, to provide the compounds of structure (15) and (16), respectively. For example, compound (13) or (14) is dissolved in a suitable organic solvent, such as acetone, 2-butanone, tetrahydrofuran, dioxane, acetonitrile, dimethylformamide, or the like, and treated with about 1 to 2 equivalents of a compound of formula R1-Hal and an excess of a suitable organic base, such as cesium carbonate or 2-tert-butylimino-2-diethylamino-1,3-dimethyl-perhydro-1,3,2-diazaphosphorine (BEMP). The reaction can be performed at 0° C. to the refluxing temperature of the solvent for about 3-24 h to give compounds of structure (15) and (16), respectively. The products can be isolated by standard aqueous workup procedures and recrystallization techniques well known in the art.

In Scheme V, step D, a compound of structure (15) or (16) is treated with a reducing agent commonly used in the art in the presence of a Lewis acid. For example, compound (15) or (16) is treated with triethylsilane and boron trifluoride diethyl etherate, in a solvent such as dichloromethane or dichloroethane, at about 22° C. up to the refluxing temperature of the solvent for about 4-24 h. Compounds of structure (17) and (18), are isolated using common aqueous extraction and chromatography techniques well known in the art.

Schemes VI(a) and VI(b) provide procedures for the synthesis of compounds of Formula I wherein, for example, R2 and R3 are substituted phenyl groups; R9 is hydroxy or amino; R12 is hydroxy; R8 and R10 are each independently hydrogen or ($C_1$-$C_6$)alkyl; and R11 and R13 are each independently ($C_1$-$C_6$)alkyl.

Schemes VI(a) and VI(b)

Scheme VI(a)

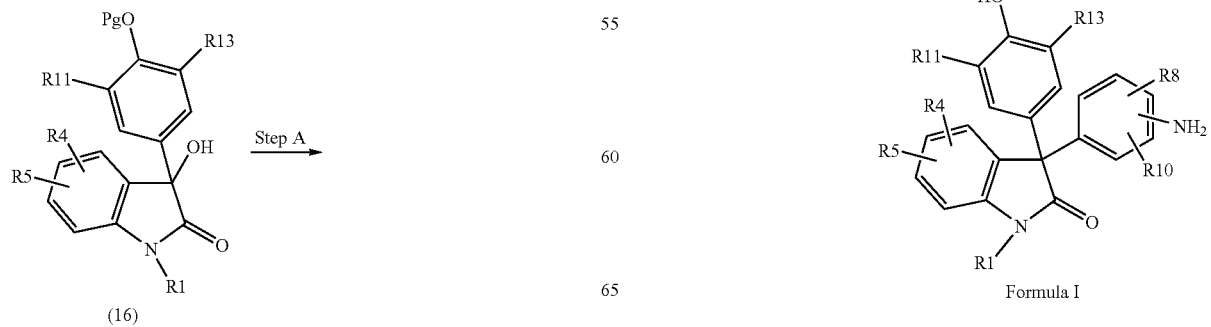

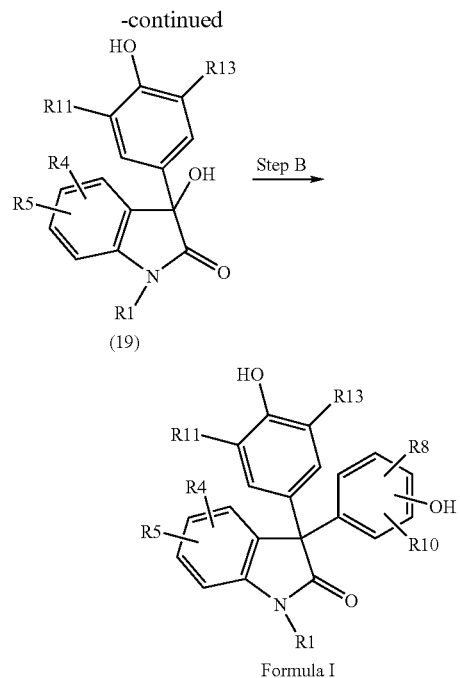

Scheme VI(b)

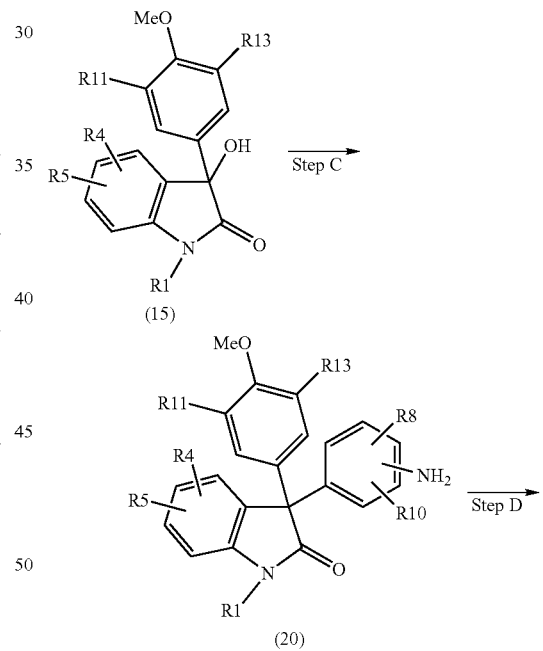

In Scheme VI(a), Step A, the compound of structure (16), wherein Pg represents a silyl protecting group, is treated with a silyl deprotecting reagent commonly used in the art such as cesium fluoride or tetrabutylammonium fluoride (TBAF) in a solvent such as tetrahydrofuran or acetonitrile at about 22-50° C. Compound (19) is then isolated by aqueous workup and chromatographic techniques well known in the art.

In Scheme VI(a), step B, the compound of structure (19) is treated with phenol or substituted phenol in a solvent such as trifluoroacetic acid at about 0-50° C. for about 1-2 h. The compound of Formula I can be isolated by common methods such as quenching with ice and extracting with ethyl acetate, followed by washing with aqueous sodium bicarbonate. The product can then be purified by standard chromatographic or recrystallization techniques well known in the art.

In Scheme VI(b), step C, the compound of structure (15) is treated with, for example, aniline or a substituted aniline in a solvent such as trifluoroacetic acid at about 0-50° C. for about 1-2 h. The compound of structure (20) can be isolated using standard methods such as quenching with ice and extracting with ethyl acetate, followed by washing with aqueous sodium bicarbonate. The product can then be purified by chromatographic or recrystallization techniques well known in the art.

In Scheme VI(b), step D, the compound of structure (20) is deprotected with an excess of pyridine hydrochloride using methods common in the art at a temperature of about 190-210° C. for about 0.5 to 2 h. Formula I is isolated by allowing the reaction to cool, dissolving the solid in ethyl acetate and 1N hydrochloric acid, and using common aqueous extraction methods. The crude material can be purified using common chromatographic techniques well known to the skilled artisan.

Schemes VII(a) and VII(b) provide procedures for the synthesis of compounds of Formula I wherein, for example, R2 and R3 are substituted phenyl groups; R9 is nitro, amino, or NHR14; R12 is hydroxy; R8 and R10 are each independently hydrogen or $(C_1-C_6)$alkyl; and R11 and R13 are $(C_1-C_6)$alkyl.

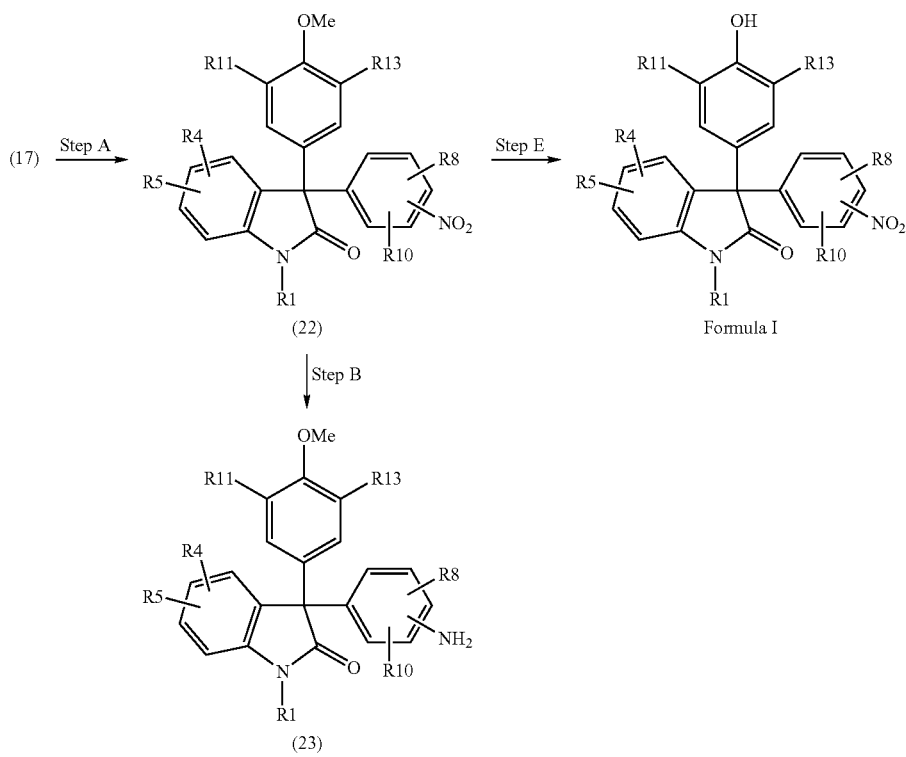

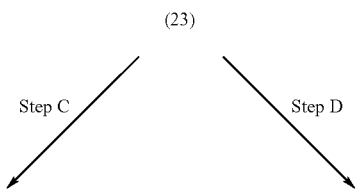

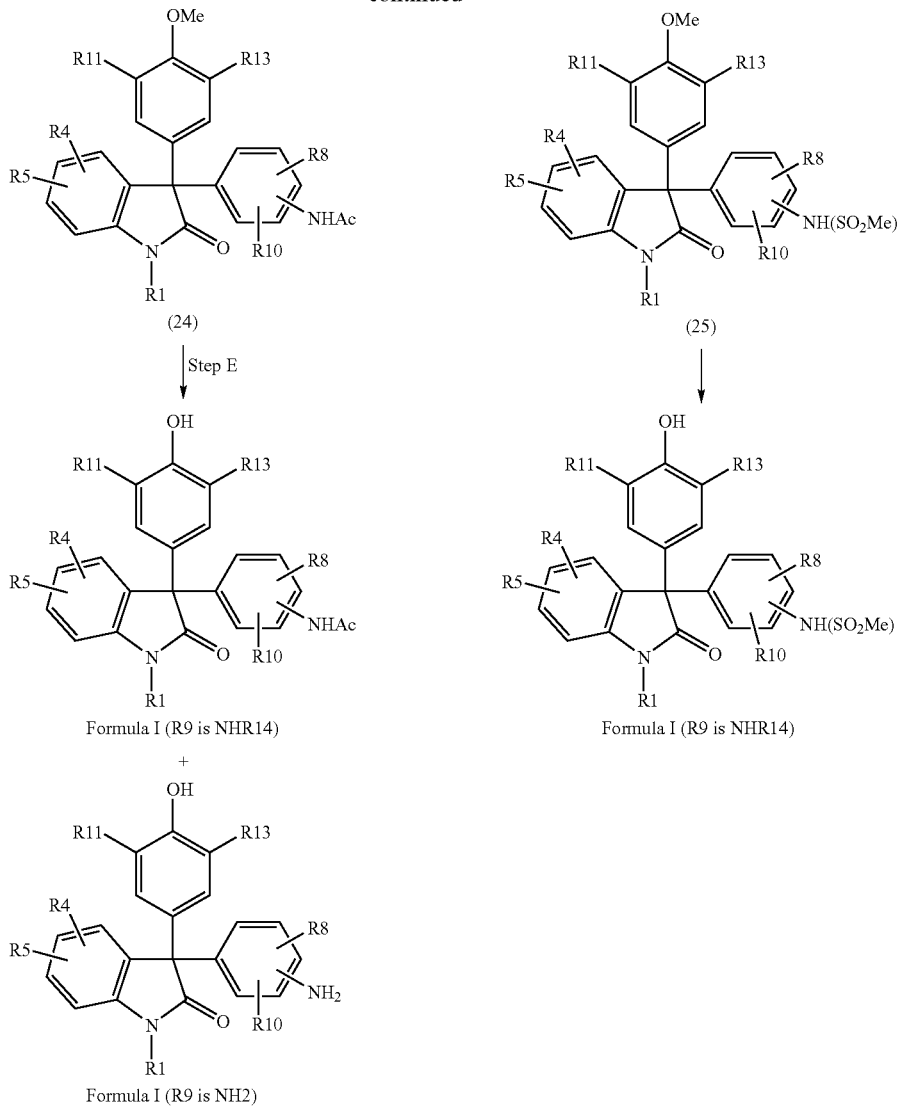

In Scheme VII(a), step A, a compound of structure (17) is treated with an appropriate base and alkylated with a p-fluoronitrobenzene to give compound (22). For example, compound (17) in a solvent such as dimethylformamide, dimethylacetamide, or tetrahydrofuran is treated with a suitable base, such as potassium, sodium or lithium bis(trimethylsilyl)amide or sodium hydride at 0-5° C. for about 10 to 20 min and then reacted with 4-fluoronitrobenzene or other substituted 4-fluoronitrobenzene at 22-150° C. for 4-24 h. Compound (22) is isolated by diluting the reaction with an organic solvent such as ethyl acetate and using standard aqueous washing methods followed by purification by chromatographic techniques.

In Scheme VII(a), step B, the nitro group of compound (22) is reduced using methods common in the art including, but limited to, catalytic hydrogenation, metals in the presence of acid, sodium dihydro(trithio)borate, sulfides or sodium borohydride with various catalysts such as dichlorobis(triphenylphosphine)nickel (II), nickelous chloride, or cobalt(II) chloride. For example, compound (22) in a solvent such as methanol, ethanol, tetrahydrofuran or dioxane, is treated with nickelous chloride (6-hydrate) and sodium borohydride at a temperature of 20-100° C. for 1-24 h. The compound of structure (23) can be isolated by evaporating the solvent and redissolving in ethyl acetate and water and then employing common extraction techniques. Compound (23) can be purified using chromatography methods common in the art.

In Scheme VII(b), step C, the compound of structure (23) is acylated using an acid chloride and a base commonly employed in the art, such as a trialkylamine. For example, Compound (23), in a solvent such as dichloromethane or tetrahydrofuran with a base such as triethylamine or N,N-diisopropylethylamine is treated with acetyl chloride at a temperature of about 22° C. to the refluxing temperature of the solvent for 1-24 h. Compound (24) is isolated by common aqueous extraction and chromatographic techniques.

In Scheme VII(b), step D, compound (23) is sulfonylated using a sulfonyl chloride and a base commonly employed in the art, such as a trialkylamine. For example, Compound (23), in a solvent such as dichloromethane or tetrahydrofuran, with a base such as triethylamine or N,N-diisopropyl-ethylamine, is treated with methane sulfonylchloride at a temperature of about 22° C. to the refluxing temperature of the solvent for 1-24 h. Compound (25) is isolated by common aqueous extraction and chromatographic techniques.

In Scheme VII(a) and VII(b), Step E, compounds of structures (22), (24), and (25) are deprotected with an excess of pyridine hydrochloride using methods common in the art at a temperature of 190-210° C. for 0.5 to 2 h. Compounds of Formula I are isolated by allowing the reaction to cool and dissolving the solid in ethyl acetate and 1N hydrochloric acid and using common aqueous extraction methods. The crude material can then be purified using common chromatographic techniques.

Schemes VIII(a) and VIII(b) provide procedures for the synthesis of compounds of Formula I wherein, for example, R2 is substituted phenyl, alkyl-substituted phenyl, alkyl, or hydroxyalkyl; R3 is substituted phenyl; R8-R10 are each independently hydrogen, hydroxy, or $(C_1-C_6)$alkyl,; R12 is hydroxy; and R11 and R13 are $(C_1-C_6)$alkyl.

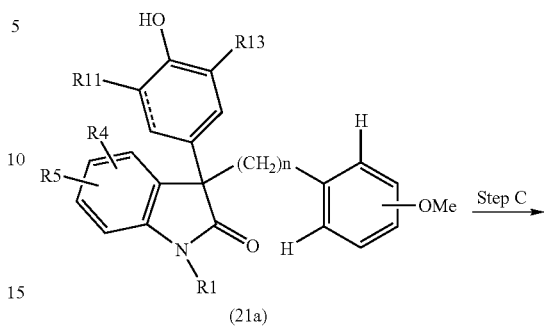

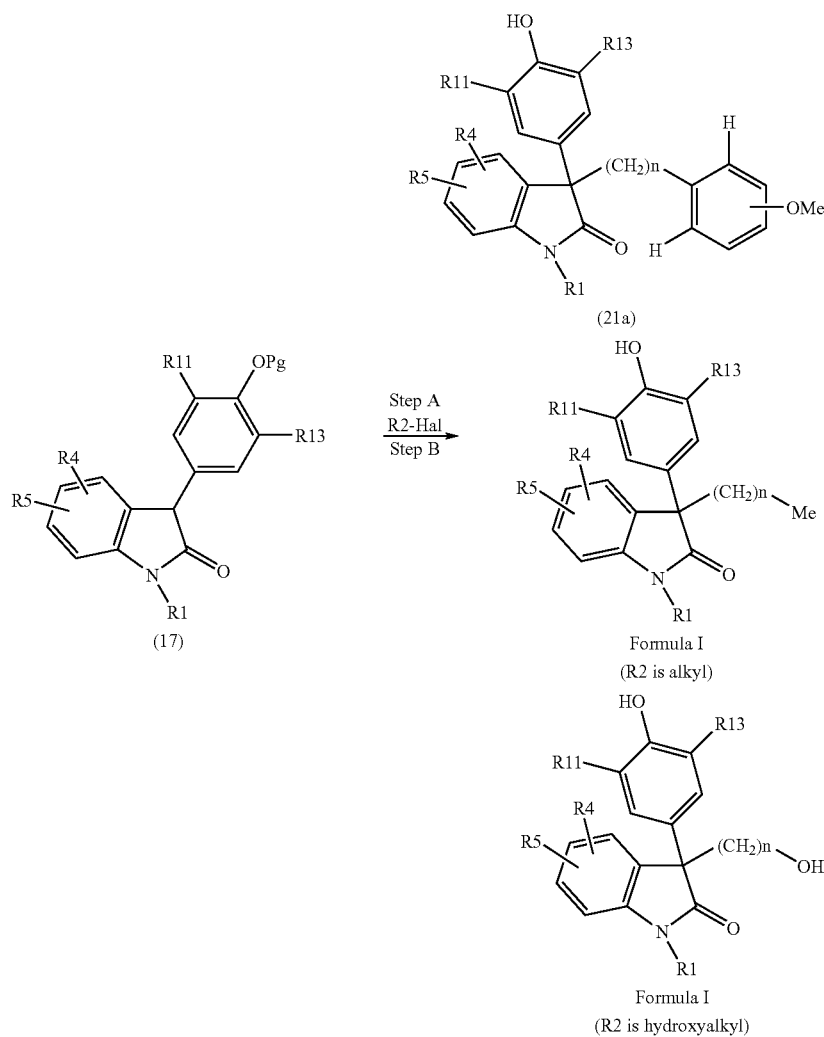

-continued

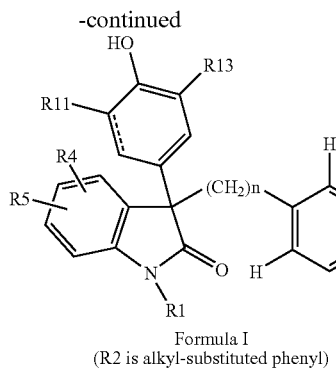

Formula I
(R2 is alkyl-substituted phenyl)

In Scheme VIII(a), step A, a compound of structure (17) is treated with an appropriate base and alkylated with a compound of the general formula R2-Hal, wherein R2 represents, for example, hydroxyalkyl, alkyl, or a group of the formula:

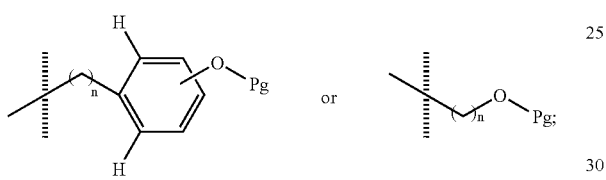

wherein "n" is 0, 1, 2, or 3; and Hal represents a chloro, bromo or iodo atom, to provide compounds of Formula I or structure (21a). For example, compound (18), prepared for example as described in Scheme V above, is dissolved in a suitable organic solvent, such as tetrahydrofuran, dioxane, dimethylformamide, or the like and treated with about 1 to 2 equivalents of base, such as sodium hydride, potassium t-butoxide, potassium, sodium or lithium bis(trimethylsilyl) amide at about 0-5° C. for about 10 to 20 min then reacted with a compound of formula R2-Hal. The reaction can be performed at 22° C. to the refluxing temperature of the solvent for about 4-24 h. The product can be isolated by standard aqueous workup procedures, or further treated in situ (step B) with a silyl deprotecting reagent commonly used in the art such as cesium fluoride or tetrabutylammonium fluoride (TBAF). Compounds of Formula I, or structure (21a), can then be isolated by aqueous workup and chromatographic techniques, well known in the art.

In Scheme VIII(b), step C, compound (21a) is deprotected with an excess of pyridine hydrochloride using methods common in the art at a temperature of about 190-210° C. for about 0.5 to 2 h. The compound of Formula I (wherein R2 is an alkyl-substituted aryl group) is isolated using common aqueous extraction methods, such as allowing the reaction to cool and dissolving the solid in ethyl acetate and 1N hydrochloric acid. The crude material can then be purified using common chromatographic techniques well known in the art.

Scheme IX provides yet additional procedures for synthesizing compounds of Formula I wherein, for example, R2 and R3 are substituted phenyl groups; R11 and R13 are $(C_1-C_6)$alkyl; R12 is hydroxy; and R8 through R10 are each independently hydrogen, hydroxy, $(C_1-C_6)$alkyl, or amino.

Scheme IX

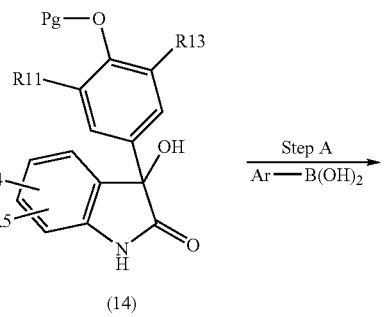

(14)
R11 and R13 are methyl

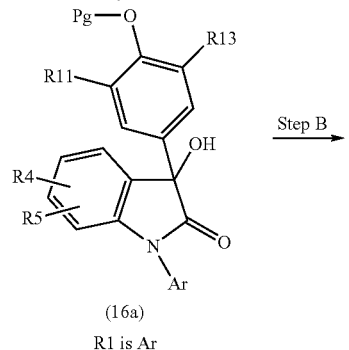

(16a)
R1 is Ar

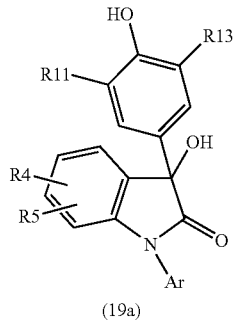

(19a)
R1 is Ar

Step C

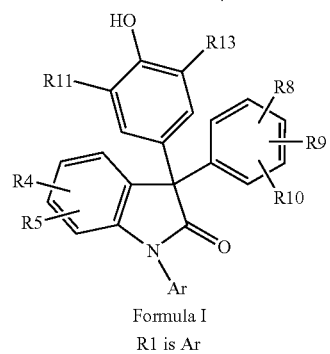

Formula I
R1 is Ar

In Scheme IX, step A, the compound of structure (14), wherein Pg is a silyl protecting group and R11 and R13 are methyl, is treated under standard conditions with a compound of formula Ar—B(OH)$_2$, wherein Ar represents an appropriately substituted or unsubstituted aryl or heterocyclic ring, to provide the compound of structure (16a). For example, compound (14) is dissolved in a suitable organic solvent, such as methylene chloride and treated with about 2 equivalents of a compound of formula Ar—B(OH)$_2$, 2 equivalents of a suitable organic base, such as triethylamine or pyridine, 1 equivalent of a suitable Cu (II) source, such as copper (II) acetate, and a drying agent, such as molecular sieves. Examples of compounds of the general formula Ar—B(OH)$_2$, suitable for the present synthesis methods, include phenylboronic acid, 3-methoxyphenylboronic acid, 2-chlorophenylboronic acid, 3-fluorophenylboronic acid, pyridine-3-boronic acid, and the like. The reaction mixture is stirred for about 16 to 200 hours at a temperature of about 25° C. under ambient atmosphere. The compound (16a) is then isolated by filtration through Celite and may be purified using chromatographic or recrystillization techniques.

The remaining synthetic steps of Scheme IX, Steps B and C, are essentially as described in Scheme VI(a), Steps A and B.

Scheme X provides yet additional procedures for synthesizing compounds of Formula I wherein, for example, R2 and R3 are substituted phenyl groups; R11 and R13 are independently hydrogen or (C$_1$-C$_6$)alkyl; R8 and R12 are hydroxy; and R9 and R10 are each independently hydrogen or (C$_1$-C$_6$)alkyl.

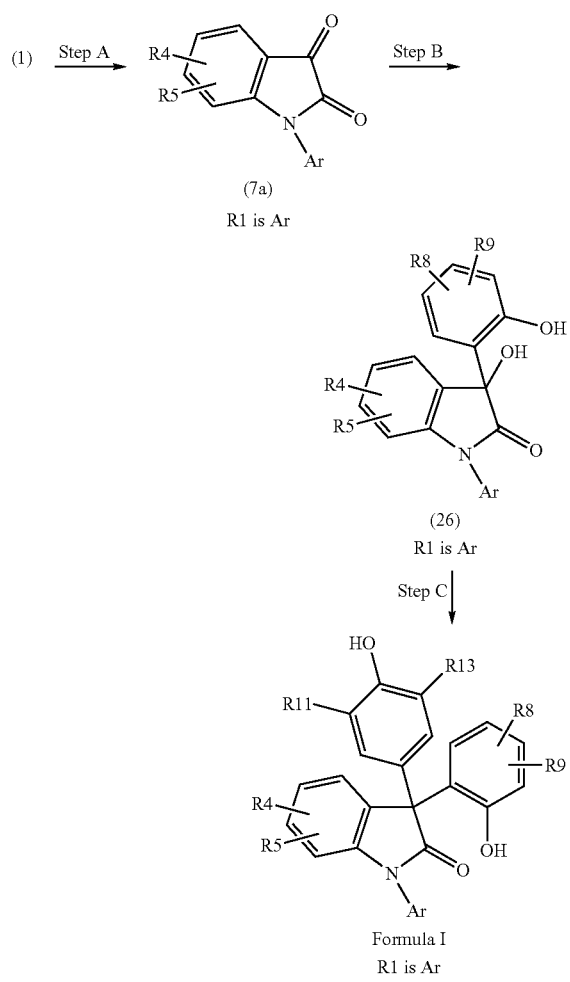

In Scheme X, Step A, the compound of structure (1) is treated the as described in the procedures for Scheme IX, Step A, above. The product, compound (7a) is then isolated and treated according to standard procedure as described by Hewawasam et al., *Tetrahedron Lett*., (1998) 39; 3981-3984, to provide the compound of structure (26). Compound (26) is then treated according to the procedures essentially as described in Scheme IX, Step C (or Scheme VI(a), Step B), above. The compound of Formula I is isolated using common aqueous extraction methods, such as allowing the reaction to cool and dissolving the solid in ethyl acetate and 1N hydrochloric acid. The crude material can then be purified using common chromatographic techniques well known in the art.

Determination of Biological Activity

To demonstrate that compounds of the present invention have affinity for steroid hormone nuclear receptors, and thus have the capacity to modulate steroid hormone nuclear receptors, soluble MR and GR binding assays are performed. All ligands, radioligands, solvents, and reagents employed in the binding assays are readily available from commercial sources, or can be readily synthesized by the ordinarily skilled artisan.

Mineralocorticoid Receptor Binding Assay:

The full length human MR gene is cloned from a human kidney or human brain cDNA library. Briefly, using synthetic oligonucleotide primers (Eli Lilly and Company, Indianapolis) directed to nucleotides 20-54 and 3700-3666 of the human MR, polymerase chain reaction (PCR) is performed under standard conditions using a human cDNA library. The PCR reaction is performed in a final volume of 50 μl containing about 1 μl of a 50× stock solution of polymerase; about 1 μl of a 50× stock solution of dNTP; about 5 μl of an appropriate PCR buffer; about 1 μl of each primer; about 5 μl of a H. kidney or H. brain cDNA library; and about 36 μl of water. The reaction is allowed to denature for about 30 seconds at 95 degrees Celsius, anneal for about 30 seconds at 55 degrees Celsius, and extend for about 5 minutes at 72 degrees Celsius, the sequence being repeated for a total of about 35 cycles. The desired PCR product (3.68 Kb) is confirmed by gel electrophoresis and subsequently cut from the gel and stored at about −20 degrees Celsius until extraction. To extract the cDNA product from the agarose gel, the QIAEX II Gel Extraction protocol (QIAGEN, Inc.) is employed according to the manufacturer's instructions. Following extraction, the MR cDNA is cloned into an appropriate cloning vector (Zero Blunt TOPO PCR Cloning Kit (Invitrogen, Inc.) and a pAcHLT-baculovirus transfer vector (B.D./Pharminogen), then expressed in SF9 insect cells, essentially according to manufacturer's instructions. Sf9 cells are grown at a scale where gram quantity cell pellets are obtained for subsequent use in the MR binding assay. Harvested cell pellets are lysed by repeated freeze-thaw cycles (about 4) in a suitable lysis buffer then centrifuged at about 1×10$^3$ G (with the supernatant being saved for future assays).

MR binding assays are performed in a final total volume of about 250 μl containing about 20-25 μg of protein and 0.5 nM of [$^3$H]-aldosterone plus varying concentrations of test compound or vehicle. The assay binding buffer consists of 30 mM sodium molybdate, 30 mM of TRIS-HCl, 5 mM sodium phosphate, 5 mM sodium pyrophosphate, and about 10% glycerol, pH=7.5.

Briefly, assays are prepared at RT in 96-well Falcon 3072 plates, each well containing 210 μl of binding buffer, 10 μl of [$^3$H]-aldosterone, 10 μl of test compound/vehicle, and 20 μl of the resuspended receptor protein extract. Incubations are carried out at 4 degrees Celsius with shaking for about 16 hours. 200 µl aliquots of each incubation are filtered onto Millipore HA 0.45 micron 96-well filter plates, pre-moistened with cold 30 mM TRIS-HCl. The filter plates are suctioned dry with vacuum and immediately washed 3× with cold 30 mM TRIS-HCl. The plates are then punched out and the amount of receptor-ligand complex is determined by liquid scintillation counting using 4 ml of Ready Protein Plus™ liquid scintillation cocktail.

$IC_{50}$ values (defined as the concentration of test compound required to decrease [$^3$H]-aldosterone binding by 50%) are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition ($IC_{50}$) of an Enzymatic Reaction, Biochem. Pharmacol., 22: 3099-31088; (1973).

Glucocorticoid Receptor Binding Assay:

To demonstrate the GR modulating potency of compounds of the present invention the following source of glucocorticoid receptor is employed. A549 human lung epithelial cells (ATCC) are grown at a scale where gram quantity cell pellets are obtained. Harvested cell pellets are washed twice in cold phosphate buffered saline, centrifuged, and resuspended in cold assay binding buffer. The assay binding buffer consists of 10% glycerol, 50 mM Tris-HCl (pH7.2), 75 mM sodium chloride, 1.5 mM magnesium chloride, 1.5 mM EDTA, and 10 mM sodium molybdate. Cell suspensions were lysed via sonication, centrifuged, and the "extract" supernatant is snap frozen and stored at −80C. until needed.

GR binding assays are performed in a final volume of 140 ul containing 50-200 ug of A549 cell extract and 1.86 nM [$^3$H]-dexamethasone (Amersham) plus varying concentrations of test compound or vehicle. Briefly, assays are prepared at RT in 96-well Fisher 3356 plates, each well containing 100 ul of A549 cell extract, 20 ul of [$^3$H]-dexamethasone, and 20 ul of test compound/vehicle. Incubations are carried out at 4 degrees celsius for 16 hours. After incubation, 70 ul of 3× dextran-coated charcoal solution is added to each reaction, mixed, and incubated for 8 minutes at RT. 3×-dextran-coated charcoal solution consists of 250 ml assay binding buffer, 3.75 g Norit A charcoal (Sigma), and 1.25 g dextran T-70 (Amersham). Charcoal/unbound radioligand complexes are removed by centrifugation of the plate and 140 ul of supernatant from each well is transferred to another 96 well Optiplate (Packard Instruments). 200 ul of Microscint-20 scinillant (Packard Instruments) is added to each well and amount of receptor bound radioligand is determined using Packard Instruments TopCount instrument.

$IC_{50}$ values, defined as the concentration of test compound required to decrease [$^3$H]-dexamethasone binding by 50%, are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition ($IC_{50}$) of an Enzymatic Reaction, Biochem. Pharmacol., 22: 3099-31088; (1973).

Binding assay protocols for PR, AR, and ER, similar to those described above for MR and GR, can be readily designed by the ordinarily skilled artisan. U.S. Pat. No. 6,166,013 provides examples of such protocols. Representative compounds of the present invention have a Ki in the MR or GR binding assay of ≦50 µM. Table I (see infra.) provides MR and GR binding data for a representative sample of the exemplified compounds of the present invention.

To demonstrate the ability of compounds of the present invention to modulate the activity of a steroid hormone receptor (i.e either agonize, antagonize, partially agonize, or partially antagonize), bioassays are performed which detect modulation of target gene expression in cells transiently transfected with a nuclear receptor protein and a hormone response element-reporter gene construct. The solvents, reagents, and ligands employed in the functional assay are readily available from commercial sources, or can be synthesized by one of ordinary skill in the art.

Functional Assay of Mineralocorticoid Receptor Modulation:

For the MR transient transfection assay, COS-7 cells are transfected with full length human MR and a 2×GRE-luciferase gene construct. Following transfection, the ability of test compounds to modulate expression of the luciferase reporter gene product is monitored. Briefly, on day one, COS cells are harvested from cell culture plates using standard procedures such as treatment with Trypsin-EDTA (GIBCO BRL). Culture medium is then added to the cells and the cell-medium mixture is plated in 96-well plates coated with poly-(d)-lysine (approximately 3×10$^4$ cells/well). Cells are grown for about 4 hours then transfected with Fugene-6 reagent with plasmids containing human MR, previously cloned into pc.DNA 3.1 expression vector, and 2×GRE-reporter gene construct (GRE-luciferase), previously cloned into pTAL-luc vector. Transfection is carried out in DMEM with 5% fetal calf serum, charcoal treated. 24 hours later cells are exposed to various concentrations of aldosterone in the presence and absence of test compound and incubated for an additional 24 hours. The reaction is terminated by the addition of lysis buffer followed by luciferin (luciferase substrate). Luciferase expression, as an indicator of ligand induced MR transactivation, is monitored by chemiluminescence measured using a microtiter plate luminometer (MLX). The kinetic inhibition constant ($K_b$ or $K_p$) can then be determined by analysis of dose-response curves for aldosterone, in the presence and absence of test compound, using standard techniques.

TABLE I

Mineralocorticoid and Glucocorticoid Receptor Binding Assay Values

| Example No. | MR Ki (nM) | GR Ki (nM) |
|---|---|---|
| 134 | +++ | +++ |
| 139 | +++ | +++ |
| 81 | +++ | +++ |
| 43 | +++ | +++ |
| 24 | +++ | ++ |
| 137 | +++ | +++ |
| 79 | +++ | +++ |
| 138 | +++ | +++ |
| 22 | +++ | +++ |
| 133 | +++ | +++ |
| 25 | +++ | ++ |
| 21 | +++ | +++ |
| 142 | +++ | ++ |
| 23 | +++ | +++ |
| 140 | +++ | +++ |
| 26 | +++ | +++ |
| 82 | +++ | +++ |
| 113 | +++ | +++ |
| 127 | +++ | +++ |

TABLE I-continued

Mineralocorticoid and Glucocorticoid Receptor Binding Assay Values

| Example No. | MR Ki (nM) | GR Ki (nM) |
|---|---|---|
| 110 | + + + | + + + |
| 77 | + + + | + + + |
| 63 | + + + | + + + |
| 20 | + + + | + + + |
| 66 | + + + | + + + |
| 129 | + + + | + + + |
| 36 | + + + | + + + |
| 97 | + + + | + + + |
| 102 | + + + | + + + |
| 130 | + + + | + + + |
| 91 | + + + | + |
| 15 | + + + | + + |
| 17 | + + + | + + + |
| 84 | + + + | + + + |
| 92 | + + + | + + + |
| 76 | + + + | + + + |
| 125 | + + + | + + + |
| 83 | + + + | + + + |
| 35 | + + + | + + + |
| 85 | + + + | + + + |
| 50 | + + + | + + + |
| 1 | + + + | + + + |
| 11 | + + + | + + + |
| 95 | + + + | + + |
| 19 | + + + | + + |
| 70 | + + + | + + + |
| 94 | + + + | + |
| 86 | + + + | + + + |
| 115 | + + + | + + + |
| 90 | + + + | + + |
| 67 | + + + | + + + |
| 126 | + + + | + + + |
| 6 | + + + | + + + |
| 65 | + + + | + + + |
| 119 | + + + | + + + |
| 132 | + + + | + + + |
| 58 | + + + | + + + |
| 53 | + + + | + + |
| 141 | + + + | + + + |
| 87 | + + + | + + + |
| 99 | + + + | + + |
| 62 | + + + | + + + |
| 68 | + + + | + + |
| 64 | + + + | + + + |
| 56 | + + + | + + + |
| 7 | + + + | + + |
| 51 | + + + | + + + |
| 128 | + + + | + + + |
| 49 | + + + | + + + |
| 44 | + + + | + + + |
| 118 | + + + | + + + |
| 10 | + + + | + |
| 89 | + + + | + + |
| 107 | + + + | + + + |
| 57 | + + + | + + + |
| 60 | + + + | + + + |
| 55 | + + + | + + + |
| 45 | + + + | + + + |
| 61 | + + + | + + + |
| 105 | + + + | + + + |
| 88 | + + + | + + + |
| 121 | + + + | + + + |
| 117 | + + + | + + + |
| 2 | + + + | + + + |
| 112 | + + + | + + + |
| 16 | + + + | + + + |
| 46 | + + + | + + + |
| 114 | + + + | + + + |
| 73 | + + + | + + + |
| 100 | + + + | + + + |
| 93 | + + + | + |
| 52 | + + + | + + + |
| 29 | + + + | + + + |
| 135 | + + + | + + + |
| 8 | + + + | + + + |
| 101 | + + + | + + + |
| 80 | + + + | + + + |
| 108 | + + + | + + + |
| 5 | + + + | + + + |
| 131 | + + + | + + + |
| 136 | + + + | + + + |
| 106 | + + + | + + + |
| 143 | + + + | + + + |
| 54 | + + + | + + |
| 103 | + + + | – – |
| 111 | + + + | + + + |
| 78 | + + + | + + + |
| 109 | + + + | + + + |
| 9 | + + + | + + + |
| 104 | + + + | – – |
| 71 | + + + | – – |
| 59 | + + + | – – |
| 96 | + + + | – – |
| 12 | + + + | + + + |
| 3 | + + + | + + + |
| 122 | + + + | – – |
| 74 | + + + | + + |
| 4 | + + | + + + |
| 73 | + + | – – |
| 14 | + + | + + + |

Legend:
"+" represents a value of ≦10,000 nM
"+ +" represents a value of ≦1,000 nM
"+ + +" represents a value of ≦500 nM
"– –" indicates the value was not determined The following preparations and examples further illustrate the invention and represent typical synthesis of the compounds of Formula I as described generally above. The reagents and starting materials are readily available to one of ordinary skill in the art. As used herein, the following terms have the meanings indicated: "i.v." refers to intravenously; "p.o." refers to orally; "i.p." refers to intraperitoneally; "eq" or "equiv." refers to equivalents; "g" refers to grams; "mg" refers to milligrams; "L" refers to liters; "mL" refers to milliliters; "μL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "$PPh_3$" refers to triphenylphosphine; "DEAD" refers to diethyl azodicarboxylate; "RT" refers to room temperature; "Pd—C" refers to palladium over carbon; $NaBH(Oac)_3$ refers to sodium triacetoxyborohydride; "Bn" refers to benzyl; "$BnNH_2$" refers to benzyl amine; $H_2$ refers to hydrogen; "$K_i$" refers to the dissociation constant of an enzyme-antagonist complex and serves as an index of ligand binding; and "$ID_{50}$" and "$ID_{100}$" refer to doses of an administered therapeutic agent which produce, respectively, a 50% and 100% reduction in a physiological response.

Analytical Methods

In the preparations and examples described herein, reference may be made to the analytical procedures denoted as System 1, System 2, and CIMS. Unless otherwise described, these methods were conducted as follows:

(System 1) Analytical HPLCs are obtained using an automated Gilson 215/306 and ELSD detection (Sedex75). A gradient of 5-100% B in A, over 3.8 min, at 3 mL/min, where solvent A is water and solvent B is acetonitrile, was employed using a YMC 4.6×5.0 mm C18 ODSa column.

(System 2) Analytical HPLC-electrospray mass spectroscopy was conducted using a Waters ZQ. A gradient of 5-100% B in A, where solvent A is water and solvent B is methanol, over 5 min, at 1.0 mL/min was employed using an ACE 2.0×50 mm C18 column and ELSD detection.

Chemical Ionization mass spectroscopy (CIMS) was conducted on Sciex API 100 using atmospheric pressure chemical ionization.

PREPARATION 1

3,3-Bis-(4-Hydroxy-3,5-dimethyl-phenyl)-1,3-dihydro-indol-2-one

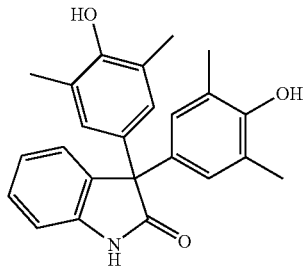

Reference: Song, H. N., et. al.; *Syn. Comm.* (1999), 29, 3303-3311.

Under a nitrogen atmosphere, combine isatin (57.30 g, 389.5 mmol) and 2,6-dimethyl phenol (99.92 g, 817.9 mmol) in glacial acetic acid (1 L) to form a bright-orange suspension. Add $AlCl_3$ (129.82 g, 973.6 mmol) in 4 portions as the mixture exotherms. Heat the reaction to 90° C. for 3 h. Monitor by TLC (5% $MeOH/CH_2Cl_2$, UV). Cool to room temperature, pour onto ice, filter, wash with $H_2O$ and vacuum dry (40° C.) to yield 125 g (86%) of the title compound as a tan solid. MS (ES): m/z=374 (M+1), 372 (M−1); NMR (DMSO-$d_6$) δ 10.49 (s, 1H), 8.17 (s, 2H), 7.18-7.15 (m, 2H), 6.96 (m, 1H), 6.87 (m, 1H), 6.66 (s, 4H), 2.05 (s, 12H).

PREPARATION 2

3,3-Bis-[4-(tert-butyl-dimethyl-silanyloxy)-3,5-dimethyl-phenyl]-1,3-dihydro-indol-2-one

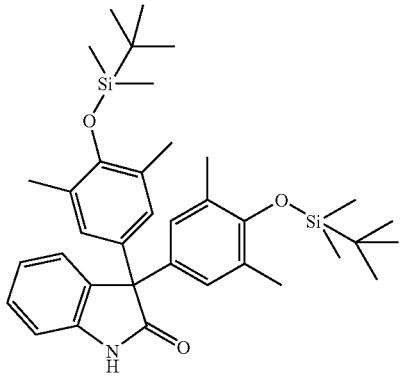

Combine 3,3-bis-(4-hydroxy-3,5-dimethyl-phenyl)-1,3-dihydro-indol-2-one(125 g, 334.7 mmol), tert-butyldimethylsilyl chloride (126.13 g, 836.8 mmol) and imidazole (91.15 g, 1.34 mol) in dry DMF (1.5 L). Flush the mixture with nitrogen and stir at room temperature 18 h. Monitor by TLC (5% $MeOH/CH_2Cl_2$ for starting material, 50% EtOAc/hexane for product, UV detection). Filter off the resulting solid, dissolve in $CH_2Cl_2$, wash with $H_2O$ (2×), and brine. Then dry ($Na_2SO_4$), filter and concentrate in vacuo to yield 68.7 g of a white solid. Concentrate in vacuo the DMF filtrate from the original reaction, add $CH_2Cl_2$ to dissolve the solids, wash with $H_2O$ and brine. Then dry and concentrate to yield an orange solid. Add $CH_2Cl_2$ again to precipitate out a solid. Wash the material with $CH_2Cl_2$, and dry to yield 24.8 g of a white solid. Concentrate the $CH_2Cl_2$ wash portion to yield 80 g of a yellow solid. Combine the three solid portions and recrystallize from EtOH/$H_2O$ to yield 151.5 g (75%) of the title compound as a white, crystalline solid. MS (ES): m/z=602 (M+1), 600 (M−1); NMR ($CDCl_3$) δ8.52 (s, 1H), 7.05 (dd, J=1.2, 7.3 Hz, 2H), 6.86 (m, 1H), 6.78 (d, J=7.6 Hz, 1H), 6.69 (s, 4H), 1.96 (s, 12H), 0.85 (s, 18H), 0.01 (s, 12H).

PREPARATION 3

3,3-Bis-(4-hydroxy-phenyl)-1,3-dihydro-indol-2-one

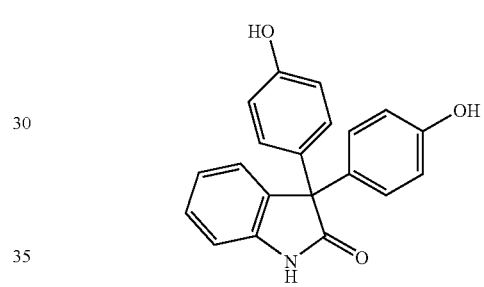

Using a method similar to Preparation 1, with isatin (1.44 g, 10 mmol) and phenol (1.88 g, 20 mmol) gives 502 mg (16%) of the title compound. MS (ES): 318 (M+H), 316 (M−H); NMR(DMSO-$d_6$): δ10.60 (s, 1H), 9.42 (s, 2H), 7.25-7.14 (m, 2H), 7.03-6.91 (m, 6H), 6.70 (d, J=8.5 Hz, 2H).

PREPARATION 4

3,3-Bis-[4-(tert-butyl-dimethyl-silanyloxy)-phenyl]-1,3-dihydro-indol-2-one

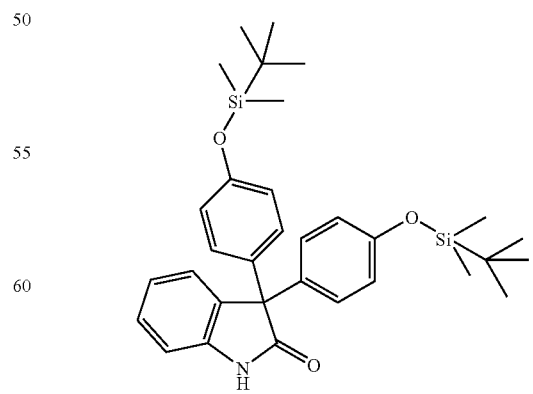

Using a method similar to Preparation 2, with 3,3-bis-(4-hydroxy-phenyl)-1,3-dihydro-indol-2-one (400 mg, 1.26 mmol) gives 543 mg (77%) of the title compound. NMR (CDCl$_3$) δ7.78 (s, 1H), 7.05-6.84 (m, 7H), 6.77 (d, J=7.5 Hz, 1H), 6.57 (d, J=8.5 Hz, 4H), 0.78 (s, 18H), 0.01 (s, 12H).

EXAMPLE 1

3,3-Bis-(4-hydroxy-3,5-dimethyl-phenyl)-1-(4-methoxy-benzyl)-1,3-dihydro-indol-2-one

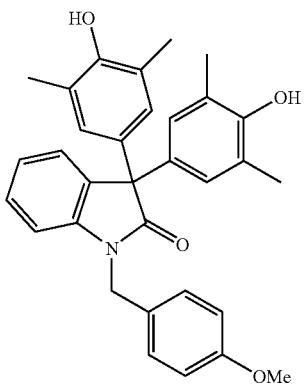

Dissolve 3,3-bis-[4-(tert-butyl-dimethyl-silanyloxy)-3,5-dimethyl-phenyl]-1,3-dihydro-indol-2-one (150 mg, 0.25 mmol) in anhydrous DMF (1.5 mL) under nitrogen. Add slowly a 1M solution of potassium t-butoxide in THF (0.260 mL, 0.260 mmol). Stir 5 min and add 4-methoxybenzyl chloride (0.037 mL, 0.275 mmol). After 1 h add a 1M solution of tetrabutylammonium fluoride in THF (0.625 mL, 0.625 mmol) and stir 2 h. Dilute with water (10 mL) and extract with ethyl acetate (3×15 mL). Wash combined organic portions with water, brine, dry (Na$_2$SO$_4$), filter and concentrate in vacuo to obtain 161 mg of a residue. Recrystallize from CH$_2$Cl$_2$ and hexane to obtain 63 mg (51%) of the title compound as a white solid. MS (ES): m/z=494 (M+1), 492 (M−1); $^1$H NMR(DMSO-d$_6$): δ8.24 (s, 2H), 7.30-7.20 (m, 4H), 7.04 (m, 2H), 6.89 (d, J=8.7 Hz, 2H), 6.68 (s, 4H), 5.77 (s, 2H), 3.72 (s, 3H), 2.07 (s, 12H).

EXAMPLE 2

1-(Fluoro-benzyl-3,3-bis-(4-hydroxy-3,5-dimethyl-phenyl)-1,3-dihydro-indol-2-one

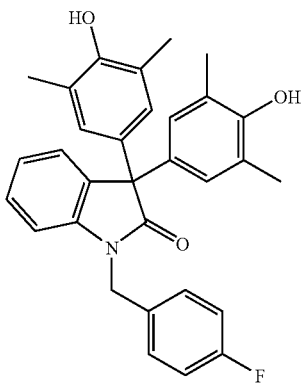

Using a method similar to Example 1, with 4-fluorobenzyl bromide gives 72 mg (60%) of the title compound as a white solid. MS (ES): m/z=482 (M+1), 480 (M−1); $^1$H NMR (DMSO-d$_6$): δ8.27 (s, 2H), 7.43-7.38 (m, 2H), 7.32-7.18 (m, 4H), 7.09 (m, 2H), 6.70 (s, 4H), 4.99 (s, 2H), 2.10 (s, 12H).

EXAMPLE 3

4-[3,3-Bis-(4-hydroxy-3,5-dimethyl-phenyl)-2-oxo-2,3-dihydro-indol-1-ylmethyl]-benzoic acid methyl ester

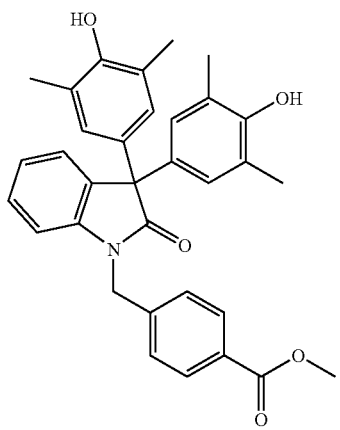

Using a method similar to Example 1, with methyl-4-(bromomethyl)benzoate gives 400 mg of a crude residue. Purify by radial chromatography (10% ethyl acetate/hexane) to give 60 mg. Triturate this material in diethyl ether to give 25 mg of the title compound. Obtain additional material from the mixed fractions by recrystallization from ethyl acetate/hexane to provide 68 mg white crystals for a total yield of 36%. MS (ES): m/z=522 (M+1), 520 (M−1); $^1$H NMR(DMSO-d$_6$): δ8.26 (s, 2H), 7.92 (d, J=8.3 Hz, 2H), 7.43 (d, J=8.3 Hz, 2H), 7.30 (d, J=7.2 Hz, 2H), 7.23 (t, J=7.4, 7.8 Hz), 7.09-7.01 (m, 2H), 6.69 (s, 4H), 5.06 (s, 2H), 3.84 (s, 3H), 8.7 Hz, 2H), 2.07 (s, 12H).

EXAMPLE 4

3,3-Bis-(4-hydroxy-3,5-dimethyl-phenyl)-1-methyl-1,3-dihydro-indol-2-one

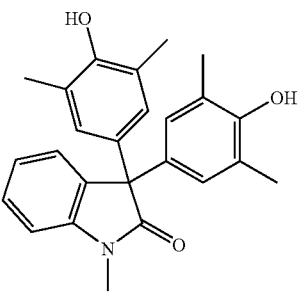

Using a method similar to Example 1, with iodomethane gives 119 mg crude product. Recrystallize from CH$_2$Cl$_2$/hexanes to give 47 mg (48%) of the title compound. MS (ES): m/z=388 (M+1); $^1$H NMR(DMSO-d$_6$): δ8.21 (s, 2H), 7.34-7.23 (m, 2H), 7.07 (m, 2H), 6.67 (s, 4H), 3.20 (s, 3H), 2.06 (s, 12H).

EXAMPLE 5

3,3-Bis-(4-hydroxy-3,5-dimethyl-phenyl)-1-propyl-1,3-dihydro-indol-2-one

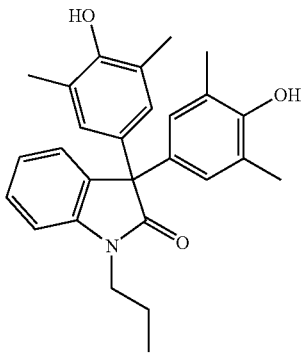

Using a method similar to Example 1, with 1-bromopropane and subsequent recrystallization from diethyl ether/hexanes gives 36 mg (35%) of the title compound as a white solid. MS (ES): m/z=416 (M+1); $^1$H NMR(DMSO-d$_6$); δ8.22 (s, 2H), 7.28 (m, 2H), 7.12 (d, J=7.6 Hz, 1H) 7.06 (t, J=7.3, 7.5 Hz, 1H), 6.67 (s, 4H), 3.70 (t, J=6.9, 7.0 Hz), 2.06 (s, 12H), 1.64 (m,2H), 0.86 (t, J=7.3, 7.4 Hz, 3H).

EXAMPLE 6

1-Cyclohexylmethyl-3,3-bis-(4-hydroxy-3,5-dimethyl-phenyl)-1,3-dihydro-indol-2-one

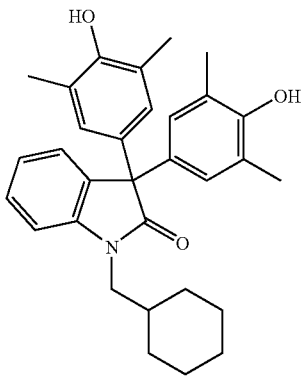

Using a method similar to Example 1, with (bromomethyl)cyclohexane gives 102 mg crude material. Recrystallize from CH$_2$Cl$_2$/hexanes two times to give 23 mg (20%) of the title compound as a white powder. MS (ES): m/z=470 (M+1), 468 (M−1); $^1$H NMR(DMSO-d$_6$): δ8.22 (s, 2H), 7.31-7.26 (m, 2H), 7.11 (d, J=8.1 Hz, 1H), 7.05 (t, J=7.4 Hz, 1H), 6.67 (s, 4H), 3.56 (d, J=7.2 Hz, 2H), (s, 2H), 2.06 (s, 12H), 1.81-1.60 (bm, 5H), 1.26-0.97 (bm, 6H).

EXAMPLE 7

1-(4-tert-Butyl-benzyl)-3,3-bis-(4-hydroxy-3,5-dimethyl-phenyl)-1,3-dihydro-indol-2-one

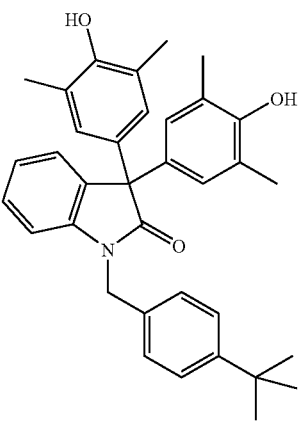

Using a method similar to Example 1, with 4-(tert-butyl)benzyl bromide gives 133 mg crude material. Recrystallize from CH$_2$Cl$_2$/diethyl ether/hexanes to obtain 55 mg (42%) of the title compound as an off-white solid. MS (ES): m/z=520 (M+1), 518 (M−1); $^1$H NMR(DMSO-d$_6$): δ8.24 (s, 2H), 7.34 (d, J=8.4 Hz, 2H), 7.28-7.20 (m, 4H), 7.08-7.01 (m, 2H), 6.68 (s, 4H), 4.92 (s, 2H), 3.72 (s, 3H), 2.07 (s, 12H), 1.25 (s, 9H).

EXAMPLE 8

3,3-Bis-(4-hydroxy-3,5-dimethyl-phenyl)-1-(3-trifluoromethoxy-benzyl)-1,3-dihydro-indol-2-one

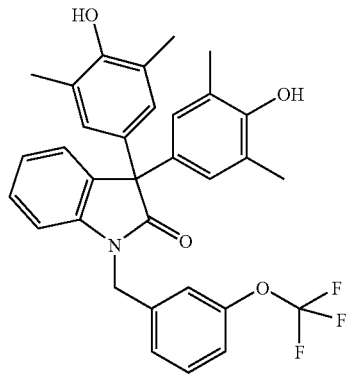

Using a method similar to Example 1, with 3-(trifluoromethoxy)benzyl bromide gives 199 mg crude material. Recrystallize from CH$_2$Cl$_2$/diethyl ether/hexanes two times to obtain 91 mg (66%) of the title compound as a white powder. MS (ES): m/z=548 (M+1), 546 (M−1); $^1$H NMR (DMSO-d$_6$): δ8.26 (s, 2H), 7.50 (t, J=7.9 Hz, 1H), 7.38 (d, J=7.8 Hz, 1H), 7.32-7.19 (m, 4H), 7.07 (t, J=7.8, 8.0 Hz, 2H), (s, 2H), 6.69 (s, 4H), 5.04 (s, 2H), 2.07 (s, 12H).

EXAMPLE 9

1-(3,5-Dimethyl-isoxazol-4-ylmethyl)-3,3-bis-(4-hydroxy-3,5-dimethyl-phenyl)-1,3-dihydro-indol-2-one

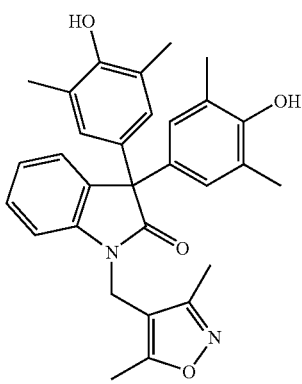

Using a method similar to Example 1, with 4-(chloromethyl)-3,5-dimethyl isoxazole gives 179 mg of crude material. Recrystallize from $CH_2Cl_2$/hexanes to obtain 89 mg (74%) of the title compound as an off-white powder. MS (ES): m/z=483 (M+1), 481 (M−1); $^1H$ NMR(DMSO-$d_6$): δ8.24 (s, 2H), 7.29 (m, 2H), 7.09-7.01 (m, 2H), 6.64 (s, 4H), 4.78 (s, 2H), 2.38 (s, 3H), 2.07 (s, 12H), 1.95 (s, 3H).

EXAMPLE 10

3,3-Bis-(4-hydroxy-3,5-dimethyl-phenyl)-1-naphthalen-1-ylmethyl-1,3-dihydro-indol-2-one

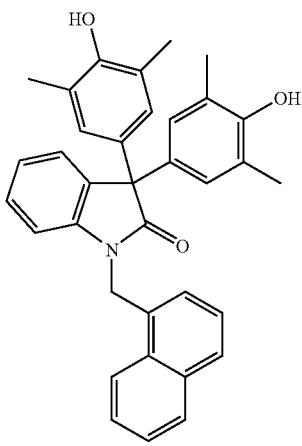

Using a method similar to Example 1, with 1-chloromethylnaphthalene gives 168 mg of crude material. Recrystallize from diethyl ether/hexanes and then $CH_2Cl_2$/hexanes to obtain 54 mg (43%) of the title compound as a white powder. MS (ES): m/z=514 (M+1), 512 (M−1); $^1H$ NMR (DMSO-$d_6$): δ8.29 (m, 1H), 8.26 (s, 2H), 7.98 (m, 1H), 7.88 (d, J=8.0 Hz, 1H), 7.58 (m, 2H), 7.42 (t, J=7.2, 8.0 Hz, 1H), 7.32 (m, 2H), 7.19 (t, J=6.9, 7.5 Hz, 1H), 7.05 (t, J=7.5, 1H), 6.96 (d, J=7.7, 1H), 6.73 (s, 4H), 5.46 (s, 2H), 2.08 (s, 12H).

EXAMPLE 11

1-(2-Chloro-benzyl)-3,3-bis-(4-hydroxy-3,5-dimethyl-phenyl)-1,3-dihydro-indol-2-one

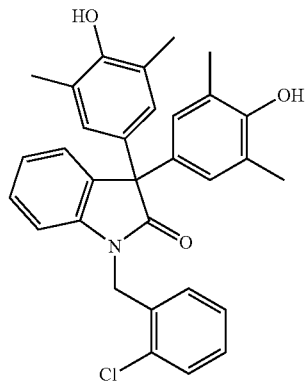

Using a method similar to Example 1, with 2-chlorobenzyl bromide gives 158 mg of crude material. Recrystallize from $CH_2Cl_2$/hexanes to obtain 68 mg (54%) of the title compound as a light pink solid. MS (ES): m/z=498 (M+1), 496 (M−1); NMR(DMSO-$d_6$): δ8.27 (s, 2H), 7.54 (dd, J=7.8 Hz, J=1.1 Hz), 7.33 (m, 2H), 7.24 (m, 2H), 7.09 (t, J=7.4, 7.0 Hz, 1H), 6.72 (s, 4H), 5.05 (s, 2H), 2.08 (s, 12H).

PREPARATION 5

1-Benzyl-1H-indole-2,3-dione

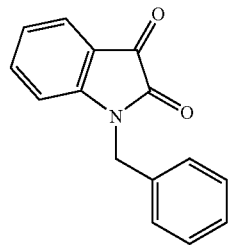

Dissolve isatin (7.36 g, 50 mmol) in anhydrous DMF (100 mL) under nitrogen and cool in an ice bath. Treat with 1M potassium tert-butoxide in THF (53 mL, 53 mmol) stir 15-20 min. Add benzyl bromide (6.2 mL, 52.5 mmol) and after 10 min remove bath and allow to warm to room temperature over 16 h. Pour into 1N HCl and wash with ethyl acetate (500 mL). Wash ethyl acetate with 1N HCl (150 mL) and then wash combined acidic portions with more ethyl acetate (150 mL). Wash the combined organic portions with brine (2×150 ml), dry ($MgSO_4$), filter and concentrate in vacuo to give 13.5 g of an orange solid. Triturate in diethyl ether and filter to give 10.0 g (84%) of the title compound. MS (ES): m/z=238 (M+1); $^1H$ NMR(CDCl$_3$): δ7.64 (dd, J=7.6 Hz, J=1 Hz, 1H), 7.5 (dt, J=7.8 Hz, J=1.3 Hz, 1H), 7.37 (m, 5H), 7.12 (t, J=7.6 Hz, 1H), 6.80 (d, J=8.0 Hz, 1H), 4.97 (s, 2H).

PREPARATION 6

1-Benzyl-5-bromo-1H-indole-2,3-dione

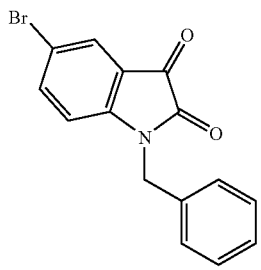

Using a method similar to Preparation 5, with 5-bromoisatin (3.39 g, 15 mmol) gives 4.97 g of crude material. Drive reaction to completion with excess of benzyl bromide (30.4 ml, 3.4 mmol). Recrystallize from diethyl ether/hexanes to obtain 2.69 g (57%) of the title compound as a dark orange-red solid. MS (ES): m/z=316, 318 (M+1); $^1$H NMR (CDCl$_3$): δ7.75 (d, J=2 Hz, 1H), 7.61 (dd, J=8 Hz, J=2 Hz, 1H), 7.37 (m, 5H), 6.70 (d, J=8.0 Hz, 1H), 4.97 (s, 2H).

PREPARATION 7

1-Benzyl-5-methoxy-1H-indole-2,3-dione

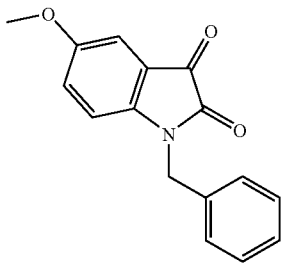

Using a method similar to Preparation 5, with 5-methoxyisatin (1.77 g, 10 mmol) gives crude material. Drive reaction to completion with later addition of potassium tert-butoxide (1 mL, 1 mmol) and benzyl bromide (0.12 ml, 1 mmol). Recrystallize from diethyl ether/hexanes to obtain 1.65 g (62%) of the title compound as a dark orange-red solid. MS (ES): m/z=267 (M+1); $^1$H NMR(CDCl$_3$): δ7.37 (m, 5H), 7.18 (d, J=2 Hz, 1H), 7.05 (dd, J=8 Hz, J=2 Hz, 1H), 6.70 (d, J=8.0 Hz, 1H), 4.94 (s, 2H), 3.81 (s, 3H).

PREPARATION 8

1-Benzyl-5-methyl-1H-indole-2,3-dione

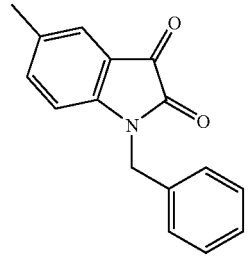

Using a method similar to Preparation 5, with 5-methylisatin (1.61 g, 10 mmol), 1M potassium tert-butoxide in THF (12 mL, 12 mmol) and benzyl bromide (1.4 mL, 12 mmol) gives 2.78 g crude material. Recrystallize from diethyl ether to obtain 1.30 g (52%) of the title compound as a dark orange-red solid. MS (ES): m/z=252 (M+1); $^1$H NMR (CDCl$_3$): δ7.45 (s, 1H), 7.39-7.32 (m, 5H), 6.68 (d, J=8.0 Hz, 1H), 4.94 (s, 2H), 2.33 (s, 3H).

PREPARATION 9

1-(2-Chloro-benzyl)-1H-indole-2,3-dione

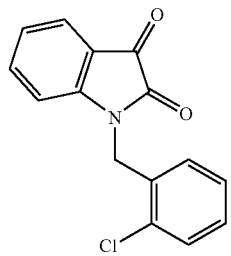

Using a method similar to Preparation 5, with isatin (5.89 g, 40 mmol), 1M potassium tert-butoxide in THF (48 mL, 48 mmol) and 2-chlorobenzyl chloride (6.1 mL, 48 mmol) gives 6.66 g (61%) of the title compound as a dark orange-red solid. MS (ES): m/z=272 (M+1); NMR(CDCl$_3$): δ7.67 (dd, J=0.9 Hz, J=7.6 Hz, 1H), 7.57-7.44 (m, 2H), 7.33-7.24 (m, 4H), 7.15 (m, 1H), 6.79 (d, J=8.0 Hz, 1H), 5.10 (s, 2H).

PREPARATION 10

5-Bromo-1-(2-chloro-benzyl)-1H-indole-2,3-dione

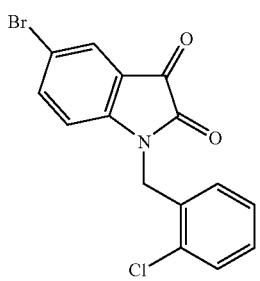

Partially dissolve 5-bromoisatin (45 mg, 0.20 mmol) in acetonitrile (2 mL) and add 2-tert-butylimino-2-diethylamino-1,3-dimethyl-perhydro-1,3,2-diazaphosphorine on polysteyrene (95 mg, 0.21 mmol, 2.2 mmol/g, Fluka) followed by adding 2-chlorobenzyl bromide (0.026 mL, 0.20 mmol). Stir 18 h and add additional base (50 mg) and bromide (0.010 mL) to drive reaction to completion after another 3 h. Dilute with MeOH and warm with heat gun to insure soluability. Filter off beads and concentrate the filtrate in vacuo to obtain 72 mg of the title compound as a dark orange solid. Use material in subsequent reaction without further purification.

PREPARATION 11

5-Bromo-1-(2-methyl-benzyl)-1H-indole-2,3-dione

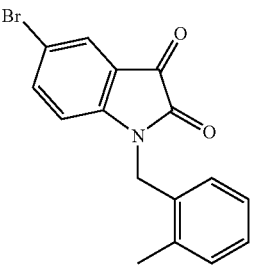

Combine 5-bromoisatin (90 mg, 0.4 mmol), 2-tert-butylimino-2-diethylamino-1,3-dimethyl-perhydro-1,3,2-diazaphosphorine on polysteyrene (270-290 mg, 0.60-0.64 mmol, 2.2 mmol/g, Fluka) and 2-methylbenzyl bromide (0.054 mL, 0.4 mmol) in acetonitrile (4 mL) in a 20 dram scintillation vial and shake on a rotator for 2.5 days. Dilute with and a small amount of CH₂Cl₂ as needed to soluabilize solids. Filter off beads, washing with MeOH, and concentrate in vacuo. Triturate the resulting solid with diethyl ether (about 4 mL) and pipet off the liquid. Dry the solid to obtain approximately 70 mg of the title compound as crude material and use without further purification.

PREPARATION 12

5-Methyl-1-(2-methyl-benzyl)-1H-indole-2,3-dione

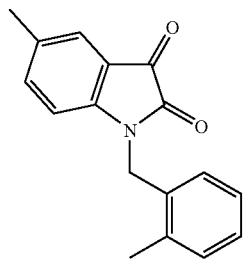

Using a method similar to Preparation 9, with 5-methylisatin (64 mg, 0.4 mmol), 2-tert-butylimino-2-diethylamino-1,3-dimethyl-perhydro-1,3,2-diazaphosphorine on polysteyrene (270-290 mg, 0.60-0.64 mmol, 2.2 mmol/g, Fluka) and 2-methylbenzyl bromide (0.054 mL, 0.4 mmol) in acetonitrile (4 mL) gives 98 mg (92%) of the title compound as crude material which is used without further purification.

PREPARATION 13

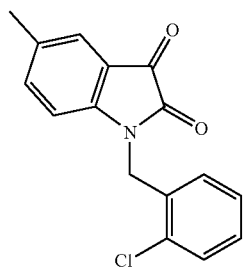

1-(2-Chloro-benzyl)-5-methyl-1H-indole-2,3-dione

Using a method similar to Preparation 12, with 5-methylisatin (64 mg, 0.4 mmol), 2-tert-butylimino-2-diethylamino-1,3-dimethyl-perhydro-1,3,2-diazaphosphorine on polysteyrene (270-290 mg, 0.60-0.64 mmol, 2.2 mmol/g, Fluka) and 2-chlorobenzyl bromide (0.052 mL, 0.4 mmol) in acetonitrile (4 mL) gives 76 mg (67%) of the title compound as crude material which is used without further purification.

PREPARATION 14

2-(5-Methyl-2,3-dioxo-2,3-dihydro-indol-1-ylmethyl)-benzonitrile

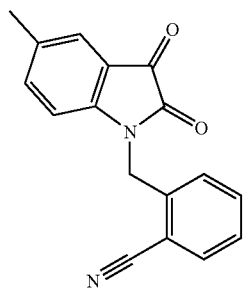

Using a method similar to Preparation 12, with 5-methylisatin (64 mg, 0.4 mmol), 2-tert-butylimino-2-diethylamino-1,3-dimethyl-perhydro-1,3,2-diazaphosphorine on polysteyrene (270-290 mg, 0.60-0.64 mmol, 2.2 mmol/g, Fluka) and 2-cyanobenzyl bromide (78 mg, 0.4 mmol) in acetonitrile (4 mL) gives 96 mg (87%) of the title compound as crude material which is used without further purification.

PREPARATION 15

1-(2-Chloro-benzyl)-7-methyl-1H-indole-2,3-dione

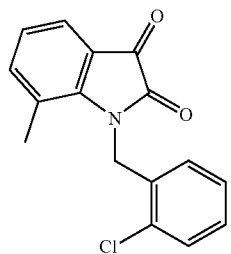

Obtain 7-methyl isatin from o-toluidine using method of Pavia, M. R., Moos, W. H., Hershenson, F. M.; *J. Org. Chem.* (1990), 55, 560-564.

Combine 7-methylisatin (80 mg, 0.5 mmol), 2-tert-butylimino-2-diethylamino-1,3-dimethyl-perhydro-1,3,2-diazaphosphorine on polystyrene beads(630-720 mg, 1.4-1.6 mmol, 2.2 mmol/g, Fluka) and 2-chlorobenzyl bromide (0.065 mL, 0.5 mmol) in acetonitrile (5 mL) in a 20 dram scintillation vial and shake on a rotator for 2.5 days at room temperature. Dilute with CH₂Cl₂ or acetonitrile and filter off beads. Concentrate in vacuo to obtain 126 mg (88%) of the title compound as crude product as a red-orange solid. MS (ES): m/z=286 (M+1).

PREPARATION 16

1-(2-Chloro-benzyl)-7-ethyl-1H-indole-2,3-dione

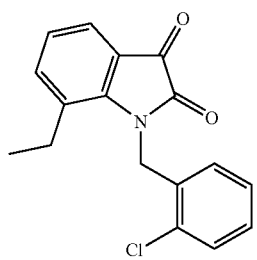

Obtain 7-ethyl isatin from 2-ethylaniline using same literature reference as in Preparation 15 or by the following: Wu, J., Ni, P., Wang, J., Xia, L.; *Zhongguo Yaowu Huaxue Zazhi*, (1990), 7(1), 57-58, 65.

Using a method similar to Preparation 15, with 7-ethylisatin (88 mg, 0.5 mmol), 2-tert-butylimino-2-diethylamino-1,3-dimethyl-perhydro-1,3,2-diazaphosphorine on polystyrene beads(630-720 mg, 1.4-1.6 mmol, 2.2 mmol/g, Fluka) and 2-chlorobenzyl bromide (0.065 mL, 0.5 mmol) gives 121 mg (85%) of the title compound as crude material as a red-orange solid. MS (ES): m/z=300 (M+1).

PREPARATION 17

4-Chloro-1-(2-chloro-benzyl)-1H-indole-2,3-dione

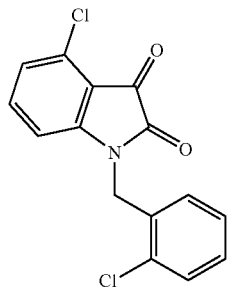

Obtain 4-chloro isatin from 1-chloro-2-nitrobenzene using method of Kraynack, E. A., Dalgard, J. E., Gaeta, F. C. A.; *Tet. Lett.* (1998), 39, 7679-7682.

Partially dissolve 4-chloro isatin (118 mg, 0.65 mmol) in acetonitrile (4 mL). Add 2-tert-butylimino-2-diethylamino-1,3-dimethyl-perhydro-1,3,2-diazaphosphorine (0.207 ml, 0.72 mmol) and after 5 min add 2-chlorobenzyl bromide (0.084 mL, 0.65 mmol). After 4 h dilute with ethyl acetate (50 mL) and wash with 1N HCl (2×20 mL), water, and brine. Dry (Na$_2$SO$_4$), filter and concentrate in vacuo to give 188 mg (94%) of the title compound as crude material as a red solid. MS (ES): m/z=306 (M+1).

EXAMPLE 12

1-Benzyl-3,3-bis-(4-hydroxy-3-methyl-phenyl)-1,3-dihydro-indol-2-one

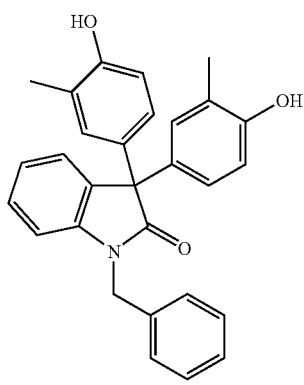

Reference: Olah, G. A., et. al.; *J. Org. Chem.* (1998), 63, 4481-4484.

Dissolve 1-benzyl-1H-indole-2,3-dione (475 mg, 2 mmol) in trifluoromethanesulfonic acid (6 ml) under nitrogen and cool in an ice bath. Add o-cresol (2.1 mL, 20 mmol). Remove ice bath after 5 min and stir for 1 h. Pour over ice and extract with toluene or ethyl acetate (2-3×). Combine all organic portions and wash carefully with saturated bicarbonate, then brine. Dry (MgSO$_4$), filter, and concentrate in vacuo to give 2.46 g of a mushy, oily solid. Purify by flash chromatography (20% EtOAc/hexanes, 25% EtOAc/hexanes, and 50% EtOAc/hexanes) to obtain an off-white solid. Triturate in cold diethyl ether and filter, washing with cold diethyl ether and dry under house vacuum to give 609 mg (70%) of the title compound as a white solid. MS (ES): m/z=436 (M+1), 434 (M−1); $^1$H NMR(DMSO-d$_6$): δ9.34 (s, 2H), 7.39-7.20 (m, 7H), 7.08-7.00 (m, 2H), 6.85-6.77 (m, 4H), 6.69 (m, 2H), 4.98 (s, 2H), 2.03 (s, 6H).

EXAMPLE 13

1-Benzyl-3,3-bis-(4-hydroxy-3-ethyl-phenyl)-1,3-dihydro-indol-2-one

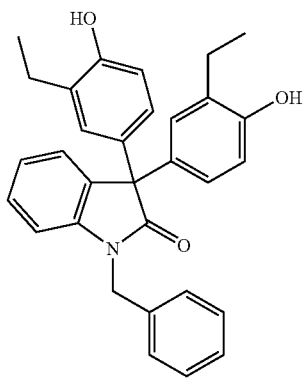

Using a method similar to Example 12, with 1-benzyl-1H-indole-2,3-dione (475 mg, 2 mmol) and 2-ethylphenol (2.4 mL, 20 mmol) in trifluoromethanesulfonic acid (6 mL) gives 2.8 g of a crude oil. Purify by flash chromatography (CH$_2$Cl$_2$ and 5% MeOH/CH$_2$Cl$_2$) to give 970 mg of a foam. Triturate in cold diethyl ether, filter and dry under house vacuum to give 621 mg (67%) of the title compound as an off-white solid. MS (ES): m/z=464 (M+1), 462 (M−1); $^1$H NMR(DMSO-d$_6$): δ9.32 (s, 2H), 7.33-7.23 (m, 7H), 7.05-7.00 (m, 2H), 6.86-6.77 (m, 4H), 6.70 (m, 2H), 4.99 (s, 2H), 2.46 (m, 4H), 1.02 (t, J=7.5 Hz, 6H).

EXAMPLE 14

1-Benzyl-3,3-bis-(3,5-dichloro-4-hydroxy-phenyl)-1,3-dihydro-indol-2-one

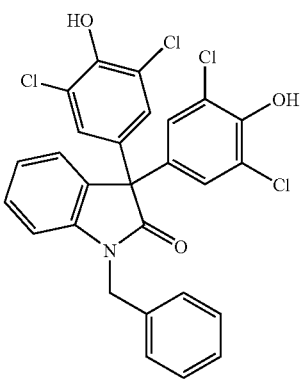

Using a method similar to Example 12, with 1-benzyl-1H-indole-2,3-dione (237 mg, 1 mmol) and 2,6-dichlorophenol (1.63 g, 10 mmol) in trifluoromethanesulfonic acid (3 mL) gives crude material. Purify by flash chromatography (CH$_2$Cl$_2$ and 5% MeOH/CH$_2$Cl$_2$) and triturate the resulting material in diethyl ether/hexane. Filter to give 271 mg (50%) of the title compound as a white powder. MS (ES): m/z=542, 544, 546, 548 (M−1); ¹H NMR(DMSO-d₆): δ10.45 (bs, 2H), 7.55 (d, J=7.4, 1H), 7.38-7.28 (m, 6H), 7.34 (m, 2H), 7.32 (s, 4H), 5.01 (s, 2H).

EXAMPLE 15

1-Benzyl-5-bromo-3,3-bis-(4-hydroxy-3,5-dimethyl-phenyl)-1,3-dihydro-indol-2-one

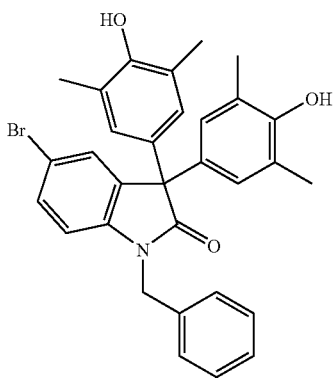

Using a method similar to Example 12, with 1-benzyl-5-bromo-1H-indole-2,3-dione (500 mg, 1.6 mmol) and 2,6-dimethylphenol (1.93 g, 15 mmol) in trifluoromethane-sulfonic acid (6 mL) gives 2.16 g crude material. Triturate in cold diethyl, filter and dry under house vacuum to give 724 mg (84%) of the title compound. MS (ES): m/z=542, 544 (M+1), 540, 542 (M−1); ¹H NMR(DMSO-d₆): δ8.30 (s, 2H), 7.45 (m, 2H), 7.37-7.28 (m, 5H), 7.03 (d, J=8 Hz, 1H), 6.68 (s, 4H), 4.97 (s, 2H), 2.08 (s, 12H).

EXAMPLE 16

1-Benzyl-3,3-bis-(4-hydroxy-3,5-dimethyl-phenyl)-5-methoxy-1,3-dihydro-indol-2-one

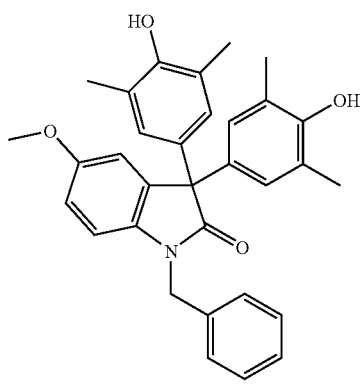

Using a method similar to Example 12, with 1-benzyl-5-methoxy-1H-indole-2,3-dione (500 mg, 1.82 mmol) and 2,6-dimethylphenol (2.28 g, 18 mmol) in trifluoromethane-sulfonic acid (6 mL) gives crude material. Triturate in cold diethyl, filter and dry under house vacuum to give 162 mg (18%) of the title compound. MS (ES): m/z=429 (M+1), 427 (M−1); ¹H NMR(DMSO-d₆): δ8.24 (s, 2H), 6.93 (d, J=8.5 Hz, 1H), 6.85 (d, J=2.4 Hz, 1H), 6.80 (dd, J=8.5 Hz, J=2.4 Hz), 6.70 (s, 4H), 4.94 (s, 2H), 3.67 (s, 3H), 2.08 (s, 12H).

EXAMPLE 17

1-Benzyl-3,3-bis-(4-hydroxy-3,5-dimethyl-phenyl)-5-methyl-1,3-dihydro-indol-2-one

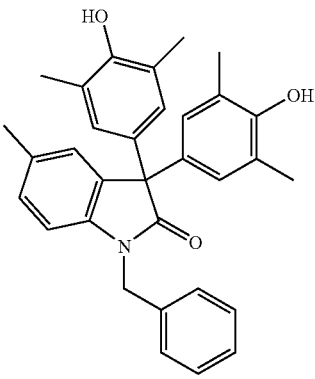

Using a method similar to Example 12, with 1-benzyl-5-methyl-1H-indole-2,3-dione (500 mg, 2 mmol) and 2,6-dimethylphenol (2.44 g, 20 mmol) in trifluoromethane-sulfonic acid (6 mL) gives 3.27 g crude material. Triturate in cold diethyl, filter and dry under house vacuum to give 790 mg (83%) of the title compound. MS (ES): m/z=478 (M+1); ¹H NMR(DMSO-d₆): δ8.24 (s, 2H), 7.33-7.27 (m, 5H), 7.06 (s, 1H), 7.03 (d, J=8 Hz, 1H), 6.90 (d, J=8 Hz, 1H), 6.68 (s, 4H), 4.94 (s, 2H), 2.24 (s, 3H), 2.07 (s, 12H).

EXAMPLE 18

1-(2-Chloro-benzyl)-3,3-bis-(4-hydroxy-phenyl)-1,3-dihydro-indol-2-one

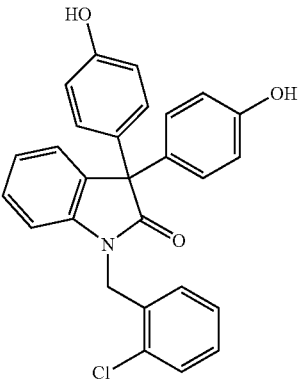

Using a method similar to Example 12, 1-(2-chloro-benzyl)-1H-indole-2,3-dione (300 mg, 1.1 mmol) and 2,6-dimethylphenol (831 mg, 8.83 mmol) in trifluoromethane-sulfonic acid (5 mL) gives a crude brown oil. Purify by flash chromatography (CH₂Cl₂, 10% EtOAc/CH₂Cl₂, 25% EtOAc/CH₂Cl₂) and recrystallize the resulting oil from diethyl ether/CH₂Cl₂/hexanes to give after drying under house vacuum 145 mg (30%) of the title compound as an off-white powder. MS (ES): m/z=442 (M+1), 440 (M−1); ¹H NMR(DMSO-d₆): δ9.46 (s, 2H), 7.52 (dd, J=1.2 Hz, J=7.8 Hz, 1H), 7.36-7.24 (m, 4H), 7.10 (t, J=7.3 Hz, 1H), 7.01-6.91 (m, 6H), 6.71 (d, J=8.7 Hz, 4H), 5.06 (s, 2H).

EXAMPLE 19

5-Bromo-1-(2-chloro-benzyl)-3,3-bis-(4-hydroxy-3,5-dimethyl-phenyl)-1,3-dihydro-indol-2-one

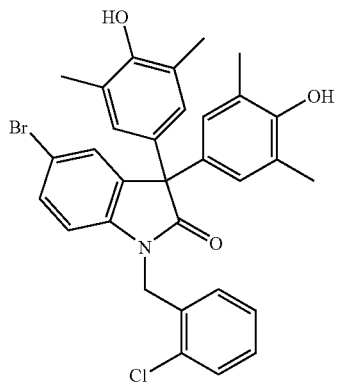

Combine crude 5-bromo-1-(2-chloro-benzyl)-1H-indole-2,3-dione (72 mg, 0.21 mmol) with 2,6-dimethylphenol (200 mg, 1.64 mmol) in trifluoromethanesulfonic acid (1 mL) and stir for 1 h. Dilute with $CH_2Cl_2$ and stir with ice water for 20 min. Pipette off ice water and stir with saturated $NaHCO_3$ solution for 20 min. Remove aqueous by pipette and pass organic layer through a 5 mL Varian Chem Elut column. Concentrate in vacuo to give 131 mg solid. Triturate in MeOH to give 50 mg (41%) of a white solid. MS (ES): m/z=576, 578 (M+1), 574, 576 (M−1); $^1$H NMR(DMSO-$d_6$): δ8.31 (s, 2H), 7.53 (d, J=7.9 Hz, 1H), 7.45 (m, 2H), 7.34 (t, J=7.6 Hz, 1H), 7.25 (t, J=7.6 Hz, 1H), 6.95 (m, 2H), 6.71 (s, 4H), 5.06 (s, 2H), 2.09 (s, 12H).

EXAMPLE 20

5-Bromo-3,3-bis-(4-hydroxy-3,5-dimethyl-phenyl)-1-(2-methyl-benzyl)-1,3-dihydro-indol-2-one

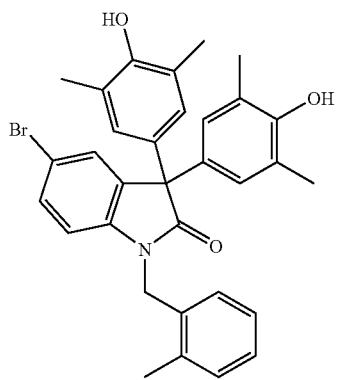

Using a method similar to Example 19, with 5-bromo-1-(2-methyl-benzyl)-1H-indole-2,3-dione (70 mg, 0.21 mmol) and 2,6-dimethylphenol (300 mg, 2.5 mmol) in trifluoromethanesulfonic acid (1.5 mL) gives crude material. Purify by radial chromatography (1-4% EtOAc/$CH_2Cl_2$) to give 20 mg (17%) of the title compound as a tan solid. MS (ES): m/z=556, 558 (M+1), 554, 556 (M−1); $^1$H NMR (DMSO-$d_6$): δ8.31 (s, 2H), 7.47-7.41 (m, 2H), 7.23 (d, J=7.1 Hz, 1H), 7.17 (t, J=7.3, 7.0 Hz, 1H), 7.04 (t, J=7.4, 7.3 Hz, 1H), 6.85 (d, J=8.3 Hz, 1H), 6.79 (d, J=7.4 Hz, 1H), 6.72 (s, 4H), 4.96 (s, 2H), 2.33 (s, 3H), 2.10 (s, 12H).

EXAMPLE 21

3,3-Bis-(4-hydroxy-3,5-dimethyl-phenyl)-5-methyl-1-(2-methyl-benzyl)-1,3-dihydro-indol-2-one

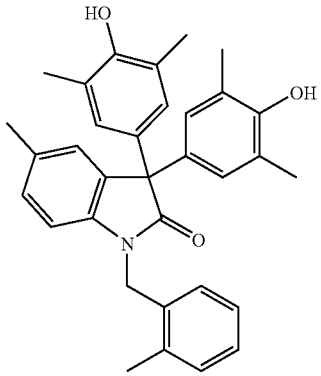

Using a method similar to Example 19, with crude 5-methyl-1-(2-methyl-benzyl)-1H-indole-2,3-dione (98 mg, 0.34 mmol) and 2,6-dimethylphenol (200-250 mg, 1.6-2.0 mmol) in trifluoromethanesulfonic acid (1 mL) gives 148 mg crude material. Purify by flash chromatography (5% MeCN/$CH_2Cl_2$) and then triturate the resulting material in diethyl ether, filtrate and dry under house vacuum to give 88 mg (53%) of the title compound. MS (ES): m/z=492 (M+1), 490 (M−1); $^1$H NMR(DMSO-$d_6$): δ8.25 (s, 2H), 7.23-7.11 (m, 3H), 7.03 (m, 2H), 6.81 (d, J=7.4 Hz, 1H), 6.73 (m, 5H), 4.92 (s, 2H), 2.34 (s, 3H), 2.26 (s, 3H), 2.09 (s, 12H).

EXAMPLE 22

1-(2-Chloro-benzyl)-3,3-bis-(4-hydroxy-3,5-dimethyl-phenyl)-5-methyl-1,3-dihydro-indol-2-one

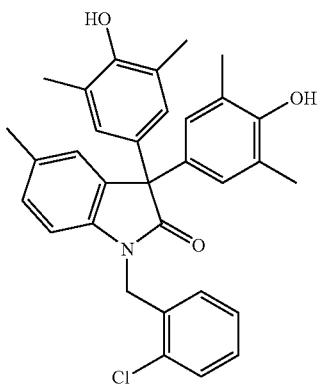

Using a method similar to Example 19, with crude 1-(2-chloro-benzyl)-5-methyl-1H-indole-2,3-dione (76 mg, 0.27 mmol) and 2,6-dimethylphenol (200-250 mg, 1.6-2.0 mmol) in trifluoromethanesulfonic acid (1 mL) gives 122 mg crude material. Purify by flash chromatography eluting (5% MeCN/$CH_2Cl_2$) and then triturate the resulting material in diethyl ether, filtrate and dry under house vacuum to give 67 mg (48%) of the title compound. MS (ES): m/z=512 (M+1), 510 (M−1); $^1$H NMR(DMSO-$d_6$): δ8.25 (s, 2H), 7.53 (d, J=7.8 Hz, 1H), 7.33 (t, J=7.5, 7.9 Hz, 1H), 7.25 (t, J=7.6, 7.5 Hz, 1H), 7.12 (s, 1H), 7.04 (d, J=7.9 Hz, 1H), 6.95 (d, J=7.3 Hz, 1H), 6.82 (d, J=8 Hz, 1H), 6.72 (s, 4H), 5.02 (s, 2H), 2.27 (s, 3H), 2.09 (s, 12H).

EXAMPLE 23

2-[3,3-Bis-(4-hydroxy-3,5-dimethyl-phenyl)-5-methyl-2-oxo-2,3-dihydro-indol-1-ylmethyl]-benzonitrile

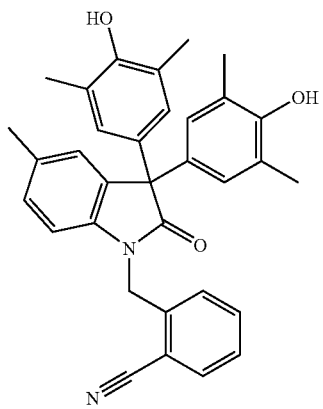

Using a method similar to Example 19, with crude 2-(5-methyl-2,3-dioxo-2,3-dihydro-indol-1-ylmethyl)-benzonitrile (96 mg, 0.35 mmol) and 2,6-dimethylphenol (200-250 mg, 1.6-2.0 mmol) in trifluoromethanesulfonic acid (1 mL) gives crude material. Purify by radial chromatography (5-20%/CH$_2$Cl$_2$) and then triturate the resulting material in diethyl ether, filtrate and dry under house vacuum to give 40 mg (24%) of the title compound. MS (ES): m/z=503 (M+1), 501 (M−1); $^1$H NMR(DMSO-d$_6$); δ8.25 (s, 2H), 7.93 (d, J=7.6 Hz, 1H), 7.62 (t, J=7.7, 1H), 7.50 (t, J=7.5, 1H), 7.08 (m, 3H), 6.94 (d, J=8 Hz, 1H), 6.69 (s, 4H), 5.15 (s, 2H), 2.27 (s, 3H), 2.08 (s, 12H).

EXAMPLE 24

1-(2-Chloro-benzyl)-3,3-bis-(4-hydroxy-3,5-dimethyl-phenyl)-7-methyl-1,3-dihydro-indol-2-one

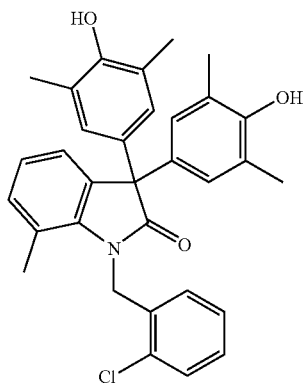

Using a method similar to Example 12, with 1-(2-chloro-benzyl)-7-methyl-1H-indole-2,3-dione (126 mg, 0.44 mmol) and 2,6-dimethylphenol (538 mg, 4.4 mmol) in trifluoromethnaesulfonic acid (2 mL) gives crude material. Purify by flash chromatography (gradient of CH$_2$Cl$_2$ up to 10% EtOAc/CH$_2$Cl$_2$). Triturate the resulting residue in CH$_2$Cl$_2$, filter and dry under house vacuum to give 88 mg (39%) of the title compound as a pale yellow solid. MS (ES): m/z=512 (M+1), 510 (M−1); $^1$H NMR(DMSO-d$_6$); δ8.27 (s, 2H), 7.57 (dd, J=1 Hz, J=7.9 Hz, 1H), 7.34 (m, 1H), 7.26-7.16 (m, 2H), 7.01 (m, 2H), 6.79 (d, J=5.7 Hz, 1H), 6.73 (s, 4H), 5.22 (s, 2H), 2.19 (s, 3H), 2.09 (s, 12H).

EXAMPLE 25

1-(2-Chloro-benzyl)-7-ethyl-3,3-bis-(4-hydroxy-3,5-dimethyl-phenyl)-1,3-dihydro-indol-2-one

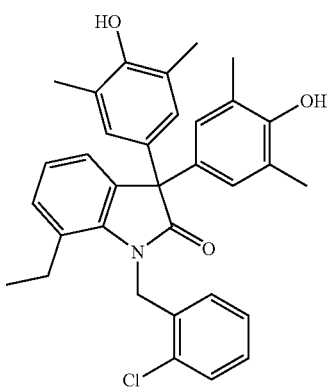

Using a method similar to Example 12, with 1-(2-chloro-benzyl)-7-ethyl-1H-indole-2,3-dione (121 mg, 0.4 mmol) and 2,6-dimethylphenol (489 mg, 4 mmol) in trifluoromethanesulfonic acid (2 mL) gives 689 mg crude material. Purify by flash chromatography (gradient of 10% EtOAc/hexanes up to 40% EtOAc/hexanes). Triturate the resulting residue in diethyl ether/CH$_2$Cl$_2$, filter and dry under house vacuum to give 47 mg (22%) of the title compound as an off-white solid. MS (ES): m/z=526 (M+1), 524 (M−1); $^1$H NMR(DMSO-d$_6$); δ8.27 (s, 2H), 7.57 (dd, J=1 Hz, J=7.9 Hz, 1H), 7.33 (m, 1H), 7.23-7.17 (m, 2H), 7.07 (m, 2H), 6.73 (m, 5H), 5.19 (s, 2H), 2.45 (q, J=7.5 Hz, 2H), 2.09 (s, 12H), 1.05 (t, J=7.5 Hz, 3H).

EXAMPLE 26

4-Chloro-1-(2-chloro-benzyl)-3,3-bis-(4-hydroxy-3,5-dimethyl-phenyl)-1,3-dihydro-indol-2-one

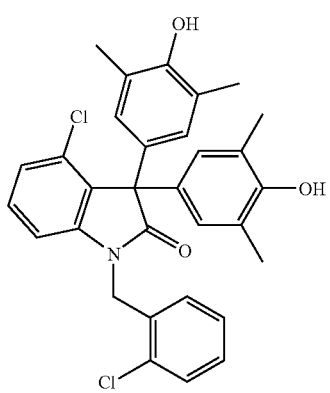

Using a method similar to Example 12, with 4-chloro-1-(2-chloro-benzyl)-1H-indole-2,3-dione (188 mg, 0.61 mmol) and 2,6-dimethylphenol (733 mg, 6 mmol) in trifluoromethanesulfonic acid (3 mL) gives 868 mg crude material. Purify by flash chromatography (gradient of $CH_2Cl_2$ up to 10% EtOAc/$CH_2Cl_2$). Triturate the resulting residue in $CH_2Cl_2$, filter and dry under house vacuum to give 212 mg (65%) of the title compound as a pale yellow solid. MS (ES): m/z=532, 534 (M+1), 530, 532 (M−1); $^1$H NMR (DMSO-$d_6$): δ8.31 (s, 2H), 7.53 (dd, J=1.2 Hz, J=7.8 Hz, 1H), 7.36-7.25 (m, 3H), 7.07 (d, J=7.8 Hz, 1H), 7.01 (m, 2H), 6.75 (s, 4H), 5.06 (s, 2H), 2.19 (s, 3H), 2.09 (s, 12H).

PREPARATION 18

3-Hydroxy-3-phenyl-1,3-dihydro-indol-2-one

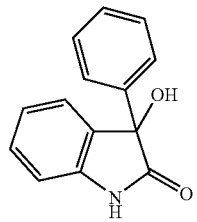

Dissolve isatin (1.47 g, 10 mmol) in anhydrous THF (40 mL) in an oven-dried flask under nitrogen. Cool in an ice bath and add slowly a 3M solution of phenylmagnesium bromide in diethyl ether (7.4 mL, 22 mmol). After 5 min remove the ice bath and stir at room temperature for 18 h. Pour the reaction over saturated $NH_4Cl$ solution and extract with ethyl acetate (200 mL, 2×100 mL). Wash combined organic portions with brine and dry ($Na_2SO_4$), filter, and concentrate in vacuo to give a yellow solid. Triturate in diethyl ether, filter and dry under house vacuum to give 1.77 g (79%) of the title compound as a yellow solid. MS (ES): m/z=208 (M+1−$H_2O$), 224 (M−1); $^1$H NMR(DMSO-$d_6$): δ10.39 (s, 1H), 7.32-7.23 (m, 6H), 7.09 (d, J=7.3 Hz, 1H), 6.96 (dt, J=0.9 Hz, J=7.5 Hz, 1H), 6.90 (d, J=7.7 Hz, 1H), 6.61 (s, 1H).

PREPARATION 19

3-(3,5-Dimethyl-phenyl)-3-hydroxy-1,3-dihydro-indol-2-one

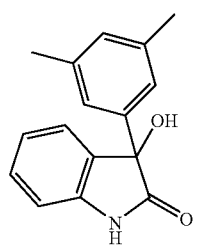

Using a method similar to Preparation 18 with isatin (1.47 g, 10 mmol) and 3,5-dimethylphenylmagnesium bromide (0.5M in THF, 42 mL, 21 mmol) gave 2.06 g (81%) of the title compound as a peach-color solid. MS (ES): m/z=236 (M+1−$H_2O$), 252 (M−1); $^1$H NMR(DMSO-$d_6$): δ10.34 (s, 1H), 7.23 (dt, J=1.3 Hz, J=7.6 Hz, 1H), 7.07 (d, J=6.7 Hz, 1H), 6.95 (dt, J=0.9 Hz, J=7.4 Hz, 1H), 6.88 (m, 4H), 6.51 (s, 1H), 2.21 (s, 6H).

PREPARATION 20

1-Benzyl-3-hydroxy-3-phenyl-1,3-dihydro-indol-2-one

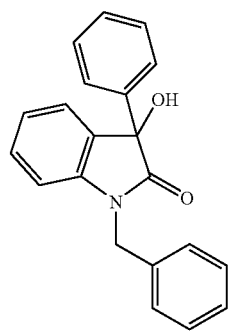

Combine 3-hydroxy-3-phenyl-1,3-dihydro-indol-2-one (225 mg, 1 mmol) and cesium carbonate (977 mg, 3 mmol) in 2-butanone (5 mL). Add benzyl bromide (0.13 mL, 1 mmol) and heat at 60° C. for 3 h. with vigorous stirring. Dilute the reaction with water and wash with ethyl acetate (2×). Wash combined organic portions with brine and then dry ($MgSO_4$), filter and concentrate in vacuo to give an oil. Purify with radial chromatography (gradient of 10% EtOAc/hexanes to 25% EtOAc/hexanes) to give 204 mg (65%) of the title compound as a white solid. MS (ES): m/z=298 (M+1−$H_2O$); $^1$H NMR(DMSO-$d_6$); δ7.37-7.27 (m, 11H), 7.18 (m, 1H), 7.05 (m, 1H), 6.98 (m, 1H), 6.87 (s, 1H), 4.92 (s, 2H).

PREPARATION 21

1-Benzyl-3-(3,5-dimethyl-phenyl)-3-hydroxy-1,3-dihydro-indol-2-one

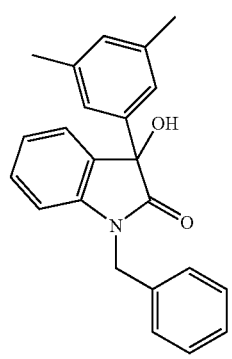

Using a method similar to Preparation 17 with 3-(3,5-dimethyl-phenyl)-3-hydroxy-1,3-dihydro-indol-2-one (50 mg, 0.20 mmol), 2-tert-butylimino-2-diethylamino-1,3-dimethyl-perhydro-1,3,2-diazaphosphorine (0.065 ml, 0.22 mmol) and benzyl bromide (0.024 mL, 0.20 mmol) in acetonitrile (1 mL) gives 68 mg (100%) of the title compound which was used without further purification.

EXAMPLE 27

1-Benzyl-3-(4-hydroxy-3,5-dimethyl-phenyl)-3-phenyl-1,3-dihydro-indol-2-one

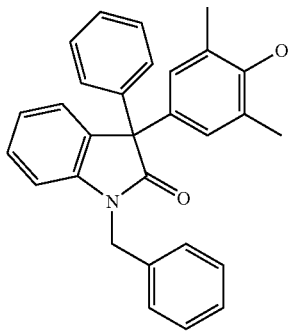

Using a method similar to Example 12, with 1-benzyl-3-hydroxy-3-phenyl-1,3-dihydro-indol-2-one (107 mg, 0.34 mmol), 2,6-dimethylphenol (208 mg, 1.7 mmol) in trifluoromethanesulfonic acid (1 mL) gives 320 mg of crude material. Purify by flash chromatography (CH$_2$Cl$_2$ and 5% MeOH/CH$_2$Cl$_2$) gives 75 mg (53%) of the title compound as a light yellow powder. MS (ES): m/z=420 (M+1), 418 (M−1); $^1$H NMR(DMSO-d$_6$): δ8.31 (s, 1H), 7.36-7.23 (m, 10H), 7.20-7.16 (m, 2H), 7.07 (t, J=6.9, 7.7 Hz, 2H), 6.70 (s, 2H), 5.00 (s, 2H), 2.07 (s, 6H).

EXAMPLE 28

1-Benzyl-3-(3,5-dimethyl-phenyl)-3-(4-hydroxy-3,5-dimethyl-phenyl)-1,3-dihydro-indol-2-one

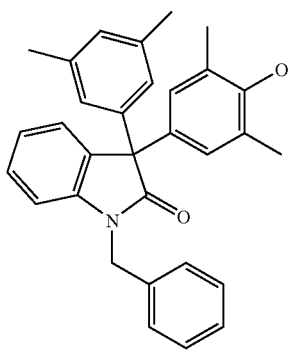

Dissolve 1-benzyl-3-(3,5-dimethyl-phenyl)-3-hydroxy-1,3-dihydro-indol-2-one (68 mg, 0.2 mmol) and 2,6-dimethylphenol (122 mg, 1.0 mmol) in trifluoroacetic acid (1 mL) and stir at room temperature for 30 min. Pour the reaction over ice water and extract with ethyl acetate (2×). Wash combined organic portions with brine and then dry (Na$_2$SO$_4$), filter and concentrate in vacuo to give an oily residue. Purify with radial chromatography (gradient of 1 EtOAc/9 hexanes and then 1 EtOAc/5 hexanes) to give 55 mg (62%) of the title compound as a white solid. MS (ES): m/z=448 (M+1), 446 (M−1); $^1$H NMR(DMSO-d$_6$): δ8.29 (s, 1H), 7.38-7.22 (m, 7H), 7.07 (m, 2H), 6.90 (s, 1H), 6.75 (s, 2H), 6.71 (s, 2H), 4.99 (s, 2H), 2.19 (s, 6H), 2.08 (s, 6H).

PREPARATION 22

5-bromo-1,3-dimethyl-2-(phenylmethoxy)-benzene

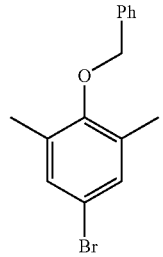

Dissolve 4-bromo-2,6-dimethyl-phenol (20.1 g, 100 mmol) in DMF (250 mL) under nitrogen. Add cesium carbonate (48.9 g, 150 mmol) and benzyl bromide (13.1 mL, 110 mmol) and heat at 70° C. stirring mechanically for 6 h. Dilute with water (400 mL) and extract with 3/1 diethyl ether/hexanes (2×400 mL). Wash combined organics with brine (300 mL) and then dry (MgSO$_4$), filter and concentrate in vacuo to give 28.67 g (99%) of the title compound as an oil which solidified on standing. $^1$H NMR(CDCl$_3$): δ7.51-7.37 (m, 5H), 7.22 (s, 2H), 4.82 (s, 2H), 2.31 (s, 6H).

PREPARATION 23

1-Benzyl-3-(4-benzyloxy-3,5-dimethyl-phenyl)-3-hydroxy-1,3-dihydro-indol-2-one

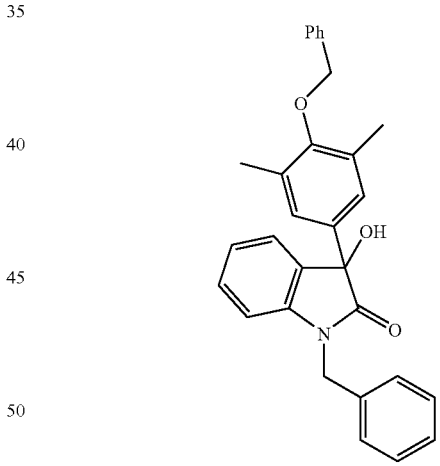

Dissolve 5-bromo-1,3-dimethyl-2-(phenylmethoxy)-benzene (2.56 g, 8.8 mmol) in ethylene glycol dimethyl ether (40 mL) under nitrogen. Cool to −70° C. with a dry ice/acetone bath and add slowly a 1.7M solution of t-butyllithium in pentane (10.4 mL, 17.6 mmol). After 15 min add 1-benzyl-1H-indole-2,3-dione (1.90 g, 8 mmol) in ethylene glycol dimethyl ether (32 mL). Remove the bath and allow to warm to room temperature with stirring for 18 h. Quench with saturated NH$_4$Cl solution and extract with ethyl acetate (2×). Wash combined organics with brine and then dry (Na$_2$SO$_4$), filter and concentrate in vacuo to give 3.42 g of a dark purple oil. Purify initially by flash chromatography (25% EtOAC/hexanes) to give 1.20 g of material which by TLC is mostly starting material and product. Purify further by chromatography (step gradient of CH₂Cl₂, 5% acetonitrile/CH₂Cl₂, 10% acetonitrile/CH₂Cl₂) to give 803 mg (22%) of the title compound as a yellow foam. MS (ES): m/z=432 (M+1−H₂O); ¹H NMR(DMSO-d₆); δ7.50-7.18 (m, 12H), 7.00 (m, 2H), 6.95 (s, 2H), 6.77 (s, 1H), 4.93 (q, J=2 Hz, J=18 Hz, 2H), 4.77 (s, 2H), 2.20 (s, 6H).

EXAMPLE 29

1-Benzyl-3-(4-hydroxy-3,5-dimethyl-phenyl)-3-(4-hydroxy-phenyl)-1,3-dihydro-indol-2-one

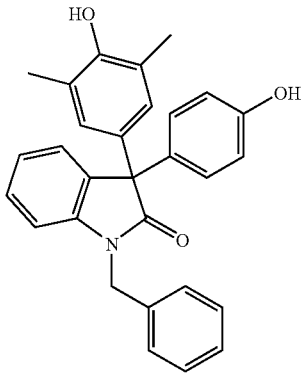

Using a method similar to Example 28, with 1-benzyl-3-(4-benzyloxy-3,5-dimethyl-phenyl)-3-hydroxy-1,3-dihydro-indol-2-one (180 mg, 0.4 mmol) and phenol (150 mg, 1.6 mmol) in TFA (2 mL) gave 0.34 g of crude material. Purify by radial chromatography (CH₂Cl₂ up to 4% MeOH/CH₂Cl₂) to give 37 mg (21%) of the title compound as a pale yellow solid. MS (ES): m/z=436 (M+1), 434 (M−1); ¹H NMR(DMSO-d₆): δ9.44 (s, 1H), 8.26 (s, 1H), 7.37-7.23 (m, 7H), 7.08-6.96 (m, 4H), 6.70 (m, 4H), 4.98 (s, 2H), 2.07 (s, 6H).

PREPARATION 24

3-Hydroxy-3-(4-methoxy-3,5-dimethyl-phenyl)-1,3-dihydro-indol-2-one

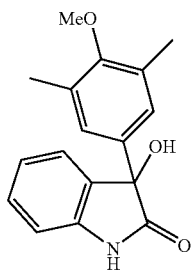

Using a method similar to Preparation 18 with isatin (1.77 g, 12 mmol) a 0.5M solution of 3,5-dimethyl-4-methoxyphenylmagnesium bromide in THF (50 mL, 25 mmol) gives 2.70 g (84%) of a yellow solid. MS (ES): m/z=266 (M+1−H₂O), 282 (M−1); ¹H NMR(DMSO-d₆): δ10.35 (s, 1H), 7.24 (dt, J=1.3 Hz, J=7.6 Hz, 1H), 7.10 (d, J=6.4 Hz, 1H), 6.98 (dd, J=0.9 Hz, J=7.5 Hz, 1H), 6.90 (m, 3H), 6.50 (s, 1H), 3.62 (s, 3H), 2.17 (s, 6H).

PREPARATION 25

1-(2-Chloro-benzyl)-3-hydroxy-3-(4-methoxy-3,5-dimethyl-phenyl)-1,3-dihydro-indol-2-one

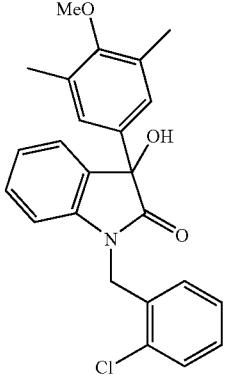

Using a method similar to Preparation 17, with 3-hydroxy-3-(4-methoxy-3,5-dimethyl-phenyl)-1,3-dihydro-indol-2-one (1.56 g, 5.8 mmol), 2-tert-butylimino-2-diethylamino-1,3-dimethyl-perhydro-1,3,2-diazaphosphorine (1.85 ml, 6.4 mmol) and 2-chlorobenzyl bromide (0.862 mL, 5.8 mmol) in acetonitrile (30 mL) gives 2.81 g of crude material. Purify by flash chromatography (gradient of CH₂Cl₂ to 5% EtOAc/CH₂Cl₂) gives 1.69 g (72%) of the title compound as a white foam. MS (ES): m/z=390, 392 (M+1−H₂O); ¹H NMR(DMSO-d₆): δ7.54 (m, 1H), 7.36-7.28 (m, 3H), 7.24-7.19 (m, 2H), 7.06 (t, J=7.5 Hz, 1H), 6.98 (s, 2H), 6.89 (d, J=7;7 Hz, 1H), 6.80 (s, 1H), 4.98 (abq, J=16.8 Hz, 2H), 3.63 (s, 3H), 2.18 (s, 6H).

PREPARATION 26

1-(2-Chloro-benzyl)-3-(4-methoxy-3,5-dimethyl-phenyl)-1,3-dihydro-indol-2-one

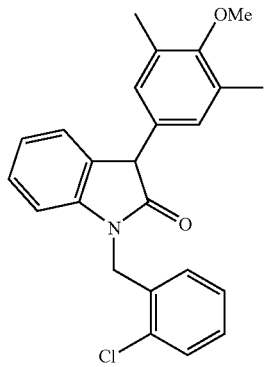

Dissolve 1-(2-chloro-benzyl)-3-hydroxy-3-(4-methoxy-3,5-dimethyl-phenyl)-1,3-dihydro-indol-2-one (430 mg, 1.05 mmol) in dichloroethane (15 mL) and treat with triethylsilane (0.503 mL, 3.15 mmol) and boron trifluoride diethyl etherate (0.038 mL, 0.3 mmol) under nitrogen. Heat at 50° C. for 24 h. Add more triethyl silane (0.250 mL, 1.57 mmol) and boron trifluoride diethyl etherate (0.030 mL, 0.24 mmol) and continue for 6 h. at which time reaction complete. Concentrate in vacuo and purify by flash chromatography (gradient of 5% EtOAc/hexanes to 25% EtOAc/hexanes) to obtain 319 mg (78%) of the title compound as a white solid. MS (ES): m/z=392 (M+1), 390 (M−1); ¹H NMR(DMSO-d₆): δ7.54 (m, 1H), 7.36-7.29 (m, 2H), 7.25 (t, J=7.9, 7.6 Hz, 1H), 7.18-7.13 (m, 2H), 7.03 (t, J=7.4 Hz, 1H), 6.88 (d, J=7.9 Hz, 1H), 6.85 (s, 2H), 5.02 (s, 2H), 4.90 (s, 1H), 3.65 (s, 3H), 2.20 (s, 6H).

PREPARATION 27

1-(2-Chloro-benzyl)-3-(4-methoxy-3,5-dimethyl-phenyl)-3-(4-nitro-phenyl)-1,3-dihydro-indol-2-one

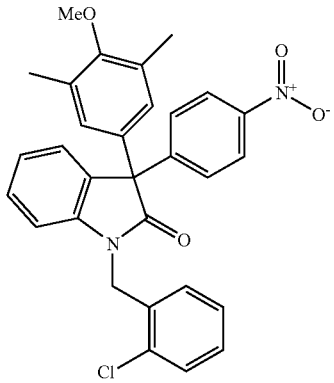

Dissolve 1-(2-chloro-benzyl)-3-(4-methoxy-3,5-dimethyl-phenyl)-1,3-dihydro-indol-2-one (222 mg, 0.57 mmol) in anhydrous DMF (5 mL) under nitrogen. Cool in an ice bath and add at 5-8° C. a 0.5M solution of potassium bis(trimethylsilyl)amide (1.2 mL, 0.6 mmol). After 10 min. remove the ice bath and allow to warm to 20° C. over 30 min. Add 1-fluoro-4-nitrobenzene (0.21 mL, 2 mmol) and heat at 80° C. for 3 h. Allow to cool to room temperature and partition between saturated NH$_4$Cl solution (25 mL) and ethyl acetate (50 mL). Separate, dilute aqueous portion with water (25 mL) and extract with ethyl acetate (2×50 mL). Combine all organic portions and wash with 1N HCl (50 mL) and brine (50 mL). Dry (MgSO$_4$), filter and concentrate in vacuo to give 704 mg of a yellow oil. Purify by flash chromatography (gradient of 50% hexanes/CH$_2$Cl$_2$ to 100% CH$_2$Cl$_2$) to give 259 mg (89%) of the title compound as a light yellow foam. MS (FAB, M+1): calcd for C$_{30}$H$_{25}$ClN$_2$O$_4$ 513.1581. found 513.1577; $^1$H NMR (DMSO-d$_6$): □8.23 (m, 2H), 7.55-4.63 (m, 4H), 7.35-7.27 (m, 3H), 7.16 (t, J=7.5, 6.8 Hz, 1H), 7.02 (m, 2H), 6.86 (s, 2H), 5.11 (s, 2H), 3.65 (s, 3H), 2.16 (s, 6H). Anal. Calcd for C$_{30}$H$_{25}$ClN$_2$O$_4$: C, 70.24; H, 4.91; N, 5.47. Found C, 70.05; H, 5.19; N, 5.42.

EXAMPLE 30

1-(2-Chloro-benzyl)-3-(4-hydroxy-3,5-dimethyl-phenyl)-3-(4-nitro-phenyl)-1,3-dihydro-indol-2-one

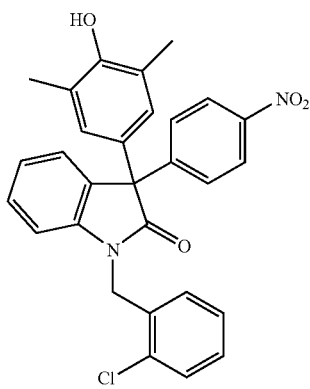

Evaporate 1-(2-chloro-benzyl)-3-(4-methoxy-3,5-dimethyl-phenyl)-3-(4-nitro-phenyl)-1,3-dihydro-indol-2-one (62 mg, 0.12 mmol) into a vial and add pyridine hydrochloride (300-500 mg). Suspend the vial, by means of a copper wire, in an oil bath heated to 180-200° C. so that the entire vial, except the cap, is immersed in the bath. When the pyridine hydrochloride melts, stir to effect a homogeneous solution. Heat for 1.5 h and then allow to cool. Treat the resulting solid with 1N HCl solution and ethyl acetate until all solids are dissolved and transferred to a separatory funnel. Extract the aqueous portion with ethyl acetate (2×). Combine the organic portions and wash with brine, then dry (MgSO$_4$), filter and concentrate in vacuo to give a yellow gum. Purify by flash chromatography (gradient of 10% EtOAc/hexanes to 33% EtOAc/hexanes) followed by trituration in diethyl ether and drying under house vacuum to obtain 24 mg (40%) of the title compound as a pale yellow solid. MS (ES): m/z=499 (M+1), 497 (M−1); $^1$H NMR (DMSO-d$_6$): δ8.43 (s, 1H), 8.24 (d, J=9 Hz, 2H), 7.57-7.43 (m, 4H), 7.37-7.23 (m, 3H), 7.15 (t, J=8 Hz, 1H), 7.01 (m, 2H), 6.76 (s, 2H), 5.11 (s, 2H), 2.12 (s, 6H).

PREPARATION 28

3-(4-Amino-phenyl)-1-(2-chloro-benzyl)-3-(4-methoxy-3,5-dimethyl-phenyl)-1,3-dihydro-indol-2-one

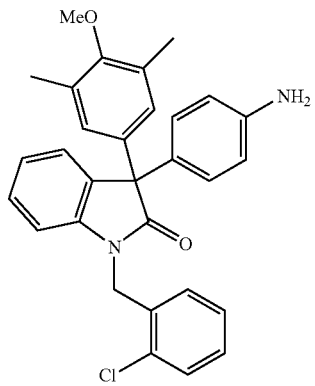

Dissolve nickelous chloride (36 mg, 0.15 mmol) in methanol (3 mL). Add sodium borohydride (17 mg) followed 1-(2-chloro-benzyl)-3-(4-hydroxy-3,5-dimethyl-phenyl)-3-(4-nitro-phenyl)-1,3-dihydro-indol-2-one (152 mg, 0.3 mmol) in THF (3 mL). Add additional sodium borohydride and stir at room temperature for 30 min. Concentrate to dryness and partition the resulting residue in water/ethyl acetate. Separate and extract aqueous with ethyl acetate (2×). Wash combined organic portions with brine and then dry (MgSO$_4$), filter and concentrate in vacuo to give 145 mg of residue. Purify by flash chromatography (gradient of 10% EtOAc/hexanes to 50% EtOAc/hexanes) to give 97 mg (67%) of the title compound as a white foam. MS (ES): m/z=483 (M+1); $^1$H NMR(DMSO-d$_6$): δ9.99 (s, 1H), 7.53 (m, 3H), 7.36-7.24 (m, 4H), 7.10 (t, J=8 Hz, 1H), 6.95 (m, 2H), 6.85 (m, 4H), 6.52 (d, J=8.5 Hz), 5.19 (bs, 2H), 5.06 (s, 2H) 3.65 (s, 3H), 2.16 (s, 6H).

PREPARATION 29

N-{4-[1-(2-Chloro-benzyl)-3-(4-methoxy-3,5-dimethyl-phenyl)-2-oxo-2,3-dihydro-1H-indol-3-yl]-phenyl}-acetamide

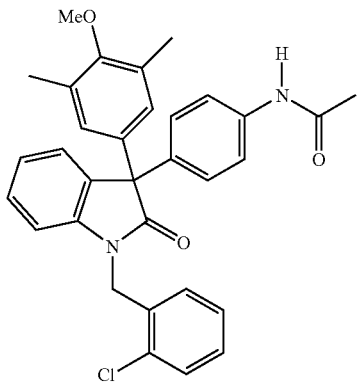

Combine 3-(4-amino-phenyl)-1-(2-chloro-benzyl)-3-(4-methoxy-3,5-dimethyl-phenyl)-1,3-dihydro-indol-2-one (126 mg, 0.26 mmol), N,N-diisopropylethylamine (0.068 mL, 0.39 mmol) and acetyl chloride (0.020 mL, 0.29 mmol) in $CH_2Cl_2$ (1 mL) and stirred at room temperature for 48 h. Dilute with $CH_2Cl_2$ and wash with water. Backwash water with $CH_2Cl_2$ and ethyl acetate. Combine all organics, dilute with more $CH_2Cl_2$ and wash with 1N HCl and brine. Dry ($MgSO_4$), filter and concentrate in vacuo to give a residual foam. Purify by flash chromatography (gradient of 33% EtOAc/hexanes to 66% EtOAc/hexanes) to give 129 mg (67%) of the title compound as a white foam. MS (ES): m/z=525 (M+1), 523 (M−1); $^1$H NMR(DMSO-$d_6$): δ9.99 (s, 1H), 7.53 (m, 3H), 7.41-7.26 (m, 4H), 7.12 (m, 3H), 6.98 (m, 2H), 6.82 (s, 2H), 5.08 (s, 2H), 3.64 (s, 3H), 2.15 (s, 6H).

EXAMPLE 31

N-{4-[1-(2-Chloro-benzyl)-3-(4-hydroxy-3,5-dimethyl-phenyl)-2-oxo-2,3-dihydro-1H-indol-3-yl]-phenyl}-acetamide

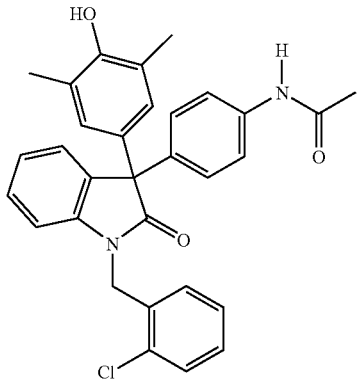

Using a method similar to Example 30, with N-{4-[1-(2-chloro-benzyl)-3-(4-methoxy-3,5-dimethyl-phenyl)-2-oxo-2,3-dihydro-1H-indol-3-yl]-phenyl}-acetamide (119 mg, 0.23 mmol) and pyridine hydrochloride (400-450 mg) in an oil bath at 195-200° C. for 30 min. gave a crude brown gum which contained two entities by TLC (50% EtOAc/hexanes). Purify and separate by radial chromatography (step gradient of 20% EtOAc/hexanes, 25% EtOAc/hexanes, 33% EtOAc/hexanes and 50% EtOAc/hexanes to obtain 42 mg (36%) of the title compound. MS (ES): m/z=511 (M+1), 509 (M−1); $^1$H NMR(DMSO-$d_6$): δ9.97 (s, 1H), 8.30 (s, 1H), 7.53 (m, 3H), 7.37-7.22 (m, 4H), 7.10 (m, 15 3H), 7.10 (t, J=5.7, 6.4, 2H), 6.72 (s, 2H), 5.07 (s, 2H), 2.09 (s, 6H), 2.03 (s, 3H).

EXAMPLE 32

3-(4-Amino-phenyl)-1-(2-chloro-benzyl)-3-(4-hydroxy-3,5-dimethyl-phenyl)-1,3-dihydro-indol-2-one

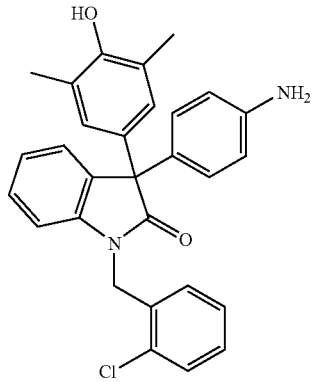

The procedure of Example 28 yields a second product from radial chromatography, 32 mg (30%) of the title compound. MS (ES): m/z=469 (M+1), 467 (M−1); $^1$H NMR(DMSO-$d_6$): δ8.11 (s, 1H), 7.40 (dd, J=1.2 Hz, J=7.8 Hz, 1H), 7.23-7.07 (m, 4H), 6.95 (t, J=7.3, 7.7 Hz, 1H), 6.80 (m, 2H), 6.71 (d, J=8.6 Hz, 2H), 6.58 (s, 2H), 6.37 (d, J=8.6 Hz, 2H), 5.10 (bs, 2H), 4.92 (s, 2H), 3.64 (s, 3H), 1.95 (s, 6H).

PREPARATION 30

N-{4-[1-(2-Chloro-benzyl)-3-(4-methoxy-3,5-dimethyl-phenyl)-2-oxo-2,3-dihydro-1H-indol-3-yl]-phenyl}-N-(methylsulfonyl)-methanesulfonamide

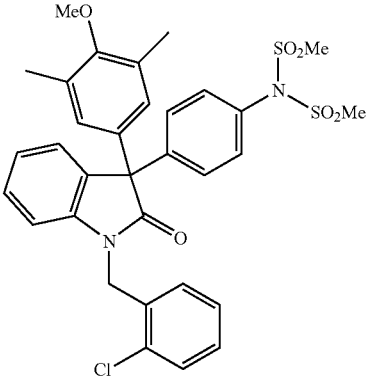

Combine 3-(4-amino-phenyl)-1-(2-chloro-benzyl)-3-(4-methoxy-3,5-dimethyl-phenyl)-1,3-dihydro-indol-2-one (73 mg, 0.15 mmol), N,N-diisopropylethylamine (0.040 mL, 0.23 mmol) and methanesulfonyl chloride (0.013 mL, 0.165 mmol) in $CH_2Cl_2$ (1 mL). After 5 h. stirring at room temperature TlC (50% EtOAc/hexanes) shows reaction not complete. Add more N,N-diisopropylethylamine (0.040 mL, 0.23 mmol) and methanesulfonyl chloride (0.013 mL, 0.165 mmol) and stir 2 h. more at which time reaction complete. Dilute with ethyl acetate and wash with water amd brine. Dry ($MgSO_4$), filter and concentrate in vacuo to give 96 mg of a residue. Purify by radial chromatography (step gradient of 10% EtOAc/hexanes, 20% EtOAc/hexanes, 25% EtOAc/hexanes and 33% EtOAc/hexanes to obtain 56 mg (58%) of the title compound. MS (ES): m/z=639 (M+1); $^1$H NMR (DMSO-d$_6$); δ7.54-7.45 (m, 4H), 7.37-7.22 (m, 5H), 7.15 (t, J=7.5, 1H), 7.00 (m, 2H), 6.87 (s, 2H), 5.09 (s, 2H), 3.64 (s, 3H), 3.53 (s, 6H), 2.17 (s, 6H).

EXAMPLE 33

N-{4-[1-(2-Chloro-benzyl)-3-(4-methoxy-3,5-dimethyl-phenyl)-2-oxo-2,3-dihydro-1H-indol-3-yl]-phenyl}-methanesulfonamide

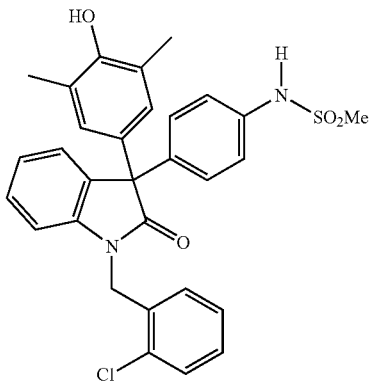

Using a method similar to Example 30, with N-{4-[1-(2-chloro-benzyl)-3-(4-methoxy-3,5-dimethyl-phenyl)-2-oxo-2,3-dihydro-1H-indol-3-yl]-phenyl}-N-(methylsulfonyl)-methanesulfonamide (52 mg, 0.094 mmol) in pyridine hydrochloride (300 mg) gives 44 mg of crude material. Purify by radial chromatography (10% EtOAc/hexanes, 25% EtOAc/hexanes) to give 6 mg (13%) of the title compound. MS (ES): m/z=547 (M+1), 545 (M−1); $^1$H NMR(DMSO-d$_6$): δ9.80 (s, 1H), 8.32 (s, 1H), 7.54 (dd, J=1.2 Hz, J=7.8 Hz, 1H), 7.38-7.22 (m, 4H), 7.16 (s, 4H), 7.11 (t, J=8.0 Hz, 7.3 Hz, 1H), 6.98 (m, 2H), 6.72 (s, 2H), 5.07 (s, 2H), 3.01 (s, 3H), 2.09 (s, 6H).

EXAMPLE 34

3-(4-Amino-3,5-dimethyl-phenyl)-1-(2-chloro-benzyl)-3-(4-methoxy-3,5-dimethyl-phenyl)-1,3-dihydro-indol-2-one

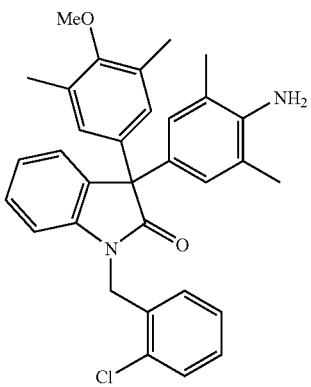

Using a method similar to Example 28, with 1-(2-chlorobenzyl)-3-hydroxy-3-(4-methoxy-3,5-dimethyl-phenyl)-1,3-dihydro-indol-2-one (142 mg, 0.35 mmol) and 0.173 mL, 1.4 mmol) trifluoroacetic acid (2 mL) gives crude material. During workup wash organic portion with 1N NaOH (2×) to free aniline from TFA salt. Purify by flash chromatography (33% EtOAc/hexanes) to give 152 mg (85%) of the title compound. MS (ES): m/z=511 (M+1); $^1$H NMR(DMSO-d$_6$): δ7.55 (dd, J=1.0 Hz, J=7.8 Hz, 1H), 7.47-7.22 (m, 4H), 7.08 (t, J=8.0 Hz, 1H), 6.97 (m, 2H), 6.83 (s, 2H), 6.65 (s, 2H), 5.06 (s, 2H), 4.60 (bs, 2H), 3.64 (s, 3H), 3.01 (s, 3H), 2.16 (s, 6H), 2.02 (s, 6H).

EXAMPLE 35

3-(4-Amino-3,5-dimethyl-phenyl)-1-(2-chloro-benzyl)-3-(4-hydroxy-3,5-dimethyl-phenyl)-1,3-dihydro-indol-2-one

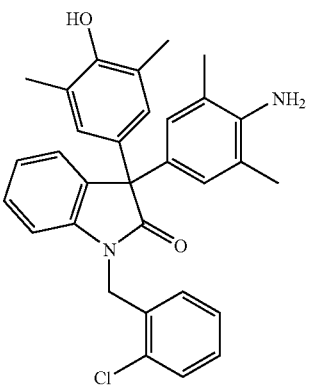

Using a method similar to Example 30, with 3-(4-amino-3,5-dimethyl-phenyl)-1-(2-chloro-benzyl)-3-(4-methoxy-3,5-dimethyl-phenyl)-1,3-dihydro-indol-2-one (152 mg, 0.30 mmol) in pyridine hydrochloride (500 mg) gives 267 mg of crude materil. Wash the organic portions with 0.5N NaOH (2×) during the workup. Purify by flash chromatography (gradient of 10% EtOAc/hexanes to 50% EtOAc/hexanes) to give 82 mg (54%) of the title compound as a pale yellow solid. MS (ES): m/z=497 (M+1), 495 (M−1); $^1$H NMR (DMSO-d$_6$): δ8.23 (s, 1H), 7.54 (dd, J=1.0 Hz, J=7.8 Hz, 1H), 7.36-7.20 (m, 4H), 7.08 (t, J=7.3 Hz, 1H), 6.97 (m, 1H), 6.92 (d, J=7.7 Hz, 1H), 6.72 (s, 2H), 6.63 (s, 2H), 5.04 (s, 2H), 4.59 (bs, 2H), 3.64 (s, 3H), 3.01 (s, 3H), 2.08 (s, 6H), 2.00 (s, 6H).

PREPARATION 31

(4-Bromo-2,6-dimethyl-phenoxy)-tert-butyl-dimethyl-silane

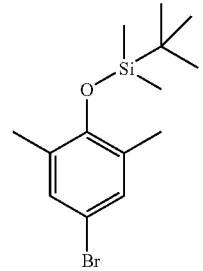

Dissolve 4-bromo-2,6-dimethylphenol (30.16 g, 150 mmol) and imidazole (26.6 g, 390 mmol) in CH$_2$Cl$_2$. Added t-butyldimethylchlorosilane (36.17 g, 240 mmol) and stirred mechanically for 3 h. The solids were vacuum filtered and the filtrate concentrated. Suspended the resulting residue in water and extracted with ethyl acetate (2×150 mL). The combined organic portions were washed with water (150 mL) and brine (150 mL) and then dried (Na$_2$SO$_4$), filtered and concentrated in vacuo to give a light brown oil. Purify on a Waters Prep 2000 LC (hexanes) to give 40.96 g of the title compound as a clear liquid. $^1$H NMR(CDCl$_3$): δ6.91 (s, 2H), 2.00 (s, 6H), 0.86 (s, 9H), 0.01 (s, 6H).

PREPARATION 32

3-[4-(tert-Butyl-dimethyl-silanyloxy)-3,5-dimethyl-phenyl]-3-hydroxy-1,3-dihydro-indol-2-one

Dissolve (4-bromo-2,6-dimethyl-phenoxy)-tert-butyl-dimethyl-silane (15.77 g, 50 mmol) in anhydrous THF (250 mL) under nitrogen and cool in a dry ice/acetone bath. Add slowly at −75 to −70° C. 1.6M n-butyl lithium in hexane (31.3 mL, 55 mmol). Stir the resulting white precipitate at −75° C. for 30 min. Add isatin (3.68 g, 25 mmol) as a solid while maintaing positive nitrogen pressure. Remove some dry ice and allow the reaction to warm up slowly to −30 to −40° C. over 3 h and then to 15° C. over 1 h. Pour the reaction into NH$_4$Cl solution and wash with EtOAc (2×500 mL, 250 mL). Wash combined organic portions with water (500 mL) and brine (500 mL). Dry (MgSO$_4$), filter and concentrate in vacuo to give 14.8 g of a yellow solid. Triturate in hexane/ether/CH$_2$Cl$_2$, filter and air dry to give 6.0 g (63%) of the title compound as a pale yellow solid. MS (ES): m/z=383 (M−1); $^1$H NMR(DMSO-d$_6$): δ10.14 (s, 1H), 7.07 (dt, J=1.1 Hz, J=7.6 Hz, 1H), 6.95 (d, J=7.0 Hz, 1H), 6.80 (t, J=7.3 Hz, 1H), 6.72 (m, 3H), 6.27 (s, 1H), 1.95 (s, 6H), 0.83 (s, 9H), 0.00 (s, 6H).

PREPARATION 33

1-Benzyl-3-[4-(tert-butyl-dimethyl-silanyloxy)-3,5-dimethyl-phenyl]-3-hydroxy-1,3-dihydro-indol-2-one

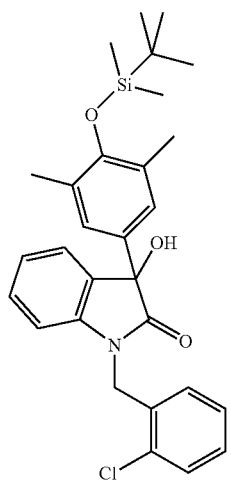

Using a method similar to Preparation 17 with 3-[4-(tert-butyl-dimethyl-silanyloxy)-3,5-dimethyl-phenyl]-3-hydroxy-1,3-dihydro-indol-2-one (3.83 g, 10 mmol), 2-tert-butylimino-2-diethylamino-1,3-dimethyl-perhydro-1,3,2-diazaphosphorine (3.5 ml, 12 mmol) and 2-chlorobenzyl bromide (1.56 mL, 12 mmol) in acetonitrile/DMF (60 mL/20 mL) gives 5.9 g of a crude yellow gum. Purify by flash chromatography (CH$_2$Cl$_2$ to 10% EtOAc/CH$_2$Cl$_2$) gives 3.84 g (76%) of the title compound as a white solid. Mp 147.1° C. MS (ES): m/z=490 (M+1−H$_2$O); $^1$H NMR (DMSO-d$_6$): δ7.52 (dd, J=1.7, 1.4 Hz, J=7.7, 7.4 Hz, 1H), 7.37-7.14 (m, 5H), 7.05 (t, J=7.7 Hz, 1H), 6.93 (s, 2H), 6.86 (d, J=7.7 Hz, 1H), 6.73 (s, 1H), 4.96 (abq, 2H), 2.11 (s, 6H), 0.98 (s, 9H), 0.16 (s, 6H).

PREPARATION 34

1-Benzyl-3-hydroxy-3-(4-hydroxy-3,5-dimethyl-phenyl)-1,3-dihydro-indol-2-one

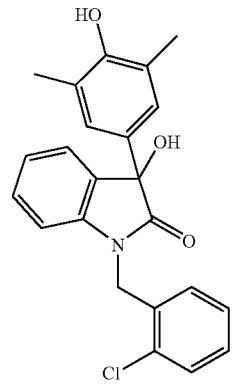

Dissolve 1-benzyl-3-[4-(tert-butyl-dimethyl-silanyloxy)-3,5-dimethyl-phenyl]-3-hydroxy-1,3-dihydro-indol-2-one (152 mg, 0.3 mmol) in THF (5 mL) and treat with 1.0M in THF tetrabutylammonium fluoride (0.36 mL, 0.36 mmol) for 6 h. Pour into ethyl acetate (25 mL) and wash with water (3×25 mL) and brine (25 mL). Dry (MgSO$_4$), filter and concentrate in vacuo to give a summy residue. Purify by flash chromatography (gradient of 5% EtOAc/hexanes to 50% EtOAc/hexanes) to give 116 mg (98%) of the title compound as a white solid. MS (ES): m/z=376 (M+1−H$_2$O); $^1$H NMR(DMSO-d$_6$): δ8.26 (s, 1H), 7.54 (dd, J=1.7, 1.4 Hz, J=7.7, 7.4 Hz, 1H), 7.38-7.15 (m, 5H), 7.05 (t, J=7.4 Hz, 1H), 6.85 (m, 3H), 6.65 (s, 1H), 4.96 (q, 2H), 2.12 (s, 6H).

EXAMPLE 36

1-(2-Chloro-benzyl)-3-(4-hydroxy-3,5-dimethyl-phenyl)-3-(4-hydroxy-phenyl)-1,3-dihydro-indol-2-one

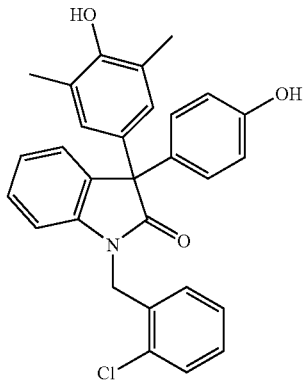

Using a method similar to Example 31, 1-benzyl-3-hydroxy-3-(4-hydroxy-3,5-dimethyl-phenyl)-1,3-dihydro-indol-2-one (61 mg, 0.16 mmol) and phenol (58 mg, 0.62 mmol) in TFA (2.5 mL) gives 80 mg of a crude residue. Purify by flash chromatography (gradient of 5% THF (inhibitor free)/hexanes to 40% THF/hexanes) to give 38 mg (52%) of the title compound as a pink solid. MS (ES): m/z=470 (M+1), 468 (M−1); $^1$H NMR(DMSO-d$_6$); δ9.45 (s, 1H), 8.27 (s, 1H), 7.54 (dd, J=1.2 Hz, J=7.9, Hz, 1H), 7.36-7.22 (m, 4H), 7.09 (t, J=7.3, 7.6 Hz, 1H), 7.01-6.92 (m, 4H), 6.72 (m, 4H), 5.06 (s, 2H), 2.08 (s, 6H).

PREPARATION 35

3-[4-(tert-Butyl-dimethyl-silanyloxy)-3,5-dimethyl-phenyl]-1-(2-chloro-benzyl)-1,3-dihydro-indol-2-one

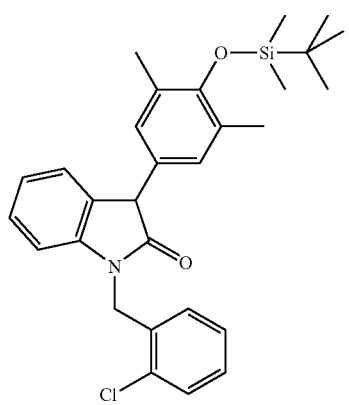

Using a method similar to Preparation 26, with 1-benzyl-3-hydroxy-3-(4-hydroxy-3,5-dimethyl-phenyl)-1,3-dihydro-indol-2-one (1.52 g, 3.0 mmol), triethylsilane (1.44 mL, 9.0 mmol) and boron trifluoride diethyl etherate (0.127 mL, 1.0 mmol) in dichloroethane (75 mL) and heating at 70° C. for 30 min. gives 1.78 g of a crude oil. Purify by flash chromatography (gradient of 10% EtOAc/hexanes to 25% EtOAC/hexanes) to give 967 mg (66%) of the title compound as an amorphous gum. MS (ES): m/z=492 (M+1), 490 (M−1); $^1$H NMR(DMSO-d$_6$): δ7.54 (m, 1H), 7.34-7.20 (m, 3H), 7.12 (m, 2H), 7.02 (t, J=7.4 Hz, 1H), 6.85 (d, J=7.8 Hz, 1H), 6.80 (s, 2H), 5.00 (s, 2H), 4.85 (s, 1H), 2.13 (s, 6H), 0.99 (s, 9H), 0.17 (s, 6H).

EXAMPLE 37

1-(2-Chloro-benzyl)-3-(4-hydroxy-3,5-dimethyl-phenyl)-3-methyl-1,3-dihydro-indol-2-one

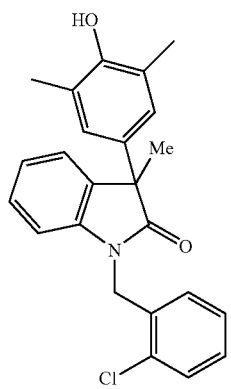

Dissolve 3-[4-(tert-butyl-dimethyl-silanyloxy)-3,5-dimethyl-phenyl]-1-(2-chloro-benzyl)-1,3-dihydro-indol-2-one (150 mg, 0.31 mmol) in anhydrous DMF (3 mL) under nitrogen and cool in an ice bath. Add a 0.5M solution of potassium bis(trimethylsilyl)amide (0.622 mL, 0.31 mmol) and stir 10 min. Add iodomethane (0.020 mL, 0.31 mmol) and after 30 min remove the ice bath and allow the reaction to warm to room temperature. After 2.5 h treat the reaction with a 1.0M solution of tetrabutylammonium fluoride (0.35 mL, 0.35 mmol) and stir 2 h. Pour the reaction into 1N HCl (20 mL) and extract with ethyl acetate (3×20 mL). Wash the combined organic portions with brine, dry (MgSO$_4$), filter and concentrate in vacuo to obtain a crude orange oil. Purify by flash chromatography (gradient of 5% EtOAc/hexanes to 33% EtOAc/hexanes) to give 70 mg (58%) of the title compound as a pink solid. MS (ES): m/z=392 (M+1), 390 (M−1); $^1$H NMR(DMSO-d$_6$): δ8.23 (s, 1H), 7.54 (dd, J=1.9, 1.5 Hz, J=7.5, 7.3 Hz, 1H), 7.38-7.20 (m, 4H), 7.09-7.02 (m, 2H), 6.89 (d, J=7.6 Hz, 1H), 6.80 (s, 2H), 5.02 (s, 2H), 2.11 (s, 6H), 1.70 (s, 3H).

EXAMPLE 38

1-(2-Chloro-benzyl)-3-(4-hydroxy-3,5-dimethyl-phenyl)-3-(3-hydroxy-propyl)-1,3-dihydro-indol-2-one

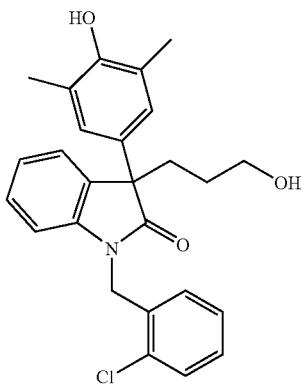

Using a method similar to Example 37, with 3-[4-(tert-butyl-dimethyl-silanyloxy)-3,5-dimethyl-phenyl]-1-(2-chloro-benzyl)-1,3-dihydro-indol-2-one (150 mg, 0.31 mmol), a 0.5M solution of potassium bis(trimethylsilyl)amide (0.622 mL, 0.31 mmol), and (3-bromopropoxy)-tert-butyldimethylsilane (0.072 mL, 0.31 mmol) in DMF (3 mL) followed by treatment with TBAF (0.70 mL, 0.70 mmol) gives a crude brown gum. Purify by flash chromatography (gradient of 25% EtOAc/hexanes to 50% EtOAc/hexanes) to give 68 mg (51%) of the title compound as a pink solid. MS (ES): m/z=436 (M+1), 434 (M−1); $^1$H NMR(DMSO-d$_6$): δ8.23 (s, 1H), 7.54 (dd, J=1.4 Hz, J=7.7 Hz, 1H), 7.37-7.22 (m, 4H), 7.12-7.04 (m, 2H), 6.90 (d, J=7.7 Hz, 1H), 6.83 (s, 2H), 5.05 (abq, J=16.7, 2H), 3.33 (m, under H$_2$O), 2.27-2.18 (m, 2H), 2.11 (s, 6H), 1.23-0.99 (m, 2H).

EXAMPLE 39

1-(2-Chloro-benzyl)-3-(4-hydroxy-3,5-dimethyl-phenyl)-3-(3-methoxy-benzyl)-1,3-dihydro-indol-2-one

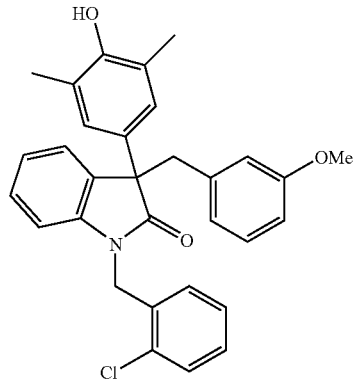

Using a method similar to Example 37, with 3-[4-(tert-butyl-dimethyl-silanyloxy)-3,5-dimethyl-phenyl]-1-(2-chloro-benzyl)-1,3-dihydro-indol-2-one (250 mg, 0.51 mmol), a 0.5M solution of potassium bis(trimethylsilyl) amide (1.04 mL, 0.52 mmol), and 3-methoxybenzyl bromide (0.073 mL, 0.31 mmol) in DMF (5 mL) followed by treatment with TBAF (0.56 mL, 0.56 mmol) gives a crude yellow solid. Purify by flash chromatography (gradient of 50% hexanes/$CH_2Cl_2$ to $CH_2Cl_2$) to give 148 mg (58%) of the title compound as a yellow powder. MS (ES): m/z=498 (M+1), 496 (M−1); $^1$H NMR(DMSO-$d_6$); δ8.28 (s, 1H), 7.56 (m, 1H), 7.45 (dd, J=1.0 Hz, J=8.0 Hz, 1H), 7.24 (m, 1H), 7.14 (m, 2H), 7.00 (s, 2H), 6.85-6.76 (m, 3H), 6.64 (d, J=8.7 Hz, 2H), 6.50 (m, 1H), 5.68 (d, J=6.6 Hz, 1H), 4.79 (abq, J=17.1 Hz, 2H), 3.68 (s, 3H), 3.60 (d, J=12.7 Hz, 1H), 2.15 (s, 6H).

EXAMPLE 40

1-(2-Chloro-benzyl)-3-(3-hydroxy-benzyl)-3-(4-hydroxy-3,5-dimethyl-phenyl)-1,3-dihydro-indol-2-one

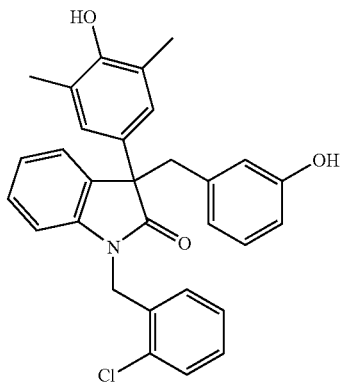

Using a method similar to Example 30, with 1-(2-chloro-benzyl)-3-(4-hydroxy-3,5-dimethyl-phenyl)-3-(3-methoxy-benzyl)-1,3-dihydro-indol-2-one (1.33 mg, 0.27 mmol) and pyridine hydrochloride (500-600 mg) gives an oil of 170 mg. Crystallize out of $CH_2Cl_2$ to give 30 mg (23%) of the title compound as a white solid. MS (ES): m/z=484 (M+1), 482 (M−1); $^1$H NMR(DMSO-$d_6$): δ9.12 (s, 1H), 8.26 (s, 1H), 7.50-7.44 (m, 2H), 7.24 (m, 1H), 7.14 (m, 2H), 6.98-6.91 (m, 3H), 6.83 (t, J=7.8 Hz, 1H), 6.58-6.49 (m, 2H), 6.39 (m, 1H), 6.26 (d, J=6.8 Hz, 1H), 5.87 (d, J=6.8 Hz, 1H), 4.81 (abq, J=17.1 Hz, 2H), 4.70 (abq, J=12.8 Hz, 2H), 2.15 (s, 6H).

EXAMPLE 41

1-(2-Chloro-benzyl)-3-(4-hydroxy-3,5-dimethyl-phenyl)-3-(4-methoxy-benzyl)-1,3-dihydro-indol-2-one

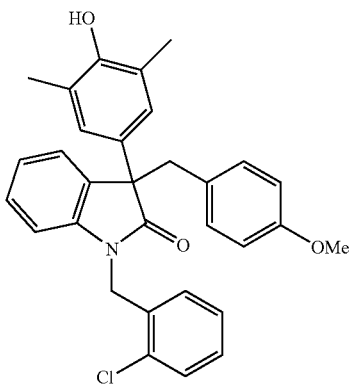

Using a method similar to Example 37, with 3-[4-(tert-butyl-dimethyl-silanyloxy)-3,5-dimethyl-phenyl]-1-(2-chloro-benzyl)-1,3-dihydro-indol-2-one (333 mg, 0.68 mmol), a 0.5M solution of potassium bis(trimethylsilyl) amide (1.38 mL, 0.69 mmol), and (4-methoxybenzyl bromide (0.094 mL, 0.69 mmol) in DMF (8 mL) followed by treatment with TBAF (0.75 mL, 0.75 mmol) gives a crude brown oil. Purify by flash chromatography (gradient of 50% hexanes/$CH_2Cl_2$ to $CH_2Cl_2$) to give material which still contains a second entity. Chromatograph again (step gradient of 5% EtOAc/hexanes, 20% EtOAc/hexanes, 33% EtOAc/hexanes) to give 215 mg (63%) of the title compound. MS (ES): m/z=498 (M+1), 496 (M−1); $^1$H NMR (DMSO-$d_6$): δ8.26 (s, 1H), 7.55 (m, 1H), 7.54 (dd, J=0.9 Hz, J=8.0 Hz, 1H), 7.24 (m, 1H), 7.14 (m, 2H), 7.00 (m, 3H), 6.90 (m, 1H), 6.75 (dd, J=2.2 Hz, J=8.0 Hz, 1H), 6.52 (m, 2H), 6.40 (m, 1H), 5.76 (d, J=6.3 Hz, 1H), 4.79 (abq, J=17.2, 2H), 3.59 (q, J=12.9, 2H), 3.46 (s, 3H), 2.15 (s, 6H).

EXAMPLE 42

1-(2-Chloro-benzyl)-3-(4-hydroxy-benzyl)-3-(4-hydroxy-3,5-dimethyl-phenyl)-1,3-dihydro-indol-2-one

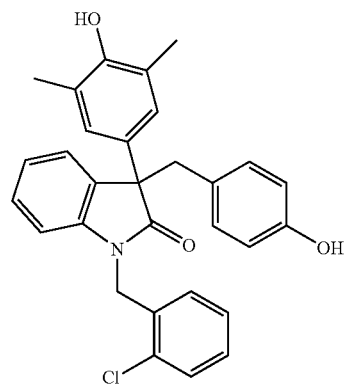

Using a method similar to Example 30, with 1-(2-Chloro-benzyl)-3-(4-hydroxy-3,5-dimethyl-phenyl)-3-(4-methoxybenzyl)-1,3-dihydro-indol-2-one (200 mg, 0.4 mmol0 and pyridine hydrochloride (700-900 mg) gives a crude residue. Purify by flash chromatography (gradient of $CH_2Cl_2$ up to 10% EtOAc/$CH_2Cl_2$) to give 135 mg (70%) of the title compound. MS (ES): m/z=484 (M+1); $^1$H NMR(DMSO-$d_6$): δ9.26 (s, 1H), 8.25 (s, 1H), 7.52 (m, 1H), 7.45 (dd, J=1.0 Hz, J=8.0 Hz, 1H), 7.24 (m, 1H), 7.12 (m, 2H), 6.94 (m, 3H), 6.64 (d, J=8.5, 2H), 6.48 (m, 3H), 5.68 (d, J=6.7 Hz, 1H), 4.78 (abq, J=17.2 Hz, 2H), 3.50 (abq, J=13.0 Hz, 2H), 2.15 (s, 6H).

EXAMPLE 43

1-(2,4-Difluoro-benzyl)-3,3-bis-(4-hydroxy-3,5-dimethyl-phenyl)-1,3-dihydro-indol-2-one

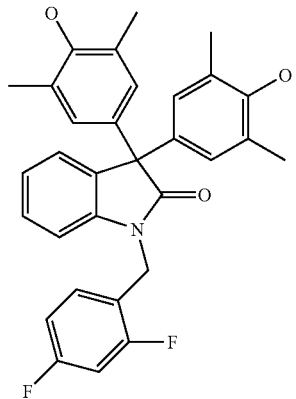

Combine a solution of 3,3-Bis-[4-(tert-butyl-dimethyl-silanyloxy)-3,5-dimethyl-phenyl]-1,3-dihydro-indol-2-one (0.15 g, 0.250 mmol) in anhydrous tetrahydrofuran (6 ml), with 0.750 mL of 1N lithium bis(trimethlysilyl)amide in tetrahydrofuran. Stir the resulting mixture at room temperature for 0.25 h. In a separate flask, prepare a solution of 2,4-difluorobenzyl bromide (0.155 g, 0.750 mmol) and sodium iodide (0.011 g, 0.075 mmol) in anhydrous tetrahydrofuran. Stir at room temperature for 0.25 h then add this solution to the 3,3-Bis-[4-(tert-butyl-dimethyl-silanyloxy)-3,5-dimethyl-phenyl]-1,3-dihydro-indol-2-one. Stir and heat the resulting mixture at 60° C. for 18 h. Cool to ambient temperature and dilute with 6 ml of methanol. Absorb the crude intermediate on 1 g of silica gel and evaporate the solvent under reduced pressure. Chromatograph this residue on a silica gel column eluting with 1:9 ethyl acetate/hexane. Combine the isolated intermediate, 3,3-Bis-[4-(tert-butyl-dimethyl-silanyloxy)-3,5-dimethyl-phenyl]-1-(2,4-difluoro-benzyl)-1,3-dihydro-indol-2-one, with 4 ml of 1N CsF in methanol. Stir and heat at 60 C for 1 h then remove solvent in vacuuo. Dissolve the residue in 10 ml of water and extract with ethyl acetate (4×7 ml). Pass the ethyl acetate solution over anhydrous sodium sulfate and concentrate under vacuum. Triturate the residue with diethyl ether to obtain 0.097 g (78%) of the titled compound as granular crystals: LCMS (system 2) $t_R$=4.13 min (100%), ESMS (M+1) m/z=499.56

Using the methods of Example 43 the compounds depicted in the following table (Table D) are prepared. As appearing in the table heading, "Ex. No." refers to the compound example number; "Name" refers to the compound chemical name; "R1", "R4", and "R5" refer to the name or symbol of the substituent that appears at the R1, R4, and R5 positions of Formula I, respectively; "Analytical" refers to the analytical physical data describing the particular compound; and "Yield(%)" refers to the percent yield obtained in the synthesis of the particular compound.

TABLE II

| Ex. No. | Name | R1 | R4 | R5 | Analytical | Yield (%) |
|---|---|---|---|---|---|---|
| 44 | 3,3-Bis-(4-hydroxy-3,5-dimethyl-phenyl)-1-[2-(2-methoxy-phenyl)-2-oxo-ethyl]-1,3-dihydro-indol-2-one | 2-(2-methoxy-phenyl)-2-oxo-ethyl | H | H | HPLC (system 1) $t_R$ = 2.82 min (100%), CIMS (M + 1) m/z = 522.92 | 7.7 |
| 45 | 3,3-Bis-(4-hydroxy-3,5-dimethyl-phenyl)-1-[2-(3-methoxy-phenyl)-2-oxo-ethyl]-1,3-dihydro-indol-2-one | 2-(3-methoxy-phenyl)-2-oxo-ethyl | H | H | HPLC (system 1) $t_R$ = 2.79 min (96.7%), CIMS (M + 1) m/z = 522.92 | 23 |
| 46 | 3,3-Bis-(4-hydroxy-3,5-dimethyl-phenyl)-1-[2-(4-methoxy-phenyl)-2-oxo-ethyl]-1,3-dihydro-indol-2-one | 2-(4-methoxy-phenyl)-2-oxo-ethyl | H | H | HPLC (system 1) $t_R$ = 2.77 min (100%), CIMS (M + 1) m/z = 522.90 | 21 |
| 47 | 3,3-Bis-(4-hydroxy-3,5-dimethyl-phenyl)-1-(2-naphthalen-2-yl-2-oxo-ethyl)-1,3-dihydro-indol-2-one | 2-naphthalen-2-yl-2-oxo-ethyl | H | H | HPLC (system 1) $t_R$ = 3.01 min (100%), CIMS (M + 1) m/z = 542.49 | 13 |
| 48 | 1-[2-(4-Bromo-phenyl)-2-oxo-ethyl]-3,3-bis-(4-hydroxy-3,5-dimethyl-phenyl)-1,3-dihydro-indol-2-one | 2-(4-Bromo-phenyl)-2-oxo-ethyl | H | H | HPLC (system 1) $t_R$ = 2.94 min (100%), CIMS (M + 1) m/z = 572.68 | 21 |
| 49 | 1-[2-(2,5-Dimethoxy-phenyl)-2-oxo-ethyl]-3,3-bis-(4-hydroxy-3,5-dimethyl-phenyl)-1,3-dihydro-indol-2-one | 2-(2,5-Dimethoxy-phenyl)-2-oxo-ethyl | H | H | HPLC (system 1) $t_R$ = 2.50 min (100%), CIMS (M + 1) m/z = 552.67 | 11 |
| 50 | 1-(2-Fluoro-benzyl)-3,3-bis-(4-hydroxy-3,5-dimethyl-phenyl)-1,3-dihydro-indol-2-one | 2-Fluoro-benzyl | H | H | HPLC (system 1) $t_R$ = 2.95 min (94.9%), CIMS (M + 1) m/z = 482.78 | 17 |
| 51 | 2-[3,3-Bis-(4-hydroxy-3,5-dimethyl-phenyl)-2-oxo-2,3-dihydro-indol-1-ylmethyl]-benzonitrile | benzonitrile | H | H | HPLC (system 1) $t_R$ = 2.94 min (100%), CIMS (M + 1) m/z = 489.43 | 16 |
| 52 | 1-(3,4-Dichloro-benzyl)-3,3-bis-(4-hydroxy-3,5-dimethyl-phenyl)-1,3-dihydro-indol-2-one | 3,4-Dichloro-benzyl | H | H | HPLC (system 1) $t_R$ = 3.28 min (100%), CIMS (M + 1) m/z = 534.12 | 23 |
| 53 | 3,3-Bis-(4-hydroxy-3,5-dimethyl-phenyl)-1-(2-trifluoromethyl-benzyl)-1,3-dihydro-indol-2-one | 2-trifluoromethyl-benzyl | H | H | HPLC (system 1) $t_R$ = 3.16 min (100%), CIMS (M + 1) m/z = 532.41 | 8 |

TABLE II-continued

| Ex. No. | Name | R1 | R4 | R5 | Analytical | Yield (%) |
|---|---|---|---|---|---|---|
| 54 | 1-Biphenyl-2-ylmethyl-3,3-bis-(4-hydroxy-3,5-dimethyl-phenyl)-1,3-dihydro-indol-2-one | 1-Biphenyl-2-ylmethyl | H | H | HPLC (system 1) $t_R$ = 3.26 min (100%), CIMS (M + 1) m/z = 540.91 | 45 |
| 55 | 3-[3,3-Bis-(4-hydroxy-3,5-dimethyl-phenyl)-2-oxo-2,3-dihydro-indol-1-ylmethyl]-benzoic acid methyl ester | benzoic acid methyl ester | H | H | HPLC (system 1) $t_R$ = 2.81 min (98.2%), CIMS (M + 1) m/z = 522.98 | 8 |
| 56 | 3,3-Bis-(4-hydroxy-3,5-dimethyl-phenyl)-1-(3-methoxy-benzyl)-1,3-dihydro-indol-2-one | 3-methoxy-benzyl | H | H | HPLC (system 1) $t_R$ = 2.83 min (100%), CIMS (M + 1) m/z = 495.02 | 37 |
| 57 | 3,3-Bis-(4-hydroxy-3,5-dimethyl-phenyl)-1-(4-trifluoromethyl-benzyl)-1,3-dihydro-indol-2-one | 4-trifluoromethyl-benzyl | H | H | HPLC (system 1) $t_R$ = 3.07 min (100%), CIMS (M + 1) m/z = 532.40 | 30 |
| 58 | 1-(4-Bromo-benzyl)-3,3-bis-(4-hydroxy-3,5-dimethyl-phenyl)-1,3-dihydro-indol-2-one | 4-Bromo-benzyl | H | H | HPLC (system 1) $t_R$ = 3.06 min (100%), CIMS (M + 1) m/z = 544.08 | 18 |
| 59 | 3,3-Bis-(4-hydroxy-3,5-dimethyl-phenyl)-1-naphthalen-2-ylmethyl-1,3-dihydro-indol-2-one | naphthalen-2-ylmethyl | H | H | HPLC (system 1) $t_R$ = 3.13 min (100%), CIMS (M + 1) m/z = 514.73 | 23 |
| 60 | 1-(3-Chloro-benzyl)-3,3-bis-(4-hydroxy-3,5-dimethyl-phenyl)-1,3-dihydro-indol-2-one | 3-Chloro-benzyl | H | H | HPLC (system 1) $t_R$ = 3.10 min (100%), CIMS (M + 1) m/z = 498.65 | 16 |
| 61 | 3,3-Bis-(4-hydroxy-3,5-dimethyl-phenyl)-1-(3-trifluoromethyl-benzyl)-1,3-dihydro-indol-2-one | 3-trifluoromethyl-benzyl | H | H | HPLC (system 1) $t_R$ = 3.02 min (100%), CIMS (M + 1) m/z = 532.42 | 45 |
| 62 | 3,3-Bis-(4-hydroxy-3,5-dimethyl-phenyl)-1-(4-nitro-benzyl)-1,3-dihydro-indol-2-one | 4-nitro-benzyl | H | H | HPLC (system 1) $t_R$ = 3.02 min (99.2%), CIMS (M + 1) m/z = 510.01 | 24 |
| 63 | 1-(2-Bromo-benzyl)-3,3-bis-(4-hydroxy-3,5-dimethyl-phenyl)-1,3-dihydro-indol-2-one | 2-Bromo-benzyl | H | H | HPLC (system 1) $t_R$ = 3.31 min (96.8%), CIMS (M + 1) m/z = 544.04 | 44 |
| 64 | 1-(3-Bromo-benzyl)-3,3-bis-(4-hydroxy-3,5-dimethyl-phenyl)-1,3-dihydro-indol-2-one | 3-Bromo-benzyl | H | H | HPLC (system 1) $t_R$ = 3.15 min (100%), CIMS (M + 1) m/z = 542.46 | 15 |
| 65 | 3,3-Bis-(4-hydroxy-3,5-dimethyl-phenyl)-1-(2-nitro-benzyl)-1,3-dihydro-indol-2-one | 2-nitro-benzyl | H | H | HPLC (system 1) $t_R$ = 2.99 min (100%), CIMS (M + 1) m/z = 509.97 | 20 |
| 66 | 1-(2,3-Difluoro-benzyl)-3,3-bis-(4-hydroxy-3,5-dimethyl-phenyl)-1,3-dihydro-indol-2-one | 2,3-Difluoro-benzyl | H | H | HPLC (system 1) $t_R$ = 3.00 min (100%), CIMS (M + 1) m/z = 500.31 | 24 |
| 67 | 3,3-Bis-(4-hydroxy-3,5-dimethyl-phenyl)-1-(4-trifluoromethoxy-benzyl)-1,3-dihydro-indol-2-one | 4-trifluoromethoxy-benzyl | H | H | HPLC (system 1) $t_R$ = 3.15 min (100%), CIMS (M + 1) m/z = 549.09 | 18 |
| 68 | 1-(2,4-Bis-trifluoromethyl-benzyl)-3,3-bis-(4-hydroxy-3,5-dimethyl-phenyl)-1,3-dihydro-indol-2-one | 2,4-Bis-trifluoromethyl-benzyl | H | H | HPLC (system 1) $t_R$ = 3.41 min (98.4%), CIMS (M + 1) m/z = 600.82 | 17 |
| 69 | 1-(3,5-Bis-trifluoromethyl-benzyl)-3,3-bis-(4-hydroxy-3,5-dimethyl-phenyl)-1,3-dihydro-indol-2-one | 3,5-Bis-trifluoromethyl-benzyl | H | H | HPLC (system 1) $t_R$ = 3.37 min (100%), CIMS (M + 1) m/z = 600.98 | 27 |
| 70 | 1-(2-Fluoro-3-methyl-benzyl)-3,3-bis-(4-hydroxy-3,5-dimethyl-phenyl)-1,3-dihydro-indol-2-one | 2-Fluoro-3-methyl-benzyl | H | H | HPLC (system 1) $t_R$ = 3.08 min (100%), CIMS (M + 1) m/z = 496.90 | 20 |
| 71 | 1-(4-Benzoyl-benzyl)-3,3-bis-(4-hydroxy-3,5-dimethyl-phenyl)-1,3-dihydro-indol-2-one | 4-Benzoyl-benzyl | H | H | HPLC (system 1) $t_R$ = 3.14 min (95.9%), CIMS (M + 1) m/z = 568.88 | 18 |
| 72 | 3,3-Bis-(4-hydroxy-3,5-dimethyl-phenyl)-1-(4-methanesulfonyl-benzyl)-1,3-dihydro-indol-2-one | 4-methanesulfonyl-benzy | H | H | HPLC (system 1) $t_R$ = 2.59 min (100%), CIMS (M + 1) m/z = 542.39 | 15 |
| 73 | 3,3-Bis-(4-hydroxy-3,5-dimethyl-phenyl)-1-(5-nitro-furan-2-ylmethyl)-1,3-dihydro-indol-2-one | 5-nitro-furan-2-ylmethyl | H | H | HPLC (system 1) $t_R$ = 2.33 min (97.5%), CIMS (M + 1) m/z = 499.04 | 16 |
| 74 | 1-(4-Benzyloxy-benzyl)-3,3-bis-(4-hydroxy-3,5-dimethyl-phenyl)-1,3-dihydro-indol-2-one | 4-Benzyloxy-benzyl | H | H | LCMS (system 2) $t_R$ = 4.47 min (100%), ESMS (M + 1) m/z = 569.71 | 33 |
| 75 | 3,3-Bis-(4-hydroxy-3,5-dimethyl-phenyl)-1-[2-(4-trifluoromethyl-phenyl)-thiazol-4-ylmethyl]-1,3-dihydro-indol-2-one | 2-(4-trifluoromethyl-phenyl)-thiazol-4-ylmethyl | H | H | LCMS (system 2) $t_R$ = 4.53 min (100%), ESMS (M + 1) m/z = 614.69 | 13 |
| 76 | 1-(2-Chloro-6-fluoro-benzyl)-3,3-bis-(4-hydroxy-3,5-dimethyl-phenyl)-1,3-dihydro-indol-2-one | 2-Chloro-6-fluoro-benzyl | H | H | LCMS (system 2) $t_R$ = 4.24 min (100%), ESMS (M + 1) m/z = 516.02 | 46 |
| 77 | 3,3-Bis-(4-hydroxy-3,5-dimethyl-phenyl)-1-pentyl-1,3-dihydro-indol-2-one | pentyl | H | H | LCMS (system 2) $t_R$ = 4.32 min (100%), ESMS (M + 1) m/z = 444.32 | 72 |
| 78 | [3,3-Bis-(4-hydroxy-3,5-dimethyl-phenyl)-2-oxo-2,3-dihydro-indol-1-yl]-acetonitrile | acetonitrile | H | H | LCMS (system 2) $t_R$ = 3.42 min (100%), ESMS (M + 1) m/z = 412.5 | 31 |
| 79 | 1-(2-Difluoromethoxy-benzyl)-3,3-bis-(4-hydroxy-3,5-dimethyl-phenyl)-1,3-dihydro-indol-2-one | 2-Difluoromethoxy-benzyl | H | H | LCMS (system 2) $t_R$ = 4.09 min (100%), ESMS (M + 1) m/z = 529.60 | 62 |

TABLE II-continued

| Ex. No. | Name | R1 | R4 | R5 | Analytical | Yield (%) |
|---|---|---|---|---|---|---|
| 80 | 1-(2-Ethoxy-ethyl)-3,3-bis-(4-hydroxy-3,5-dimethyl-phenyl)-1,3-dihydro-indol-2-one | 2-Ethoxy-ethyl | H | H | LCMS (system 2) $t_R$ = 3.73 min (100%), ESMS (M + 1) m/z = 445.56 | 66 |
| 81 | 1-(4-Bromo-2-fluoro-benzyl)-3,3-bis-(4-hydroxy-3,5-dimethyl-phenyl)-1,3-dihydro-indol-2-one | 4-Bromo-2-fluoro-benzyl | H | H | LCMS (system 2) $t_R$ = 4.35 min (100%), ESMS (M + 1) m/z = 559.12 | 67 |
| 82 | 1-(2,4-Difluoro-benzyl)-3,3-bis-(4-hydroxy-3,5-dimethyl-phenyl)-1,3-dihydro-indol-2-one | 2,4-difluoro-benzyl | H | H | LCMS (system 2) $t_R$ = 4.30 min (100%), ESMS (M + 1) m/z = 515.20 | 81 |
| 83 | 1-(4-Chloro-2-fluoro-benzyl)-3,3-bis-(4-hydroxy-3,5-dimethyl-phenyl)-1,3-dihydro-indol-2-one | 4-Chloro-2-fluoro-benzyl | H | H | LCMS (system 2) $t_R$ = 3.90 min (100%), ESMS (M + 1) m/z = 547.70 | 85 |
| 84 | 3,3-Bis-(4-hydroxy-3,5-dimethyl-phenyl)-1-(4-[1,2,3]thiadiazol-4-yl-benzyl)-1,3-dihydro-indol-2-one | 4-[1,2,3]thiadiazol-4-yl-benzyl | H | H | LCMS (system 2) $t_R$ = 3.86 min (100%), ESMS (M + 1) m/z = 508.60 | 8 |
| 85 | 3,3-Bis-(4-hydroxy-3,5-dimethyl-phenyl)-1-(3-nitro-benzyl)-1,3-dihydro-indol-2-one | 3-nitro-benzyl | H | H | LCMS (system 2) $t_R$ = 3.95 min (100%), ESMS (M + 1) m/z = 509.61 | 47 |
| 86 | 1-(5-Cyclobutyl-[1,2,4]oxadiazol-3-ylmethyl)-3,3-bis-(4-hydroxy-3,5-dimethyl-phenyl)-1,3-dihydro-indol-2-one | 5-Cyclobutyl-[1,2,4]oxadiazol-3-ylmethyl | H | H | LCMS (system 2) $t_R$ = 3.86 min (100%), ESMS (M + 1) m/z = 521.20 | 54 |
| 87 | 1-(5-Furan-2-yl-[1,2,4]oxadiazol-3-ylmethyl)-3,3-bis-(4-hydroxy-3,5-dimethyl-phenyl)-1,3-dihydro-indol-2-one | 5-Furan-2-yl-[1,2,4]oxadiazol-3-ylmethyl | H | H | LCMS (system 2) $t_R$ = 3.64 min (100%), ESMS (M + 1) m/z = 479.57 | 83 |
| 88 | 1-(4-Hydroxy-benzyl)-3,3-bis-(4-hydroxy-3,5-dimethyl-phenyl)-1,3-dihydro-indol-2-one | 4-Hydroxy-benzyl | H | H | LCMS (system 2) $t_R$ = 3.76 min (100%), ESMS (M + 1) m/z = 484.62 | 66 |
| 89 | 3,3-Bis-(4-hydroxy-3,5-dimethyl-phenyl)-1-(2-methyl-thiazol-4-ylmethyl)-1,3-dihydro-indol-2-one | 2-methyl-thiazol-4-ylmethyl | H | H | LCMS (system 2) $t_R$ = 3.94 min (100%), ESMS (M + 1) m/z = 498.65 | 12 |
| 90 | 1-(2-Ethyl-thiazol-4-ylmethyl)-3,3-bis-(4-hydroxy-3,5-dimethyl-phenyl)-1,3-dihydro-indol-2-one | 2-Ethyl-thiazol-4-ylmethyl | H | H | LCMS (system 2) $t_R$ = 4.23 min (100%), ESMS (M + 1) m/z = 546.69 | 80 |
| 91 | 3,3-Bis-(4-hydroxy-3,5-dimethyl-phenyl)-1-(2-phenyl-thiazol-4-ylmethyl)-1,3-dihydro-indol-2-one | 2-phenyl-thiazol-4-ylmethyl | H | H | LCMS (system 2) $t_R$ = 4.34 min (100%), ESMS (M + 1) m/z = 560.72 | 56 |
| 92 | 3,3-Bis-(4-hydroxy-3,5-dimethyl-phenyl)-5-methyl-1-(2-phenyl-thiazol-4-ylmethyl)-1,3-dihydro-indol-2-one | 2-phenyl-thiazol-4-ylmethyl | H | Me | LCMS (system 2) $t_R$ = 3.89 min (100%), ESMS (M + 1) m/z = 499.29 | 12 |
| 93 | 3,3-Bis-(4-hydroxy-3,5-dimethyl-phenyl)-5-methyl-1-(2-methyl-thiazol-4-ylmethyl)-1,3-dihydro-indol-2-one | 2-methyl-thiazol-4-ylmethyl | H | Me | LCMS (system 2) $t_R$ = 4.25 min (100%), ESMS (M + 1) m/z = 576.72 | 80 |
| 94 | 3,3-Bis-(4-hydroxy-3,5-dimethyl-phenyl)-1-[2-(4-methoxy-phenyl)-thiazol-4-ylmethyl]-1,3-dihydro-indol-2-one | 2-(4-methoxy-phenyl)-thiazol-4-ylmethyl | H | H | LCMS (system 2) $t_R$ = 4.37 min (100%), ESMS (M + 1) m/z = 590.75 | 81 |
| 95 | 3,3-Bis-(4-hydroxy-3,5-dimethyl-phenyl)-1-[2-(4-methoxy-phenyl)-thiazol-4-ylmethyl]-5-methyl-1,3-dihydro-indol-2-one | 2-(4-methoxy-phenyl)-thiazol-4-ylmethyl | H | Me | LCMS (system 2) $t_R$ = 4.47 min (100%), ESMS (M + 1) m/z = 626.37 | 6 |
| 96 | 2-[3,3-Bis-(4-hydroxy-3,5-dimethyl-phenyl)-2-oxo-2,3-dihydro-indol-1-yl]-N-cyclohexyl-acetamide | N-cyclohexyl-acetamidyl | H | H | HPLC (system 1) tR = 2.75 min (93%), CIMS (M + 1) m/z = 512.6 | 20 |
| 97 | 3,3-Bis-(4-hydroxy-3,5-dimethyl-phenyl)-1-quinolin-2-ylmethyl-1,3-dihydro-indol-2-one | quinolin-2-ylmethyl | H | H | LCMS (system 2) $t_R$ = 4.02 min (100%), ESMS (M − 1) m/z = 513.4 | 20 |
| 98 | 3,3-Bis-(4-hydroxy-3,5-dimethyl-phenyl)-1-[5-(2-methoxy-phenyl)-[1,2,4]oxadiazol-3-ylmethyl]-1,3-dihydro-indol-2-one | 5-(2-methoxy-phenyl)-[1,2,4]oxadiazol-3-ylmethyl | H | H | HPLC (system 1) tR = 3.00 min (100%), CIMS (M + 1) m/z = 562.3 | 11 |
| 99 | 3,3-Bis-(4-hydroxy-3,5-dimethyl-phenyl)-1-[5-(4-methoxy-phenyl)-[1,2,4]oxadiazol-3-ylmethyl]-1,3-dihydro-indol-2-one | 5-(4-methoxy-phenyl)-[1,2,4]oxadiazol-3-ylmethyl | H | H | LCMS (system 2) $t_R$ = 4.20 min (100%), ESMS (M − 1) m/z = 560.4 | 21 |
| 100 | 3,3-Bis-(4-hydroxy-3,5-dimethyl-phenyl)-1-pyridin-2-ylmethyl-1,3-dihydro-indol-2-one | pyridin-2-ylmethyl | H | H | LCMS (system 2) $t_R$ = 3.64 min (100%), ESMS (M − 1) m/z = 463.3 | 20 |
| 101 | 3,3-Bis-(4-hydroxy-3,5-dimethyl-phenyl)-1-prop-2-ynyl-1,3-dihydro-indol-2-one | prop-2-ynyl | H | H | HPLC (system 1) tR = 2.67 min (100%), CIMS (M + 1) m/z = 412.3 | 15 |

TABLE II-continued

| Ex. No. | Name | R1 | R4 | R5 | Analytical | Yield (%) |
|---|---|---|---|---|---|---|
| 102 | 3,3-Bis-(4-hydroxy-3,5-dimethyl-phenyl)-1-(3-methyl-but-2-enyl)-1,3-dihydro-indol-2-one | 3-methyl-but-2-enyl | H | H | LCMS (system 2) $t_R$ = 4.14 min (100%), ESMS (M − 1) m/z = 440.3 | 20 |
| 103 | 3,3-Bis-(4-hydroxy-3,5-dimethyl-phenyl)-1-pyridin-3-ylmethyl-1,3-dihydro-indol-2-one | pyridin-3-ylmethyl | H | H | HPLC (system 1) tR = 1.86 min (100%), CIMS (M + 1) m/z = 465.5 | 25 |
| 104 | 1-Allyl-3,3-bis-(4-hydroxy-3,5-dimethyl-phenyl)-1,3-dihydro-indol-2-one | Allyl | H | H | HPLC (system 1) tR = 2.67 min (100%), CIMS (M + 1) m/z = 414.7 | 20 |
| 105 | 1-Cyclopropylmethyl-3,3-bis-(4-hydroxy-3,5-dimethyl-phenyl)-1,3-dihydro-indol-2-one | Cyclopropylmethyl | H | H | HPLC (system 1) tR = 2.78 min (99%), CIMS (M + 1) m/z = 428.5 | 20 |
| 106 | 3,3-Bis-(4-hydroxy-3,5-dimethyl-phenyl)-1-(2-methyl-allyl)-1,3-dihydro-indol-2-one | 2-methyl-allyl | H | H | HPLC (system 1) tR = 2.82 min (100%), CIMS (M + 1) m/z = 428.5 | 18 |
| 107 | 1-(2,6-Dimethyl-benzyl)-3,3-bis-(4-hydroxy-3,5-dimethyl-phenyl)-1,3-dihydro-indol-2-one | 2,6-Dimethyl-benzyl | H | H | HPLC (system 1) tR = 3.13 min (100%), CIMS (M + 1) m/z = 492.7 | 40 |
| 108 | 5-[3,3-Bis-(4-hydroxy-3,5-dimethyl-phenyl)-2-oxo-2,3-dihydro-indol-1-ylmethyl]-furan-2-carboxylic acid methyl ester | furan-2-carboxylic acid methyl ester | H | H | LCMS (system 2) $t_R$ = 3.84 min (100%), ESMS (M + 1) m/z = 512.2 | 41 |
| 109 | [3,3-Bis-(4-hydroxy-3,5-dimethyl-phenyl)-2-oxo-2,3-dihydro-indol-1-yl]-acetic acid ethyl ester | acetic acid ethyl ester | H | H | LCMS (system 2) $t_R$ = 3.75 min (100%), ESMS (M + 1) m/z = 460.2 | 60 |
| 110 | 1-(2-Cyclohexyl-ethyl)-3,3-bis-(4-hydroxy-3,5-dimethyl-phenyl)-1,3-dihydro-indol-2-one | 2-Cyclohexyl-ethyl | H | H | LCMS (system 2) $t_R$ = 4.58 min (100%), ESMS (M + 1) m/z = 484.3 | 91 |
| 111 | 3,3-Bis-(4-hydroxy-3,5-dimethyl-phenyl)-1-pyridin-4-ylmethyl-1,3-dihydro-indol-2-one | pyridin-4-ylmethyl | H | H | LCMS (system 2) $t_R$ = 3.30 min (100%), ESMS (M + 1) m/z = 465.2 | 72 |
| 112 | 1-(2-Fluoro-5-trifluoromethyl-benzyl)-3,3-bis-(4-hydroxy-3,5-dimethyl-phenyl)-1,3-dihydro-indol-2-one | 2-Fluoro-5-trifluoromethyl-benzyl | H | H | LCMS (system 2) $t_R$ = 4.30 min (100%), ESMS (M + 1) m/z = 550.2 | 97 |
| 113 | 1-(2,6-Dichloro-benzyl)-3,3-bis-(4-hydroxy-3,5-dimethyl-phenyl)-1,3-dihydro-indol-2-one | 2,6-dichlorobenzyl | H | H | HPLC (system 1) $t_R$ = 3.01 min (100%), CIMS (M + 1) m/z = 532.4 | 59 |
| 114 | 1-Cyclopentyl-3,3-bis-(4-hydroxy-3,5-dimethyl-phenyl)-1,3-dihydro-indol-2-one | cyclopentyl | H | H | LCMS (system 2) $t_R$ = 4.22 min (100%), ESMS (M + 1) m/z = 442.3, $^1$H NMR(CDCl3): 7.24-7.18(m, 2H), 7.02(dd, 1H, J=6Hz, J=6Hz), 6.97(d, 1H, J=6Hz), 6.79(s, 4H), 4.90-4.79(m, 1H), 4.52(s, 2H), 2.18-2.02(m, 14H), 1.98-1.86 (2, 4H), 1.74-1.63(m, 2H). | 23 |
| 115 | 1-(2,6-Difluoro-benzyl)-3,3-bis-(4-hydroxy-3,5-dimethyl-phenyl)-1,3-dihydro-indol-2-one | 2,6-difluoro-benzyl | H | H | LCMS (system 2) $t_R$ = 4.12 min (100%), ESMS (M + 1) m/z = 499.36. | 10 |
| 116 | 1-(2,6-Difluoro-benzyl)-3-[4-(2,6-difluoro-benzyloxy)-3,5-dimethyl-phenyl]-3-(4-hydroxy-3,5-dimethyl-phenyl)-1,3-dihydro-indol-2-one | 2,6-difluoro-benzyl | H | H | LCMS (system 2) $t_R$ = 4.47 min (100%), ESMS (M + 1) m/z = 626.37. | |

EXAMPLE 117

11-(4-Amino-benzyl)-3,3-bis-(4-hydroxy-3,5-dimethyl-phenyl)-1,3-dihydro-indol-2-one

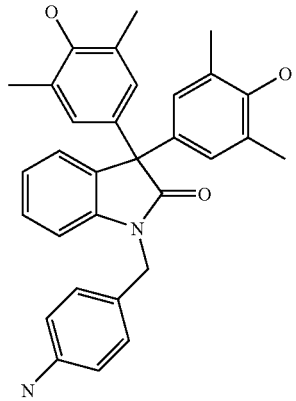

Combine a solution of 3,3-Bis-[4-(tert-butyl-dimethyl-silanyloxy)-3,5-dimethyl-phenyl]-1,3-dihydro-indol-2-one (0.15 g, 0.250 mmol) in anhydrous tetrahydrofuran (6 ml), with 0.750 mL of 1N lithium bis(trimethlysilyl)amide in tetrahydrofuran. Stir the resulting mixture at room temperature for 0.25 h. In a separate flask, prepare a solution of 4-nitrobenzyl bromide (0.162 g, 0.750 mmol) and sodium iodide (0.011 g, 0.075 mmol) in anhydrous tetrahydrofuran. Stir at room temperature for 0.25 h then add this solution to the 3,3-Bis-[4-(tert-butyl-dimethyl-silanyloxy)-3,5-dimethyl-phenyl]-1,3-dihydro-indol-2-one. Stir and heat the resulting mixture at 60° C. for 18 h. Cool to ambient temperature and dilute with 6 ml of methanol. Absorb the crude intermediate on 1 g of silica gel and evaporate the solvent under reduced pressure. Chromatograph this residue on a silica gel column eluting with 1:9 ethyl acetate/hexane. Combine the isolated intermediate, 3,3-Bis-(4-hydroxy-3,5-dimethyl-phenyl)-1-(4-nitro-benzyl)-1,3-dihydro-indol-2-one, with Tin(II)chloride dihydrate (113 mg, 0.5 mmol)in 1:1 methanol/tetrahydrofuran. Stir at ambient temperature for 24 h then remove solvent in vacuuo. Dissolve the residue in 10 ml of ethyl acetate and extract with of 1N aqueous sodium hydroxide (4×7 ml). Dry the ethyl acetate solution (anhydrous sodium sulfate) and concentrate under vacuum. Chromatograph this residue on a silica gel column eluting with 1:9 ethyl acetate/hexane.

Combine the isolated intermediate, 1-(4-Amino-benzyl)-3,3-bis-[4-(tert-butyl-dimethyl-silanyloxy)-3,5-dimethyl-phenyl]-1,3-dihydro-indol-2-one, with 4 ml of 1N CsF in methanol. Stir and heat at 60° C. for 1 h then remove solvent in vacuuo. Dissolve the residue in 10 ml of water and extract with ethyl acetate (4×7 ml). Dry the ethyl acetate solution (anhydrous sodium sulfate) and concentrate under vacuum. Triterate the residue with diethyl ether to obtain 0.015 g (13%) of the titled compound as granular crystals: LCMS (system 2) $t_R$=3.23 min (100%), ESMS (M+1) m/z=478.60

By the methods of Example 117 the following compounds were prepared.

EXAMPLE 120

1-Benzenesulfonyl-3,3-bis-(4-hydroxy-3,5-dimethyl-phenyl)-1,3-dihydro-indol-2-one

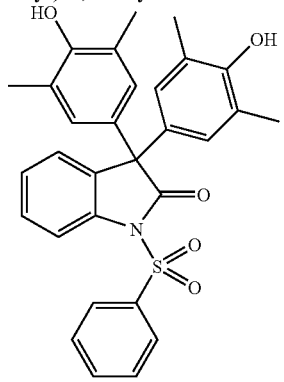

In a 40-mL vial, combine 0.15 g (1.0 mmol) of 3,3-Bis-[4-(tert-butyl-dimethyl-silanyloxy)-3,5-dimethyl-phenyl]-1,3-dihydro-indol-2-one with 15 mL of dry THF under nitrogen. Add 1.0 equivalent of sodium hydride and stir the resulting mixture 30 minutes under nitrogen. Add 2.0 equivalence of benzenesulfonyl chloride and stir an additional 30 minutes. Remove solvent in vacuuo and chromatograph the crude intermediate (1-Benzenesulfonyl-3,3-bis-[4-(tert-butyl-dimethyl-silanyloxy)-3,5-dimethyl-phenyl]-1,3-dihydro-indol-2-one) using 1:4 ethyl acetate/hexane to elute. Dissolve the intermediate in refluxing 1:1 THF/methanol and add excess cesium fluoride. Stir for 10 minutes, remove solvent in vacuuo, and add 10 mL of water. Extract with ethyl acetate to obtain 0.06 g (47%) of the titled compound as an off-white solid: LCMS (system 2) $t_R$=4.05 min (100%), ESMS (M+1) m/z=514.2; $^1$H NMR (DMSO-$d_6$); 8.28 (s, 1H), 7.98 (d, 2H), 7.90 (d, 1H), 7.81 (t, 1H), 7.65 (t, 2H), 7.39 (m, 1H), 7.20 (m, 2H), 6.30 (s, 4H), 1.93 (s, 12H).

EXAMPLE 121

3,3-Bis-(4-hydroxy-3,5-dimethyl-phenyl)-1-[2-(4-methyl-thiazol-5-yl)-ethyl]-1,3-dihydro-indol-2-one

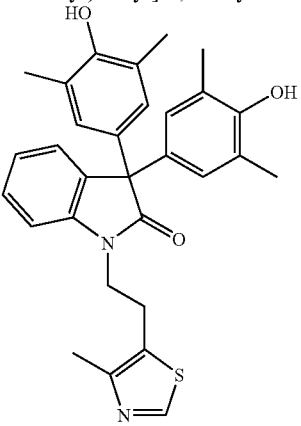

| Ex. No. | Name | R1 | R4 | R5 | Analytical | Yield (%) |
|---|---|---|---|---|---|---|
| 118 | 1-(3-Amino-benzyl)-3,3-bis-(4-hydroxy-3,5-dimethyl-phenyl)-1,3-dihydro-indol-2-one | 3-Amino-benzyl | H | H | LCMS (system 2) $t_R$ = 3.40 min (100%), ESMS (M + 1) m/z = 478.60 | 13 |
| 119 | 1-(2-Amino-benzyl)-3,3-bis-(4-hydroxy-3,5-dimethyl-phenyl)-1,3-dihydro-indol-2-one | 2-Amino-benzyl | H | H | LCMS (system 2) $t_R$ = 3.71 min (100%), ESMS (M + 1) m/z = 478.60 | 13 |

Combine 3,3-bis-[4-(tert-butyl-dimethyl-silanyloxy)-3,5-dimethyl-phenyl]-1,3-dihydro-indol-2-one (100 mg, 0.166 mmol), 2-(4-methyl-thiazol-5-yl)-ethanol (80 □L, 0.664 mL), (4-diphenylphosphanyl-phenyl)-dimethyl-amine (203 mg, 0.664 mmol), and anhydrous tetrahydrofuran (3 mL). Add a few activated 4A molecular sieves and allow the reaction mixture to gently stir for 0.5 h. Add diethyl azodicarboxylate (118 mL, 0.747 mmol) to the reaction mixture in a slow dropwise manner over 5 minutes. Allow the reaction mixture to stir for 1 h and then add additional (4-diphenylphosphanyl-phenyl)-dimethyl-amine (203 mg, 0.664 mmol) followed by diethyl azodicarboxylate (118 mL, 0.747 mmol). Let the reaction mixture stir for 2 h and then dilute the reaction mixture with ethyl acetate and then filter off the molecular sieves. Wash the ethyl acetate solution with 3:1 water:brine (3×). Dry the ethyl acetate layer (anhydrous magnesium sulfate), and then remove the solvent under reduced pressure. Purify the crude product by column chromatography using silica gel, starting with straight hexanes and then slowly introduce ethyl acetate until the solvent system reaches 30% ethyl acetate in hexanes. The semi-purified N-alkylated intermediate 3,3-bis-[4-(tert-butyl-dimethyl-silanyloxy)-3,5-dimethyl-phenyl]-1-[2-(4-methyl-thiazol-5-yl)-ethyl]-1,3-dihydro-indol-2-one (contaminated by a small amount of the O-alkylated regioisomer) can be used as is in the next step.

Add a solution of tetrabutylammonium fluoride (41 mg, 0.157 mmol) in anhydrous tetrahydrofuran (0.5 mL) to a solution the semi-purified intermediate from above in anhydrous tetrahydrofuran (2 mL) and stir for 3 h. Dilute the reaction mixture with ethyl acetate and then wash with 3:1 water:brine (3×). Dry the ethyl acetate layer (anhydrous magnesium sulfate), and then remove the solvent under reduced pressure. Purify the crude product by column chromatography using silica gel starting with 10% ethyl acetate in hexanes and then gradually increasing the amount of ethyl acetate until the solvent system reaches 60% ethyl acetate in hexanes. Remove of solvent under reduced pressure from the combined product containing fractions to give 36 mg (33%) of the title compound: HPLC (system 1) $t_R$=2.10 min (100%), CIMS (M+1) m/z=499.4, $^1$H NMR(CDCl$_3$); 8.51 (s, 1H), 7.25-7.20 (m, 2H), 7.04 (dd, 1H, J=6 Hz, J=6 Hz), 6.77 (d, 1H, J=6 Hz), 6.74 (d, 4H), 4.59 (s, 2H), 3.97 (t, 2H, J=5.5 Hz), 3.17 (t, 2H, J=5.5 Hz), 2.29 (s, 3H), 2.13 (s, 12H).

EXAMPLE 122

3,3-Bis-(4-hydroxy-3,5-dimethyl-phenyl)-1-(2-pyridin-2-yl-ethyl)-1,3-dihydro-indol-2-one

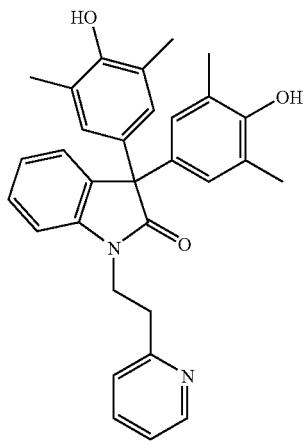

Using a method similar to Example 121, using 2-pyridin-2-yl-ethanol gives 19.2 mg (16%) of the title compound as an off-white solid: HPLC (system 1) $t_R$=1.86 min (98%), CIMS (M+1) m/z=479.4, $^1$H NMR(CDCl$_3$): δ8.53 (d, 1H, J=4 Hz), 7.43 (dt, 1H, J=1.5 Hz, J=6 Hz, J=6 Hz), 7.20-7.15 (m, 2H), 7.08 (dd, 1H, J=4.0 Hz, J=4.5 Hz), 7.04-6.80 (m, 2H), 6.87 (d, 1H, J=6 Hz), 6.79 (s, 4H), 4.65 (s, 2H), 4.18 (t, 2H, J=5.5 Hz), 3.18 (t, 2H, J=5.5 Hz), 2.16 (s, 12H).

EXAMPLE 123

3,3-Bis-(4-hydroxy-3,5-dimethyl-phenyl)-1-[2-(2-methoxy-ethoxy)-ethyl]-1,3-dihydro-indol-2-one

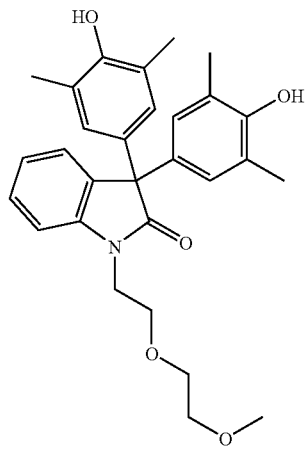

Using a method similar to Example 121, using 2-(2-Methoxy-ethoxy)-ethanol gives 25.3 mg (21%) of the title compound as a white solid: HPLC (system 1) $t_R$=2.49 min (100%), CIMS (M+1) m/z=476.7.

EXAMPLE 124

2-Cyclopentyloxy-3,3-bis-(4-hydroxy-3,5-dimethyl-phenyl)-3H-indole

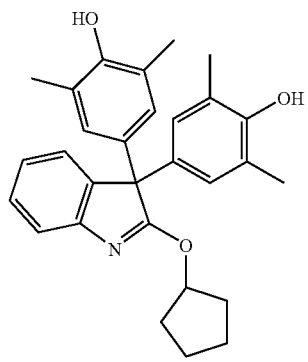

Using a method similar to Example 121, using cyclopentanol gives 25.3 mg (21%) of the title compound as a white solid: LCMS (system 2) $t_R$=4.08 min (100%), ESMS (M+1) m/z=442.3, $^1$H NMR(CDCl$_3$): δ7.37 (d, 1H, J=4 Hz), 7.22 (dt, 1H, J=1.5 Hz, J=6 Hz, J=6 Hz), 7.11 (d, 1H, J=6 Hz), 7.03 (dt, 1H, J=1.5 Hz, J=6 Hz, J=6 Hz), 6.76 (s, 4H), 5.52-5.45 (m, 1H), 4.52 (s, 2H), 2.13 (s, 12H), 1.85-1.75 (2, 4H), 1.63-1.53 (m, 4H).

EXAMPLE 125

3,3-Bis-(4-hydroxy-3,5-dimethyl-phenyl)-1-p-tolyl-1,3-dihydro-indol-2-one

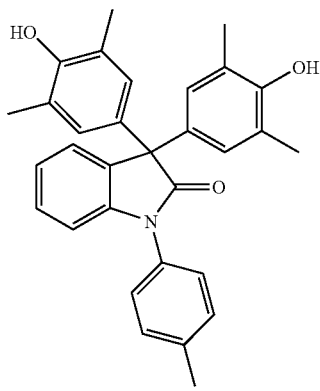

Combine 3,3-Bis-[4-(tert-butyl-dimethyl-silanyloxy)-3,5-dimethyl-phenyl]-1,3-dihydro-indol-2-one (0.886 g, 1.47 mmol), p-tolylboronic acid (0.40 g, 2.94 mmol), copper (II) acetate (0.267 g, 1.47 mmol), triethylamine (0.41 mL, 2.94 mmol), 4 angstrom molecular sieves, and dichloromethane (20 mL). Stir at room temperature overnight under ambient atmosphere. Filter the reaction through Celite. Elute through a column of silica gel with 70% dichloromethane in hexanes and concentrate. Dissolve the resulting compound (0.340 g, 0.492 mmol), in THF (2 mL). Add a solution of tetrabutylammonium fluoride (1.0 M) in THF (1.23 mL). Stir for 1 h. Add 1N aqueous HCl(10 mL), water (40 mL), and ethyl acetate (50 mL). Separate the layers and concentrate the organic layer in vacuo. Chromatograph on silica gel eluting with ethyl acetate to give 0.215 g (32%) of the title compound: mass spectrum (FAB): m/z=464(M+1); $^1$H NMR (DMSO-$d_6$): δ8.23 (s, 2H), 7.37-7.28 (m, 5H), 7.21 (td, 1H), 7.08 (td, 1H), 6.74-6.73 (m, 5H), 2.37 (s, 3H) 2.07 (s, 12H).

EXAMPLE 126

3,3-Bis-(4-hydroxy-3,5-dimethyl-phenyl)-1-phenyl-1,3-dihydro-indol-2-one

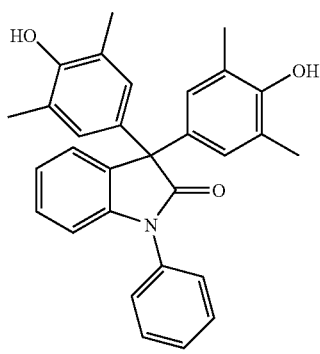

Combine 3,3-Bis-[4-(tert-butyl-dimethyl-silanyloxy)-3,5-dimethyl-phenyl]-1,3-dihydro-indol-2-one (0.816 g, 1.36 mmol), phenylboronic acid (0.330 g, 2.71 mmol), copper (II) acetate (0.25 g, 1.36 mmol), triethylamine (0.38 mL, 2.71 mmol), 4 angstrom molecular sieves, and dichloromethane (20 mL). Stir at room temperature for 72 h under ambient atmosphere. Filter the reaction through Celite. Elute through a column of silica gel with 70% dichloromethane in hexanes and concentrate. Dissolve the resulting compound in (0.446 g, 0.655 mmol), Add a solution of tetrabutylammonium fluoride (1.0 M) in THF (1.64 mL). Stir for 1 h. Add 1N aqueous HCl (10 mL), water (40 mL), and ethyl acetate (50 mL). Separate the layers, and concentrate the organic layer in vacuo. Chromatograph on silica gel eluting with ethyl acetate to give 0.236 g (39%) of the title compound: mass spectrum (FAB): m/z=450(M+1); $^1$H NMR(DMSO-$d_6$): δ8.24 (s, 2H), 7.58-7.54 (m, 2H), 7.48-7.41 (m, 3H), 7.32 (dd, 1H), 7.22 (td, 1H), 7.10 (td, 1H), 6.77 (d, 1H), 6.74 (s, 4H), 2.07 (s, 12H).

EXAMPLE 127

3,3-Bis-(4-hydroxy-3,5-dimethyl-phenyl)-1-(3-trifluoromethyl-phenyl)-1,3-dihydro-indol-2-one

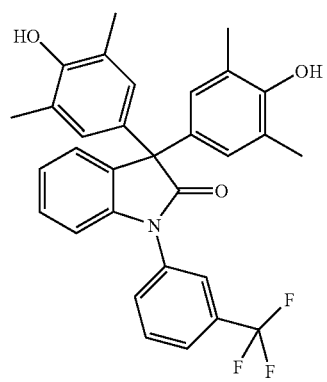

Combine 3,3-Bis-[4-(tert-butyl-dimethyl-silanyloxy)-3,5-dimethyl-phenyl]-1,3-dihydro-indol-2-one (0.710 g, 1.18 mmol), 3-(trifluoromethyl)phenylboronic acid (0.448 g, 2.36 mmol), copper (II) acetate (0.214 g, 1.18 mmol), triethylamine (0.41 mL, 2.36 mmol), 4 angstrom molecular sieves, and dichloromethane (20 mL). Stir at room temperature overnight under ambient atmosphere. Filter the reaction through Celite. Elute through a column of silica gel with 70% dichloromethane in hexanes and concentrate. Dissolve the resulting compound (0.812 g, 1.09 mmol), in THF (5 mL). Add a solution of tetrabutylammonium fluoride (1.0 M) in THF (2.72 mL). Stir for 1 h. Add 1N aqueous HCl (10 mL), water (40 mL), and ethyl acetate (50 mL). Separate the layers and concentrate the organic layer in vacuo. Chromatograph on silica gel eluting with ethyl acetate to give 0.353 g (58%) of the title compound: mass spectrum (FAB): m/z=518(M+1); $^1$H NMR(DMSO-$d_6$): δ8.25 (s, 2H), 7.84-7.79 (m, 4H), 7.33 (d, 1H), 7.26 (td, 1H), 7.14 (td, 1H), 6.85 (d, 1H), 6.75 (s, 4H), 2.07 (s, 12H).

EXAMPLE 128

3,3-Bis-(4-hydroxy-3,5-dimethyl-phenyl)-1-(4-methoxy-phenyl)-1,3-dihydro-indol-2-one

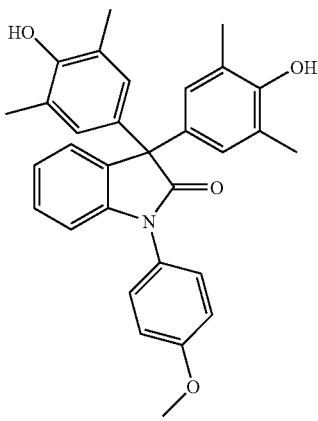

Combine 3,3-Bis-[4-(tert-butyl-dimethyl-silanyloxy)-3,5-dimethyl-phenyl]-1,3-dihydro-indol-2-one (0.580 g, 0.963 mmol), 4-methoxyphenylboronic acid (0.293 g, 1.93 mmol), copper (II) acetate (0.175 g, 0.963 mmol), triethylamine (0.27 mL, 1.93 mmol), 4 angstrom molecular sieves, and dichloromethane (15 mL). Stir at room temperature overnight under ambient atmosphere. Filter the reaction through Celite. Elute through a column of silica gel with 80% dichloromethane in hexanes and concentrate. Dissolve the resulting compound (0.501 g, 0.708 mmol), in THF (5 mL). Add a solution of tetrabutylammonium fluoride (1.0 M) in THF (1.80 mL). Stir for 1 h. Add 1N aqueous HCl(10 mL), water (40 mL), and add ethyl acetate (50 mL). Separate the layers, and concentrate the organic layer in vacuo. Chromatograph on silica gel eluting with ethyl acetate to give 0.285 g (62%) of the title compound: mass spectrum (FAB): m/z=480(M+1); $^1$H NMR(DMSO-d$_6$): δ8.23 (s, 2H), 7.33-7.29 (m, 3H), 7.21 (td, 1H), 7.11-7.06 (m, 3H), 6.73 (s, 4H), 6.70 (d, 1), 3.70 (s, 3H), 2.07 (s, 12H).

EXAMPLE 129

1-(2-Chloro-phenyl)-3,3-bis-(4-hydroxy-3,5-dimethyl-phenyl)-1,3-dihydro-indol-2-one

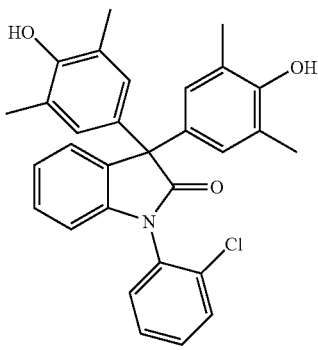

Combine 3,3-Bis-[4-(tert-butyl-dimethyl-silanyloxy)-3,5-dimethyl-phenyl]-1,3-dihydro-indol-2-one (0.680 g, 1.13 mmol), 2-chloroyphenylboronic acid (0.353 g, 2.26 mmol), copper (II) acetate (0.205 g, 1.13 mmol), triethylamine (0.32 mL, 2.26 mmol), 4 angstrom molecular sieves, and dichloromethane (15 mL). Stir at room temperature 120 h under ambient atmosphere. Filter the reaction through Celite. Elute through a column of silica gel with 70% dichloromethane in hexanes and concentrate. Dissolve the resulting compound (0.124 g, 0.174 mmol), in THF (3 mL). Add a solution of tetrabutylammonium fluoride (1.0 M) in THF (0.44 mL). Stir for 1 h. Add 1N aqueous HCl(10 mL), water (40 mL), and add ethyl acetate (50 mL). Separate the layers and concentrate the organic layer in vacuo. Chromatograph on silica gel eluting with ethyl acetate to give 0.067 g (13%) of the title compound: mass spectrum (FAB): m/z=484(M+1); $^1$H NMR(DMSO-d$_6$): δ8.2 (s, 1H), 8.23 (s, 1H), 7.75-7.72 (m, 1H), 7.59-7.49 (m, 3H), 7.34 (d, 1H), 7.20 (td, 1H), 7.10 (td, 1H), 6.79 (s, 2H), 6.76 (s, 2H), 6.44 (d, 1H) 2.08 (s, 6H), 2.05 (s, 6H).

EXAMPLE 130

1-(3-Fluoro-phenyl)-3,3-bis-(4-hydroxy-3,5-dimethyl-phenyl)-1,3-dihydro-indol-2-one

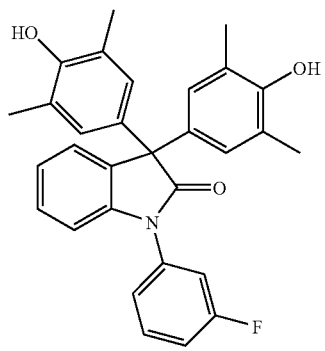

Combine 3,3-Bis-[4-(tert-butyl-dimethyl-silanyloxy)-3,5-dimethyl-phenyl]-1,3-dihydro-indol-2-one (0.563 g, 0.935 mmol), 3-fluorophenylboronic acid (0.262 g, 1.87 mmol), copper (II) acetate (0.169 g, 0.935 mmol), triethylamine (0.26 mL, 1.87 mmol), 4 angstrom molecular sieves, and dichloromethane (15 mL). Stir at room temperature overnight under ambient atmosphere. Filter the reaction through Celite. Elute through a column of silica gel with 70% dichloromethane in hexanes and concentrate. Dissolve the resulting compound (0.508 g, 0.730 mmol), in THF (4 mL). Add a solution of tetrabutylammonium fluoride (1.0 M) in THF (1.70 mL). Stir for 1 h. Add 1N aqueous HCl(10 mL), water(40 mL), and add ethyl acetate (50 mL). Separate the layers and concentrate the organic layer in vacuo. Chromatograph on silica gel eluting with ethyl acetate to give 0.259 g (59%) of the title compound: mass spectrum (FAB): m/z=468(M+1); $^1$H NMR(DMSO-d$_6$): δ8.30 (s, 2H), 7.69-7.63 (m, 1H), 7.47 (dt, 1H), 7.40-7.35 (m, 3H), 7.31 (td, 1H), 7.18 (td, 1H), 6.93 (d, 1H), 6.80 (s, 4H), 2.13 (s, 12H).

EXAMPLE 131

3,3-Bis-(4-hydroxy-3,5-dimethyl-phenyl)-1-(4-trifluoromethyl-phenyl)-1,3-dihydro-indol-2-one

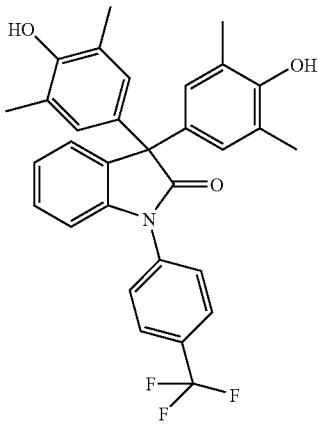

Combine 3,3-Bis-[4-(tert-butyl-dimethyl-silanyloxy)-3,5-dimethyl-phenyl]-1,3-dihydro-indol-2-one (0.561 g, 0.932 mmol), 4-(trifluoromethyl)phenylboronic acid (0.354 g, 1.86 mmol), copper (II) acetate (0.169 g, 0.932 mmol), triethylamine (0.26 mL, 1.86 mmol), 4 angstrom molecular sieves, and dichloromethane (15 mL). Stir at room temperature overnight under ambient atmosphere. Filter the reaction through Celite. Elute through a column of silica gel with 70% dichloromethane in hexanes and concentrate. Dissolve the resulting compound (0.498 g, 0.667 mmol), in THF (4 mL). Add a solution of tetrabutylammonium fluoride (1.0 M) in THF (1.80 mL). Stir for 1 h. Add 1N aqueous HCl(10 mL), water (40 mL), and ethyl acetate (50 mL). Separate the layers and concentrate the organic layer in vacuo. Chromatograph on silica gel eluting with ethyl acetate to give 0.283 g (59%) of the title compound: mass spectrum (FAB): m/z=518(M+1); $^1$H NMR(DMSO-d$_6$): δ8.32 (s, 2H), 7.98 (d, 2H), 7.79 (d, 2H), 7.40 (d, 1H), 7.32 (td, 1H), 7.21 (td, 1H), 6.99 (d, 1H), 6.80 (s, 4H), 2.13 (s, 12H).

EXAMPLE 132

3,3-Bis-(4-hydroxy-3,5-dimethyl-phenyl)-1-o-tolyl-1,3-dihydro-indol-2-one

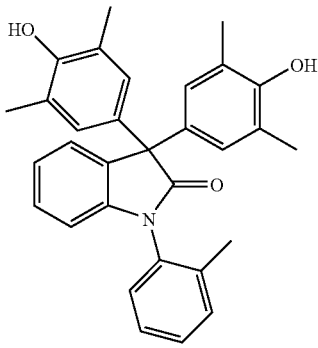

Combine 3,3-Bis-[4-(tert-butyl-dimethyl-silanyloxy)-3,5-dimethyl-phenyl]-1,3-dihydro-indol-2-one (0.700 g, 1.16 mmol), o-tolylboronic acid (0.316 g, 2.33 mmol), copper (II) acetate (0.211 g, 1.16 mmol), triethylamine (0.325 mL, 2.33 mmol), 4 angstrom molecular sieves, and dichloromethane (15 mL). Stir at room temperature overnight under ambient atmosphere. Filter the reaction through Celite. Elute through a column of silica gel with 70% dichloromethane in hexanes and concentrate. Dissolve the resulting compound (0.256 g, 3.70 mmol), in THF (4 mL). Add a solution of tetrabutylammonium fluoride (1.0 M) in THF (0.92 mL). Stir for 1 h. Add 1N aqueous HCl(10 mL), water (40 mL), and ethyl acetate (50 mL). Separate the layers and concentrate the organic layer in vacuo. Chromatograph on silica gel eluting with ethyl acetate to give 0.086 g (16%) of the title compound: mass spectrum (FAB): m/z=464(M+1); $^1$H NMR (DMSO-d$_6$): δ8.25 (s, 1H), 8.23 (s, 1H), 7.46-7.33 (m, 7H), 6.76 (s, 2H), 6.75 (s, 2H), 6.41 (d, 1H), 2.08 (s, 6H), 2.06 (s, 6H), 1.98 (s, 3H).

EXAMPLE 133

3,3-Bis-(4-hydroxy-3,5-dimethyl-phenyl)-1-m-tolyl-1,3-dihydro-indol-2-one

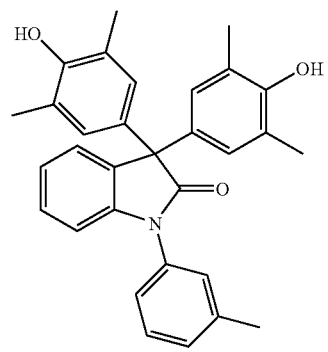

Combine 3,3-Bis-[4-(tert-butyl-dimethyl-silanyloxy)-3,5-dimethyl-phenyl]-1,3-dihydro-indol-2-one (0.650 g, 1.08 mmol), m-tolylboronic acid (0.294 g, 2.16 mmol), copper (II) acetate (0.196 g, 1.08 mmol), triethylamine (0.301 mL, 2.16 mmol), 4 angstrom molecular sieves, and dichloromethane (15 mL). Stir at room temperature overnight under ambient atmosphere. Filter the reaction through Celite. Elute through a column of silica gel with 70% dichloromethane in hexanes and concentrate. Dissolve the resulting compound (0.298 g, 0.431 mmol), in THF (4 mL). Add a solution of tetrabutylammonium fluoride (1.0 M) in THF (1.08 mL). Stir for 1 h. Add 1N aqueous HCl(10 mL),water (40 mL), and add ethyl acetate (50 mL). Separate the layers and concentrate the organic layer in vacuo. Chromatograph on silica gel eluting with ethyl acetate to give 0.170 g (34%) of the title compound: mass spectrum (FAB): m/z=413(M+1); $^1$H NMR(DMSO-d$_6$): δ8.10 (s, 2H), 7.31 (t, 1H), 7.18-7.06 (m, 5H), 6.96 (t, 1H), 6.66-6.60 (m, 5H) 2.23 (s, 3H), 1.92 (s, 12H).

EXAMPLE 134

3,3-Bis-(4-hydroxy-3,5-dimethyl-phenyl)-1-(3-methoxy-phenyl)-1,3-dihydro-indol-2-one

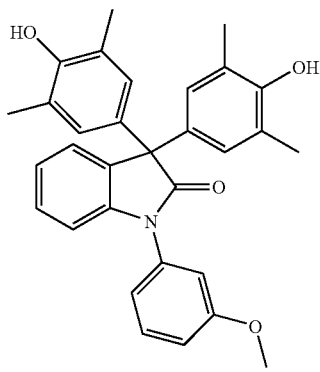

Combine 3,3-Bis-[4-(tert-butyl-dimethyl-silanyloxy)-3,5-dimethyl-phenyl]-1,3-dihydro-indol-2-one (0.680 g, 1.13 mmol), 3-methoxyphenylboronic acid (0.343 g, 2.26 mmol), copper (II) acetate (0.205 g, 1.13 mmol), triethylamine (0.32 mL, 2.26 mmol), 4 angstrom molecular sieves, and dichloromethane (15 mL). Stir at room temperature overnight under ambient atmosphere. Filter the reaction through Celite, and elute through a column of silica gel with 70% dichloromethane in hexanes and concentrate. Dissolve the resulting compound (0.417 g, 0.589 mmol), in THF (4 mL). Add a solution of tetrabutylammonium fluoride (1.0 M) in THF (1.47 mL). Stir for 1 h. Add 1N aqueous HCl(10 mL), water (40 mL), and ethyl acetate (50 mL). Separate the layers and concentrate the organic layer in vacuo. Chromatograph on silica gel eluting with ethyl acetate to give 0.155 g (29%) of the title compound: mass spectrum (FAB): m/z=480(M+1); $^1$H NMR(DMSO-d$_6$): δ8.23 (s, 2H), 7.46 (t, 1H), 7.31 (d, 1H), 7.23 (td, 1H), 7.10 (td, 1H), 7.05-7.02 (m, 1H), 6.98-6.95 (m, 2H), 6.81 (d, 1H), 6.73 (s, 4H), 3.79 (s, 3H), 2.07 (s, 12H).

EXAMPLE 135

3,3-Bis-(4-hydroxy-3,5-dimethyl-phenyl)-1-pyridin-3-yl-1,3-dihydro-indol-2-one

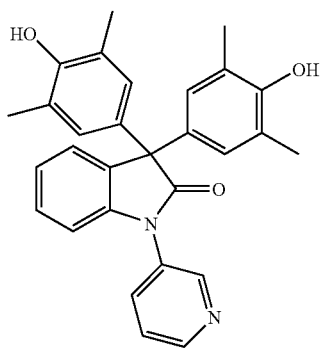

Combine 3,3-Bis-[4-(tert-butyl-dimethyl-silanyloxy)-3,5-dimethyl-phenyl]-1,3-dihydro-indol-2-one (0.622 g, 1.03 mmol), pyridine-3-boronic acid (0.254 g, 2.07 mmol), copper (II) acetate (0.187 g, 1.03 mmol), triethylamine (0.29 mL, 2.07 mmol), 4 angstrom molecular sieves, and dichloromethane (15 mL). Stir at room temperature overnight under ambient atmosphere. Filter the reaction through Celite. Elute through a column of silica gel with 50% dichloromethane in hexanes. Dissolve the resulting compound (0.103 g, 0.152 mmol), in THF (4 mL). Add a solution of tetrabutylammonium fluoride (1.0M) in THF (0.40 mL). Stir for 1 h. Add 1N aqueous HCl(10 mL), water (40 mL), and ethyl acetate (50 mL). Separate the layers and concentrate the organic layer in vacuo. Chromatograph on silica gel eluting with ethyl acetate to give 0.036 g (8%) of the title compound: mass spectrum (ion spray): m/z=451 (M+1); $^1$H NMR(DMSO-d$_6$): δ8.70 (d, 1H), 8.65 (dd, 1H), 8.25 (s, 2H), 7.98-7.94 (m, 1H), 7.62-7.59 (m, 1H), 7.34 (d, 1H), 7.25 (td, 1H), 7.14 (td, 1H), 6.84 (d, 1H), 6.75 (s, 4H), 2.07 (s, 12H).

EXAMPLE 136

3,3-Bis-(4-hydroxy-3,5-dimethyl-phenyl)-1-pyridin-4-yl-1,3-dihydro-indol-2-one

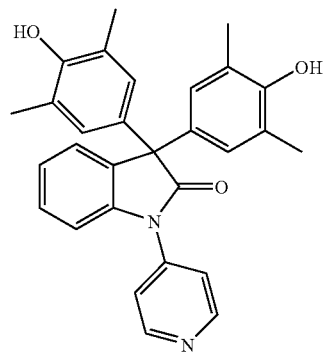

Combine 3,3-Bis-[4-(tert-butyl-dimethyl-silanyloxy)-3,5-dimethyl-phenyl]-1,3-dihydro-indol-2-one (0.700 g, 1.16 mmol), pyridine-4-boronic acid (0.286 g, 2.33 mmol), copper (II) acetate (0.211 g, 1.16 mmol), triethylamine (0.33 mL, 2.33 mmol), 4 angstrom molecular sieves, and dichloromethane (15 mL). Stir at room temperature overnight under ambient atmosphere. Filter the reaction through Celite. Elute through a column of silica gel with 10% ethyl acetate in hexanes. Dissolve the resulting compound (0.103 g, 0.152 mmol), in THF (4 mL). Add a solution of tetrabutylammonium fluoride (1.0 M) in THF (0.40 mL). Stir for 1 h. Add saturated aqueous ammonium chloride(10 mL), water (40 mL)m and ethyl acetate (50 mL). Separate the layers and concentrate the organic layer in vacuo. Chromatograph on silica gel eluting with a gradient from 50% to 75% ethyl acetate in hexanes to give 0.109 g (21%) of the title compound: mass spectrum (ion spray): m/z=451(M+1); $^1$H NMR(DMSO-d$_6$): δ8.46 (dd, 2H), 8.27 (s, 2H), 7.59 (dd, 2H), 7.34 (d, 1H), 7.29 (t, 1H), 7.16 (t, 1H), 7.06(d, 1H), 6.73 (s, 4H), 2.06(s, 12H).

EXAMPLE 137

1-(3-Ethoxy-phenyl)-3,3-bis-(4-hydroxy-3,5-dimethyl-phenyl)-1,3-dihydro-indol-2-one

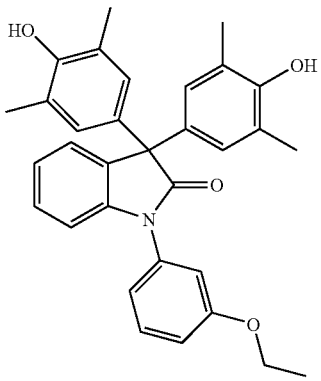

Combine 3,3-Bis-[4-(tert-butyl-dimethyl-silanyloxy)-3,5-dimethyl-phenyl]-1,3-dihydro-indol-2-one (0.500 g, 0.831 mmol), 3-ethoxyphenylboronic acid (0.276 g, 1.66 mmol), copper (II) acetate (0.151 g, 0.831 mmol), triethylamine (0.23 mL, 1.66 mmol), 4 angstrom molecular sieves, and dichloromethane (20 mL). Stir at room temperature overnight under ambient atmosphere. Filter the reaction through Celite. Elute through a column of silica gel with 70% dichloromethane in hexanes and concentrate. Dissolve the resulting compound (0.603 g, 0.83 mmol), in THF (4 mL). Add a solution of tetrabutylammonium fluoride (1.0M) in THF (2.1 mL). Stir for 1 h. Quench with saturated aqueous ammonium chloride(10 mL), water (40 mL) and ethyl acetate (50 mL). Separate the layers and concentrate the organic layer in vacuo. Chromatograph on silica gel eluting with 25% to 50% ethyl acetate in hexanes to give 0.255 g (62%) of the title compound: mass spectrum (ion spray): m/z=494(M+1); $^1$H NMR(DMSO-d$_6$); δ8.28 (s, 2H), 7.51 (t, 1H), 7.37 (d, 1H), 7.29 (td, 1H), 7.16 (td, 1h), 7.08-7.06 (m, 1H), 7.02-6.98 (m, 2H), 6.87 (d, 1H), 6.80 (s, 4H), 4.12 (q, 2H), 2.12(s, 12H), 1.38 (t, 3H).

EXAMPLE 138

3,3-Bis-(4-hydroxy-3,5-dimethyl-phenyl)-1-(3-isopropyl-phenyl)-1,3-dihydro-indol-2-one

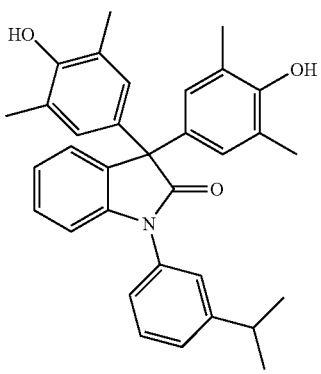

Combine 3,3-Bis-[4-(tert-butyl-dimethyl-silanyloxy)-3,5-dimethyl-phenyl]-1,3-dihydro-indol-2-one (0.350 g, 0.581 mmol), 3isopropylphenylboronic acid (0.190 g, 1.16 mmol), copper (II) acetate (0.106 g, 0.581 mmol), triethylamine (0.16 mL, 1.16 mmol), 4 angstrom molecular sieves, and dichloromethane (10 mL). Stir at room temperature overnight under ambient atmosphere. Filter the reaction through Celite. Elute through a column of silica gel with 70% dichloromethane in hexanes and concentrate. Dissolve the resulting compound (0.189 g, 0.268 mmol), in THF (4 mL). Add a solution of tetrabutylammonium fluoride (1.0 M) in THF (0.67 mL). Stir for 1 h. Add saturated aqueous ammonium chloride(10 mL), water and ethyl acetate (50 mL). Separate the layers and concentrate the organic layer in vacuo. Chromatograph on silica gel eluting with 25% to 50% ethyl acetate in hexanes to give 0.089 g (31%) of the title compound: mass Spectrum (ion spray): m/z=492(M+1); $^1$H NMR(DMSO-d$_6$); δ8.36 (s, 2H), 7.54 (t, 1H), 7.41-7.37 (m, 2H), 7.32-7.27 (m, 3H), 7.16 (t, 1H), 6.83-6.80 (m, 5H), 3.05-3.01 (m, 1H), 2.13 (s, 12H), 1.28 (d, 6H).

EXAMPLE 139

1-(3-Bromo-phenyl)-3,3-bis-(4-hydroxy-3,5-dimethyl-phenyl)-1,3-dihydro-indol-2-one

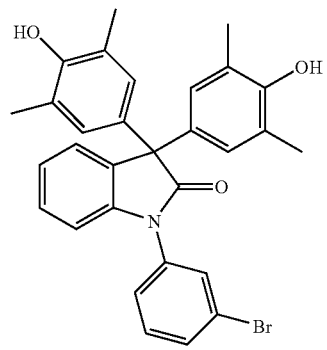

Combine 3,3-Bis-[4-(tert-butyl-dimethyl-silanyloxy)-3,5-dimethyl-phenyl]-1,3-dihydro-indol-2-one (2.0 g, 3.32 mmol), 3-bromophenylboronic acid (1.33 g, 6.64 mmol), copper (II) acetate (0.603 g, 3.32 mmol), triethylamine (0.93 mL, 6.64 mmol), 4 angstrom molecular sieves, and dichloromethane (50 mL). Stir at room temperature overnight under ambient atmosphere. Filter the reaction through Celite. Elute through a column of silica gel with 70% dichloromethane in hexanes to obtain 1.08 grams. Dissolve some of the resulting compound (0.167 g, 0.83 mmol) in THF (4 mL). Add a solution of tetrabutylammonium fluoride (1.0 M) in THF (2.1 mL). Stir for 1 h. Quench with saturated aqueous ammonium chloride(10 mL), water (40 mL) and ethyl acetate (50 mL). Separate the layers and concentrate the organic layer in vacuo. Chromatograph on silica gel eluting with 25% to 50% ethyl acetate in hexanes to give 0.255 g (62%) of the title compound: mass spectrum (ion spray): m/z=529(M+1), 531(M+3); $^1$H NMR(DMSO-d$_6$): δ8.24 (s, 2H), 7.70-7.65 (m, 2H), 7.64-7.46 (m, 2H), 7.31 (d, 1H), 7.25 (td, 1H), 7.12 (t, 1H), 6.84 (d, 1H), 6.73 (s, 4H), 2.07 (s,12H).

EXAMPLE 140

1-(3,4-Dimethoxy-phenyl)-3,3-bis-(4-hydroxy-3,5-dimethyl-phenyl)-1,3-dihydro-indol-2-one

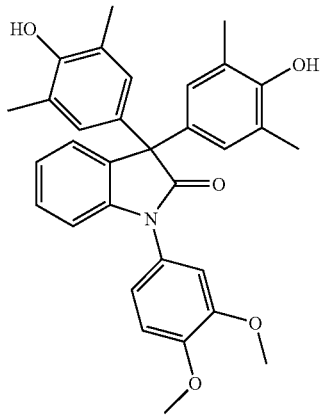

Combine 3,3-Bis-[4-(tert-butyl-dimethyl-silanyloxy)-3,5-dimethyl-phenyl]-1,3-dihydro-indol-2-one (0.583 g, 0.968 mmol), 3,4-dimethoxybenzeneboronic acid (0.353 g, 1.94 mmol), copper (II) acetate (0.176 g, 0.968 mmol), triethylamine (0.27 mL, 1.94 mmol), 4 angstrom molecular sieves, and dichloromethane (15 mL). Stir at room temperature overnight under ambient atmosphere. Filter the reaction through Celite. Elute through a column of silica gel with 70% dichloromethane in hexanes and concentrate. Dissolve the resulting compound (0.399 g, 0.511 mmol), in THF (4 mL). Add a solution of tetrabutylammonium fluoride (1.0M) in THF (1.35 mL). Stir for 1 h. Add saturated aqueous ammonium chloride(10 mL) water (40 mL) and ethyl acetate (50 mL). Separate the layers and concentrate the organic layer in vacuo. Chromatograph on silica gel eluting with a gradient from 25% to 50% ethyl acetate in hexanes to give 0.153 g (31%) of the title compound: mass spectrum (ion spray): m/z=510(M+1); $^1$H NMR(DMSO-d$_6$): δ8.23 (s, 2H), 7.31 (d, 1H), 7.21 (td, 1H), 7.11-7.06 (m, 2H), 6.94-6.89 (m, 2H), 6.76-6.74 (m, 5H), 3.80 (s, 3H), 3.75 (s, 3H), 2.07 (s, 12H).

PREPARATION 36

{3,3-Bis-[4-(tert-butyl-dimethyl-silanyloxy)-3,5-dimethyl-phenyl]-2-oxo-2,3-dihydro-indol-1-yl}-acetonitrile

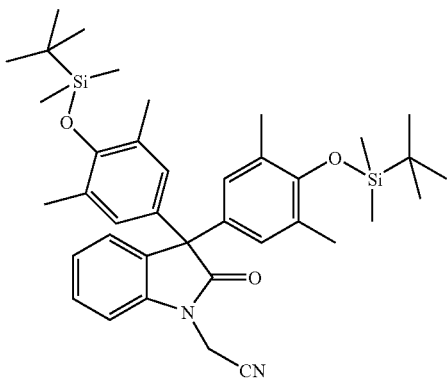

Under an N$_2$ atmosphere, dissolve 3,3-Bis-[4-(tert-butyl-dimethyl-silanyloxy)-3,5-dimethyl-phenyl]-1,3-dihydro-indol-2-one (2.5 g, 4.15 mmol) in dry DMF (50 mL). Cool the reaction to 0° C. Add a solution of potassium t-butoxide (1.0 M) in THF (4.57 mL). Allow the reaction to stir at 0° C. for 10 minutes. Add bromoacetonitrile (0.32 mL, 4.57 mmol), and allow the reaction to warm to room temperature. Stir the reaction at room temperature overnight. Dilute the reaction with water (200 mL) and diethyl ether (200 mL). Separate the layers and wash the aqueous layer with diethyl ether (100 mL). Combine the organic layers. Wash the diethyl ether with brine (100 mL), and separate the layers. Dry the organic layer with sodium sulfate and concentrate in vacuo. Purify the crude oil by flash column chromatography. Elute the column with 20% ethyl acetate in hexanes to give 1.92 g (72%) of the title compound: $^1$H NMR(CDCl$_3$): δ7.36 (td, 1H), 7.29-7.26 (m, 1H), 7.17 (td, 1H), 7.06 (d, 1H), 6.77 (s, 4H), 4.72 (s, 2H), 2.12 (s, 12H), 1.01 (s, 18H), 0.16 (s, 6H) 0.16 (s, 6H).

EXAMPLE 141

3-{5-[3,3-Bis-(4-hydroxy-3,5-dimethyl-phenyl)-2-oxo-2,3-dihydro-indol-1-ylmethyl]-[1,2,4]oxadiazol-3-yl}-benzoic acid methyl ester

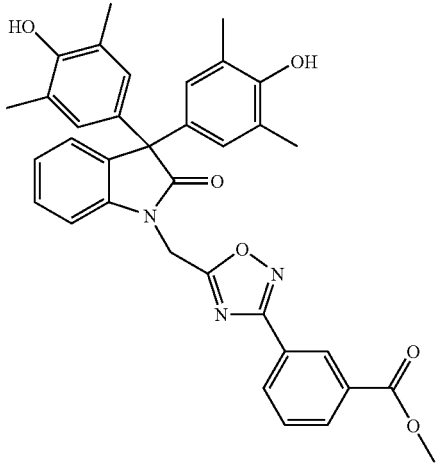

Under an N$_2$ atmosphere combine [3,3-Bis-(4-hydroxy-3,5-dimethyl-phenyl)-2-oxo-2,3-dihydro-indol-1-yl]-acetonitrile (0.501 g, 0.782 mmol), 3-[chloro(hydroxyimino)methyl]-benzoic acid methyl ester (1.17 g, 5.47 mmol), and diethyl ether (20 mL). Add a solution of triethylamine (0.84 mL, 6.02 mmol) in diethyl ether (10 mL) over 30 minutes. Stir the reaction at room temperature overnight. Dilute the reaction with ethyl acetate (200 mL) and water (200 mL). Separate the layers, and dry the organic layer with sodium sulfate. Concentrate in vacuo. Chromatograph on silica gel eluting with 20% ethyl acetate in hexanes and concentrate. Dissolve the resulting compound (0.124 g, 0.152 mmol) in THF (1 mL). Add a solution of tetrabutylammonium fluoride (1.0 M) in THF (0.38 mL) and stir the reaction at room temperature for 30 minutes. Add 1N aqueous HCl(10 mL), ethyl acetate (50 mL), and water (40 mL). Separate the layers and wash the organic layer with brine (50 mL). Dry the ethyl acetate with sodium sulfate, and concentrate in vacuo. Chromatograph on silica gel eluting with a gradient from 25% to 50% ethyl acetate in hexanes to give 0.037 g of the title compound: mass spectrum (ion spray): m/z=590 (M+1); $^1$H NMR(DMSO-d$_6$): δ8.24 (s, 2H), 8.10-8.03 (m, 4H), 7.29-7.25 (m, 2H), 7.17 (d, 1H), 7.09 (t, 1H) 6.71 (s, 1H), 5.48 (s, 2H), 3.87 (s, 3H), 2.04 (s, 12H).

EXAMPLE 142

3,3-Bis-(4-hydroxy-3,5-dimethyl-phenyl)-1-[3-(4-methoxy-phenyl)-[1,2,4]oxadiazol-5-ylmethyl]-1,3-dihydro-indol-2-one

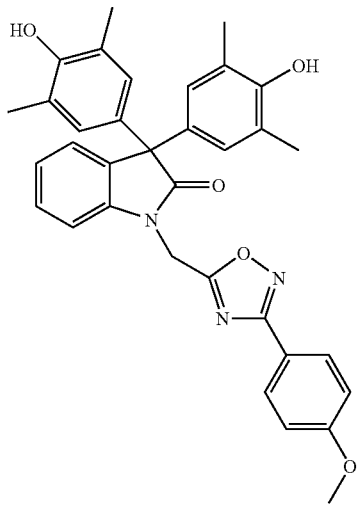

Combine [3,3-Bis-(4-hydroxy-3,5-dimethyl-phenyl)-2-oxo-2,3-dihydro-indol-1-yl]-acetonitrile (0.563 g, 0.878 mmol), N-hydroxy-4-methoxy-benzenecarboximidoyl chloride (1.63 g, 8.78 mmol), and diethyl ether (20 mL). Add a solution of triethylamine (1.35 mL, 9.66 mmol) in diethyl ether (10 mL) over 30 minutes. Stir the reaction at room temperature overnight. Dilute the reaction with ethyl acetate (200 mL) and water (200 mL). Separate the layers, and dry the organic layer with sodium sulfate. Concentrate in vacuo. Chromatograph on silica gel eluting with 20% ethyl acetate in hexanes and concentrate. Dissolve the resulting compound (0.217 g, 0.275 mmol) in THF (2 mL). Add a solution of tetrabutylammonium fluoride (1.0 M) in THF (0.69 mL) and stir the reaction at room temperature for 30 minutes. Quench with 1N aqueous HCl (10 mL), ethyl acetate (50 mL), and water (40 mL). Separate the layers and wash the organic layer with brine (50 mL). Dry the ethyl acetate with sodium sulfate, and concentrate in vacuo. Chromatograph on silica gel eluting with a gradient from 25% to 50% ethyl acetate in hexanes to give 0.137 g of the title compound: mass spectrum (ion spray): m/z=562(M+1); $^1$H NMR (DMSO-d$_6$): δ8.23 (s, 2H), 7.84-7.82 (m, 2H), 7.28-7.25 (m, 2H), 7.16-7.04 (m, 6H), 6.71 (s, 4H), 5.42 (s, 2H), 3.81 (s, 3H), 2.04 (s, 12H).

PREPARATION 37

3,3-Bis-[4-(tert-butyl-dimethyl-silanyloxy)-3,5-dimethyl-phenyl]-1-(2-chloro-pyrimidin-4-yl)-1,3-dihydro-indol-2-one

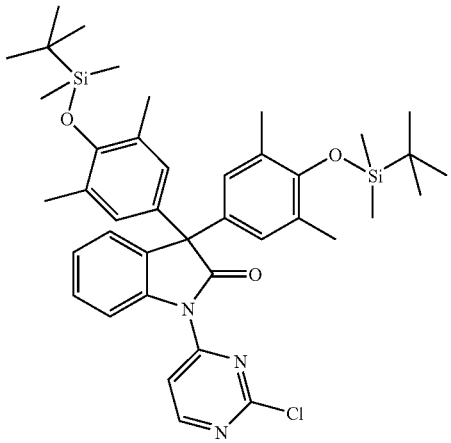

Under an N$_2$ atmosphere, dissolve 3,3-Bis-[4-(tert-butyl-dimethyl-silanyloxy)-3,5-dimethyl-phenyl]-1,3-dihydro-indol-2-one (0.519 g, 0.862 mmol) in dry THF (2 mL). Cool the reaction to 0° C. Add a solution of potassium t-butoxide (1.0 M) in THF (0.95 mL). Allow the reaction to stir at 0° C. for 10 minutes. Add 2,4-dichloro-pyrmidine (0.141 g, 0.948 mmol), and remove the ice bath. Heat the reaction to 55° C. and stir overnight. Dilute the reaction with water (200 mL) and diethyl ether (200 mL). Separate the layers and wash the aqueous layer with diethyl ether (100 mL). Combine the organic layers. Dry the organic layer with sodium sulfate and concentrate in vacuo. Purify the crude oil by flash column chromatography. Elute the column with 20% ethyl acetate in hexanes to give 0.289 g (47%) of the title compound: $^1$H NMR(DMSO-d$_6$); δ8.60 (d, 1H), 8.41 (d, 1H), 8.28 (d, 1H), 7.41-7.38 (m, 1H), 7.25-7.22 (m, 1H), 7.17-7.14 (m, 1H), 6.78 (s, 4H), 2.11 (s, 12H), 1.00 (s, 18H), 0.15 (s, 6H), 0.15 (s, 6H).

EXAMPLE 143

3,3-Bis-(4-hydroxy-3,5-dimethyl-phenyl)-1-(2-methoxy-pyrimidin-4-yl)-1,3-dihydro-indol-2-one

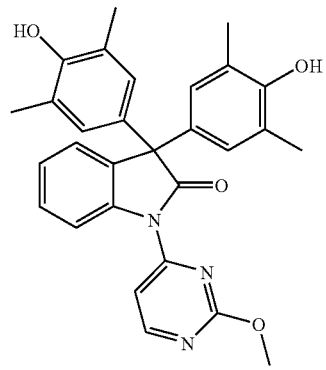

Under an N$_2$ atmosphere, combine 3,3-Bis-[4-(tert-butyl-dimethyl-silanyloxy)-3,5-dimethyl-phenyl]-1-(2-chloro-pyrimidin-4-yl)-1,3-dihydro-indol-2-one and sodium methoxide solution (0.5 M) in methanol (2.0 mL). Add THF (5.0 mL) and stir for 3 h at room temperature. Quench the reaction with saturated aqueous ammonium chloride (25 mL). Add ethyl acetate (25 mL) and separate the layers. Dry the organic layer with sodium sulfate and concentrate in vacuo. Dissolve the crude residue in THF (2 mL), and add a solution of tetrabutylammonium fluoride (1.0 M) in THF (0.84 mL). Stir the reaction at room temperature for 1 h. Quench the reaction with saturated aqueous ammonium chloride (25 mL). Add ethyl acetate (25 mL) and separate the layers. Dry the organic layer with sodium sulfate and concentrate in vacuo. Purify by flash column chromatography eluting with a gradient from 25% to 50% ethyl acetate in hexanes to give 0.289 g (%) of the title compound: mass Spectrum (ion spray): m/z=482(M+1); $^1$H NMR (DMSO-$d_6$): $\delta$8.67 (d, 1H), 8.29 (s, 2H), 8.21 (d, 1H), 7.36 (td, 1H), 7.30, (dd, 1H), 7.22 (td, 1H), 6.69 (s, 4H), 3.97 (s, 3H), 2.05 (s, 12H).

PREPARATION 38

3-[4-(tert-Butyl-dimethyl-silanyloxy)-3,5-dimethyl-phenyl]-1-(3-methoxy-phenyl)-1,3-dihydro-indol-2-one

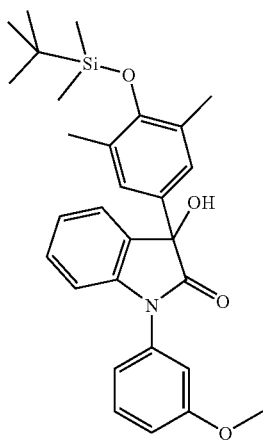

Combine 3-[4-(tert-Butyl-dimethylsilanyloxy)-3,5-dimethyl-phenyl]-3-hydroxy-1,3-dihydro-indol-2-one (15.34 g, 40 mmol), 3-methoxyphenylboronic acid (12.16 g, 80 mmol), copper (II) acetate (7.27 g, 40 mmol), triethyl amine (11.2 ml, 80 mmol) and 4A sieves (100 g) in dichloromethane (1 L) and heat at 32° C. for 1 day stirring mechanically. Add more 3-methoxyphenylboronic acid (6.0 g, 39 mmol), copper (II) acetate (7.27 g, 40 mmol), triethyl amine (5.6 ml, 40 mmol) and 4A sieves (50 g) and continue heating for 3 days. Filter the reaction through Celite washing liberally with dichloromethane. Add ethyl acetate to get more precipitate and refilter through Celite. Evaporate in vacuo to obtain an oil of about 30 g. Purify by preparative HPLC (gradient of 15% ethyl acetate/dichloromethane to 50% ethyl acetate/dichloromethane) to obtain 9.60 g of an orange foam. MS (ES): m/z=490 (M+1); $^1$H NMR (DMSO-$d_6$); $\delta$7.50 (t, 1H), 7.28-7.23 (m, 2H), 7.12-6.98 (m, 6H), 6.82 (d, 1H), 6.72 (s, 1H), 3.81 (s, 3H), 2.14 (s, 6H), 0.99 (s, 9H), 0.17 (s, 6H).

PREPARATION 39

3-Hydroxy-3-(4-hydroxy-3,5-dimethyl-phenyl)-1-(3-methoxy-phenyl)-1,3-dihydro-indol-2-one

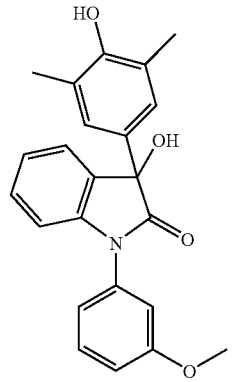

Using a method similar to Preparation 34, with 3-[4-(tert-Butyl-dimethyl-silanyloxy)-3,5-dimethyl-phenyl]-1-(3-methoxy-phenyl)-1,3-dihydro-indol-2-one (5.03 g, 10.3 mmol)and tetrabutyl ammonium fluoride (11.3 ml, 11.3 mmol, 1.0M in THF) in THF (140 mL) provides 4.50 g of an orange solid after workup. Purify by tituration in dichloromethane with 5-10% hexane to obtain 3.77 g (97%) of a yellow solid. MS (ES): m/z=376 (M+1); $^1$H NMR (DMSO-$d_6$); $\delta$8.21 (s, 1H), 7.46 (t, 1H), 7.25-7.18 (m, 2H), 7.08-6.93 (m, 4H), 6.88 (s, 2H), 6.79 (d, 1H), 6.60 (s, 1H), 3.78 (s, 3H), 2.10 (s, 6H).

The following examples were made using a method similar to Example 28. Use the appropriate phenol or aniline with 3-hydroxy-3-(4-hydroxy-3,5-dimethyl-phenyl)-1-(3-methoxy-phenyl)-1,3-dihydro-indol-2-one in trifluoroacetic acid at room temperature for 30-60 min. Pour over ice and extract with ethyl acetate (2×). Wash organic portion with 1N NaOH (2 to 3 times), water, brine, dry (MgSO4), filter and concentrate in vacuo. Purify by flash chromatography.

EXAMPLE 144

3-(4-Hydroxy-3,5-dimethyl-phenyl)-3-(2-hydroxy-3,4-dimethyl-phenyl)-1-(3-methoxy-phenyl)-1,3-dihydro-indol-2-one

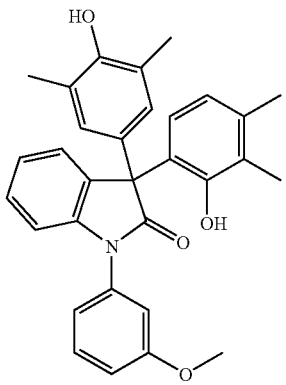

MS (ES): m/z=480 (M+1), 478 (m−1); $^1$H NMR (DMSO-$d_6$): $\square$8.47 (s, 1H), 8.29 (s, 1H), 7.47 (t, 1H), 7.21 (m, 1H), 7.07-6.94 (m, 7H), 6.77 (d, 1H), 6.61 (d, 1H), 6.48 (d, 1H), 3.81 (s, 3H), 2.16 (s, 3H), 2.09 (s, 6H), 2.00 (s, 3H).

EXAMPLE 145

3-(4-Hydroxy-3,5-dimethyl-phenyl)-3-(2-hydroxy-5-methyl-phenyl)-1-(3-methoxy-phenyl)-1,3-dihydro-indol-2-one

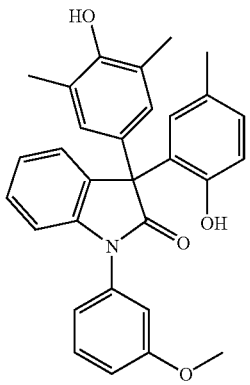

MS (ES): m/z=466 (M+1), 464 (m−1); $^1$H NMR (DMSO-$d_6$): δ9.39 (s, 1H), 8.32 (s, 1H), 7.46 (t, 1H), 7.21 (m, 1H), 7.07-6.93 (m, 7H), 6.88 (dd, 1H), 6.75 (d, 1H), 6.59-6.56 (m, 2H), 3.80 (s, 3H), 2.12 (s, 6H), 2.11 (s, 3H).

EXAMPLE 146

3-(4-Hydroxy-3,5-dimethyl-phenyl)-3-(2-hydroxy-3,5-dimethyl-phenyl)-1-(3-methoxy-phenyl)-1,3-dihydro-indol-2-one

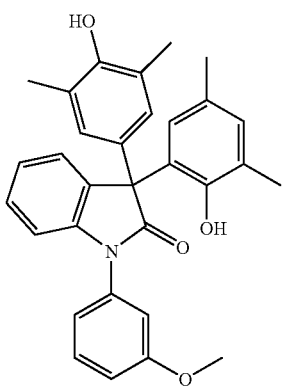

MS (ES): m/z=480 (M+1), 478 (m−1); $^1$H NMR (DMSO-$d_6$): δ8.35 (s, 1H), 8.30 (s, 1H), 7.46 (t, 1H), 7.21 (m, 1H), 7.07-6.98 (m, 5H), 6.95 (bs, 2H), 6.81 (d, 1H), 6.76 (d, 1H), 6.41 (d, 1H), 3.80 (s, 3H), 2.11 (s, 6H), 2.08 (s, 3H), 2.07 (s, 3H).

EXAMPLE 147

3-(3,4-Dihydroxy-5-methyl-phenyl)-3-(4-Hydroxy-3,5-dimethyl-phenyl)-1-(3-methoxy-phenyl)-1,3-dihydro-indol-2-one

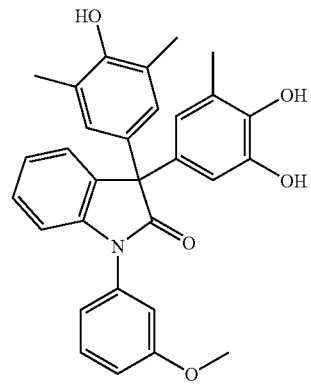

MS (ES): m/z=482 (M+1), 480 (m−1); $^1$H NMR (DMSO-$d_6$): δ9.16 (s, 1H), 8.24 (s, 1H), 8.20 (s, 1H), 7.50 (t, 1H), 7.32-7.23 (m, 2H), 7.13 (t, 1H), 7.06 (m, 1H), 6.98 (m, 2H) 6.83 (d, 1H), 6.79 (s, 2H), 6.56 (d, 1H), 6.36 (d, 1H), 3.81 (s, 3H), 2.10 (s, 6H), 2.03 (s, 3H).

EXAMPLE 148

3-(4-Hydroxy-3,5-dimethyl-phenyl)-3-(4-hydroxy-3-methyl-5-propyl-phenyl)-1-(3-methoxy-phenyl)-1,3-dihydro-indol-2-one

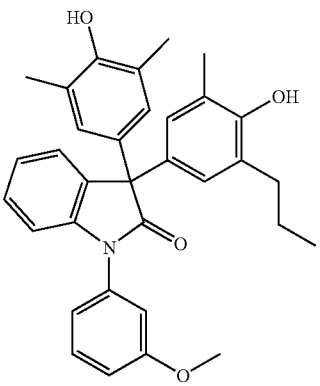

MS (ES): m/z=508 (M+1), 506 (m−1); $^1$H NMR (DMSO-$d_6$): δ8.24 (s, 1H), 8.18 (s, 1H), 7.49 (t, 1H), 7.32-7.22 (m, 2H), 7.14-7.04 (m, 2H), 6.98 (m, 2H), 6.85 (d, 1H), 6.75 (m, 4H), 3.81 (s, 3H), 2.47 (m, 2H), 2.09 (s, 9H), 1.45 (quint, 2H), 0.83 (qu, 3H).

EXAMPLE 149

3-(4-Hydroxy-3,5-dimethyl-phenyl)-3-(4-hydroxy-3-methyl-phenyl)-1-(3-methoxy-phenyl)-1,3-dihydro-indol-2-one

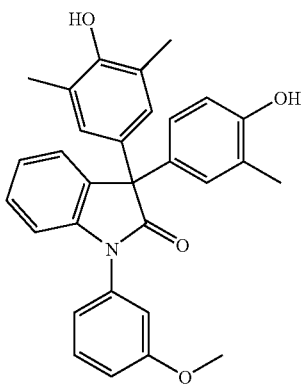

MS (ES): m/z=466 (M+1); $^1$H NMR (DMSO-d$_6$); δ9.32 (s, 1H), 8.25 (s, 1H), 7.49 (t, 1H), 7.32 (d, 1H), 7.25 (t, 1H), 7.12 (t, 1H), 7.05 (m, 1H), 6.98 (m, 2H), 6.91 (m, 1H), 6.84 (m, 2H), 6.76 (s, 2H), 6.72 (d, 1H), 3.81 (s, 3H), 2.09 (s, 6H), 2.05 (s, 3H).

EXAMPLE 150

3-(4-Hydroxy-3,5-dimethyl-phenyl)-3-(4-hydroxy-phenyl)-1-(3-methoxy-phenyl)-1,3-dihydro-indol-2-one

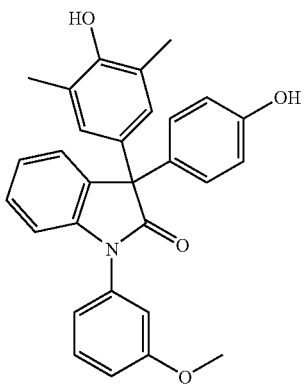

MS (ES): m/z=452 (M+1), 450 (M−1); $^1$H NMR (DMSO-d$_6$): δ9.43 (s, 1H), 8.26 (s, 1H), 7.50 (t, 1H), 7.33-7.23 (m, 2H), 7.12 (t, 1H), 7.07-6.98 (m, 5H), 6.84 (d, 1H), 6.77 (s, 2H), 6.72 (d, 2H), 3.81 (s, 3H), 2.10 (s, 6H).

EXAMPLE 151

3-(3,4-Dimethyl-phenyl)-3-(4-hydroxy-3,5-dimethyl-phenyl)-1-(3-methoxy-phenyl)-1,3-dihydro-indol-2-one

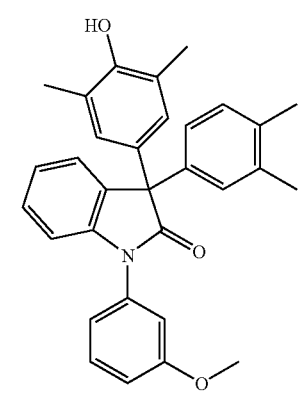

MS (ES): m/z=464 (M+1); $^1$H NMR (DMSO-d$_6$): δ8.28 (s, 1H), 7.49 (t, 1H), 7.33 (d, 1H), 7.26 (t, 1H), 7.15-7.05 (m, 3H), 6.99 (m, 3H), 6.92 (m, 1H), 6.84 (d, 1H), 6.77 (s, 2H), 3.81 (s, 3H), 2.18 (s, 3H), 2.16 (s, 3H), 2.10 (s, 6H).

EXAMPLE 152

3-(4-Hydroxy-3,5-dimethyl-phenyl)-1-(3-methoxy-phenyl)-3-(3,4,5-trimethyl-phenyl)-1,3-dihydro-indol-2-one

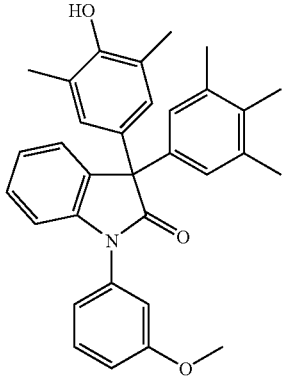

MS (ES): m/z=478 (M+1); $^1$H NMR (DMSO-d$_6$): δ8.27 (s, 1H), 7.49 (t, 1H), 7.35 (d, 1H), 7.26 (t, 1H), 7.13 (t, 1H), 7.05 (m, 1H), 6.98 (m, 2H), 6.84 (d, 3H), 6.77 (s, 2H), 3.81 (s, 3H), 2.17 (s, 6H), 2.09 (s, 9H).

EXAMPLE 153

3-(4-Amino-3,5-dimethyl-phenyl)-3-(4-hydroxy-3,5-dimethyl-phenyl)-1-(3-methoxy-phenyl)-1,3-dihydro-indol-2-one

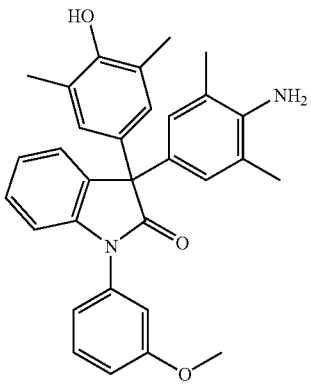

MS (ES): m/z=479 (M+1), 477 (M−1); $^1$H NMR (DMSO-$d_6$): δ8.21 (s, 1H), 7.48 (t, 1H), 7.29 (d, 1H), 7.24 (t, 1H), 7.13-7.03 (m, 2H), 6.97 (m, 2H), 6.82 (d, 1H), 6.76 (s, 2H), 6.67 (s, 2H), 4.56 (bs, 2H), 3.81 (s, 3H), 2.09 (s, 6H), 2.01 (s, 6H).

EXAMPLE 154

3-(4-Amino-3-chloro-5-methyl-phenyl)-3-(4-hydroxy-3,5-dimethyl-phenyl)-1-(3-methoxy-phenyl)-1,3-dihydro-indol-2-one

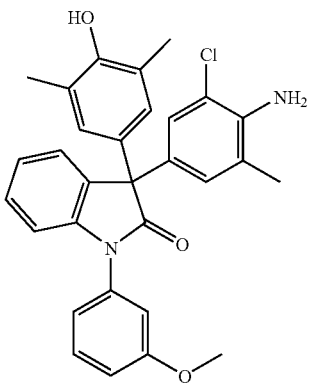

MS (ES): m/z=499 (M+1), 497 (M−1); $^1$H NMR (DMSO-$d_6$): δ8.28 (s, 1H), 7.49 (t, 1H), 7.35 (d, 1H), 7.27 (t, 1H), 7.14 (t, 1H), 7.05 (m, 1H), 6.99 (m, 2H), 6.85-6.80 (m, 3H), 6.77 (s, 2H), 5.09 (bs, 2H), 3.81 (s, 3H), 2.10 (s, 6H), 2.08 (s, 3H).

EXAMPLE 155

3-(4-Amino-3-methyl-phenyl)-3-(4-hydroxy-3,5-dimethyl-phenyl)-1-(3-methoxy-phenyl)-1,3-dihydro-indol-2-one

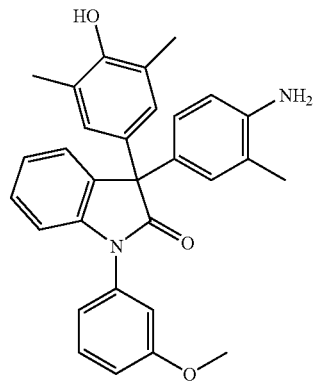

MS (ES): m/z=465 (M+1), 463 (M−1); $^1$H NMR (DMSO-$d_6$): δ8.22 (s, 1H), 7.48 (t, 1H), 7.29 (d, 1H), 7.24 (t, 1H), 7.12 (d, 1H), 7.07 (m, 1H), 6.97 (m, 2H), 6.82 (d, 1H), 6.77-6.73 (m, 4H), 6.53 (d, 1H), 4.86 (bs, 2H), 3.81 (s, 3H), 2.09 (s, 6H), 1.98 (s, 3H).

EXAMPLE 156

3(2,4-Dihydroxy-phenyl)-3-(4hydroxy-3,5-dimethyl-phenyl)-1-(3-methoxy-phenyl)-1,3-hydro-indol-2-one

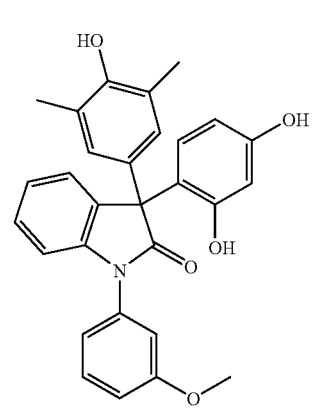

MS (ES): m/z=468 (M+1), 466 (M−1); $^1$H NMR (DMSO-$d_6$): □9.42 (s, 1H), 9.17 bs, 1H), 8.28 (bs, 1H), 7.46 (t, 1H), 7.22-7.17 (m, 1H), 7.07-6.91 (m, 7H), 6.73 (d, 1H), 6.50 (d, 1H), 6.16-6.11 (m, 2H), 3.79 (s, 3H), 2.11 (s, 6H).

EXAMPLE 157

3-(2,4-Dihydroxy-3-methyl-phenyl)-3-(4-hydroxy-3,5-dimethyl-phenyl)-1-(3-methoxy-phenyl)-1,3-dihydro-indol-2-one

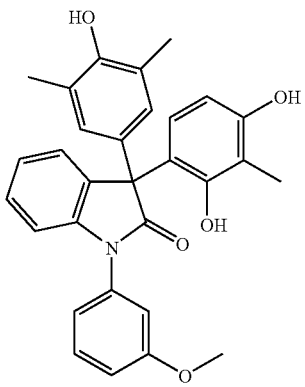

MS (ES): m/z=482 (M+1), 480 (M−1); $^1$H NMR (DMSO-d$_6$): □9.14 (s, 1H), 8.44 (s, 1H), 8.26 (s, 1H), 7.46 (t, 1H), 7.22-7.17 (m, 1H), 7.07-6.98 (m, 5H), 6.94 (s, 2H), 6.75 (d, 1H), 6.37 (d, 1H), 6.27 (m, 1H), 3.80 (s, 3H), 2.10 (s, 6H), 1.91 (s, 3H).

PREPARATION 40

1-(3-Methoxy-phenyl)-1H-indol-2,3-dione

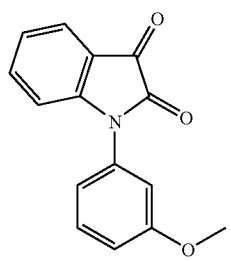

Using a method similar to Preparation 38, with isatin (2.94 g, 20 mmol), 3-methoxyphenylboronic acid (6.08 g, 40 mmol), copper (II) acetate (3.63 g, 20 mmol), pyridine (3.2 ml, 40 mmol) and powdered 4A sieves (15-25 g) in dichloromethane (60 mL). Follow reaction by TLC (50% ethyl acetate/hexane). Stir mechanically for 1 day and add more powdered 4A sieves (10-15 g). Stir for 3 days and add 3-methoxyphenylboronic acid (1.52 g, 10 mmol), copper (II) acetate (1.82 g, 10 mmol), pyridine (1.6 ml, 20 mmol) and powdered 4A sieves (10-15 g). Workup and purify by flash chromatography (dichloromethane) to provide 4.09 g (81%) of an orange solid. MS (ES): m/z=254 (M+1); $^1$H NMR (DMSO-d$_6$): δ7.66-7.58 (m, 2H), 7.51 (t, 1H), 7.19 (t, 1H), 7.09-7.04 (m, 3H) 6.85 (d, 1H), 3.80 (s, 3H).

PREPARATION 41

3-(3-Ethyl-2-hydroxy-phenyl)-3-hydroxy-1-(3-methoxy-phenyl)-1,3-dihydro-indol-2-one

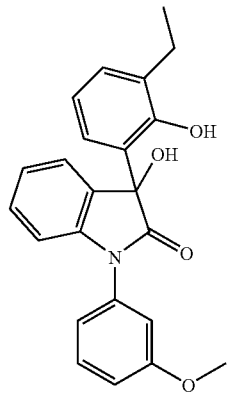

Using the method of Hewawasam, P. and Erway, M; *Tetrahedron Lett.* (1998), 39, 3981-3984 with 2-ethylphenol (0.283 mL, 2.4 mmol) and ethylmagnesium bromide (0.74 mL, 2.2 mmol, 3.0M in diethyl ether) and 1-(3-methoxyphenyl)-1H-indol-2,3-dione (507 mg, 2.0 mmol) gave 816 mg of crude material after workup. Purify by flash chromatography (20% ethyl acetate/hexane to 50% ethyl acetate/hexane) to obtain 553 mg (61%) of a yellow foam. MS (ES): m/z=356 (M+1−H$_2$O), 374 (M−1); $^1$H NMR (DMSO-d$_6$): δ8.65 (s, 1H), 7.50 (m, 2H), 7.24-7.19 (m, 1H), 7.09-6.96 (m, 6H), 6.90-6.85 (m, 2H), 6.77 (d, 1H), 3.83 (s, 3H), 2.52 (m, 2H), 1.07 (t, 3H).

PREPARATION 42

3-Hydroxy-3-(2-hydroxy-phenyl)-1-(3-methoxy-phenyl)-1,3-dihydro-indol-2-one

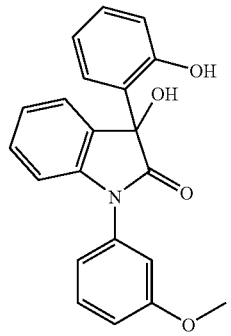

Using a method similar to Preparation 41 with phenol (113 mg, 1.2 mmol) and ethylmagnesium bromide (0.37 mL, 1.1 mmol, 3.0M in diethyl ether) and 1-(3-methoxy-phenyl)-1H-indol-2,3-dione (253 mg, 1.0 mmol) gave 387 mg of crude material after workup. Purify by passing over a pad of silica (33% ethyl acetate/hexane) to obtain 306 mg (88%) of a yellow foam. MS (ES): m/z=330 (M+1−H$_2$O), 346 (M−1); $^1$H NMR (DMSO-d$_6$): δ9.57 (s, 1H), 7.87 (dd, 1H), 7.57 (t, 1H), 7.28-7.15 (m, 2H), 7.12-7.07 (m, 2H), 7.03-6.94 (m, 4H), 6.84-6.69 (d, 3H), 3.88 (s, 3H).

The following examples were made using a method similar to Example 28 with 2,6-dimethyl phenol or o-cresol and 3-(3-Ethyl-2-hydroxy-phenyl)-3-hydroxy-1-(3-methoxy-phenyl)-1,3-dihydro-indol-2-one or 3-Hydroxy-3-(2-hydroxy-phenyl)-1-(3-methoxy-phenyl)-1,3-dihydro-indol-2-one from Preparations 41 and 42 in trifluoroacetic acid at room temperature for 30-60 min. Pour over ice and extract with ethyl acetate (2×). Wash organic portion with 1N NaOH and NaHCO₃, water, brine, dry (MgSO₄), filter and concentrate in vacuo. Purify by flash chromatography (5% ETOAc/CH₂Cl₂) followed by tituration in diethyl ether/hexane to obtain products as solids.

EXAMPLE 158

3-(3-Ethyl-2-hydroxy-phenyl)-3-(4-hydroxy-3,5-dimethyl-phenyl)-1-(3-methoxy-phenyl)-1,3-dihydro-indol-2-one

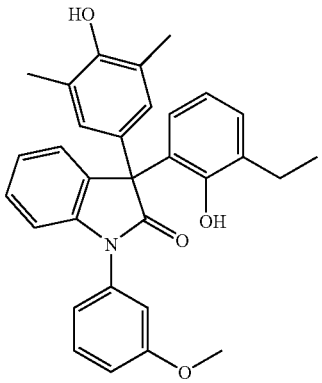

MS (ES): m/z=480 (M+1); ¹H NMR (DMSO-d₆): δ8.54 (s, 1H), 8.31 (s, 1H), 7.47 (t, 1H), 7.22 (dt, 1H), 7.08-6.99 (m, 6H), 6.95 (bs, 2H), 6.80-6.72 (m, 2H), 6.60 (dd, 1H), 3.81 (s, 3H), 2.52 (m, 2H), 2.10 (s, 6H), 1.07 (t, 3H).

EXAMPLE 159

3-(3-Ethyl-2-hydroxy-phenyl)-3-(4-hydroxy-3-methyl-phenyl)-1-(3-methoxy-phenyl)-1,3-dihydro-indol-2-one

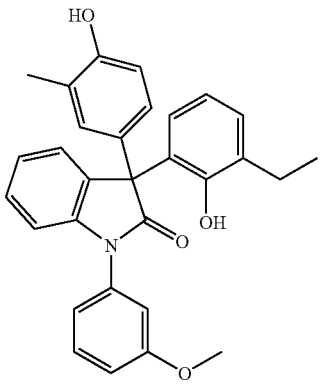

MS (ES): m/z=466 (M+1), 464 (M−1); ¹H NMR (DMSO-d₆): δ9.39 (s, 1H), 8.56 (s, 1H), 7.47 (t, 1H), 7.22 (dt, 1H), 7.13 (s, 1H), 7.08-7.00 (m, 7H), 6.80-6.72 (m, 2H) 6.61 (dd, 1H), 3.81 (s, 3H), 2.52 (m, 2H), 2.07 (s, 3H), 1.07 (t, 3H).

EXAMPLE 160

3-(4-Hydroxy-3,5-dimethyl-phenyl)-3-(2-hydroxy-phenyl)-1-(3-methoxy-phenyl)-1,3-dihydro-indol-2-one

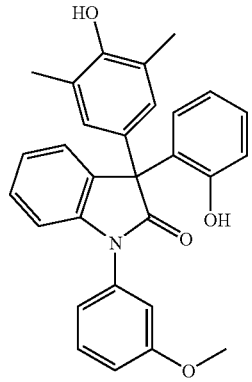

MS (ES): m/z=452 (M+1), 450 (m−1); ¹H NMR (DMSO-d₆): δ9.64 (s, 1H), 8.32 (s, 1H), 7.47 (t, 1H), 7.21 (m, 1H), 7.11-6.94 (m, 8H), 6.75 (m, 3H), 6.68 (d, 1H), 3.80 (s, 3H), 2.12 (s, 6H).

PREPARATION 43

3-[4-(tert-Butyl-dimethyl-silanyloxy)-3,5-dimethyl-phenyl]-3-hydroxy-1-m-tolyl-1,3-dihydro-indol-2-one

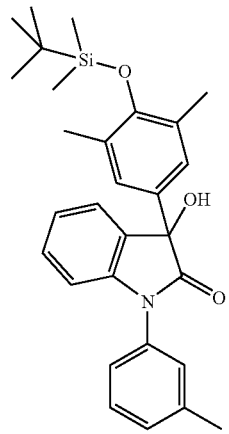

Using a method similar to Preparation 38, with 3-[4-(tert-Butyl-dimethylsilanyloxy)-3,5-dimethyl-phenyl]-3-hydroxy-1,3-dihydro-indol-2-one (11.51 g, 30 mmol), m-tolylboronic acid (8.16 g, 60 mmol), copper (II) acetate (5.45 g, 30 mmol), pyridine (4.9 ml, 60 mmol) and powdered 4A sieves (15 g) in dichloromethane (100 mL) and heat at 32° C. for 1 day stirring mechanically. Add more m-tolylboronic acid (4.08 g, 30 mmol), copper (II) acetate (2.73 g, 15 mmol), pyridine (5.0 ml, 62 mmol) and powdered 4A sieves (15 g) and continue heating for 1 day. Dilute with dichloromethane/ethyl acetate and filter slowly through a pad of Celite and silica gel. Use three such pads to filter the entire reaction washing liberally with ethyl acetate. After the filtration is complete stir the pads in additional ethyl acetate and refilter. Evaporate the organics in vacuo to obtain 17.55 g of a yellow oil. Purify by preparative HPLC (5% ethyl acetate/hexanes for 5 minutes and then use gradient up to 25% ethyl acetate/hexanes) to obtain 9.05 g (64%) of a yellow gum. MS (ES): m/z=474 (M+1); ¹H NMR (DMSO-d$_6$); δ7.47 (t, 1H), 7.30-7.23 (m, 5H), 7.09 (t, 1H), 6.77 (d, 1H), 6.72 (s, 1H), 2.39 (s, 3H), 2.14 (s, 6H), 0.99 (s, 9H), 0.17 (s, 6H).

PREPARATION 44

3-Hydroxy-3-(4-hydroxy-3,5-dimethyl-phenyl)-1-m-tolyl-1,3-dihydro-indol-2-one

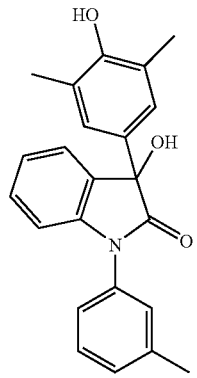

Using a method similar to Preparation 34, with 3-[4-(tert-butyl-dimethyl-silanyloxy)-3,5-dimethyl-phenyl]-3-hydroxy-1-m-tolyl-1,3-dihydro-indol-2-one (9.04 g, 19.1 mmol) and tetrabutylammonium fluoride (21 mL, 21 mmol, 1.0M in THF) in THF followed by workup and concentration in vacuo to obtain a slurry of product in ethyl acetate. Cool, filter, and wash with cold ethyl acetate to obtain 5.49 g (80%) of a white powder. MS (ES): m/z=360 (M+1), 358 (M−1); $^1$H NMR (DMSO-d$_6$): δ8.23 (s, 1H), 7.47 (t, 1H), 7.29-7.21 (m, 5H), 7.08 (t, 1H), 6.91 (s, 2H), 6.77 (d, 1H), 6.63 (s, 1H), 2.39 (s, 3H), 2.13 (s, 6H).

The following examples were made using a method similar to Example 28. Use the appropriate phenol with 3-Hydroxy-3-(4-hydroxy-3,5-dimethyl-phenyl)-1-m-tolyl-1,3-dihydro-indol-2-one in trifluoroacetic acid at room temperature for 30-60 min. Pour over ice and extract with ethyl acetate (2×). Wash organic portion with 1N NaOH and NaHCO$_3$, water, brine, dry (MgSO$_4$), filter and concentrate in vacuo. Purify by flash chromatography with ethyl acetate/hexanes or ethyl acetate/dichloromethane.

EXAMPLE 161

3-(4-Hydroxy-3,5-dimethyl-phenyl)-3-(2-hydroxy-3,4-dimethyl-phenyl)-1-m-tolyl-1,3-dihydro-indol-2-one

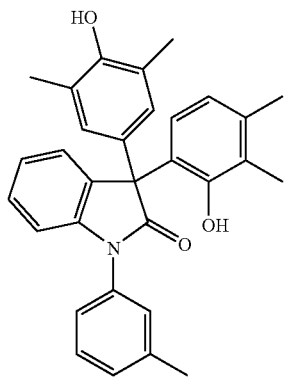

MS (ES): m/z=464 (M+1), 462 (M−1); $^1$H NMR (DMSO-d$_6$); δ8.45 (bs, 1H), 8.29 (bs, 1H), 7.44 (t, 1H), 7.26-7.18 (m, 4H), 7.04-6.97 (m, 2H), 6.93 (s, 2H), 6.72 (d, 1H), 6.61 (d, 1H), 6.48 (d, 1H), 2.38 (s, 3H), 2.16 (s, 3H), 2.09 (s, 6H), 2.01 (s, 3H).

EXAMPLE 162

3-(2,4-Dihydroxy-3-methyl-phenyl)-3-(4-hydroxy-3,5-dimethyl-phenyl)-1-m-tolyl-1,3-dihydro-indol-2-one

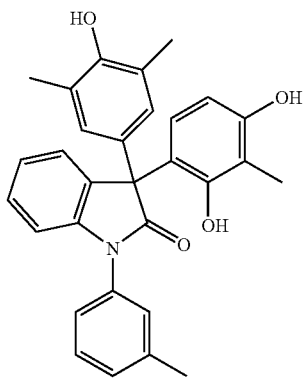

MS (ES): m/z=466 (M+1), 464 (M−1); $^1$H NMR (DMSO-d$_6$); δ9.14 (s, 1H), 8.43 (s, 1H), 8.26 (s, 1H), 7.44 (t, 1H), 7.26-7.17 (m, 4H), 7.07-6.99 (m, 2H), 6.93 (s, 2H), 6.70 (d, 1H), 6.38 (d, 1H), 6.27 (d, 1H), 2.38 (s, 3H), 2.10 (s, 6H), 1.91 (s, 3H).

EXAMPLE 163

R & S-3-(2,4-Dihydroxy-3-methyl-phenyl)-3-(4-hydroxy-3,5-dimethyl-phenyl)-1-m-tolyl-1,3-dihydro-indol-2-one

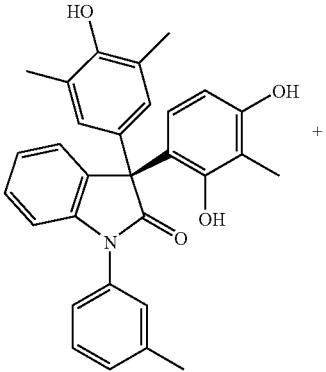

+

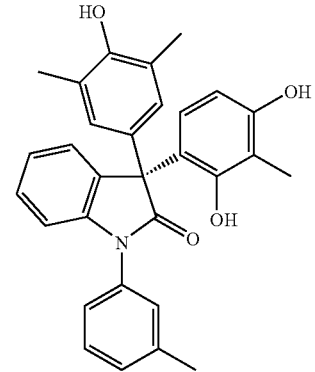

Separate racemic 3-(2,4-Dihydroxy-3-methyl-phenyl)-3-(4-hydroxy-3,5-dimethyl-phenyl)-1-m-tolyl-1,3-dihydro-indol-2-one (2.78 g) by chiral chromatography. Use a Chiralpak AD column of 4.6×250 mm and elute with 10% ethyl alcohol/heptane at a flow rate of 1.0 mL/min with UV detection set at 240 nm. Obtain 792 mg of Isomer 1 with ee=99.0% and 820 mg of Isomer 2 with ee=94.4%.

EXAMPLE 164

3-(5-Fluoro-2-hydroxy-3-methoxy-phenyl)-3-(4-hydroxy-3,5-dimethyl-phenyl)-1-m-tolyl-1,3-dihydro-indol-2-one

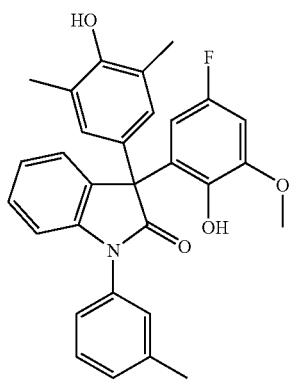

MS (ES): m/z=484 (M+1), 482 (M−1); $^1$H NMR (DMSO-d$_6$); δ8.97 (s, 1H), 8.38 (s, 1H), 7.46 (t, 1H), 7.30-7.24 (m, 2H), 7.18-7.09 (m, 4H), 6.93 (s, 2H), 6.79 (d, 1H), 6.76 (s, 1H), 6.44 (d, 1H), 2.38 (s, 3H), 2.12 (s, 6H).

EXAMPLE 165

3-(4-Hydroxy-3,5-dimethyl-phenyl)-3-(2-hydroxy-5-methyl-phenyl)-1-m-tolyl-1,3-dihydro-indol-2-one

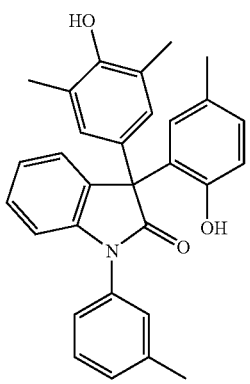

MS (ES): m/z=450 (M+1), 448 (m−1); $^1$H NMR (DMSO-d$_6$): δ9.37 (s, 1H), 8.31 (s, 1H), 7.43 (t, 1H), 7.26-7.17 (m, 4H), 7.03 (d, 2H), 6.97 (s, 2H), 6.86 (dd, 1H), 6.70 (d, 1H), 6.59-6.56 (m, 2H), 3.80 (s, 3H), 2.37 (s, 3H), 2.11 (s, 9H).

EXAMPLE 166

3-(5-Fluoro-2-hydroxy-3-methyl-phenyl)-3-(4-hydroxy-3,5-dimethyl-phenyl)-1-m-tolyl-1,3-dihydro-indol-2-one

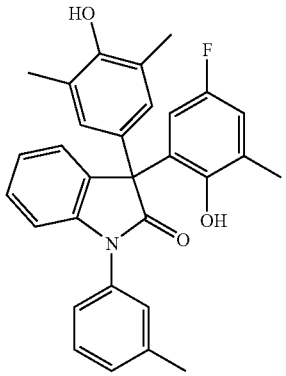

MS (ES): m/z=468 (M+1), 466 (M−1); $^1$H NMR (DMSO-d$_6$): δ8.58 (s, 1H), 8.38 (s, 1H), 7.44 (t, 1H), 7.27-7.20 (m, 4H), 7.06 (d, 2H), 6.97 (s, 2H), 6.89 (dd, 1H), 6.73 (d, 1H), 6.30 (dd, 1H), 2.38 (s, 3H), 2.12 (s, 9H).

EXAMPLE 167

3-(5-Fluoro-2-hydroxy-4-methyl-phenyl)-3-(4-hydroxy-3,5-dimethyl-phenyl)-1-m-tolyl-1,3-dihydro-indol-2-one

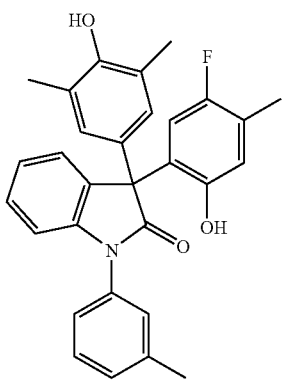

MS (ES): m/z=468 (M+1), 466 (M−1); $^1$H NMR (DMSO-d$_6$): δ9.54 (s, 1H), 8.37 (s, 1H), 7.44 (t, 1H), 7.27-7.16 (m, 4H), 7.09-7.02 (m, 2H), 6.99 (s, 2H), 6.71 (d, 1H), 6.54 (d, 1H), 6.40 (d, 1H), 2.37 (s, 3H), 2.12 (s, 9H).

EXAMPLE 168

3-(4-Hydroxy-3,5-dimethyl-phenyl)-3-(2-hydroxy-4-methyl-phenyl)-1-m-tolyl-1,3-dihydro-indol-2-one

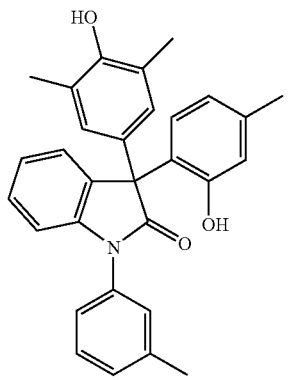

MS (ES): m/z=450 (M+1), 448 (M−1); $^1$H NMR (DMSO-$d_6$): δ9.48 (s, 1H), 8.30 (s, 1H), 7.44 (t, 1H), 7.26-7.17 (m, 4H), 7.06-6.96 (m, 4H), 6.71 (d, 1H), 6.63 (d, 1H), 6.53 (d, 1H), 6.50 (s, 1H), 2.37 (s, 3H), 2.18 (s, 3H), 2.11 (s, 6H).

PREPARATION 45

3-[4-(tert-Butyl-dimethyl-silanyloxy)-3,5-dimethyl-phenyl]-3-hydroxy-1-(3-trifluoromethoxy-phenyl)-1,3-dihydro-indol-2-one

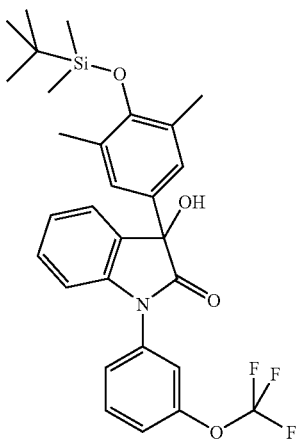

Using a method similar to Preparation 38, with 3-[4-(tert-Butyl-dimethylsilanyloxy)-3,5-dimethyl-phenyl]-3-hydroxy-1,3-dihydro-indol-2-one (15.34 g, 40 mmol), 3-(trifluoromethoxy)phenylboronic acid (16.47 g, 80 mmol), copper (II) acetate (7.27 g, 40 mmol), pyridine (6.5 ml, 80 mmol) and powdered 4A sieves (25 g) in dichloromethane (130 mL) and heat at 32° C. for 1 day stirring mechanically. Add more 3-(trifluoromethoxy)phenylboronic acid (8.24 g, 40 mmol), copper (II) acetate (3.64 g, 20 mmol), pyridine (6.5 ml, 80 mmol) and powdered 4A sieves (25 g) and continue heating for 1 day. Dilute with ethyl acetate (150 mL) and filter slowly through a pads of Celite and silica gel. After the filtration is complete stir the pads in additional ethyl acetate and refilter. Evaporate the organics in vacuo and apply the resulting residue to a silica pad with dichloromethane/acetone. Elute with 2% ethyl acetate/dichloromethane and concentrate in vacuo to obtain 17.45 g of a yellow solid. Titurate the solid in diethyl ether, filter, and dry to obtain 9.47 g (44%) of a white solid. MS (ES): m/z=526 (M+1−H$_2$O); $^1$H NMR (DMSO-$d_6$): δ7.71 (t, 1H), 7.58-7.52 (m, 3H), 7.32-7.25 (m, 2H), 7.13 (t, 1H), 7.01 (s, 2H), 6.87 (d, 1H), 6.76 (s, 1H), 2.14 (s, 6H), 0.99 (s, 9H), 0.17 (s, 6H).

PREPARATION 46

3-Hydroxy-3-(4-hydroxy-3,5-dimethyl-phenyl)-1-(3-trifluoromethoxy-phenyl)-1,3-dihydro-indol-2-one

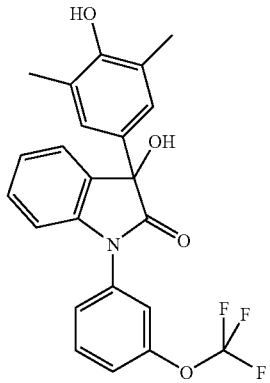

Using a method similar to Preparation 34, with 3-[4-(tert-Butyl-dimethyl-silanyloxy)-3,5-dimethyl-phenyl]-3-hydroxy-1-(3-trifluoromethoxy-phenyl)-1,3-dihydro-indol-2-one (9.43 g, 17.3 mmol) and tetrabutylammonium fluoride (19 mL, 19 mmol, 1.0M in THF) in THF after followed by workup and concentration in vacuo provides a residue. Titurate the residue in diethyl ether, cool, filter, and wash with additional diethyl ether to obtain 4.91 g (66%) of a white solid. MS (ES): m/z=412 (M+1−H$_2$O), 428 (M−1); $^1$H NMR (DMSO-$d_6$): δ8.25 (s, 1H), 7.73 (m, 1H), 7.57-7.48 (m, 3H), 7.31-7.24 (m, 2H), 7.13 (t, 1H), 6.92 (s, 2H), 6.87 (d, 1H), 6.67 (s, 1H), 2.13 (s, 6H).

The following examples were made using a method similar to Example 28. Use the appropriate phenol with 3-Hydroxy-3-(4-hydroxy-3,5-dimethyl-phenyl)-1-(3-trifluoromethoxy-phenyl)-1,3-dihydro-indol-2-one in trifluoroacetic acid at room temperature for 30-60 min. Pour over ice and extract with ethyl acetate (2×). Wash organic portion with 1N NaOH and NaHCO$_3$, water, brine, dry (MgSO$_4$), filter and concentrate in vacuo. Purify by flash chromatography with ethyl acetate/hexanes or ethyl acetate/dichloromethane.

EXAMPLE 169

3-(4-Hydroxy-3,5-dimethyl-phenyl)-3-(2-hydroxy-5-methyl-phenyl)-1-(3-trifluoromethoxy-phenyl)-1,3-dihydro-indol-2-one

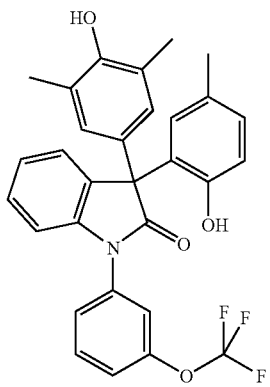

MS (ES): m/z=520 (M+1), 518 (m−1); ¹H NMR (DMSO-d₆): δ9.42 (s, 1H), 8.34 (s, 1H), 7.70 (t, 1H), 7.51-7.42 (m, 3H), 7.24 (dt, 1H), 7.11-7.03 (m, 2H), 6.97 (s, 2H), 6.89 (dd, 1H), 6.81 (d, 1H), 6.58 (m, 2H), 2.11 (s, 9H).

EXAMPLE 170

3-(4-Hydroxy-3,5-dimethyl-phenyl)-3-(2-hydroxy-3,4-dimethyl-phenyl)-1-(3-trifluoromethoxy-phenyl)-1,3-dihydro-indol-2-one

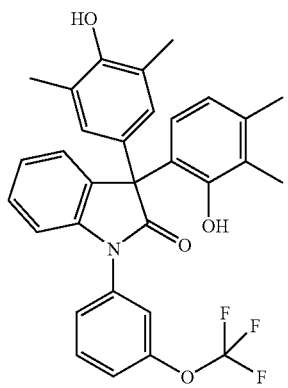

MS (ES): m/z=534 (M+1), 532 (M−1); ¹H NMR (DMSO-d₆): δ8.46 (s, 1H), 8.32 (s, 1H), 7.70 (t, 1H), 7.55-7.45 (m, 3H), 7.25 (dt, 1H), 7.08 (t, 1H), 6.99 (dd, 1H) 6.94 (s, 2H), 6.82 (d, 1H), 6.63 (d, 1H), 6.48 (d, 1H), 2.16 (s, 3H), 2.09 (s, 6H), 2.00 (s, 3H).

EXAMPLE 171

3-(2,4-Dihydroxy-3-methyl-phenyl)-3-(4-hydroxy-3,5-dimethyl-phenyl)-1-(3-trifluoromethoxy-phenyl)-1,3-dihydro-indol-2-one

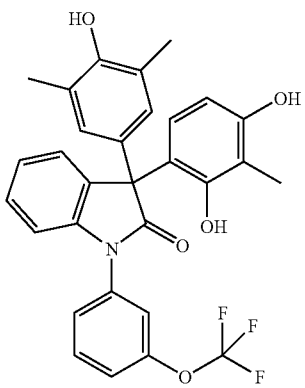

MS (ES): m/z=436 (M+1), 434 (M−1); ¹H NMR (DMSO-d₆): δ9.16 (s, 1H), 8.42 (s, 1H), 8.29 (s, 1H), 7.70 (t, 1H), 7.54-7.44 (m, 3H), 7.23 (t, 1H), 7.08 (t, 1H), 7.00 (d, 1H), 6.94 (s, 2H), 6.81 (d, 1H), 6.38 (d, 1H), 6.28 (d, 1H), 2.10 (s, 6H), 1.91 (s, 3H).

EXAMPLE 172

3-(5-Ethyl-2-hydroxy-phenyl)-3-(4-hydroxy-3,5-dimethyl-phenyl)-1-(3-trifluoromethoxy-phenyl)-1,3-dihydro-indol-2-one

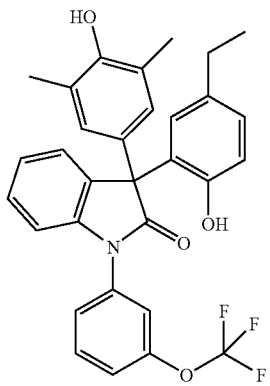

MS (ES): m/z=534 (M+1), 532 (M−1); ¹H NMR (DMSO-d₆): δ9.44 (s, 1H), 8.34 (s, 1H), 7.70 (t, 1H), 7.51-7.42 (m, 3H), 7.25 (dt, 1H), 7.11-6.91 (m, 5H), 6.82 (d, 1H), 6.62 (m, 2H), 2.40 (q, 2H), 2.11 (s, 6H), 1.04 (t, 3H).

We claim:
1. A compound of Formula I:

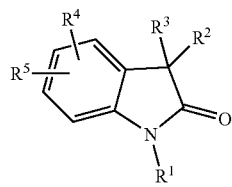

Formula I wherein
R¹ represents a phenyl moiety substituted one to two times independently with a substituent selected from the group consisting of of (C₁-C₆)alkyl, (C₁-C₆)alkoxy, halo, heterocycle, N,N(C₁-C₆)dialkylamine, NH(C₁-C₆)alkylamine, trifluoromethyl, trifluoromethoxy, difluoromethyl, difluoromethoxy or a heterocycle further substituted with one to two moieties selected from the group consisting of (C₁-C₆)alkyl, (C₃-C₇)cycloalkyl, halogen, hydroxy, (C₁-C₆)alkoxy, difluoromethyl, difluoromethoxy, trifluoromethyl, trifluoromethoxy, CF₂CF₃, nitro, amino, N,N(C₁-C₆)dialkylamine, or NH(C₁-C₆)alkylamine; or R¹ represents a substituted benzyl wherein the phenyl group of said benzyl is substituted one to two times independently with a substituent selected from the group consisting of halogen, hydroxy, cyano, nitro, amino, (C₁-C₆)alkyl, (C₁-C₄)alkylsulfonyl, (C₁-C₆)alkoxy, aryl, heterocycle, (C₁-C₆)alkoxycarbonyl, difluoromethyl, difluoromethoxy, trifluoromethyl, trifluoromethoxy, and benzoyl R² and R³ each represent 4-hydroxy-3,5 dimethyl phenyl; and R⁴ and R⁵ each independently represent hydrogen;
or a pharmaceutically acceptable salt thereof.

2. The compound or salt according to claim 1 wherein $R^1$ represents a substituted phenyl moiety further provided that at least one of the substitutions occurs at the meta position of said phenyl moiety.

3. The compound or salt according to claim 2 wherein the compound of Formula I is one wherein $R^1$ represents 3-methyl phenyl, 3-trifluoromethyl-phenyl, 3-isopropyl-phenyl, 3-methoxy-phenyl, 3,4-dimethoxy-phenyl, 3-ethoxy-phenyl, 3-fluoro-phenyl, or 3-bromo-phenyl.

4. The compound or salt according to claim 1 wherein the compound of Formula 1 is one wherein $R^1$ represents 4-methoxy-benzyl, 3-methoxy benzyl, 4-Hydroxy-benzyl, 4-fluoro-benzyl, 2-Fluoro-benzyl, 4-Bromo-benzyl, 2,6-difluoro-benzyl, 2-Bromo-benzyl, 3-Bromo-benzyl, 2,4-Difluoro-benzyl, 2,3-Difluoro-benzyl, 2,6-difluoro-benzyl, 2-Chloro-benzyl, 3-Chloro-benzyl, 3,4-Dichloro-benzyl, 2,6-dichloro-benzyl, 2-Chloro-6-fluoro-benzyl, 4-Bromo-2-fluoro-benzyl, 4-Chloro-2-fluoro-benzyl, 2-methyl-benzyl, 2,6-Dimethyl-benzyl, 2-cyano-benzyl, 4-methoxycarbonyl benzyl, 3-methoxycarbonyl benzyl, 4-methanesulfonyl-benzyl, 4-tert-butyl benzyl, 2-Difluoromethoxy-benzyl, 2-trifluoromethyl-benzyl, 3-trifluoromethoxy-benzyl, 3-trifluoromethyl-benzyl, 4-trifluoromethyl-benzyl, 4-trifluoromethoxy-benzyl, 2,4-Bis-trifluoromethyl-benzyl, 3,5-Bis-trifluoromethyl-benzyl, 2-Fluoro-3-methyl-benzyl, 2-Fluoro-5-trifluoromethyl-benzyl, 4-nitro-benzyl, 2-nitro-benzyl, 3-nitro-benzyl, 2-Amino-benzyl, 3-Amino-benzyl, 4-Amino-benzyl, 4-Benzoyl-benzyl, 1-Biphenyl-2-ylmethyl, or 4-[1,2,3]thiadiazol-4-yl-benzyl.

5. A method of treating diastolic or systolic congestive heart failure comprising administering to a patient in need thereof an effective amount of a compound or salt according to claim 1.

6. A pharmaceutical composition comprising a compound or salt according to claim 1, in combination with a pharmaceutically acceptable carrier.

7. A compound selected from the group consisting of 3,3-Bis-(4-hydroxy-3,5-dimethyl-phenyl)-1-(3-trifluoromethyl-phenyl)-1,3-dihydro-indol-2-one; 3,3-Bis-(4-hydroxy-3,5-dimethyl-phenyl)-1-m-tolyl-1,3-dihydro-indol-2-one; 3,3-Bis-(4-hydroxy-3,5-dimethyl-phenyl)-1-(3-methoxy-phenyl)-1,3-dihydro-indol-2-one; 1-(3-Ethoxy-phenyl)-3,3-bis-(4-hydroxy-3,5-dimethyl-phenyl)-1,3-dihydro-indol-2-one; 1-(2-Chloro-benzyl)-3,3-bis-(4-hydroxy-3,5-dimethyl-phenyl)-1,3-dihydro-indol-2-one; 1-(2,4-Difluoro-benzyl)-3,3-bis-(4-hydroxy-3,5-dimethyl-phenyl)-1,3-dihydro-indol-2-one; and 3,3-Bis-(4-hydroxy-3,5-dimethyl-phenyl)-1-(2-trifluoromethyl-benzyl)-1,3-dihydro-indol-2-one, or a pharmaceutically acceptable salt thereof.

8. A method of treating diastolic or systolic congestive heart failure comprising administering to a patient in need thereof an effective amount of a compound selected from the group consisting of 3,3-Bis-(4-hydroxy-3,5-dimethyl-phenyl)-1-(3-trifluoromethyl-phenyl)-1,3-dihydro-indol-2-one; 3,3-Bis-(4-hydroxy-3,5-dimethyl-phenyl)-1-m-tolyl-1,3-dihydro-indol-2-one; 3,3-Bis-(4-hydroxy-3,5-dimethyl-phenyl)-1-(3-methoxy-phenyl)-1,3-dihydro-indol-2-one; 1-(3-Ethoxy-phenyl)-3,3-bis-(4-hydroxy-3,5-dimethyl-phenyl)-1,3-dihydro-indol-2-one; 1-(2-Chloro-benzyl)-3,3-bis-(4-hydroxy-3,5-dimethyl-phenyl)-1,3-dihydro-indol-2-one; 1-(2,4-Difluoro-benzyl)-3,3-bis-(4-hydroxy-3,5-dimethyl-phenyl)-1,3-dihydro-indol-2-one; and 3,3-Bis-(4-hydroxy-3,5-dimethyl-phenyl)-1-(2-trifluoromethyl-benzyl)-1,3-dihydro-indol-2-one, or a pharmaceutically acceptable salt thereof.

9. A pharmaceutical composition comprising a compound selected from the group consisting of 3,3-Bis-(4-hydroxy-3,5-dimethyl-phenyl)-1-(3-trifluoromethyl-phenyl)-1,3-dihydro-indol-2-one; 3,3-Bis-(4-hydroxy-3,5-dimethyl-phenyl)-1-m-tolyl-1,3-dihydro-indol-2-one; 3,3-Bis-(4-hydroxy-3,5-dimethyl-phenyl)-1-(3-methoxy-phenyl)-1,3-dihydro-indol-2-one; 1-(3-Ethoxy-phenyl)-3,3-bis-(4-hydroxy-3,5-dimethyl-phenyl)-1,3-dihydro-indol-2-one; 1-(2-Chloro-benzyl)-3,3-bis-(4-hydroxy-3,5-dimethyl-phenyl)-1,3-dihydro-indol-2-one; 1-(2,4-Difluoro-benzyl)-3,3-bis-(4-hydroxy-3,5-dimethyl-phenyl)-1,3-dihydro-indol-2-one; and 3,3-Bis-(4-hydroxy-3,5-dimethyl-phenyl)-1-(2-trifluoromethyl-benzyl)-1,3-dihydro-indol-2-one, or a pharmaceutically acceptable salt thereof, in combination with a pharmaceutically acceptable carrier.

* * * * *